United States Patent
Aldridge et al.

(10) Patent No.: US 11,324,527 B2
(45) Date of Patent: May 10, 2022

(54) ULTRASONIC AND ELECTROSURGICAL DEVICES

(71) Applicant: Cilag GmbH International, Zug (CH)

(72) Inventors: Jeffrey L. Aldridge, Lebanon, OH (US); Craig N. Faller, Batavia, OH (US); Kevin D. Felder, Cincinnati, OH (US); Jacob S. Gee, Cincinnati, OH (US); William D. Kelly, Los Altos, CA (US); Robert J. Laird, Morrow, OH (US); Amy L. Marcotte, Mason, OH (US); Jeffrey D. Messerly, Cincinnati, OH (US); Emily H. Monroe, George's Mills, NH (US); Scott A. Nield, Morrow, OH (US); Daniel W. Price, Loveland, OH (US); Patrick J. Scoggins, Loveland, OH (US); John B. Schulte, West Chester, OH (US); Geoffrey S. Strobl, Williamsburg, OH (US); James W. Voegele, Cincinnati, OH (US); John A. Weed, III, Monroe, OH (US); William B. Weisenburgh, II, Maineville, OH (US); Patrick A. Weizman, Liberty Township, OH (US); John W. Willis, Batavia, OH (US)

(73) Assignee: Cilag GmbH International, Zug (CH)

( * ) Notice: Subject to any disclaimer, the term of this patent is extended or adjusted under 35 U.S.C. 154(b) by 348 days.

(21) Appl. No.: 14/627,792

(22) Filed: Feb. 20, 2015

(65) Prior Publication Data

US 2015/0164538 A1    Jun. 18, 2015

Related U.S. Application Data

(62) Division of application No. 13/843,295, filed on Mar. 15, 2013, now abandoned.

(Continued)

(51) Int. Cl.
*A61B 18/14*    (2006.01)
*A61B 17/32*    (2006.01)
(Continued)

(52) U.S. Cl.
CPC ...... *A61B 17/29* (2013.01); *A61B 17/320092* (2013.01); *A61B 18/1206* (2013.01);
(Continued)

(58) Field of Classification Search
CPC .... A61B 17/320092; A61B 17/320068; A61B 2017/320072; A61B 2017/320088;
(Continued)

(56) References Cited

U.S. PATENT DOCUMENTS

| 969,528 A | 9/1910 | Disbrow |
| 1,570,025 A | 1/1926 | Young |

(Continued)

FOREIGN PATENT DOCUMENTS

| AU | 2003241752 A1 | 9/2003 |
| CA | 2535467 A1 | 4/1993 |

(Continued)

OTHER PUBLICATIONS

Technology Overvew. printed from www.harmonicscalpel.com, Internet site, website accessed on Jun. 13, 2007, (3 pages).

(Continued)

*Primary Examiner* — Katherine H Schwiker

(57) ABSTRACT

A surgical instrument comprising a waveguide, an end effector, and an electrical switch is disclosed. The waveguide comprises a proximal end and a distal end, wherein the proximal end is configured to couple to an ultrasonic transducer and one output of a radio frequency (RF) generator. The end effector may comprise an ultrasonic blade and a clamp arm. The ultrasonic blade is mechanically coupled to the distal end of the waveguide and electrically coupled to (Continued)

the waveguide. The clamp arm comprises a movable jaw member electrically coupled to another output of the RF generator. The electrical switch is operable to cause the surgical instrument to deliver electrical current from the RF generator to the movable jaw member for a first period, and to cause the surgical instrument to deliver ultrasonic energy to the ultrasonic blade for a second period.

20 Claims, 62 Drawing Sheets

Related U.S. Application Data

(60) Provisional application No. 61/726,890, filed on Nov. 15, 2012.

(51) Int. Cl.
*A61B 17/29* (2006.01)
*F15D 1/00* (2006.01)
*A61B 18/12* (2006.01)
*A61B 18/00* (2006.01)
*A61B 90/00* (2016.01)
*A61B 17/00* (2006.01)

(52) U.S. Cl.
CPC ........ *A61B 18/1445* (2013.01); *F15D 1/0015* (2013.01); *A61B 2017/005* (2013.01); *A61B 2017/2927* (2013.01); *A61B 2017/2929* (2013.01); *A61B 2017/2936* (2013.01); *A61B 2017/2939* (2013.01); *A61B 2017/320074* (2017.08); *A61B 2017/320078* (2017.08); *A61B 2017/320084* (2013.01); *A61B 2017/320088* (2013.01); *A61B 2017/320093* (2017.08); *A61B 2017/320094* (2017.08); *A61B 2017/320095* (2017.08); *A61B 2018/00023* (2013.01); *A61B 2018/00083* (2013.01); *A61B 2018/00101* (2013.01); *A61B 2018/00107* (2013.01); *A61B 2018/00178* (2013.01); *A61B 2018/00916* (2013.01); *A61B 2018/00922* (2013.01); *A61B 2018/00958* (2013.01); *A61B 2018/00994* (2013.01); *A61B 2090/035* (2016.02); *A61B 2090/0436* (2016.02); *A61B 2090/0472* (2016.02); *A61B 2090/0813* (2016.02); *A61B 2217/005* (2013.01); *Y10T 137/2087* (2015.04)

(58) Field of Classification Search
CPC ............ A61B 18/1445; A61B 18/1442; A61B 2017/320069; A61B 2017/32007; A61B 2017/320071; A61B 2017/320073; A61B 2017/320074; A61B 2017/320075; A61B 2017/320077; A61B 2017/320078; A61B 2017/320082; A61B 2017/320093; A61B 2017/320094; A61B 2017/320095; A61B 2017/320098; A61B 2017/320084; A61B 2017/320089; A61B 2017/32009; A61B 2017/320097; A61B 2018/0063
See application file for complete search history.

(56) References Cited

U.S. PATENT DOCUMENTS

| | | | |
|---|---|---|---|
| 1,813,902 A | 7/1931 | Bovie |
| 2,188,497 A | 1/1940 | Calva |
| 2,366,274 A | 1/1945 | Luth et al. |
| 2,425,245 A | 8/1947 | Johnson |
| 2,442,966 A | 6/1948 | Wallace |
| 2,458,152 A | 1/1949 | Eakins |
| 2,510,693 A | 6/1950 | Green |
| 2,597,564 A | 5/1952 | Bugg |
| 2,704,333 A | 3/1955 | Calosi et al. |
| 2,736,960 A | 3/1956 | Armstrong |
| 2,748,967 A | 6/1956 | Roach |
| 2,845,072 A | 7/1958 | Shafer |
| 2,849,788 A | 9/1958 | Creek |
| 2,867,039 A | 1/1959 | Zach |
| 2,874,470 A | 2/1959 | Richards |
| 2,990,616 A | 7/1961 | Balamuth et al. |
| RE25,033 E | 8/1961 | Balamuth et al. |
| 3,015,961 A | 1/1962 | Roney |
| 3,033,407 A | 5/1962 | Alfons |
| 3,053,124 A | 9/1962 | Balamuth et al. |
| 3,082,805 A | 3/1963 | Royce |
| 3,166,971 A | 1/1965 | Stoecker |
| 3,322,403 A | 5/1967 | Murphy |
| 3,432,691 A | 3/1969 | Shoh |
| 3,433,226 A | 3/1969 | Boyd |
| 3,489,930 A | 1/1970 | Shoh |
| 3,513,848 A | 5/1970 | Winston et al. |
| 3,514,856 A | 6/1970 | Camp et al. |
| 3,525,912 A | 8/1970 | Wallin |
| 3,526,219 A | 9/1970 | Balamuth |
| 3,554,198 A | 1/1971 | Tatoian et al. |
| 3,580,841 A | 5/1971 | Cadotte et al. |
| 3,606,682 A | 9/1971 | Camp et al. |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |
| 3,668,486 A | 6/1972 | Silver |
| 3,702,948 A | 11/1972 | Balamuth |
| 3,703,651 A | 11/1972 | Blowers |
| 3,776,238 A | 12/1973 | Peyman et al. |
| 3,777,760 A | 12/1973 | Essner |
| 3,805,787 A | 4/1974 | Banko |
| 3,809,977 A | 5/1974 | Balamuth et al. |
| 3,830,098 A | 8/1974 | Antonevich |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 3,989,952 A | 11/1976 | Hohmann |
| 4,005,714 A | 2/1977 | Hiltebrandt |
| 4,012,647 A | 3/1977 | Balamuth et al. |
| 4,034,762 A | 7/1977 | Cosens et al. |
| 4,058,126 A | 11/1977 | Leveen |
| 4,074,719 A | 2/1978 | Semm |
| 4,156,187 A | 5/1979 | Murry et al. |
| 4,167,944 A | 9/1979 | Banko |
| 4,188,927 A | 2/1980 | Harris |
| 4,200,106 A | 4/1980 | Douvas et al. |
| 4,203,430 A | 5/1980 | Takahashi |
| 4,203,444 A | 5/1980 | Bonnell et al. |
| 4,220,154 A | 9/1980 | Semm |
| 4,237,441 A | 12/1980 | van Konynenburg et al. |
| 4,244,371 A | 1/1981 | Farin |
| 4,281,785 A | 8/1981 | Brooks |
| 4,300,083 A | 11/1981 | Heiges |
| 4,302,728 A | 11/1981 | Nakamura |
| 4,304,987 A | 12/1981 | van Konynenburg |
| 4,306,570 A | 12/1981 | Matthews |
| 4,314,559 A | 2/1982 | Allen |
| 4,353,371 A | 10/1982 | Cosman |
| 4,409,981 A | 10/1983 | Lundberg |
| 4,445,063 A | 4/1984 | Smith |
| 4,461,304 A | 7/1984 | Kuperstein |
| 4,463,759 A | 8/1984 | Garito et al. |
| 4,491,132 A | 1/1985 | Aikins |
| 4,492,231 A | 1/1985 | Auth |
| 4,494,759 A | 1/1985 | Kieffer |

(56) References Cited

U.S. PATENT DOCUMENTS

| | | |
|---|---|---|
| 4,504,264 A | 3/1985 | Kelman |
| 4,512,344 A | 4/1985 | Barber |
| 4,526,571 A | 7/1985 | Wuchinich |
| 4,535,773 A | 8/1985 | Yoon |
| 4,541,638 A | 9/1985 | Ogawa et al. |
| 4,545,374 A | 10/1985 | Jacobson |
| 4,545,926 A | 10/1985 | Fouts, Jr. et al. |
| 4,549,147 A | 10/1985 | Kondo |
| 4,550,870 A | 11/1985 | Krumme et al. |
| 4,553,544 A | 11/1985 | Nomoto et al. |
| 4,562,838 A | 1/1986 | Walker |
| 4,574,615 A | 3/1986 | Bower et al. |
| 4,582,236 A | 4/1986 | Hirose |
| 4,593,691 A | 6/1986 | Lindstrom et al. |
| 4,608,981 A | 9/1986 | Rothfuss et al. |
| 4,617,927 A | 10/1986 | Manes |
| 4,633,119 A | 12/1986 | Thompson |
| 4,633,874 A | 1/1987 | Chow et al. |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,674,502 A | 6/1987 | Imonti |
| 4,694,835 A | 9/1987 | Strand |
| 4,708,127 A | 11/1987 | Abdelghani |
| 4,712,722 A | 12/1987 | Hood et al. |
| 4,735,603 A | 4/1988 | Goodson et al. |
| 4,761,871 A | 8/1988 | O'Connor et al. |
| 4,808,154 A | 2/1989 | Freeman |
| 4,819,635 A | 4/1989 | Shapiro |
| 4,827,911 A | 5/1989 | Broadwin et al. |
| 4,830,462 A | 5/1989 | Karny et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,849,133 A | 7/1989 | Yoshida et al. |
| 4,850,354 A | 7/1989 | McGurk-Burleson et al. |
| 4,852,578 A | 8/1989 | Companion et al. |
| 4,860,745 A | 8/1989 | Farin et al. |
| 4,862,890 A | 9/1989 | Stasz et al. |
| 4,865,159 A | 9/1989 | Jamison |
| 4,867,157 A | 9/1989 | McGurk-Burleson et al. |
| 4,878,493 A | 11/1989 | Pasternak et al. |
| 4,880,015 A | 11/1989 | Nierman |
| 4,881,550 A | 11/1989 | Kothe |
| 4,896,009 A | 1/1990 | Pawlowski |
| 4,903,696 A | 2/1990 | Stasz et al. |
| 4,910,389 A | 3/1990 | Sherman et al. |
| 4,915,643 A | 4/1990 | Samejima et al. |
| 4,920,978 A | 5/1990 | Colvin |
| 4,922,902 A | 5/1990 | Wuchinich et al. |
| 4,936,842 A | 6/1990 | D'Amelio et al. |
| 4,954,960 A | 9/1990 | Lo et al. |
| 4,965,532 A | 10/1990 | Sakurai |
| 4,979,952 A | 12/1990 | Kubota et al. |
| 4,981,756 A | 1/1991 | Rhandhawa |
| 5,001,649 A | 3/1991 | Lo et al. |
| 5,009,661 A | 4/1991 | Michelson |
| 5,013,956 A | 5/1991 | Kurozumi et al. |
| 5,015,227 A | 5/1991 | Broadwin et al. |
| 5,020,514 A | 6/1991 | Heckele |
| 5,026,370 A | 6/1991 | Lottick |
| 5,026,387 A | 6/1991 | Thomas |
| 5,035,695 A | 7/1991 | Weber, Jr. et al. |
| 5,042,461 A | 8/1991 | Inoue et al. |
| 5,042,707 A | 8/1991 | Taheri |
| 5,052,145 A | 10/1991 | Wang |
| 5,061,269 A | 10/1991 | Muller |
| 5,075,839 A | 12/1991 | Fisher et al. |
| 5,084,052 A | 1/1992 | Jacobs |
| 5,099,840 A | 3/1992 | Goble et al. |
| 5,104,025 A | 4/1992 | Main et al. |
| 5,105,117 A | 4/1992 | Yamaguchi |
| 5,106,538 A | 4/1992 | Barma et al. |
| 5,108,383 A | 4/1992 | White |
| 5,109,819 A | 5/1992 | Custer et al. |
| 5,112,300 A | 5/1992 | Ureche |
| 5,113,139 A | 5/1992 | Furukawa |
| 5,123,903 A | 6/1992 | Quaid et al. |
| 5,126,618 A | 6/1992 | Takahashi et al. |
| D327,872 S | 7/1992 | McMills et al. |
| 5,152,762 A | 10/1992 | McElhenney |
| 5,156,633 A | 10/1992 | Smith |
| 5,160,334 A | 11/1992 | Billings et al. |
| 5,162,044 A | 11/1992 | Gahn et al. |
| 5,163,421 A | 11/1992 | Bernstein et al. |
| 5,163,537 A | 11/1992 | Radev |
| 5,163,945 A | 11/1992 | Ortiz et al. |
| 5,167,619 A | 12/1992 | Wuchinich |
| 5,167,725 A | 12/1992 | Clark et al. |
| 5,172,344 A | 12/1992 | Ehrlich |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grezeszykowski |
| 5,188,102 A | 2/1993 | Idemoto et al. |
| D334,173 S | 3/1993 | Liu et al. |
| 5,190,517 A | 3/1993 | Zieve et al. |
| 5,190,518 A | 3/1993 | Takasu |
| 5,190,541 A | 3/1993 | Abele et al. |
| 5,196,007 A | 3/1993 | Ellman et al. |
| 5,205,459 A | 4/1993 | Brinkerhoff et al. |
| 5,205,817 A | 4/1993 | Idemoto et al. |
| 5,209,719 A | 5/1993 | Baruch et al. |
| 5,213,569 A | 5/1993 | Davis |
| 5,214,339 A | 5/1993 | Naito |
| 5,217,460 A | 6/1993 | Knoepfler |
| 5,218,529 A | 6/1993 | Meyer et al. |
| 5,221,282 A | 6/1993 | Wuchinich |
| 5,222,937 A | 6/1993 | Kagawa |
| 5,226,909 A | 7/1993 | Evans et al. |
| 5,226,910 A | 7/1993 | Kajiyama et al. |
| 5,231,989 A | 8/1993 | Middleman et al. |
| 5,234,428 A | 8/1993 | Kaufman |
| 5,241,236 A | 8/1993 | Sasaki et al. |
| 5,241,968 A | 9/1993 | Slater |
| 5,242,339 A | 9/1993 | Thornton |
| 5,242,460 A | 9/1993 | Klein et al. |
| 5,246,003 A | 9/1993 | DeLonzor |
| 5,254,129 A | 10/1993 | Alexander |
| 5,257,988 A | 11/1993 | L'Esperanee, Jr. |
| 5,258,004 A | 11/1993 | Bales et al. |
| 5,258,006 A | 11/1993 | Rydell et al. |
| 5,261,922 A | 11/1993 | Hood |
| 5,263,957 A | 11/1993 | Davison |
| 5,264,925 A | 11/1993 | Shipp et al. |
| 5,269,297 A | 12/1993 | Weng et al. |
| 5,275,166 A | 1/1994 | Vaitekunas et al. |
| 5,275,607 A | 1/1994 | Lo et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,285,945 A | 2/1994 | Brinkerhoff et al. |
| 5,290,286 A | 3/1994 | Parins |
| 5,293,863 A | 3/1994 | Zhu et al. |
| 5,300,068 A | 4/1994 | Rosar et al. |
| 5,304,115 A | 4/1994 | Pflueger et al. |
| D347,474 S | 5/1994 | Olson |
| 5,307,976 A | 5/1994 | Olson et al. |
| 5,309,927 A | 5/1994 | Welch |
| 5,312,023 A | 5/1994 | Green et al. |
| 5,312,425 A | 5/1994 | Evans et al. |
| 5,318,525 A | 6/1994 | West et al. |
| 5,318,563 A | 6/1994 | Malis et al. |
| 5,318,564 A | 6/1994 | Eggers |
| 5,318,570 A | 6/1994 | Hood et al. |
| 5,318,589 A | 6/1994 | Lichtman |
| 5,322,055 A | 6/1994 | Davison et al. |

(56) References Cited

U.S. PATENT DOCUMENTS

| | | |
|---|---|---|
| 5,324,299 A | 6/1994 | Davison et al. |
| 5,326,013 A | 7/1994 | Green et al. |
| 5,326,342 A | 7/1994 | Pflueger et al. |
| 5,330,471 A | 7/1994 | Eggers |
| 5,330,502 A | 7/1994 | Hassler et al. |
| 5,334,183 A | 8/1994 | Wuchinich |
| 5,339,723 A | 8/1994 | Huitema |
| 5,342,356 A | 8/1994 | Ellman et al. |
| 5,342,359 A | 8/1994 | Rydell |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A | 10/1994 | Good et al. |
| 5,357,164 A | 10/1994 | Imabayashi et al. |
| 5,357,423 A | 10/1994 | Weaver et al. |
| 5,359,994 A | 11/1994 | Krauter et al. |
| 5,361,583 A | 11/1994 | Huitema |
| 5,366,466 A | 11/1994 | Christian et al. |
| 5,368,557 A | 11/1994 | Nita et al. |
| 5,370,645 A | 12/1994 | Klicek et al. |
| 5,371,429 A | 12/1994 | Manna |
| 5,374,813 A | 12/1994 | Shipp |
| D354,564 S | 1/1995 | Medema |
| 5,381,067 A | 1/1995 | Greenstein et al. |
| 5,383,874 A | 1/1995 | Jackson et al. |
| 5,383,917 A | 1/1995 | Desai et al. |
| 5,387,207 A | 2/1995 | Dyer et al. |
| 5,387,215 A | 2/1995 | Fisher |
| 5,389,098 A | 2/1995 | Tsuruta et al. |
| 5,394,187 A | 2/1995 | Shipp |
| 5,395,033 A | 3/1995 | Byrne et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,400,267 A | 3/1995 | Denen et al. |
| 5,403,312 A | 4/1995 | Yates et al. |
| 5,403,334 A | 4/1995 | Evans et al. |
| 5,406,503 A | 4/1995 | Williams, Jr. et al. |
| 5,408,268 A | 4/1995 | Shipp |
| D358,887 S | 5/1995 | Feinberg |
| 5,411,481 A | 5/1995 | Allen et al. |
| 5,417,709 A | 5/1995 | Slater |
| 5,419,761 A | 5/1995 | Narayanan et al. |
| 5,421,829 A | 6/1995 | Olichney et al. |
| 5,423,844 A | 6/1995 | Miller |
| 5,428,504 A | 6/1995 | Bhatia |
| 5,429,131 A | 7/1995 | Scheinman et al. |
| 5,438,997 A | 8/1995 | Sieben et al. |
| 5,441,499 A | 8/1995 | Fritzsch |
| 5,443,463 A | 8/1995 | Stern et al. |
| 5,445,638 A | 8/1995 | Rydell et al. |
| 5,445,639 A | 8/1995 | Kuslich et al. |
| 5,447,509 A | 9/1995 | Mills et al. |
| 5,449,370 A | 9/1995 | Vaitekunas |
| 5,451,053 A | 9/1995 | Garrido |
| 5,451,161 A | 9/1995 | Sharp |
| 5,451,220 A | 9/1995 | Ciervo |
| 5,451,227 A | 9/1995 | Michaelson |
| 5,456,684 A | 10/1995 | Schmidt et al. |
| 5,458,598 A | 10/1995 | Feinberg et al. |
| 5,462,604 A | 10/1995 | Shibano et al. |
| 5,465,895 A | 11/1995 | Knodel et al. |
| 5,471,988 A | 12/1995 | Fujio et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,490,860 A | 2/1996 | Middle et al. |
| 5,496,317 A | 3/1996 | Goble et al. |
| 5,499,992 A | 3/1996 | Meade et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,507,297 A | 4/1996 | Slater et al. |
| 5,507,738 A | 4/1996 | Ciervo |
| 5,509,922 A | 4/1996 | Aranyi et al. |
| 5,511,556 A | 4/1996 | DeSantis |
| 5,520,704 A | 5/1996 | Castro et al. |
| 5,522,832 A | 6/1996 | Kugo et al. |
| 5,522,839 A | 6/1996 | Pilling |
| 5,527,331 A | 6/1996 | Kresch et al. |
| 5,531,744 A | 7/1996 | Nardella et al. |
| 5,540,681 A | 7/1996 | Strul et al. |
| 5,540,693 A | 7/1996 | Fisher |
| 5,542,916 A | 8/1996 | Hirsch et al. |
| 5,548,286 A | 8/1996 | Craven |
| 5,549,637 A | 8/1996 | Crainich |
| 5,553,675 A | 9/1996 | Pitzen et al. |
| 5,558,671 A | 9/1996 | Yates |
| 5,562,609 A | 10/1996 | Brumbach |
| 5,562,610 A | 10/1996 | Brumbach |
| 5,562,659 A | 10/1996 | Morris |
| 5,562,703 A | 10/1996 | Desai |
| 5,563,179 A | 10/1996 | Stone et al. |
| 5,569,164 A | 10/1996 | Lurz |
| 5,571,121 A | 11/1996 | Heifetz |
| 5,573,424 A | 11/1996 | Poppe |
| 5,573,533 A | 11/1996 | Strul |
| 5,573,534 A | 11/1996 | Stone |
| 5,577,654 A | 11/1996 | Bishop |
| 5,584,830 A | 12/1996 | Ladd et al. |
| 5,591,187 A | 1/1997 | Dekel |
| 5,593,414 A | 1/1997 | Shipp et al. |
| 5,599,350 A | 2/1997 | Schulze et al. |
| 5,600,526 A | 2/1997 | Russell et al. |
| 5,601,601 A | 2/1997 | Tal et al. |
| 5,603,773 A | 2/1997 | Campbell |
| 5,607,436 A | 3/1997 | Pratt et al. |
| 5,607,450 A | 3/1997 | Zvenyatsky et al. |
| 5,609,573 A | 3/1997 | Sandock |
| 5,611,813 A | 3/1997 | Lichtman |
| 5,618,304 A | 4/1997 | Hart et al. |
| 5,618,307 A | 4/1997 | Donlon et al. |
| 5,618,492 A | 4/1997 | Auten et al. |
| 5,620,447 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,626,608 A | 5/1997 | Cuny et al. |
| 5,628,760 A | 5/1997 | Knoepfler |
| 5,630,420 A | 5/1997 | Vaitekunas |
| 5,632,432 A | 5/1997 | Schulze et al. |
| 5,632,717 A | 5/1997 | Yoon |
| 5,640,741 A | 6/1997 | Yano |
| D381,077 S | 7/1997 | Hunt |
| 5,647,871 A | 7/1997 | Levine et al. |
| 5,649,937 A | 7/1997 | Bito |
| 5,649,955 A | 7/1997 | Hashimoto et al. |
| 5,651,780 A | 7/1997 | Jackson et al. |
| 5,653,713 A | 8/1997 | Michelson |
| 5,655,100 A | 8/1997 | Ebrahim et al. |
| 5,658,281 A | 8/1997 | Heard |
| 5,662,662 A | 9/1997 | Bishop et al. |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,678,568 A | 10/1997 | Uchikubo et al. |
| 5,688,270 A | 11/1997 | Yates et al. |
| 5,690,269 A | 11/1997 | Bolanos et al. |
| 5,693,051 A | 12/1997 | Schulze et al. |
| 5,694,936 A | 12/1997 | Fujimoto et al. |
| 5,695,510 A | 12/1997 | Hood |

(56) References Cited

U.S. PATENT DOCUMENTS

| | | | |
|---|---|---|---|
| 5,700,261 A * | 12/1997 | Brinkerhoff | A61B 18/1445 606/205 |
| 5,704,534 A | 1/1998 | Huitema et al. | |
| 5,704,791 A | 1/1998 | Gillio | |
| 5,707,369 A | 1/1998 | Vaitekunas et al. | |
| 5,709,680 A | 1/1998 | Yates et al. | |
| 5,711,472 A | 1/1998 | Bryan | |
| 5,713,896 A | 2/1998 | Nardella | |
| 5,715,817 A | 2/1998 | Stevens-Wright et al. | |
| 5,716,366 A | 2/1998 | Yates | |
| 5,717,306 A | 2/1998 | Shipp | |
| 5,720,742 A | 2/1998 | Zacharias | |
| 5,720,744 A | 2/1998 | Eggleston et al. | |
| 5,722,980 A | 3/1998 | Schulz et al. | |
| 5,723,970 A | 3/1998 | Bell | |
| 5,728,130 A | 3/1998 | Ishikawa et al. | |
| 5,730,752 A | 3/1998 | Alden et al. | |
| 5,733,074 A | 3/1998 | Stöck et al. | |
| 5,735,848 A | 4/1998 | Yates et al. | |
| 5,741,226 A | 4/1998 | Strukel et al. | |
| 5,743,906 A | 4/1998 | Parins et al. | |
| 5,752,973 A | 5/1998 | Kieturakis | |
| 5,755,717 A | 5/1998 | Yates et al. | |
| 5,762,255 A | 6/1998 | Chrisman et al. | |
| 5,766,164 A | 6/1998 | Mueller et al. | |
| 5,772,659 A | 6/1998 | Becker et al. | |
| 5,776,130 A | 7/1998 | Buysse et al. | |
| 5,776,155 A | 7/1998 | Beaupre et al. | |
| 5,779,130 A | 7/1998 | Alesi et al. | |
| 5,779,701 A | 7/1998 | McBrayer et al. | |
| 5,782,834 A | 7/1998 | Lucey et al. | |
| 5,792,135 A | 8/1998 | Madhani et al. | |
| 5,792,138 A | 8/1998 | Shipp | |
| 5,792,165 A | 8/1998 | Klieman et al. | |
| 5,796,188 A | 8/1998 | Bays | |
| 5,797,941 A | 8/1998 | Schulze et al. | |
| 5,797,958 A | 8/1998 | Yoon | |
| 5,797,959 A | 8/1998 | Castro et al. | |
| 5,800,432 A | 9/1998 | Swanson | |
| 5,800,449 A | 9/1998 | Wales | |
| 5,805,140 A | 9/1998 | Rosenberg et al. | |
| 5,807,393 A | 9/1998 | Williamson, IV et al. | |
| 5,808,396 A | 9/1998 | Boukhny | |
| 5,810,811 A | 9/1998 | Yates et al. | |
| 5,810,828 A | 9/1998 | Lightman et al. | |
| 5,810,859 A | 9/1998 | DiMatteo et al. | |
| 5,817,033 A | 10/1998 | DeSantis et al. | |
| 5,817,084 A | 10/1998 | Jensen | |
| 5,817,093 A | 10/1998 | Williamson, IV et al. | |
| 5,817,119 A | 10/1998 | Klieman et al. | |
| 5,823,197 A | 10/1998 | Edwards | |
| 5,827,271 A | 10/1998 | Buysse et al. | |
| 5,827,323 A | 10/1998 | Klieman et al. | |
| 5,828,160 A | 10/1998 | Sugishita | |
| 5,833,696 A | 11/1998 | Whitfield et al. | |
| 5,836,897 A | 11/1998 | Sakurai et al. | |
| 5,836,909 A | 11/1998 | Cosmescu | |
| 5,836,943 A | 11/1998 | Miller, III | |
| 5,836,957 A | 11/1998 | Schulz et al. | |
| 5,836,990 A | 11/1998 | Li | |
| 5,843,109 A | 12/1998 | Mehta et al. | |
| 5,851,212 A | 12/1998 | Zirps et al. | |
| 5,853,412 A | 12/1998 | Mayenberger | |
| 5,854,590 A | 12/1998 | Dalstein | |
| 5,858,018 A | 1/1999 | Shipp et al. | |
| 5,865,361 A | 2/1999 | Milliman et al. | |
| 5,873,873 A | 2/1999 | Smith et al. | |
| 5,873,882 A | 2/1999 | Straub et al. | |
| 5,876,401 A | 3/1999 | Schulze et al. | |
| 5,878,193 A | 3/1999 | Wang et al. | |
| 5,879,364 A | 3/1999 | Bromfield et al. | |
| 5,880,668 A | 3/1999 | Hall | |
| 5,883,615 A | 3/1999 | Fago et al. | |
| 5,891,142 A | 4/1999 | Eggers et al. | |
| 5,893,835 A | 4/1999 | Witt et al. | |
| 5,897,523 A | 4/1999 | Wright et al. | |
| 5,897,569 A | 4/1999 | Kellogg et al. | |
| 5,903,607 A | 5/1999 | Tailliet | |
| 5,904,681 A | 5/1999 | West, Jr. | |
| 5,906,625 A | 5/1999 | Bito et al. | |
| 5,906,627 A | 5/1999 | Spaulding | |
| 5,906,628 A | 5/1999 | Miyawaki et al. | |
| 5,910,129 A | 6/1999 | Koblish et al. | |
| 5,911,699 A | 6/1999 | Anis et al. | |
| 5,913,823 A | 6/1999 | Hedberg et al. | |
| 5,916,229 A | 6/1999 | Evans | |
| 5,921,956 A | 7/1999 | Grinberg et al. | |
| 5,929,846 A | 7/1999 | Rosenberg et al. | |
| 5,935,143 A | 8/1999 | Hood | |
| 5,935,144 A | 8/1999 | Estabrook | |
| 5,938,633 A | 8/1999 | Beaupre | |
| 5,944,718 A | 8/1999 | Austin et al. | |
| 5,944,737 A | 8/1999 | Tsonton et al. | |
| 5,947,984 A | 9/1999 | Whipple | |
| 5,954,717 A | 9/1999 | Behl et al. | |
| 5,954,736 A | 9/1999 | Bishop et al. | |
| 5,954,746 A | 9/1999 | Holthaus et al. | |
| 5,957,882 A | 9/1999 | Nita et al. | |
| 5,957,943 A | 9/1999 | Vaitekunas | |
| 5,968,007 A | 10/1999 | Simon et al. | |
| 5,968,060 A | 10/1999 | Kellogg | |
| 5,974,342 A | 10/1999 | Petrofsky | |
| D416,089 S | 11/1999 | Barton et al. | |
| 5,980,510 A | 11/1999 | Tsonton et al. | |
| 5,980,546 A | 11/1999 | Hood | |
| 5,984,938 A | 11/1999 | Yoon | |
| 5,987,344 A | 11/1999 | West | |
| 5,989,274 A | 11/1999 | Davison et al. | |
| 5,989,275 A | 11/1999 | Estabrook et al. | |
| 5,993,465 A | 11/1999 | Shipp et al. | |
| 5,993,972 A | 11/1999 | Reich et al. | |
| 5,994,855 A | 11/1999 | Lundell et al. | |
| 6,003,517 A | 12/1999 | Sheffield et al. | |
| 6,004,335 A | 12/1999 | Vaitekunas et al. | |
| 6,013,052 A | 1/2000 | Durman et al. | |
| 6,024,741 A | 2/2000 | Williamson, IV et al. | |
| 6,024,744 A | 2/2000 | Kese et al. | |
| 6,024,750 A | 2/2000 | Mastri et al. | |
| 6,027,515 A | 2/2000 | Cimino | |
| 6,031,526 A | 2/2000 | Shipp | |
| 6,033,375 A | 3/2000 | Brumbach | |
| 6,033,399 A | 3/2000 | Gines | |
| 6,036,667 A | 3/2000 | Manna et al. | |
| 6,036,707 A | 3/2000 | Spaulding | |
| 6,039,734 A | 3/2000 | Goble | |
| 6,048,224 A | 4/2000 | Kay | |
| 6,050,943 A | 4/2000 | Slayton et al. | |
| 6,050,996 A | 4/2000 | Schmaltz et al. | |
| 6,051,010 A | 4/2000 | DiMatteo et al. | |
| 6,056,735 A | 5/2000 | Okada et al. | |
| 6,063,098 A | 5/2000 | Houser et al. | |
| 6,066,132 A | 5/2000 | Chen et al. | |
| 6,066,151 A | 5/2000 | Miyawaki et al. | |
| 6,068,627 A | 5/2000 | Orszulak et al. | |
| 6,068,629 A | 5/2000 | Haissaguerre et al. | |
| 6,068,647 A | 5/2000 | Witt et al. | |
| 6,074,389 A | 6/2000 | Levine et al. | |
| 6,077,285 A | 6/2000 | Boukhny | |
| 6,080,149 A | 6/2000 | Huang et al. | |
| 6,083,191 A | 7/2000 | Rose | |
| 6,086,584 A | 7/2000 | Miller | |
| 6,090,120 A | 7/2000 | Wright et al. | |
| 6,091,995 A | 7/2000 | Ingle et al. | |
| 6,096,033 A | 8/2000 | Tu et al. | |
| 6,099,483 A | 8/2000 | Palmer et al. | |
| 6,099,542 A | 8/2000 | Cohn et al. | |
| 6,099,550 A | 8/2000 | Yoon | |
| 6,109,500 A | 8/2000 | Alli et al. | |
| 6,110,127 A | 8/2000 | Suzuki | |
| 6,113,594 A | 9/2000 | Savage | |
| 6,113,598 A | 9/2000 | Baker | |
| 6,117,152 A | 9/2000 | Huitema | |
| H001904 H | 10/2000 | Yates et al. | |
| 6,126,629 A | 10/2000 | Perkins | |

(56) References Cited

U.S. PATENT DOCUMENTS

| | | | |
|---|---|---|---|
| 6,126,658 A | 10/2000 | Baker |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,429 A | 10/2000 | Baker |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,144,402 A | 11/2000 | Norsworthy et al. |
| 6,147,560 A | 11/2000 | Erhage et al. |
| 6,152,902 A | 11/2000 | Christian et al. |
| 6,152,923 A | 11/2000 | Ryan |
| 6,154,198 A | 11/2000 | Rosenberg |
| 6,156,029 A | 12/2000 | Mueller |
| 6,159,160 A | 12/2000 | Hsei et al. |
| 6,159,175 A | 12/2000 | Strukel et al. |
| 6,162,194 A | 12/2000 | Shipp |
| 6,162,208 A | 12/2000 | Hipps |
| 6,165,150 A | 12/2000 | Banko |
| 6,174,309 B1 | 1/2001 | Wrublewski et al. |
| 6,174,310 B1 | 1/2001 | Kirwan, Jr. |
| 6,176,857 B1 | 1/2001 | Ashley |
| 6,179,853 B1 | 1/2001 | Sachse et al. |
| 6,183,426 B1 | 2/2001 | Akisada et al. |
| 6,187,003 B1 | 2/2001 | Buysse et al. |
| 6,190,386 B1 | 2/2001 | Rydell |
| 6,193,709 B1 | 2/2001 | Miyawaki et al. |
| 6,204,592 B1 | 3/2001 | Hur |
| 6,205,383 B1 | 3/2001 | Hermann |
| 6,205,855 B1 | 3/2001 | Pfeiffer |
| 6,206,844 B1 | 3/2001 | Reichel et al. |
| 6,206,876 B1 | 3/2001 | Levine et al. |
| 6,210,337 B1 | 4/2001 | Dunham et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,228,080 B1 | 5/2001 | Gines |
| 6,231,565 B1 | 5/2001 | Tovey et al. |
| 6,232,899 B1 | 5/2001 | Craven |
| 6,233,476 B1 | 5/2001 | Strommer et al. |
| 6,238,366 B1 | 5/2001 | Savage et al. |
| 6,241,724 B1 | 6/2001 | Fleischman et al. |
| 6,245,065 B1 | 6/2001 | Panescu et al. |
| 6,251,110 B1 | 6/2001 | Wampler |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,259,230 B1 | 7/2001 | Chou |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,292,700 B1 | 9/2001 | Morrison et al. |
| 6,299,591 B1 | 10/2001 | Banko |
| 6,306,131 B1 | 10/2001 | Hareyama |
| 6,306,157 B1 | 10/2001 | Shchetvinsky |
| 6,309,400 B2 | 10/2001 | Beaupre |
| 6,311,783 B1 | 11/2001 | Harpell |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,338,657 B1 | 1/2002 | Harper et al. |
| 6,340,352 B1 | 1/2002 | Okada et al. |
| 6,340,878 B1 | 1/2002 | Oglesbee |
| 6,350,269 B1 | 2/2002 | Shipp et al. |
| 6,352,532 B1 | 3/2002 | Kramer et al. |
| 6,356,224 B1 | 3/2002 | Wohlfarth |
| 6,358,246 B1 | 3/2002 | Behl et al. |
| 6,358,264 B2 | 3/2002 | Banko |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,094 B1 | 5/2002 | Eitenmuller |
| 6,387,109 B1 | 5/2002 | Davison et al. |
| 6,388,657 B1 | 5/2002 | Natoli |
| 6,390,973 B1 | 5/2002 | Ouchi |
| 6,391,026 B1 | 5/2002 | Hung et al. |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,184 B1 | 6/2002 | Bohme et al. |
| 6,405,733 B1 | 6/2002 | Fogarty et al. |
| 6,409,722 B1 | 6/2002 | Hoey et al. |
| H002037 H | 7/2002 | Yates et al. |
| 6,416,469 B1 | 7/2002 | Phung et al. |
| 6,416,486 B1 | 7/2002 | Wampler |
| 6,419,675 B1 | 7/2002 | Gallo, Sr. |
| 6,423,073 B2 | 7/2002 | Bowman |
| 6,423,082 B1 | 7/2002 | Houser et al. |
| 6,425,906 B1 | 7/2002 | Young et al. |
| 6,428,538 B1 | 8/2002 | Blewett et al. |
| 6,428,539 B1 | 8/2002 | Baxter et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,128 B1 | 10/2002 | Schulze |
| 6,458,130 B1 | 10/2002 | Frazier et al. |
| 6,458,142 B1 | 10/2002 | Faller et al. |
| 6,459,363 B1 | 10/2002 | Walker et al. |
| 6,461,363 B1 | 10/2002 | Gadberry et al. |
| 6,464,689 B1 | 10/2002 | Qin et al. |
| 6,464,702 B2 | 10/2002 | Schulze et al. |
| 6,468,270 B1 | 10/2002 | Hovda et al. |
| 6,475,211 B2 | 11/2002 | Chess et al. |
| 6,475,215 B1 | 11/2002 | Tanrisever |
| 6,480,796 B2 | 11/2002 | Wiener |
| 6,485,490 B2 | 11/2002 | Wampler et al. |
| 6,491,690 B1 | 12/2002 | Goble et al. |
| 6,491,701 B2 | 12/2002 | Tierney et al. |
| 6,491,708 B2 | 12/2002 | Madan et al. |
| 6,497,715 B2 | 12/2002 | Satou |
| 6,500,112 B1 | 12/2002 | Khouri |
| 6,500,176 B1 | 12/2002 | Truckai et al. |
| 6,500,188 B2 | 12/2002 | Harper et al. |
| 6,500,312 B2 | 12/2002 | Wedekamp |
| 6,503,248 B1 | 1/2003 | Levine |
| 6,506,208 B2 | 1/2003 | Hunt et al. |
| 6,511,478 B1 | 1/2003 | Burnside |
| 6,511,480 B1 | 1/2003 | Tetzlaff et al. |
| 6,511,493 B1 | 1/2003 | Moutafis et al. |
| 6,514,252 B2 | 2/2003 | Nezhat et al. |
| 6,514,267 B2 | 2/2003 | Jewett |
| 6,517,565 B1 | 2/2003 | Whitman et al. |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,531,846 B1 | 3/2003 | Smith |

(56) References Cited

U.S. PATENT DOCUMENTS

| | | |
|---|---|---|
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,561,983 B2 | 5/2003 | Cronin et al. |
| 6,562,035 B1 | 5/2003 | Levin |
| 6,562,037 B2 | 5/2003 | Paton et al. |
| 6,565,558 B1 | 5/2003 | Lindenmeier et al. |
| 6,572,563 B2 | 6/2003 | Ouchi |
| 6,572,632 B2 | 6/2003 | Zisterer et al. |
| 6,572,639 B1 | 6/2003 | Ingle et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| 6,584,360 B2 | 6/2003 | Francischelli et al. |
| D477,408 S | 7/2003 | Bromley |
| 6,585,735 B1 | 7/2003 | Frazier et al. |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,590,733 B1 | 7/2003 | Wilson et al. |
| 6,599,288 B2 | 7/2003 | Maguire et al. |
| 6,602,252 B2 | 8/2003 | Mollenauer |
| 6,602,262 B2 | 8/2003 | Griego et al. |
| 6,607,540 B1 | 8/2003 | Shipp |
| 6,610,059 B1 | 8/2003 | West, Jr. |
| 6,610,060 B2 | 8/2003 | Mulier et al. |
| 6,611,793 B1 | 8/2003 | Burnside et al. |
| 6,616,450 B2 | 9/2003 | Mossie et al. |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,632,221 B1 | 10/2003 | Edwards et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,651,669 B1 | 11/2003 | Burnside |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,132 B1 | 12/2003 | Ouchi |
| 6,656,177 B2 | 12/2003 | Truckai et al. |
| 6,656,198 B2 | 12/2003 | Tsonton et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,710 B2 | 12/2003 | Moutafis et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,685,700 B2 | 2/2004 | Behl et al. |
| 6,685,701 B2 | 2/2004 | Orszulak et al. |
| 6,685,703 B2 | 2/2004 | Pearson et al. |
| 6,689,145 B2 | 2/2004 | Lee et al. |
| 6,689,146 B1 | 2/2004 | Himes |
| 6,690,960 B2 | 2/2004 | Chen et al. |
| 6,695,840 B2 | 2/2004 | Schulze |
| 6,702,821 B2 | 3/2004 | Bonutti |
| 6,716,215 B1 | 4/2004 | David et al. |
| 6,719,692 B2 | 4/2004 | Kleffner et al. |
| 6,719,765 B2 | 4/2004 | Bonutti |
| 6,719,776 B2 | 4/2004 | Baxter |
| 6,722,552 B2 | 4/2004 | Fenton, Jr. |
| 6,723,091 B2 | 4/2004 | Goble et al. |
| D490,059 S | 5/2004 | Conway et al. |
| 6,730,080 B2 | 5/2004 | Harano et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauhi et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,766,202 B2 | 7/2004 | Underwood et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,773,435 B2 | 8/2004 | Schulze et al. |
| 6,773,443 B2 | 8/2004 | Truwit et al. |
| 6,773,444 B2 | 8/2004 | Messerly |
| 6,775,575 B2 | 8/2004 | Bommannan et al. |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,173 B2 | 9/2004 | Saadat et al. |
| 6,790,216 B1 | 9/2004 | Ishikawa |
| 6,794,027 B1 | 9/2004 | Araki et al. |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,811,842 B1 | 11/2004 | Ehrnsperger et al. |
| 6,814,731 B2 | 11/2004 | Swanson |
| 6,819,027 B2 | 11/2004 | Saraf |
| 6,821,273 B2 | 11/2004 | Mollenauer |
| 6,827,712 B2 | 12/2004 | Tovey et al. |
| 6,828,712 B2 | 12/2004 | Battaglin et al. |
| 6,835,082 B2 | 12/2004 | Gonnering |
| 6,835,199 B2 | 12/2004 | McGuckin, Jr. et al. |
| 6,840,938 B1 | 1/2005 | Morley et al. |
| 6,843,789 B2 | 1/2005 | Goble |
| 6,849,073 B2 | 2/2005 | Hoey et al. |
| 6,860,878 B2 | 3/2005 | Brock |
| 6,860,880 B2 | 3/2005 | Treat et al. |
| 6,863,676 B2 | 3/2005 | Lee et al. |
| 6,866,671 B2 | 3/2005 | Tierney et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,252 B1 | 5/2005 | Okada et al. |
| 6,893,435 B2 | 5/2005 | Goble |
| 6,898,536 B2 | 5/2005 | Wiener et al. |
| 6,899,685 B2 | 5/2005 | Kermode et al. |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,923,806 B2 | 8/2005 | Hooven et al. |
| 6,926,712 B2 | 8/2005 | Phan |

(56) References Cited

U.S. PATENT DOCUMENTS

| | | |
|---|---|---|
| 6,926,716 B2 | 8/2005 | Baker et al. |
| 6,926,717 B1 | 8/2005 | Garito et al. |
| 6,929,602 B2 | 8/2005 | Hirakui et al. |
| 6,929,622 B2 | 8/2005 | Chian |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,660 B2 | 9/2005 | Pantera et al. |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| 6,953,461 B2 | 10/2005 | McClurken et al. |
| 6,958,070 B2 | 10/2005 | Witt et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,984,231 B2 | 1/2006 | Goble et al. |
| 6,988,295 B2 | 1/2006 | Tillim |
| 6,994,708 B2 | 2/2006 | Manzo |
| 6,994,709 B2 | 2/2006 | Iida |
| 7,000,818 B2 | 2/2006 | Shelton, IV et al. |
| 7,001,335 B2 | 2/2006 | Adachi et al. |
| 7,001,379 B2 | 2/2006 | Behl et al. |
| 7,001,382 B2 | 2/2006 | Gallo, Sr. |
| 7,004,951 B2 | 2/2006 | Gibbens, III |
| 7,011,657 B2 | 3/2006 | Truckai et al. |
| 7,014,638 B2 | 3/2006 | Michelson |
| 7,018,389 B2 | 3/2006 | Camerlengo |
| 7,025,732 B2 | 4/2006 | Thompson et al. |
| 7,033,356 B2 | 4/2006 | Latterell et al. |
| 7,033,357 B2 | 4/2006 | Baxter et al. |
| 7,037,306 B2 | 5/2006 | Podany |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,052,494 B2 | 5/2006 | Goble et al. |
| 7,055,731 B2 | 6/2006 | Shelton, IV et al. |
| 7,063,699 B2 | 6/2006 | Hess et al. |
| 7,066,893 B2 | 6/2006 | Hibner et al. |
| 7,066,895 B2 | 6/2006 | Podany |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,075 B2 | 8/2006 | Swayze et al. |
| 7,083,613 B2 | 8/2006 | Treat |
| 7,083,618 B2 | 8/2006 | Couture |
| 7,083,619 B2 | 8/2006 | Truckai et al. |
| 7,087,054 B2 | 8/2006 | Truckai et al. |
| 7,090,637 B2 | 8/2006 | Danitz et al. |
| 7,090,672 B2 | 8/2006 | Underwood et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| 7,113,831 B2 | 9/2006 | Hooven |
| D531,311 S | 10/2006 | Guerra et al. |
| 7,117,034 B2 | 10/2006 | Kronberg |
| 7,118,564 B2 | 10/2006 | Ritchie et al. |
| 7,118,570 B2 | 10/2006 | Tetzlaff et al. |
| 7,118,587 B2 | 10/2006 | Dycus et al. |
| 7,119,516 B2 | 10/2006 | Denning |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,131,970 B2 | 11/2006 | Moses et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,144,403 B2 | 12/2006 | Booth |
| 7,147,138 B2 | 12/2006 | Shelton, IV |
| 7,153,315 B2 | 12/2006 | Miller |
| D536,093 S | 1/2007 | Nakajima et al. |
| 7,156,189 B1 | 1/2007 | Bar-Cohen et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,259 B2 | 1/2007 | Tardy et al. |
| 7,160,296 B2 | 1/2007 | Pearson et al. |
| 7,160,298 B2 | 1/2007 | Lawes et al. |
| 7,160,299 B2 | 1/2007 | Baily |
| 7,163,548 B2 | 1/2007 | Stulen et al. |
| 7,166,103 B2 | 1/2007 | Carmel et al. |
| 7,169,144 B2 | 1/2007 | Hoey et al. |
| 7,169,146 B2 | 1/2007 | Truckai et al. |
| 7,169,156 B2 | 1/2007 | Hart |
| 7,179,254 B2 | 2/2007 | Pendekanti et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,198,635 B2 | 4/2007 | Danek et al. |
| 7,204,820 B2 | 4/2007 | Akahoshi |
| 7,207,471 B2 | 4/2007 | Heinrich et al. |
| 7,207,997 B2 | 4/2007 | Shipp et al. |
| 7,208,005 B2 | 4/2007 | Frecker et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | Ei-Gailey et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,447 B2 | 6/2007 | Uchida et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,071 B2 | 6/2007 | Gonnering |
| 7,235,073 B2 | 6/2007 | Levine et al. |
| 7,241,294 B2 | 7/2007 | Reschke |
| 7,244,262 B2 | 7/2007 | Wiener et al. |
| 7,251,531 B2 | 7/2007 | Mosher et al. |
| 7,252,641 B2 | 8/2007 | Thompson et al. |
| 7,252,667 B2 | 8/2007 | Moses et al. |
| 7,258,688 B1 | 8/2007 | Shah et al. |
| 7,264,618 B2 | 9/2007 | Murakami et al. |
| 7,267,677 B2 | 9/2007 | Johnson et al. |
| 7,267,685 B2 | 9/2007 | Butaric et al. |
| 7,269,873 B2 | 9/2007 | Brewer et al. |
| 7,273,483 B2 | 9/2007 | Wiener et al. |
| D552,241 S | 10/2007 | Bramley et al. |
| 7,282,048 B2 | 10/2007 | Goble et al. |
| 7,285,895 B2 | 10/2007 | Beaupré |
| 7,287,682 B1 | 10/2007 | Ezzat et al. |
| 7,297,149 B2 | 11/2007 | Vitali et al. |
| 7,300,431 B2 | 11/2007 | Dubrovsky |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,531 B2 | 12/2007 | Lee et al. |
| 7,303,557 B2 | 12/2007 | Wham et al. |
| 7,306,597 B2 | 12/2007 | Manzo |
| 7,307,313 B2 | 12/2007 | Ohyanagi et al. |
| 7,309,849 B2 | 12/2007 | Truckai et al. |

(56) References Cited

U.S. PATENT DOCUMENTS

| | | |
|---|---|---|
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,353,068 B2 | 4/2008 | Tanaka et al. |
| 7,354,440 B2 | 4/2008 | Truckai et al. |
| 7,357,287 B2 | 4/2008 | Shelton, IV et al. |
| 7,357,802 B2 | 4/2008 | Palanker et al. |
| 7,361,172 B2 | 4/2008 | Cimino |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,412,008 B2 | 8/2008 | Lliev |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| 7,422,582 B2 | 9/2008 | Malackowski et al. |
| D578,643 S | 10/2008 | Shumer et al. |
| D578,644 S | 10/2008 | Shumer et al. |
| D578,645 S | 10/2008 | Shumer et al. |
| 7,431,694 B2 | 10/2008 | Stefanchik et al. |
| 7,431,704 B2 | 10/2008 | Babaev |
| 7,431,720 B2 | 10/2008 | Pendekanti et al. |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,449,004 B2 | 11/2008 | Yamada et al. |
| 7,451,904 B2 | 11/2008 | Shelton, IV |
| 7,455,208 B2 | 11/2008 | Wales et al. |
| 7,455,641 B2 | 11/2008 | Yamada et al. |
| 7,462,181 B2 | 12/2008 | Kraft et al. |
| 7,464,846 B2 | 12/2008 | Shelton, IV et al. |
| 7,464,849 B2 | 12/2008 | Shelton, IV et al. |
| 7,472,815 B2 | 1/2009 | Shelton, IV et al. |
| 7,473,145 B2 | 1/2009 | Ehr et al. |
| 7,473,253 B2 | 1/2009 | Dycus et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,488,319 B2 | 2/2009 | Yates |
| 7,491,201 B2 | 2/2009 | Shields et al. |
| 7,491,202 B2 | 2/2009 | Odom et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,502,234 B2 | 3/2009 | Goliszek et al. |
| 7,503,893 B2 | 3/2009 | Kucklick |
| 7,503,895 B2 | 3/2009 | Rabinet et al. |
| 7,506,790 B2 | 3/2009 | Shelton, IV |
| 7,506,791 B2 | 3/2009 | Omaits et al. |
| 7,507,239 B2 | 3/2009 | Shadduck |
| 7,510,107 B2 | 3/2009 | Timm et al. |
| 7,510,556 B2 | 3/2009 | Nguyen et al. |
| 7,513,025 B2 | 4/2009 | Fischer |
| 7,517,349 B2 | 4/2009 | Truckai et al. |
| 7,524,320 B2 | 4/2009 | Tierney et al. |
| 7,530,986 B2 | 5/2009 | Beaupre et al. |
| 7,534,243 B1 | 5/2009 | Chin et al. |
| 7,535,233 B2 | 5/2009 | Kojovic et al. |
| D594,983 S | 6/2009 | Price et al. |
| 7,540,871 B2 | 6/2009 | Gonnering |
| 7,540,872 B2 | 6/2009 | Schechter et al. |
| 7,543,730 B1 | 6/2009 | Marczyk |
| 7,544,200 B2 | 6/2009 | Houser |
| 7,549,564 B2 | 6/2009 | Boudreaux |
| 7,550,216 B2 | 6/2009 | Ofer et al. |
| 7,553,309 B2 | 6/2009 | Buysse et al. |
| 7,554,343 B2 | 6/2009 | Bromfield |
| 7,559,450 B2 | 7/2009 | Wales et al. |
| 7,559,452 B2 | 7/2009 | Wales et al. |
| 7,563,259 B2 | 7/2009 | Takahashi |
| 7,566,318 B2 | 7/2009 | Haefner |
| 7,567,012 B2 | 7/2009 | Namikawa |
| 7,568,603 B2 | 8/2009 | Shelton, IV et al. |
| 7,569,057 B2 | 8/2009 | Liu et al. |
| 7,572,266 B2 | 8/2009 | Young et al. |
| 7,572,268 B2 | 8/2009 | Babaev |
| 7,578,820 B2 | 8/2009 | Moore et al. |
| 7,582,084 B2 | 9/2009 | Swanson et al. |
| 7,582,086 B2 | 9/2009 | Privitera et al. |
| 7,582,087 B2 | 9/2009 | Tetzlaff et al. |
| 7,582,095 B2 | 9/2009 | Shipp et al. |
| 7,585,181 B2 | 9/2009 | Olsen |
| 7,586,289 B2 | 9/2009 | Andruk et al. |
| 7,587,536 B2 | 9/2009 | McLeod |
| 7,588,176 B2 | 9/2009 | Timm et al. |
| 7,588,177 B2 | 9/2009 | Racenet |
| 7,594,925 B2 | 9/2009 | Danek et al. |
| 7,597,693 B2 | 10/2009 | Garrison |
| 7,601,119 B2 | 10/2009 | Shahinian |
| 7,601,136 B2 | 10/2009 | Akahoshi |
| 7,604,150 B2 | 10/2009 | Boudreaux |
| 7,607,557 B2 | 10/2009 | Shelton, IV et al. |
| 7,617,961 B2 | 11/2009 | Viola |
| 7,621,930 B2 | 11/2009 | Houser |
| 7,625,370 B2 | 12/2009 | Hart et al. |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,240 B2 | 1/2010 | Thompson et al. |
| 7,645,277 B2 | 1/2010 | McClurken et al. |
| 7,645,278 B2 | 1/2010 | Ichihashi et al. |
| 7,648,499 B2 | 1/2010 | Orszulak et al. |
| 7,649,410 B2 | 1/2010 | Andersen et al. |
| 7,654,431 B2 | 2/2010 | Hueil et al. |
| 7,655,003 B2 | 2/2010 | Lorang et al. |
| 7,658,311 B2 | 2/2010 | Boudreaux |
| 7,659,833 B2 | 2/2010 | Warner et al. |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,667,592 B2 | 2/2010 | Ohyama et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,105 B2 | 3/2010 | McGreevy et al. |
| 7,678,125 B2 | 3/2010 | Shipp |
| 7,682,366 B2 | 3/2010 | Sakurai et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,095 B2 | 4/2010 | Bednarek et al. |
| 7,691,098 B2 | 4/2010 | Wallace et al. |
| 7,696,441 B2 | 4/2010 | Kataoka |
| 7,699,846 B2 | 4/2010 | Ryan |

(56) References Cited

U.S. PATENT DOCUMENTS

| | | |
|---|---|---|
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,708,768 B2 | 5/2010 | Danek et al. |
| 7,713,202 B2 | 5/2010 | Boukhny et al. |
| 7,713,267 B2 | 5/2010 | Pozzato |
| 7,714,481 B2 | 5/2010 | Sakai |
| 7,717,312 B2 | 5/2010 | Beetel |
| 7,717,914 B2 | 5/2010 | Kimura |
| 7,717,915 B2 | 5/2010 | Miyazawa |
| 7,721,935 B2 | 5/2010 | Racenet et al. |
| 7,722,527 B2 | 5/2010 | Bouchier et al. |
| 7,722,607 B2 | 5/2010 | Dumbauld et al. |
| D618,797 S | 6/2010 | Price et al. |
| 7,726,537 B2 | 6/2010 | Olson et al. |
| 7,727,177 B2 | 6/2010 | Bayat |
| 7,731,717 B2 | 6/2010 | Odom et al. |
| 7,738,969 B2 | 6/2010 | Bleich |
| 7,740,594 B2 | 6/2010 | Hibner |
| 7,744,615 B2 | 6/2010 | Couture |
| 7,749,240 B2 | 7/2010 | Takahashi et al. |
| 7,751,115 B2 | 7/2010 | Song |
| 7,753,245 B2 | 7/2010 | Boudreaux et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| D621,503 S | 8/2010 | Otten et al. |
| 7,766,210 B2 | 8/2010 | Shelton, IV et al. |
| 7,766,693 B2 | 8/2010 | Sartor et al. |
| 7,766,910 B2 | 8/2010 | Hixson et al. |
| 7,768,510 B2 | 8/2010 | Tsai et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,776,036 B2 | 8/2010 | Schechter et al. |
| 7,776,037 B2 | 8/2010 | Odom |
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,662 B2 | 8/2010 | Wales et al. |
| 7,784,663 B2 | 8/2010 | Shelton, IV |
| 7,789,883 B2 | 9/2010 | Takashino et al. |
| 7,793,814 B2 | 9/2010 | Racenet et al. |
| 7,794,475 B2 | 9/2010 | Hess et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,027 B2 | 9/2010 | Hafner |
| 7,799,045 B2 | 9/2010 | Masuda |
| 7,803,152 B2 | 9/2010 | Honda et al. |
| 7,803,156 B2 | 9/2010 | Eder et al. |
| 7,803,168 B2 | 9/2010 | Gifford et al. |
| 7,806,891 B2 | 10/2010 | Nowlin et al. |
| 7,810,693 B2 | 10/2010 | Broehl et al. |
| 7,811,283 B2 | 10/2010 | Moses et al. |
| 7,815,238 B2 | 10/2010 | Cao |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,819 B2 | 10/2010 | Quick et al. |
| 7,819,872 B2 | 10/2010 | Johnson et al. |
| 7,821,143 B2 | 10/2010 | Wiener |
| D627,066 S | 11/2010 | Romero |
| 7,824,401 B2 | 11/2010 | Manzo et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,484 B2 | 11/2010 | Sartor |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,846,160 B2 | 12/2010 | Payne et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,862,561 B2 | 1/2011 | Swanson et al. |
| 7,867,228 B2 | 1/2011 | Nobis et al. |
| 7,871,392 B2 | 1/2011 | Sartor |
| 7,871,423 B2 | 1/2011 | Livneh |
| 7,876,030 B2 | 1/2011 | Taki et al. |
| D631,965 S | 2/2011 | Price et al. |
| 7,877,852 B2 | 2/2011 | Unger et al. |
| 7,878,991 B2 | 2/2011 | Babaev |
| 7,879,029 B2 | 2/2011 | Jimenez |
| 7,879,033 B2 | 2/2011 | Sartor et al. |
| 7,879,035 B2 | 2/2011 | Garrison et al. |
| 7,879,070 B2 | 2/2011 | Ortiz et al. |
| 7,883,475 B2 | 2/2011 | Dupont et al. |
| 7,892,606 B2 | 2/2011 | Thies et al. |
| 7,896,875 B2 | 3/2011 | Heim et al. |
| 7,897,792 B2 | 3/2011 | Iikura et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,909,820 B2 | 3/2011 | Lipson et al. |
| 7,909,824 B2 | 3/2011 | Masuda et al. |
| 7,918,848 B2 | 4/2011 | Lau et al. |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,611 B2 | 4/2011 | Novak et al. |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,936,203 B2 | 5/2011 | Zimiich |
| 7,951,095 B2 | 5/2011 | Makin et al. |
| 7,951,165 B2 | 5/2011 | Golden et al. |
| 7,955,331 B2 | 6/2011 | Truckai et al. |
| 7,956,620 B2 | 6/2011 | Gilbert |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,972,328 B2 | 7/2011 | Wham et al. |
| 7,972,329 B2 | 7/2011 | Refior et al. |
| 7,975,895 B2 | 7/2011 | Milliman |
| 7,976,544 B2 | 7/2011 | McClurken et al. |
| 7,980,443 B2 | 7/2011 | Scheib et al. |
| 7,981,050 B2 | 7/2011 | Ritchart et al. |
| 7,981,113 B2 | 7/2011 | Truckai et al. |
| 7,997,278 B2 | 8/2011 | Utley et al. |
| 7,998,157 B2 | 8/2011 | Culp et al. |
| 8,002,732 B2 | 8/2011 | Visconti |
| 8,002,770 B2 | 8/2011 | Swanson et al. |
| 8,020,743 B2 | 9/2011 | Shelton, IV |
| 8,028,885 B2 | 10/2011 | Smith et al. |
| 8,033,173 B2 | 10/2011 | Ehlert et al. |
| 8,034,049 B2 | 10/2011 | Odom et al. |
| 8,038,693 B2 | 10/2011 | Allen |
| 8,048,070 B2 | 11/2011 | O'Brien et al. |
| 8,052,672 B2 | 11/2011 | Laufer et al. |
| 8,055,208 B2 | 11/2011 | Lilla et al. |
| 8,056,720 B2 | 11/2011 | Hawkes |
| 8,056,787 B2 | 11/2011 | Boudreaux et al. |
| 8,057,468 B2 | 11/2011 | Konesky |
| 8,057,498 B2 | 11/2011 | Robertson |
| 8,058,771 B2 | 11/2011 | Giordano et al. |
| 8,061,014 B2 | 11/2011 | Smith et al. |
| 8,066,167 B2 | 11/2011 | Measamer et al. |
| 8,070,036 B1 | 12/2011 | Knodel |
| 8,070,711 B2 | 12/2011 | Bassinger et al. |
| 8,070,762 B2 | 12/2011 | Escudero et al. |

(56) References Cited

U.S. PATENT DOCUMENTS

| | | |
|---|---|---|
| 8,075,555 B2 | 12/2011 | Truckai et al. |
| 8,075,558 B2 | 12/2011 | Truckai et al. |
| 8,089,197 B2 | 1/2012 | Rinner et al. |
| 8,092,475 B2 | 1/2012 | Cotter et al. |
| 8,096,459 B2 | 1/2012 | Ortiz et al. |
| 8,097,012 B2 | 1/2012 | Kagarise |
| 8,100,894 B2 | 1/2012 | Mucko et al. |
| 8,105,230 B2 | 1/2012 | Honda et al. |
| 8,105,323 B2 | 1/2012 | Buysse et al. |
| 8,105,324 B2 | 1/2012 | Palanker et al. |
| 8,114,104 B2 | 2/2012 | Young et al. |
| 8,118,276 B2 | 2/2012 | Sanders et al. |
| 8,128,624 B2 | 3/2012 | Couture et al. |
| 8,133,218 B2 | 3/2012 | Daw et al. |
| 8,136,712 B2 | 3/2012 | Zingman |
| 8,141,762 B2 | 3/2012 | Bedi et al. |
| 8,142,421 B2 | 3/2012 | Cooper et al. |
| 8,142,461 B2 | 3/2012 | Houser et al. |
| 8,147,485 B2 | 4/2012 | Wham et al. |
| 8,147,488 B2 | 4/2012 | Masuda |
| 8,147,508 B2 | 4/2012 | Madan et al. |
| 8,152,801 B2 | 4/2012 | Goldberg et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,170,717 B2 | 5/2012 | Sutherland et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,502 B2 | 5/2012 | Stulen et al. |
| 8,186,560 B2 | 5/2012 | Hess et al. |
| 8,186,877 B2 | 5/2012 | Klimovitch et al. |
| 8,187,267 B2 | 5/2012 | Pappone et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,207,651 B2 | 6/2012 | Gilbert |
| 8,210,411 B2 | 7/2012 | Yates et al. |
| 8,211,100 B2 | 7/2012 | Podhajsky et al. |
| 8,220,688 B2 | 7/2012 | Laurent et al. |
| 8,221,306 B2 | 7/2012 | Okada et al. |
| 8,221,415 B2 | 7/2012 | Francischelli |
| 8,221,418 B2 | 7/2012 | Prakash et al. |
| 8,226,580 B2 | 7/2012 | Govari et al. |
| 8,226,675 B2 | 7/2012 | Houser et al. |
| 8,231,607 B2 | 7/2012 | Takuma |
| 8,235,917 B2 | 8/2012 | Joseph et al. |
| 8,236,018 B2 | 8/2012 | Yoshimine et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,271 B2 | 8/2012 | Millman et al. |
| 8,241,282 B2 | 8/2012 | Unger et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,246,575 B2 | 8/2012 | Viola |
| 8,246,615 B2 | 8/2012 | Behnke |
| 8,246,616 B2 | 8/2012 | Amoah et al. |
| 8,246,618 B2 | 8/2012 | Bucciaglia et al. |
| 8,246,642 B2 | 8/2012 | Houser et al. |
| 8,251,994 B2 | 8/2012 | McKenna et al. |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,262,563 B2 | 9/2012 | Bakos et al. |
| 8,267,300 B2 | 9/2012 | Boudreaux |
| 8,267,935 B2 | 9/2012 | Couture et al. |
| 8,273,087 B2 | 9/2012 | Kimura et al. |
| D669,992 S | 10/2012 | Schafer et al. |
| D669,993 S | 10/2012 | Merchant et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,886 B2 | 10/2012 | Kerr et al. |
| 8,292,888 B2 | 10/2012 | Whitman |
| 8,292,905 B2 | 10/2012 | Taylor et al. |
| 8,295,902 B2 | 10/2012 | Salahieh et al. |
| 8,298,223 B2 | 10/2012 | Wham et al. |
| 8,298,225 B2 | 10/2012 | Gilbert |
| 8,298,232 B2 | 10/2012 | Unger |
| 8,298,233 B2 | 10/2012 | Mueller |
| 8,303,576 B2 | 11/2012 | Brock |
| 8,303,579 B2 | 11/2012 | Shibata |
| 8,303,580 B2 | 11/2012 | Wham et al. |
| 8,303,583 B2 | 11/2012 | Hosier et al. |
| 8,303,613 B2 | 11/2012 | Crandall et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,802 B2 | 12/2012 | Deville et al. |
| 8,328,833 B2 | 12/2012 | Cuny |
| 8,328,834 B2 | 12/2012 | Isaacs et al. |
| 8,333,764 B2 | 12/2012 | Francischelli et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,947 B2 | 1/2013 | Takashino et al. |
| 8,348,967 B2 | 1/2013 | Stulen |
| 8,353,297 B2 | 1/2013 | Dacquay et al. |
| 8,357,103 B2 | 1/2013 | Mark et al. |
| 8,357,144 B2 | 1/2013 | Whitman et al. |
| 8,357,149 B2 | 1/2013 | Govari et al. |
| 8,357,158 B2 | 1/2013 | McKenna et al. |
| 8,361,066 B2 | 1/2013 | Long et al. |
| 8,361,072 B2 | 1/2013 | Dumbauld et al. |
| 8,361,569 B2 | 1/2013 | Saito et al. |
| 8,366,727 B2 | 2/2013 | Witt et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,372,102 B2 | 2/2013 | Stiller et al. |
| 8,374,670 B2 | 2/2013 | Selkee |
| 8,377,044 B2 | 2/2013 | Coe et al. |
| 8,377,059 B2 | 2/2013 | Deville et al. |
| 8,377,085 B2 | 2/2013 | Smith et al. |
| 8,382,748 B2 | 2/2013 | Geisei |
| 8,382,775 B1 | 2/2013 | Bender et al. |
| 8,382,782 B2 | 2/2013 | Robertson et al. |
| 8,382,792 B2 | 2/2013 | Chojin |
| 8,388,646 B2 | 3/2013 | Chojin |
| 8,388,647 B2 | 3/2013 | Nau, Jr. et al. |
| 8,393,514 B2 | 3/2013 | Shelton, IV et al. |
| 8,394,115 B2 | 3/2013 | Houser et al. |
| 8,397,971 B2 | 3/2013 | Yates et al. |
| 8,398,394 B2 | 3/2013 | Sauter et al. |
| 8,403,926 B2 | 3/2013 | Nobis et al. |
| 8,403,945 B2 | 3/2013 | Whitfield et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,234 B2 | 4/2013 | Stahler et al. |

(56) References Cited

U.S. PATENT DOCUMENTS

| | | |
|---|---|---|
| 8,414,577 B2 | 4/2013 | Boudreaux et al. |
| 8,418,073 B2 | 4/2013 | Mohr et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,423,182 B2 | 4/2013 | Robinson et al. |
| 8,425,410 B2 | 4/2013 | Murray et al. |
| 8,425,545 B2 | 4/2013 | Smith et al. |
| 8,430,811 B2 | 4/2013 | Hess et al. |
| 8,430,874 B2 | 4/2013 | Newton et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,437,832 B2 | 5/2013 | Govari et al. |
| 8,439,912 B2 | 5/2013 | Cunningham et al. |
| 8,439,939 B2 | 5/2013 | Deville et al. |
| 8,444,637 B2 | 5/2013 | Podmore et al. |
| 8,444,662 B2 | 5/2013 | Palmer et al. |
| 8,444,663 B2 | 5/2013 | Houser et al. |
| 8,444,664 B2 | 5/2013 | Balanev et al. |
| 8,453,906 B2 | 6/2013 | Huang et al. |
| 8,454,599 B2 | 6/2013 | Inagaki et al. |
| 8,454,639 B2 | 6/2013 | Du et al. |
| 8,459,525 B2 | 6/2013 | Yates et al. |
| 8,460,284 B2 | 6/2013 | Aronow et al. |
| 8,460,288 B2 | 6/2013 | Tamai et al. |
| 8,460,292 B2 | 6/2013 | Truckai et al. |
| 8,461,744 B2 | 6/2013 | Wiener et al. |
| 8,469,981 B2 | 6/2013 | Robertson et al. |
| 8,471,685 B2 | 6/2013 | Shingai |
| 8,479,969 B2 | 7/2013 | Shelton, IV |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| 8,491,625 B2 | 7/2013 | Homer |
| 8,496,682 B2 | 7/2013 | Guerra et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,336 B2 | 8/2013 | Couture |
| 8,512,337 B2 | 8/2013 | Francischelli et al. |
| 8,512,359 B2 | 8/2013 | Whitman et al. |
| 8,512,364 B2 | 8/2013 | Kowalski et al. |
| 8,512,365 B2 | 8/2013 | Wiener et al. |
| 8,521,331 B2 | 8/2013 | Itkowitz |
| 8,523,882 B2 | 9/2013 | Huitema et al. |
| 8,523,889 B2 | 9/2013 | Stulen et al. |
| 8,528,563 B2 | 9/2013 | Gruber |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,308 B2 | 9/2013 | Govari et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,546,996 B2 | 10/2013 | Messerly et al. |
| 8,546,999 B2 | 10/2013 | Houser et al. |
| 8,551,077 B2 | 10/2013 | Main et al. |
| 8,551,086 B2 | 10/2013 | Kimura et al. |
| 8,556,929 B2 | 10/2013 | Harper et al. |
| 8,561,870 B2 | 10/2013 | Baxter, III et al. |
| 8,562,592 B2 | 10/2013 | Conlon et al. |
| 8,562,598 B2 | 10/2013 | Falkenstein et al. |
| 8,562,600 B2 | 10/2013 | Kirkpatrick et al. |
| 8,562,604 B2 | 10/2013 | Nishimura |
| 8,568,390 B2 | 10/2013 | Mueller |
| 8,568,397 B2 | 10/2013 | Horner et al. |
| 8,568,400 B2 | 10/2013 | Gilbert |
| 8,568,412 B2 | 10/2013 | Brandt et al. |
| 8,569,997 B2 | 10/2013 | Lee |
| 8,573,461 B2 | 11/2013 | Shelton, IV et al. |
| 8,573,465 B2 | 11/2013 | Shelton, IV |
| 8,574,231 B2 | 11/2013 | Boudreaux et al. |
| 8,574,253 B2 | 11/2013 | Gruber et al. |
| 8,579,176 B2 | 11/2013 | Smith et al. |
| 8,579,897 B2 | 11/2013 | Vakharia et al. |
| 8,579,928 B2 | 11/2013 | Robertson et al. |
| 8,579,937 B2 | 11/2013 | Gresham |
| 8,585,727 B2 | 11/2013 | Polo |
| 8,588,371 B2 | 11/2013 | Ogawa et al. |
| 8,591,459 B2 | 11/2013 | Clymer et al. |
| 8,591,506 B2 | 11/2013 | Wham et al. |
| 8,591,536 B2 | 11/2013 | Robertson |
| D695,407 S | 12/2013 | Price et al. |
| D696,631 S | 12/2013 | Price et al. |
| 8,596,513 B2 | 12/2013 | Olson et al. |
| 8,597,193 B2 | 12/2013 | Grunwald et al. |
| 8,597,287 B2 | 12/2013 | Benamou et al. |
| 8,602,031 B2 | 12/2013 | Reis et al. |
| 8,602,288 B2 | 12/2013 | Shelton, IV et al. |
| 8,603,085 B2 | 12/2013 | Jimenez |
| 8,603,089 B2 | 12/2013 | Viola |
| 8,608,044 B2 | 12/2013 | Hueil et al. |
| 8,608,045 B2 | 12/2013 | Smith et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,617,152 B2 | 12/2013 | Werneth et al. |
| 8,617,194 B2 | 12/2013 | Beaupre |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,044 B2 | 1/2014 | Timm et al. |
| 8,628,529 B2 | 1/2014 | Aldridge et al. |
| 8,628,534 B2 | 1/2014 | Jones et al. |
| 8,632,461 B2 | 1/2014 | Glossop |
| 8,636,736 B2 | 1/2014 | Yates et al. |
| 8,638,428 B2 | 1/2014 | Brown |
| 8,640,788 B2 | 2/2014 | Dachs, II et al. |
| 8,641,663 B2 | 2/2014 | Kirschenman et al. |
| 8,647,350 B2 | 2/2014 | Mohan et al. |
| 8,650,728 B2 | 2/2014 | Wan et al. |
| 8,652,120 B2 | 2/2014 | Giordano et al. |
| 8,652,155 B2 | 2/2014 | Houser et al. |
| 8,657,489 B2 | 2/2014 | Ladurner et al. |
| 8,659,208 B1 | 2/2014 | Rose et al. |
| 8,663,214 B2 | 3/2014 | Weinberg et al. |
| 8,663,220 B2 | 3/2014 | Wiener et al. |
| 8,663,222 B2 | 3/2014 | Anderson et al. |
| 8,663,223 B2 | 3/2014 | Masuda et al. |
| 8,663,262 B2 | 3/2014 | Smith et al. |
| 8,668,691 B2 | 3/2014 | Heard |
| 8,668,710 B2 | 3/2014 | Slipszenko et al. |
| 8,684,253 B2 | 4/2014 | Giordano et al. |
| 8,685,016 B2 | 4/2014 | Wham et al. |
| 8,685,020 B2 | 4/2014 | Weizman et al. |
| 8,690,582 B2 | 4/2014 | Rohrbach et al. |
| 8,695,866 B2 | 4/2014 | Leimbach et al. |
| 8,696,366 B2 | 4/2014 | Chen et al. |
| 8,696,665 B2 | 4/2014 | Hunt et al. |
| 8,696,666 B2 | 4/2014 | Sanai et al. |
| 8,696,917 B2 | 4/2014 | Petisce et al. |
| 8,702,609 B2 | 4/2014 | Hadjicostis |
| 8,702,704 B2 | 4/2014 | Shelton, IV et al. |
| 8,704,425 B2 | 4/2014 | Giordano et al. |
| 8,708,213 B2 | 4/2014 | Shelton, IV et al. |
| 8,709,008 B2 | 4/2014 | Willis et al. |
| 8,709,031 B2 | 4/2014 | Stuien |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,721,657 B2 | 5/2014 | Kondoh et al. |
| 8,733,613 B2 | 5/2014 | Huitema et al. |
| 8,734,443 B2 | 5/2014 | Hixson et al. |
| 8,738,110 B2 | 5/2014 | Tabada et al. |

(56) References Cited

U.S. PATENT DOCUMENTS

| | | |
|---|---|---|
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,749,116 B2 | 6/2014 | Messerly et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,758,342 B2 | 6/2014 | Bales et al. |
| 8,758,352 B2 | 6/2014 | Cooper et al. |
| 8,758,391 B2 | 6/2014 | Swayze et al. |
| 8,764,735 B2 | 7/2014 | Coe et al. |
| 8,764,747 B2 | 7/2014 | Cummings et al. |
| 8,767,970 B2 | 7/2014 | Eppolito |
| 8,770,459 B2 | 7/2014 | Racenet et al. |
| 8,771,269 B2 | 7/2014 | Sherman et al. |
| 8,771,270 B2 | 7/2014 | Burbank |
| 8,771,293 B2 | 7/2014 | Surti et al. |
| 8,773,001 B2 | 7/2014 | Wiener et al. |
| 8,777,944 B2 | 7/2014 | Frankhouser et al. |
| 8,777,945 B2 | 7/2014 | Floume et al. |
| 8,779,648 B2 | 7/2014 | Giordano et al. |
| 8,783,541 B2 | 7/2014 | Shelton, IV et al. |
| 8,784,415 B2 | 7/2014 | Malackowski et al. |
| 8,784,418 B2 | 7/2014 | Romero |
| 8,790,342 B2 | 7/2014 | Stulen et al. |
| 8,795,274 B2 | 8/2014 | Hanna |
| 8,795,275 B2 | 8/2014 | Hafner |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,710 B2 | 8/2014 | Ullrich et al. |
| 8,801,752 B2 | 8/2014 | Fortier et al. |
| 8,808,204 B2 | 8/2014 | Irisawa et al. |
| 8,808,319 B2 | 8/2014 | Houser et al. |
| 8,814,856 B2 | 8/2014 | Elmouelhi et al. |
| 8,814,870 B2 | 8/2014 | Paraschiv et al. |
| 8,820,605 B2 | 9/2014 | Shelton, IV |
| 8,821,388 B2 | 9/2014 | Naito et al. |
| 8,827,992 B2 | 9/2014 | Koss et al. |
| 8,827,995 B2 | 9/2014 | Schaller et al. |
| 8,834,466 B2 | 9/2014 | Cummings et al. |
| 8,834,518 B2 | 9/2014 | Faller et al. |
| 8,844,789 B2 | 9/2014 | Shelton, IV et al. |
| 8,845,537 B2 | 9/2014 | Tanaka et al. |
| 8,845,630 B2 | 9/2014 | Mehta et al. |
| 8,848,808 B2 | 9/2014 | Dress |
| 8,851,354 B2 | 10/2014 | Swensgard et al. |
| 8,852,184 B2 | 10/2014 | Kucklick |
| 8,858,547 B2 | 10/2014 | Brogna |
| 8,862,955 B2 | 10/2014 | Cesari |
| 8,864,749 B2 | 10/2014 | Okada |
| 8,864,757 B2 | 10/2014 | Klimovitch et al. |
| 8,864,761 B2 | 10/2014 | Johnson et al. |
| 8,870,865 B2 | 10/2014 | Frankhouser et al. |
| 8,874,220 B2 | 10/2014 | Draghici et al. |
| 8,876,726 B2 | 11/2014 | Amit et al. |
| 8,876,858 B2 | 11/2014 | Braun |
| 8,882,766 B2 | 11/2014 | Couture et al. |
| 8,882,791 B2 | 11/2014 | Stolen |
| 8,888,776 B2 | 11/2014 | Dietz et al. |
| 8,888,783 B2 | 11/2014 | Young |
| 8,888,809 B2 | 11/2014 | Davison et al. |
| 8,899,462 B2 | 12/2014 | Kostrzewski et al. |
| 8,900,259 B2 | 12/2014 | Houser et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,920,412 B2 | 12/2014 | Fritz et al. |
| 8,920,414 B2 | 12/2014 | Stone et al. |
| 8,920,421 B2 | 12/2014 | Rupp |
| 8,926,607 B2 | 1/2015 | Norvell et al. |
| 8,926,608 B2 | 1/2015 | Bacher et al. |
| 8,926,620 B2 | 1/2015 | Chasmawala et al. |
| 8,931,682 B2 | 1/2015 | Timm et al. |
| 8,932,282 B2 | 1/2015 | Gilbert |
| 8,932,299 B2 | 1/2015 | Bono et al. |
| 8,936,614 B2 | 1/2015 | Allen, IV |
| 8,939,974 B2 | 1/2015 | Boudreaux et al. |
| 8,945,126 B2 | 2/2015 | Garrison et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,960,520 B2 | 2/2015 | McCuen |
| 8,961,515 B2 | 2/2015 | Twomey et al. |
| 8,961,547 B2 | 2/2015 | Dietz et al. |
| 8,967,443 B2 | 3/2015 | McCuen |
| 8,968,283 B2 | 3/2015 | Kharin |
| 8,968,294 B2 | 3/2015 | Maass et al. |
| 8,968,296 B2 | 3/2015 | McPherson |
| 8,968,355 B2 | 3/2015 | Malkowski et al. |
| 8,974,447 B2 | 3/2015 | Kimball et al. |
| 8,974,477 B2 | 3/2015 | Yamada |
| 8,974,479 B2 | 3/2015 | Ross et al. |
| 8,974,932 B2 | 3/2015 | McGahan et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,287 B2 | 3/2015 | Park et al. |
| 8,986,297 B2 | 3/2015 | Daniel et al. |
| 8,986,302 B2 | 3/2015 | Aldridge et al. |
| 8,989,855 B2 | 3/2015 | Murphy et al. |
| 8,989,903 B2 | 3/2015 | Weir et al. |
| 8,991,678 B2 | 3/2015 | Wellman et al. |
| 8,992,422 B2 | 3/2015 | Spivey et al. |
| 8,992,526 B2 | 3/2015 | Brodbeck et al. |
| 8,998,891 B2 | 4/2015 | Garito et al. |
| 9,005,199 B2 | 4/2015 | Beckman et al. |
| 9,011,437 B2 | 4/2015 | Woodruff et al. |
| 9,011,471 B2 | 4/2015 | Timm et al. |
| 9,017,326 B2 | 4/2015 | DiNardo et al. |
| 9,017,372 B2 | 4/2015 | Artale et al. |
| 9,023,070 B2 | 5/2015 | Levine et al. |
| 9,023,071 B2 | 5/2015 | Miller et al. |
| 9,028,397 B2 | 5/2015 | Naito |
| 9,028,476 B2 | 5/2015 | Bonn |
| 9,028,478 B2 | 5/2015 | Mueller |
| 9,028,481 B2 | 5/2015 | Behnke, II |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,973 B2 | 5/2015 | Krapohl et al. |
| 9,035,741 B2 | 5/2015 | Hamel et al. |
| 9,037,259 B2 | 5/2015 | Mathur |
| 9,039,690 B2 | 5/2015 | Kersten et al. |
| 9,039,695 B2 | 5/2015 | Giordano et al. |
| 9,039,696 B2 | 5/2015 | Assmus et al. |
| 9,039,705 B2 | 5/2015 | Takashino |
| 9,039,731 B2 | 5/2015 | Joseph |
| 9,043,018 B2 | 5/2015 | Mohr |
| 9,044,227 B2 | 6/2015 | Shelton, IV et al. |
| 9,044,238 B2 | 6/2015 | Orszulak |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,093 B2 | 6/2015 | Aldridge et al. |
| 9,050,098 B2 | 6/2015 | Deville et al. |
| 9,050,123 B2 | 6/2015 | Krause et al. |
| 9,050,124 B2 | 6/2015 | Houser |
| 9,055,961 B2 | 6/2015 | Manzo et al. |
| 9,059,547 B2 | 6/2015 | McLawhorn |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,060,778 B2 | 6/2015 | Condie et al. |
| 9,066,720 B2 | 6/2015 | Ballakur et al. |
| 9,066,723 B2 | 6/2015 | Beller et al. |
| 9,066,747 B2 | 6/2015 | Robertson |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,072,538 B2 | 7/2015 | Suzuki et al. |

(56) References Cited

U.S. PATENT DOCUMENTS

| | | |
|---|---|---|
| 9,072,539 B2 | 7/2015 | Messerly et al. |
| 9,084,624 B2 | 7/2015 | Larkin et al. |
| 9,089,327 B2 | 7/2015 | Worrell et al. |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,385 B2 | 8/2015 | Shelton, IV et al. |
| 9,107,684 B2 | 8/2015 | Ma |
| 9,107,689 B2 | 8/2015 | Robertson et al. |
| 9,107,690 B2 | 8/2015 | Bales, Jr. et al. |
| 9,113,900 B2 | 8/2015 | Buysse et al. |
| 9,113,907 B2 | 8/2015 | Allen, IV et al. |
| 9,113,940 B2 | 8/2015 | Twomey |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,144,453 B2 | 9/2015 | Rencher et al. |
| 9,147,965 B2 | 9/2015 | Lee |
| 9,149,324 B2 | 10/2015 | Huang et al. |
| 9,149,325 B2 | 10/2015 | Worrell et al. |
| 9,161,803 B2 | 10/2015 | Yates et al. |
| 9,165,114 B2 | 10/2015 | Jain et al. |
| 9,168,054 B2 | 10/2015 | Turner et al. |
| 9,168,085 B2 | 10/2015 | Juzkiw et al. |
| 9,168,089 B2 | 10/2015 | Buysse et al. |
| 9,173,656 B2 | 11/2015 | Schurr et al. |
| 9,179,912 B2 | 11/2015 | Yates et al. |
| 9,186,199 B2 | 11/2015 | Strauss et al. |
| 9,186,204 B2 | 11/2015 | Nishimura et al. |
| 9,186,796 B2 | 11/2015 | Ogawa |
| 9,192,380 B2 | 11/2015 | (Tarinelli) Racenet et al. |
| 9,192,421 B2 | 11/2015 | Garrison |
| 9,192,428 B2 | 11/2015 | Houser et al. |
| 9,192,431 B2 | 11/2015 | Woodruff et al. |
| 9,198,714 B2 | 12/2015 | Worrell et al. |
| 9,198,715 B2 | 12/2015 | Livneh |
| 9,198,718 B2 | 12/2015 | Marczyk et al. |
| 9,198,776 B2 | 12/2015 | Young |
| 9,204,879 B2 | 12/2015 | Shelton, IV |
| 9,204,891 B2 | 12/2015 | Weitzman |
| 9,204,918 B2 | 12/2015 | Germain et al. |
| 9,204,923 B2 | 12/2015 | Manzo et al. |
| 9,216,050 B2 | 12/2015 | Condie et al. |
| 9,216,051 B2 | 12/2015 | Fischer et al. |
| 9,216,062 B2 | 12/2015 | Duque et al. |
| 9,220,483 B2 | 12/2015 | Frankhouser et al. |
| 9,220,527 B2 | 12/2015 | Houser et al. |
| 9,220,559 B2 | 12/2015 | Worrell et al. |
| 9,226,750 B2 | 1/2016 | Weir et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,232,979 B2 | 1/2016 | Parihar et al. |
| 9,237,891 B2 | 1/2016 | Shelton, IV |
| 9,237,921 B2 | 1/2016 | Messerly et al. |
| 9,241,060 B1 | 1/2016 | Fujisaki |
| 9,241,692 B2 | 1/2016 | Gunday et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,241,768 B2 | 1/2016 | Sandhu et al. |
| 9,247,953 B2 | 2/2016 | Palmer et al. |
| 9,254,165 B2 | 2/2016 | Aronow et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,926 B2 | 2/2016 | Strobl et al. |
| 9,265,973 B2 | 2/2016 | Akagane |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,289,256 B2 | 3/2016 | Shelton, IV et al. |
| 9,295,514 B2 | 3/2016 | Shelton, IV et al. |
| 9,301,759 B2 | 4/2016 | Spivey et al. |
| 9,305,497 B2 | 4/2016 | Seo et al. |
| 9,307,388 B2 | 4/2016 | Liang et al. |
| 9,307,986 B2 | 4/2016 | Hall et al. |
| 9,308,009 B2 | 4/2016 | Madan et al. |
| 9,308,014 B2 | 4/2016 | Fischer |
| 9,314,261 B2 | 4/2016 | Bales, Jr. et al. |
| 9,314,292 B2 | 4/2016 | Trees et al. |
| 9,314,301 B2 | 4/2016 | Ben-Haim et al. |
| 9,326,754 B2 | 5/2016 | Polster |
| 9,326,788 B2 | 5/2016 | Batross et al. |
| 9,333,025 B2 | 5/2016 | Monson et al. |
| 9,333,034 B2 | 5/2016 | Hancock |
| 9,339,289 B2 | 5/2016 | Robertson |
| 9,339,323 B2 | 5/2016 | Eder et al. |
| 9,339,326 B2 | 5/2016 | McCullagh et al. |
| 9,345,481 B2 | 5/2016 | Hall et al. |
| 9,345,534 B2 | 5/2016 | Artale et al. |
| 9,345,900 B2 | 5/2016 | Wu et al. |
| 9,351,642 B2 | 5/2016 | Nadkarni et al. |
| 9,351,726 B2 | 5/2016 | Leimbach et al. |
| 9,351,754 B2 | 5/2016 | Vakharia et al. |
| 9,352,173 B2 | 5/2016 | Yamada et al. |
| 9,358,065 B2 | 6/2016 | Ladtkow et al. |
| 9,364,171 B2 | 6/2016 | Harris et al. |
| 9,364,230 B2 | 6/2016 | Shelton, IV et al. |
| 9,364,279 B2 | 6/2016 | Houser et al. |
| 9,370,364 B2 | 6/2016 | Smith et al. |
| 9,370,400 B2 | 6/2016 | Parihar |
| 9,370,611 B2 | 6/2016 | Ross et al. |
| 9,375,232 B2 | 6/2016 | Hunt et al. |
| 9,375,256 B2 | 6/2016 | Cunningham et al. |
| 9,375,264 B2 | 6/2016 | Horner et al. |
| 9,375,267 B2 | 6/2016 | Kerr et al. |
| 9,385,831 B2 | 7/2016 | Marr et al. |
| 9,386,983 B2 | 7/2016 | Swensgard et al. |
| 9,393,037 B2 | 7/2016 | Olson et al. |
| 9,393,070 B2 | 7/2016 | Gelfand et al. |
| 9,398,911 B2 | 7/2016 | Auld |
| 9,402,680 B2 | 8/2016 | Ginnebaugh et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,853 B2 | 8/2016 | Stulen et al. |
| 9,414,880 B2 | 8/2016 | Monson et al. |
| 9,421,060 B2 | 8/2016 | Monson et al. |
| 9,427,249 B2 | 8/2016 | Robertson et al. |
| 9,427,279 B2 | 8/2016 | Muniz-Medina et al. |
| 9,439,668 B2 | 9/2016 | Timm et al. |
| 9,439,669 B2 | 9/2016 | Wiener et al. |
| 9,439,671 B2 | 9/2016 | Akagane et al. |
| 9,442,288 B2 | 9/2016 | Tanimura |
| 9,445,784 B2 | 9/2016 | O'Keeffe |
| 9,445,832 B2 | 9/2016 | Wiener et al. |
| 9,451,967 B2 | 9/2016 | Jordan et al. |
| 9,456,863 B2 | 10/2016 | Moua |
| 9,456,864 B2 | 10/2016 | Witt et al. |
| 9,468,498 B2 | 10/2016 | Sigmon, Jr. |
| 9,474,542 B2 | 10/2016 | Slipszenko et al. |
| 9,486,236 B2 | 11/2016 | Price et al. |
| 9,492,146 B2 | 11/2016 | Kostrzewski et al. |
| 9,492,224 B2 | 11/2016 | Boudreaux et al. |
| 9,498,245 B2 | 11/2016 | Voegele et al. |
| 9,498,275 B2 | 11/2016 | Wham et al. |
| 9,504,483 B2 | 11/2016 | Houser et al. |
| 9,504,520 B2 | 11/2016 | Worrell et al. |
| 9,504,524 B2 | 11/2016 | Behnke, II |
| 9,504,855 B2 | 11/2016 | Messerly et al. |
| 9,510,850 B2 | 12/2016 | Robertson et al. |
| 9,510,906 B2 | 12/2016 | Boudreaux et al. |
| 9,522,029 B2 | 12/2016 | Yates et al. |
| 9,522,032 B2 | 12/2016 | Behnke |
| 9,526,564 B2 | 12/2016 | Rusin |
| 9,526,565 B2 | 12/2016 | Strobl |
| 9,545,253 B2 | 1/2017 | Worrell et al. |
| 9,545,497 B2 | 1/2017 | Wenderow et al. |

(56) References Cited

U.S. PATENT DOCUMENTS

| | | |
|---|---|---|
| 9,554,846 B2 | 1/2017 | Boudreaux |
| 9,554,854 B2 | 1/2017 | Yates et al. |
| 9,560,995 B2 | 2/2017 | Addison et al. |
| 9,561,038 B2 | 2/2017 | Shelton, IV et al. |
| 9,572,592 B2 | 2/2017 | Price et al. |
| 9,574,644 B2 | 2/2017 | Parihar |
| 9,585,714 B2 | 3/2017 | Livneh |
| 9,592,072 B2 | 3/2017 | Akagane |
| 9,597,143 B2 | 3/2017 | Madan et al. |
| 9,603,669 B2 | 3/2017 | Govari et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,623,237 B2 | 4/2017 | Turner et al. |
| 9,636,135 B2 | 5/2017 | Stulen |
| 9,636,165 B2 | 5/2017 | Larson et al. |
| 9,636,167 B2 | 5/2017 | Gregg |
| 9,638,770 B2 | 5/2017 | Dietz et al. |
| 9,642,644 B2 | 5/2017 | Houser et al. |
| 9,642,669 B2 | 5/2017 | Takashino et al. |
| 9,643,052 B2 | 5/2017 | Tchao et al. |
| 9,649,111 B2 | 5/2017 | Shelton, IV et al. |
| 9,649,126 B2 | 5/2017 | Robertson et al. |
| 9,649,173 B2 | 5/2017 | Choi et al. |
| 9,655,670 B2 | 5/2017 | Larson et al. |
| 9,662,131 B2 | 5/2017 | Omori et al. |
| 9,668,806 B2 | 6/2017 | Unger et al. |
| 9,671,860 B2 | 6/2017 | Ogawa et al. |
| 9,675,374 B2 | 6/2017 | Stulen et al. |
| 9,675,375 B2 | 6/2017 | Houser et al. |
| 9,681,884 B2 | 6/2017 | Clem et al. |
| 9,687,290 B2 | 6/2017 | Keller |
| 9,690,362 B2 | 6/2017 | Leimbach et al. |
| 9,693,817 B2 | 7/2017 | Mehta et al. |
| 9,700,309 B2 | 7/2017 | Jaworek et al. |
| 9,700,339 B2 | 7/2017 | Nield |
| 9,700,343 B2 | 7/2017 | Messerly et al. |
| 9,705,456 B2 | 7/2017 | Gilbert |
| 9,707,004 B2 | 7/2017 | Houser et al. |
| 9,707,027 B2 | 7/2017 | Ruddenklau et al. |
| 9,707,030 B2 | 7/2017 | Davison et al. |
| 9,713,507 B2 | 7/2017 | Stulen et al. |
| 9,717,548 B2 | 8/2017 | Couture |
| 9,717,552 B2 | 8/2017 | Cosman et al. |
| 9,724,118 B2 | 8/2017 | Schulte et al. |
| 9,724,120 B2 | 8/2017 | Faller et al. |
| 9,724,152 B2 | 8/2017 | Horlle et al. |
| 9,730,695 B2 | 8/2017 | Leimbach et al. |
| 9,737,326 B2 | 8/2017 | Worrell et al. |
| 9,737,355 B2 | 8/2017 | Yates et al. |
| 9,737,358 B2 | 8/2017 | Beckman et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,757,142 B2 | 9/2017 | Shimizu |
| 9,757,150 B2 | 9/2017 | Alexander et al. |
| 9,757,186 B2 | 9/2017 | Boudreaux et al. |
| 9,764,164 B2 | 9/2017 | Wiener et al. |
| 9,770,285 B2 | 9/2017 | Zoran et al. |
| 9,782,214 B2 | 10/2017 | Houser et al. |
| 9,788,851 B2 | 10/2017 | Dannaher et al. |
| 9,795,405 B2 | 10/2017 | Price et al. |
| 9,795,436 B2 | 10/2017 | Yates et al. |
| 9,795,808 B2 | 10/2017 | Messerly et al. |
| 9,801,648 B2 | 10/2017 | Houser et al. |
| 9,802,033 B2 | 10/2017 | Hibner et al. |
| 9,808,246 B2 | 11/2017 | Shelton, IV et al. |
| 9,808,308 B2 | 11/2017 | Faller et al. |
| 9,814,514 B2 | 11/2017 | Shelton, IV et al. |
| 9,820,768 B2 | 11/2017 | Gee et al. |
| 9,820,771 B2 | 11/2017 | Norton et al. |
| 9,820,806 B2 | 11/2017 | Lee et al. |
| 9,839,443 B2 | 12/2017 | Brockman et al. |
| 9,848,901 B2 | 12/2017 | Robertson et al. |
| 9,848,902 B2 | 12/2017 | Price et al. |
| 9,848,937 B2 | 12/2017 | Trees et al. |
| 9,861,381 B2 | 1/2018 | Johnson |
| 9,861,428 B2 | 1/2018 | Trees et al. |
| 9,867,651 B2 | 1/2018 | Wham |
| 9,867,670 B2 | 1/2018 | Brannan et al. |
| 9,872,722 B2 | 1/2018 | Lech |
| 9,872,725 B2 | 1/2018 | Worrell et al. |
| 9,872,726 B2 | 1/2018 | Morisaki |
| 9,877,720 B2 | 1/2018 | Worrell et al. |
| 9,877,776 B2 | 1/2018 | Boudreaux |
| 9,878,184 B2 | 1/2018 | Beaupre |
| 9,883,884 B2 | 2/2018 | Neurohr et al. |
| 9,888,919 B2 | 2/2018 | Leimbach et al. |
| 9,888,958 B2 | 2/2018 | Evans et al. |
| 9,901,321 B2 | 2/2018 | Harks et al. |
| 9,901,383 B2 | 2/2018 | Hassler, Jr. |
| 9,901,754 B2 | 2/2018 | Yamada |
| 9,907,563 B2 | 3/2018 | Germain et al. |
| 9,913,656 B2 | 3/2018 | Stulen |
| 9,913,680 B2 | 3/2018 | Voegele et al. |
| 9,918,730 B2 | 3/2018 | Trees et al. |
| 9,925,003 B2 | 3/2018 | Parihar et al. |
| 9,949,785 B2 | 4/2018 | Price et al. |
| 9,949,788 B2 | 4/2018 | Boudreaux |
| 9,962,182 B2 | 5/2018 | Dietz et al. |
| 9,974,539 B2 | 5/2018 | Yates et al. |
| 10,004,526 B2 | 6/2018 | Dycus et al. |
| 10,004,527 B2 | 6/2018 | Gee et al. |
| 10,010,341 B2 | 7/2018 | Houser et al. |
| 10,016,207 B2 | 7/2018 | Suzuki et al. |
| 10,022,142 B2 | 7/2018 | Aranyi et al. |
| 10,028,761 B2 | 7/2018 | Leimbach et al. |
| 10,034,684 B2 | 7/2018 | Weisenburgh, II et al. |
| 10,039,588 B2 | 8/2018 | Harper et al. |
| 10,045,810 B2 | 8/2018 | Schall et al. |
| 10,070,916 B2 | 9/2018 | Artale |
| 10,080,609 B2 | 9/2018 | Hancock et al. |
| 10,085,792 B2 | 10/2018 | Johnson et al. |
| 10,092,310 B2 | 10/2018 | Boudreaux et al. |
| 10,092,348 B2 | 10/2018 | Boudreaux |
| 10,092,350 B2 | 10/2018 | Rothweiler et al. |
| 10,105,140 B2 | 10/2018 | Malinouskas et al. |
| 10,111,699 B2 | 10/2018 | Boudreaux |
| 10,111,703 B2 | 10/2018 | Cosman, Jr. et al. |
| 10,117,702 B2 | 11/2018 | Danziger et al. |
| 10,123,835 B2 | 11/2018 | Keller et al. |
| 10,130,410 B2 | 11/2018 | Strobl et al. |
| 10,130,412 B2 | 11/2018 | Wham |
| 10,154,848 B2 | 12/2018 | Chernov et al. |
| 10,154,852 B2 | 12/2018 | Conlon et al. |
| 10,159,524 B2 | 12/2018 | Yates et al. |
| 10,166,060 B2 | 1/2019 | Johnson et al. |
| 10,172,665 B2 | 1/2019 | Heckel et al. |
| 10,172,669 B2 | 1/2019 | Felder et al. |
| 10,179,022 B2 | 1/2019 | Yates et al. |
| 10,188,455 B2 | 1/2019 | Hancock et al. |
| 10,194,972 B2 | 2/2019 | Yates et al. |
| 10,194,973 B2 | 2/2019 | Wiener et al. |
| 10,194,976 B2 | 2/2019 | Boudreaux |
| 10,194,977 B2 | 2/2019 | Yang |
| 10,194,999 B2 | 2/2019 | Bacher et al. |
| 10,201,364 B2 | 2/2019 | Leimbach et al. |
| 10,231,747 B2 | 3/2019 | Stulen et al. |
| 10,238,385 B2 | 3/2019 | Yates et al. |
| 10,238,391 B2 | 3/2019 | Leimbach et al. |
| 10,245,095 B2 | 4/2019 | Boudreaux |
| 10,245,104 B2 | 4/2019 | McKenna et al. |
| 10,251,664 B2 | 4/2019 | Shelton, IV et al. |
| 10,263,171 B2 | 4/2019 | Wiener et al. |
| 10,265,118 B2 | 4/2019 | Gerhardt |
| 10,271,840 B2 | 4/2019 | Sapre |
| 10,278,721 B2 | 5/2019 | Dietz et al. |
| 10,285,750 B2 | 5/2019 | Coulson et al. |
| 10,299,810 B2 | 5/2019 | Robertson et al. |
| 10,299,821 B2 | 5/2019 | Shelton, IV et al. |
| 10,314,638 B2 | 6/2019 | Gee et al. |
| 10,321,950 B2 | 6/2019 | Yates et al. |
| 10,335,182 B2 | 7/2019 | Stulen et al. |
| 10,335,183 B2 | 7/2019 | Worrell et al. |

(56) References Cited

U.S. PATENT DOCUMENTS

| | | | |
|---|---|---|---|
| 10,335,614 B2 | 7/2019 | Messerly et al. |
| 10,342,602 B2 | 7/2019 | Strobl et al. |
| 10,342,606 B2 | 7/2019 | Cosman et al. |
| 10,349,999 B2 | 7/2019 | Yates et al. |
| 10,357,303 B2 | 7/2019 | Conlon et al. |
| 10,363,084 B2 | 7/2019 | Friedrichs |
| 10,376,305 B2 | 8/2019 | Yates et al. |
| 10,398,466 B2 | 9/2019 | Stulen et al. |
| 10,413,352 B2 | 9/2019 | Thomas et al. |
| 10,420,579 B2 | 9/2019 | Wiener et al. |
| 10,420,607 B2 | 9/2019 | Woloszko et al. |
| 10,426,507 B2 | 10/2019 | Wiener et al. |
| 10,507,033 B2 | 12/2019 | Dickerson et al. |
| 10,561,560 B2 | 2/2020 | Boutoussov et al. |
| 10,617,420 B2 | 4/2020 | Shelton, IV et al. |
| RE47,996 E | 5/2020 | Turner et al. |
| 10,677,764 B2 | 6/2020 | Ross et al. |
| 10,856,896 B2 | 12/2020 | Eichmann et al. |
| 10,874,465 B2 | 12/2020 | Weir et al. |
| 2001/0025173 A1 | 9/2001 | Ritchie et al. |
| 2001/0025183 A1 | 9/2001 | Shahidi et al. |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0002380 A1 | 1/2002 | Bishop |
| 2002/0019649 A1 | 2/2002 | Sikora et al. |
| 2002/0022836 A1 | 2/2002 | Goble et al. |
| 2002/0029036 A1 | 3/2002 | Goble et al. |
| 2002/0029055 A1 | 3/2002 | Bonutti |
| 2002/0049551 A1 | 4/2002 | Friedman et al. |
| 2002/0052617 A1 | 5/2002 | Anis et al. |
| 2002/0077550 A1 | 6/2002 | Rabiner et al. |
| 2002/0107517 A1 | 8/2002 | Witt et al. |
| 2002/0156466 A1 | 10/2002 | Sakurai et al. |
| 2002/0156493 A1 | 10/2002 | Houser et al. |
| 2002/0177862 A1 | 11/2002 | Aranyi et al. |
| 2003/0014053 A1 | 1/2003 | Nguyen et al. |
| 2003/0014087 A1 | 1/2003 | Fang et al. |
| 2003/0036705 A1 | 2/2003 | Hare et al. |
| 2003/0040758 A1 | 2/2003 | Wang et al. |
| 2003/0050572 A1 | 3/2003 | Brautigam et al. |
| 2003/0055443 A1 | 3/2003 | Spotnitz |
| 2003/0109778 A1 | 6/2003 | Rashidi |
| 2003/0109875 A1 | 6/2003 | Tetzlaff et al. |
| 2003/0109876 A1* | 6/2003 | Yamauchi ......... A61B 18/1442 606/48 |
| 2003/0114851 A1 | 6/2003 | Trackai et al. |
| 2003/0130693 A1 | 7/2003 | Levin et al. |
| 2003/0139741 A1 | 7/2003 | Goble et al. |
| 2003/0144680 A1 | 7/2003 | Keliogg et al. |
| 2003/0158548 A1 | 8/2003 | Phan et al. |
| 2003/0171747 A1 | 9/2003 | Kanehira et al. |
| 2003/0181898 A1 | 9/2003 | Bowers |
| 2003/0199794 A1 | 10/2003 | Sakurai et al. |
| 2003/0204193 A1 | 10/2003 | Novak et al. |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0225332 A1 | 12/2003 | Okada et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0087943 A1 | 5/2004 | Dycus et al. |
| 2004/0092921 A1 | 5/2004 | Kadziauskas et al. |
| 2004/0092992 A1 | 5/2004 | Adams et al. |
| 2004/0097911 A1 | 5/2004 | Murakami et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0122423 A1 | 6/2004 | Dycus et al. |
| 2004/0132383 A1 | 7/2004 | Langford et al. |
| 2004/0138621 A1 | 7/2004 | Jahns et al. |
| 2004/0142667 A1 | 7/2004 | Lochhead et al. |
| 2004/0147934 A1 | 7/2004 | Kiester |
| 2004/0147945 A1 | 7/2004 | Fritzsch |
| 2004/0158237 A1 | 8/2004 | Abboud et al. |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0193150 A1 | 9/2004 | Sharkey et al. |
| 2004/0193153 A1 | 9/2004 | Sartor et al. |
| 2004/0199193 A1 | 10/2004 | Hayashi et al. |
| 2004/0204728 A1 | 10/2004 | Haefner |
| 2004/0215132 A1 | 10/2004 | Yoon |
| 2004/0243147 A1 | 12/2004 | Lipow |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2004/0267311 A1 | 12/2004 | Viola et al. |
| 2005/0015125 A1 | 1/2005 | Mioduski et al. |
| 2005/0020967 A1 | 1/2005 | Ono |
| 2005/0021018 A1 | 1/2005 | Anderson et al. |
| 2005/0021065 A1 | 1/2005 | Yamada et al. |
| 2005/0021078 A1 | 1/2005 | Vleugels et al. |
| 2005/0033278 A1 | 2/2005 | McClurken et al. |
| 2005/0033337 A1 | 2/2005 | Muir et al. |
| 2005/0049546 A1 | 3/2005 | Messerly et al. |
| 2005/0070800 A1 | 3/2005 | Takahashi |
| 2005/0080427 A1 | 4/2005 | Govari et al. |
| 2005/0088285 A1 | 4/2005 | Jei |
| 2005/0090817 A1 | 4/2005 | Phan |
| 2005/0096683 A1 | 5/2005 | Ellins et al. |
| 2005/0099824 A1 | 5/2005 | Dowling et al. |
| 2005/0103819 A1 | 5/2005 | Racenet et al. |
| 2005/0107777 A1 | 5/2005 | West et al. |
| 2005/0131390 A1 | 6/2005 | Heinrich et al. |
| 2005/0143769 A1 | 6/2005 | White et al. |
| 2005/0149108 A1 | 7/2005 | Cox |
| 2005/0165345 A1 | 7/2005 | Laufer et al. |
| 2005/0165429 A1 | 7/2005 | Douglas et al. |
| 2005/0171522 A1 | 8/2005 | Christopherson |
| 2005/0177184 A1 | 8/2005 | Easley |
| 2005/0182339 A1 | 8/2005 | Lee et al. |
| 2005/0188743 A1 | 9/2005 | Land |
| 2005/0192610 A1 | 9/2005 | Houser et al. |
| 2005/0192611 A1 | 9/2005 | Houser |
| 2005/0209620 A1 | 9/2005 | Du et al. |
| 2005/0222598 A1 | 10/2005 | Ho et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261581 A1 | 11/2005 | Hughes et al. |
| 2005/0261588 A1 | 11/2005 | Makin et al. |
| 2005/0262175 A1 | 11/2005 | Iino et al. |
| 2005/0267464 A1 | 12/2005 | Truckai et al. |
| 2005/0271807 A1 | 12/2005 | Iljima et al. |
| 2005/0273090 A1 | 12/2005 | Nieman et al. |
| 2005/0288653 A1 | 12/2005 | Kimura et al. |
| 2006/0025757 A1 | 2/2006 | Heim |
| 2006/0030737 A1 | 2/2006 | Zhou et al. |
| 2006/0030848 A1 | 2/2006 | Craig et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0066181 A1 | 3/2006 | Bromfield et al. |
| 2006/0074442 A1 | 4/2006 | Noriega et al. |
| 2006/0079874 A1 | 4/2006 | Faller et al. |
| 2006/0079879 A1 | 4/2006 | Faller et al. |
| 2006/0084963 A1 | 4/2006 | Messerly |
| 2006/0095046 A1 | 5/2006 | Trieu et al. |
| 2006/0109061 A1 | 5/2006 | Dobson et al. |
| 2006/0159731 A1 | 7/2006 | Shoshan |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217729 A1 | 9/2006 | Eskridge et al. |
| 2006/0224160 A1 | 10/2006 | Trieu et al. |

(56) References Cited

U.S. PATENT DOCUMENTS

| | | |
|---|---|---|
| 2006/0235306 A1 | 10/2006 | Cotter et al. |
| 2006/0247558 A1 | 11/2006 | Yamada |
| 2006/0253050 A1 | 11/2006 | Yoshimine et al. |
| 2006/0259026 A1 | 11/2006 | Godara et al. |
| 2006/0264803 A1 | 11/2006 | Hansmann et al. |
| 2006/0264995 A1 | 11/2006 | Fanton et al. |
| 2006/0265035 A1 | 11/2006 | Yachi et al. |
| 2006/0270916 A1 | 11/2006 | Skwarek et al. |
| 2006/0271030 A1 | 11/2006 | Francis et al. |
| 2006/0293656 A1 | 12/2006 | Shadduck et al. |
| 2007/0016235 A1 | 1/2007 | Tanaka et al. |
| 2007/0016236 A1 | 1/2007 | Beaupre |
| 2007/0021738 A1 | 1/2007 | Hasser et al. |
| 2007/0027468 A1 | 2/2007 | Wales et al. |
| 2007/0032704 A1 | 2/2007 | Gandini et al. |
| 2007/0055228 A1 | 3/2007 | Berg et al. |
| 2007/0056596 A1 | 3/2007 | Fanney et al. |
| 2007/0060915 A1 | 3/2007 | Kucklick |
| 2007/0060935 A1 | 3/2007 | Schwardt et al. |
| 2007/0063618 A1 | 3/2007 | Bromfield |
| 2007/0066971 A1 | 3/2007 | Podhajsky |
| 2007/0067123 A1 | 3/2007 | Jungerman |
| 2007/0073185 A1 | 3/2007 | Nakao |
| 2007/0073341 A1 | 3/2007 | Smith et al. |
| 2007/0074584 A1 | 4/2007 | Talarico et al. |
| 2007/0078458 A1 | 4/2007 | Dumbauid et al. |
| 2007/0106317 A1 | 5/2007 | Shelton, IV et al. |
| 2007/0118115 A1 | 5/2007 | Artale et al. |
| 2007/0129716 A1 | 6/2007 | Daw et al. |
| 2007/0130771 A1 | 6/2007 | Ehlert et al. |
| 2007/0131034 A1 | 6/2007 | Ehlert et al. |
| 2007/0135803 A1 | 6/2007 | Belson |
| 2007/0149881 A1 | 6/2007 | Rabin |
| 2007/0156163 A1 | 7/2007 | Davison et al. |
| 2007/0162050 A1 | 7/2007 | Sartor |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0175949 A1 | 8/2007 | Shelton, IV et al. |
| 2007/0175955 A1 | 8/2007 | Shelton et al. |
| 2007/0185380 A1 | 8/2007 | Kucklick |
| 2007/0185474 A1 | 8/2007 | Nahen |
| 2007/0191712 A1 | 8/2007 | Messerly et al. |
| 2007/0191713 A1 | 8/2007 | Eichmann et al. |
| 2007/0203483 A1 | 8/2007 | Kim et al. |
| 2007/0208336 A1 | 9/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0239028 A1 | 10/2007 | Houser et al. |
| 2007/0239101 A1 | 10/2007 | Kellogg |
| 2007/0249941 A1 | 10/2007 | Salehi et al. |
| 2007/0260234 A1 | 11/2007 | McCullagh et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0265620 A1 | 11/2007 | Kraas et al. |
| 2007/0275348 A1 | 11/2007 | Lemon |
| 2007/0282335 A1 | 12/2007 | Young et al. |
| 2007/0287933 A1 | 12/2007 | Phan et al. |
| 2007/0288055 A1 | 12/2007 | Lee |
| 2007/0299895 A1 | 12/2007 | Johnson et al. |
| 2008/0005213 A1 | 1/2008 | Holtzman |
| 2008/0009848 A1 | 1/2008 | Paraschiv et al. |
| 2008/0013809 A1 | 1/2008 | Zhu et al. |
| 2008/0015575 A1 | 1/2008 | Odom et al. |
| 2008/0033465 A1 | 2/2008 | Schmitz et al. |
| 2008/0039746 A1 | 2/2008 | Hissong et al. |
| 2008/0051812 A1 | 2/2008 | Schmitz et al. |
| 2008/0058585 A1 | 3/2008 | Novak et al. |
| 2008/0058648 A1 * | 3/2008 | Novak ............ A61B 17/22004 600/471 |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0077145 A1 | 3/2008 | Boyden et al. |
| 2008/0062039 A1 | 4/2008 | Babaev |
| 2008/0082098 A1 | 4/2008 | Tanaka et al. |
| 2008/0097501 A1 | 4/2008 | Blier |
| 2008/0114355 A1 | 5/2008 | Whayne et al. |
| 2008/0114364 A1 | 5/2008 | Goldin et al. |
| 2008/0122496 A1 | 5/2008 | Wagner |
| 2008/0125768 A1 | 5/2008 | Tahara et al. |
| 2008/0140158 A1 | 6/2008 | Hamel et al. |
| 2008/0147058 A1 | 6/2008 | Horrell et al. |
| 2008/0147062 A1 | 6/2008 | Truckai et al. |
| 2008/0147092 A1 | 6/2008 | Rogge et al. |
| 2008/0171938 A1 | 7/2008 | Masuda et al. |
| 2008/0172051 A1 | 7/2008 | Masuda et al. |
| 2008/0177268 A1 | 7/2008 | Daum et al. |
| 2008/0188755 A1 | 8/2008 | Hart |
| 2008/0188878 A1 | 8/2008 | Young |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243106 A1 | 10/2008 | Coe et al. |
| 2008/0243162 A1 | 10/2008 | Shibata et al. |
| 2008/0245371 A1 | 10/2008 | Gruber |
| 2008/0249553 A1 | 10/2008 | Gruber et al. |
| 2008/0255413 A1 | 10/2008 | Zemlok et al. |
| 2008/0255423 A1 | 10/2008 | Kondo et al. |
| 2008/0262490 A1 | 10/2008 | Williams |
| 2008/0275440 A1 | 11/2008 | Kratoska et al. |
| 2008/0281200 A1 | 11/2008 | Voic et al. |
| 2008/0281315 A1 | 11/2008 | Gines |
| 2008/0281322 A1 | 11/2008 | Sherman et al. |
| 2008/0287944 A1 | 11/2008 | Pearson et al. |
| 2008/0287948 A1 | 11/2008 | Newton et al. |
| 2008/0296346 A1 | 12/2008 | Shelton, IV et al. |
| 2008/0300588 A1 | 12/2008 | Groth et al. |
| 2009/0012516 A1 | 1/2009 | Curtis et al. |
| 2009/0023985 A1 | 1/2009 | Ewers |
| 2009/0024141 A1 | 1/2009 | Stabler et al. |
| 2009/0043293 A1 | 2/2009 | Pankratov et al. |
| 2009/0048537 A1 | 2/2009 | Lydon et al. |
| 2009/0048589 A1 | 2/2009 | Takashino et al. |
| 2009/0054886 A1 | 2/2009 | Yachi et al. |
| 2009/0054889 A1 | 2/2009 | Newton et al. |
| 2009/0054894 A1 | 2/2009 | Yachi |
| 2009/0065565 A1 | 3/2009 | Cao |
| 2009/0076506 A1 | 3/2009 | Baker |
| 2009/0082716 A1 | 3/2009 | Akahoshi |
| 2009/0082766 A1 | 3/2009 | Unger et al. |
| 2009/0088738 A1 | 4/2009 | Guerra et al. |
| 2009/0088785 A1 | 4/2009 | Masuda |
| 2009/0090763 A1 | 4/2009 | Zemlok et al. |
| 2009/0112229 A1 | 4/2009 | Omori et al. |
| 2009/0118751 A1 | 5/2009 | Wiener et al. |
| 2009/0118802 A1 | 5/2009 | Mioduski et al. |
| 2009/0138006 A1 | 5/2009 | Bales et al. |
| 2009/0143678 A1 | 6/2009 | Keast et al. |
| 2009/0143799 A1 | 6/2009 | Smith et al. |
| 2009/0143800 A1 | 6/2009 | Deville et al. |
| 2009/0143806 A1 | 6/2009 | Witt et al. |
| 2009/0149801 A1 | 6/2009 | Crandall et al. |
| 2009/0163807 A1 | 6/2009 | Sliwa |
| 2009/0177119 A1 | 7/2009 | Heidner et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0198272 A1 | 8/2009 | Kerver et al. |
| 2009/0204114 A1 | 8/2009 | Odom |
| 2009/0207923 A1 | 8/2009 | Dress |
| 2009/0216157 A1 | 8/2009 | Yamada |
| 2009/0223033 A1 | 9/2009 | Houser |
| 2009/0240244 A1 | 9/2009 | Malis et al. |
| 2009/0248021 A1 | 10/2009 | McKenna |

(56) References Cited

U.S. PATENT DOCUMENTS

| | | |
|---|---|---|
| 2009/0254077 A1 | 10/2009 | Craig |
| 2009/0254080 A1 | 10/2009 | Honda |
| 2009/0259149 A1 | 10/2009 | Tahara et al. |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270891 A1 | 10/2009 | Beaupre |
| 2009/0270899 A1 | 10/2009 | Carusillo et al. |
| 2009/0275940 A1 | 11/2009 | Malackowski et al. |
| 2009/0287205 A1 | 11/2009 | Ingle |
| 2009/0292283 A1 | 11/2009 | Odom |
| 2009/0299141 A1 | 12/2009 | Downey et al. |
| 2009/0318945 A1 | 12/2009 | Yoshimine et al. |
| 2009/0327715 A1 | 12/2009 | Smith et al. |
| 2010/0004508 A1 | 1/2010 | Naito et al. |
| 2010/0016785 A1 | 1/2010 | Takuma |
| 2010/0016852 A1 | 1/2010 | Manzo et al. |
| 2010/0022825 A1 | 1/2010 | Yoshie |
| 2010/0030233 A1 | 2/2010 | Whitman et al. |
| 2010/0030248 A1 | 2/2010 | Palmer et al. |
| 2010/0034605 A1 | 2/2010 | Huckins et al. |
| 2010/0036370 A1 | 2/2010 | Mirel et al. |
| 2010/0036405 A1* | 2/2010 | Giordano ............. A61B 5/0538 606/169 |
| 2010/0042077 A1 | 2/2010 | Okada |
| 2010/0042093 A9 | 2/2010 | Wham et al. |
| 2010/0049180 A1 | 2/2010 | Wells et al. |
| 2010/0057118 A1 | 3/2010 | Dietz et al. |
| 2010/0063525 A1 | 3/2010 | Beaupre et al. |
| 2010/0063528 A1 | 3/2010 | Beaupré |
| 2010/0069940 A1 | 3/2010 | Miller et al. |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0106173 A1 | 4/2010 | Yoshimine |
| 2010/0109480 A1 | 5/2010 | Forslund et al. |
| 2010/0158307 A1 | 6/2010 | Kubota et al. |
| 2010/0168741 A1 | 7/2010 | Sanai et al. |
| 2010/0181966 A1 | 7/2010 | Sakakibara |
| 2010/0187283 A1 | 7/2010 | Crainich et al. |
| 2010/0204721 A1 | 8/2010 | Young et al. |
| 2010/0222714 A1 | 9/2010 | Muir et al. |
| 2010/0222752 A1 | 9/2010 | Collins, Jr. et al. |
| 2010/0228250 A1 | 9/2010 | Brogna |
| 2010/0228264 A1 | 9/2010 | Robinson et al. |
| 2010/0234906 A1 | 9/2010 | Koh |
| 2010/0262134 A1 | 10/2010 | Jensen et al. |
| 2010/0274160 A1 | 10/2010 | Yachi et al. |
| 2010/0274278 A1 | 10/2010 | Fleenor et al. |
| 2010/0280368 A1 | 11/2010 | Can et al. |
| 2010/0280407 A1 | 11/2010 | Polster |
| 2010/0292691 A1 | 11/2010 | Brogna |
| 2010/0298743 A1 | 11/2010 | Nield et al. |
| 2010/0298851 A1 | 11/2010 | Nield |
| 2010/0331742 A1 | 12/2010 | Masuda |
| 2011/0004233 A1 | 1/2011 | Muir et al. |
| 2011/0009850 A1 | 1/2011 | Main et al. |
| 2011/0015650 A1 | 1/2011 | Choi et al. |
| 2011/0028964 A1 | 2/2011 | Edwards |
| 2011/0071523 A1 | 3/2011 | Dickhans |
| 2011/0077648 A1 | 3/2011 | Lee et al. |
| 2011/0082486 A1* | 4/2011 | Messerly ....... A61B 17/320092 606/169 |
| 2011/0087218 A1 | 4/2011 | Boudreaux et al. |
| 2011/0106141 A1 | 5/2011 | Nakamura |
| 2011/0112400 A1 | 5/2011 | Emery et al. |
| 2011/0112526 A1 | 5/2011 | Fritz et al. |
| 2011/0125149 A1 | 5/2011 | El-Galley et al. |
| 2011/0125151 A1 | 5/2011 | Strauss et al. |
| 2011/0125174 A1 | 5/2011 | Babaev |
| 2011/0144806 A1 | 6/2011 | Sandhu et al. |
| 2011/0160725 A1 | 6/2011 | Kabaya et al. |
| 2011/0224689 A1 | 9/2011 | Larkin et al. |
| 2011/0238010 A1 | 9/2011 | Kirschenman et al. |
| 2011/0238065 A1 | 9/2011 | Hunt et al. |
| 2011/0257650 A1 | 10/2011 | Deville et al. |
| 2011/0270126 A1 | 11/2011 | Gunday et al. |
| 2011/0273465 A1 | 11/2011 | Konishi et al. |
| 2011/0278343 A1 | 11/2011 | Knodel et al. |
| 2011/0279268 A1 | 11/2011 | Konishi et al. |
| 2011/0284014 A1 | 11/2011 | Cadeddu et al. |
| 2011/0290853 A1 | 12/2011 | Shelton, IV et al. |
| 2011/0290856 A1 | 12/2011 | Shelton, IV et al. |
| 2011/0295242 A1 | 12/2011 | Spivey et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0004655 A1 | 1/2012 | Kim et al. |
| 2012/0016413 A1 | 1/2012 | Timm et al. |
| 2012/0022519 A1 | 1/2012 | Huang et al. |
| 2012/0022525 A1 | 1/2012 | Dietz et al. |
| 2012/0022526 A1 | 1/2012 | Aldridge et al. |
| 2012/0022530 A1 | 1/2012 | Woodruff et al. |
| 2012/0022583 A1 | 1/2012 | Sugalski et al. |
| 2012/0041358 A1 | 2/2012 | Mann et al. |
| 2012/0053597 A1 | 3/2012 | Anvari et al. |
| 2012/0059286 A1 | 3/2012 | Hastings et al. |
| 2012/0059289 A1 | 3/2012 | Nield et al. |
| 2012/0065628 A1 | 3/2012 | Naito |
| 2012/0071863 A1 | 3/2012 | Lee et al. |
| 2012/0078139 A1 | 3/2012 | Aldridge et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078278 A1 | 3/2012 | Bales, Jr. et al. |
| 2012/0080332 A1 | 4/2012 | Shelton, IV et al. |
| 2012/0080344 A1 | 4/2012 | Shelton, IV |
| 2012/0101495 A1 | 4/2012 | Young et al. |
| 2012/0101501 A1 | 4/2012 | Nishimura et al. |
| 2012/0109159 A1 | 5/2012 | Jordan et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0116266 A1 | 5/2012 | Houser et al. |
| 2012/0116373 A1 | 5/2012 | Yates et al. |
| 2012/0116381 A1 | 5/2012 | Houser et al. |
| 2012/0116391 A1 | 5/2012 | Houser et al. |
| 2012/0116394 A1 | 5/2012 | Timm et al. |
| 2012/0116395 A1 | 5/2012 | Madan |
| 2012/0130256 A1 | 5/2012 | Buysse et al. |
| 2012/0130365 A1 | 5/2012 | McLawhorn |
| 2012/0136279 A1 | 5/2012 | Tanaka et al. |
| 2012/0136354 A1 | 5/2012 | Rupp |
| 2012/0136386 A1 | 5/2012 | Kishida et al. |
| 2012/0138660 A1 | 6/2012 | Shelton, IV |
| 2012/0143211 A1 | 6/2012 | Kishi |
| 2012/0150049 A1 | 6/2012 | Zielinski et al. |
| 2012/0150169 A1 | 6/2012 | Zielinksi et al. |
| 2012/0150170 A1 | 6/2012 | Buysse et al. |
| 2012/0165816 A1 | 6/2012 | Kersten et al. |
| 2012/0172873 A1 | 7/2012 | Artale et al. |
| 2012/0172904 A1 | 7/2012 | Muir et al. |
| 2012/0177005 A1 | 7/2012 | Liang et al. |
| 2012/0184946 A1 | 7/2012 | Price et al. |
| 2012/0191091 A1 | 7/2012 | Allen |
| 2012/0199630 A1 | 8/2012 | Shelton, IV |
| 2012/0199632 A1 | 8/2012 | Spivey et al. |
| 2012/0203143 A1* | 8/2012 | Sanai ............ A61B 17/320092 601/3 |
| 2012/0203247 A1 | 8/2012 | Shelton, IV et al. |
| 2012/0209289 A1 | 8/2012 | Duque et al. |
| 2012/0209303 A1 | 8/2012 | Frankhouser et al. |
| 2012/0210223 A1 | 8/2012 | Eppolito |
| 2012/0211542 A1 | 8/2012 | Racenet |
| 2012/0215220 A1 | 8/2012 | Manzo et al. |
| 2012/0245582 A1 | 9/2012 | Kimball et al. |
| 2012/0253328 A1 | 10/2012 | Cunningham et al. |
| 2012/0253370 A1 | 10/2012 | Ross et al. |
| 2012/0265241 A1 | 10/2012 | Hart et al. |
| 2012/0269676 A1 | 10/2012 | Houser et al. |
| 2012/0277778 A1* | 11/2012 | Masuda ......... A61B 17/320092 606/169 |

(56) References Cited

U.S. PATENT DOCUMENTS

| | | |
|---|---|---|
| 2012/0296325 A1 | 11/2012 | Takashino |
| 2012/0296371 A1 | 11/2012 | Kappus et al. |
| 2012/0330307 A1 | 12/2012 | Ladtkow et al. |
| 2013/0012957 A1 | 1/2013 | Shelton, IV et al. |
| 2013/0023925 A1 | 1/2013 | Mueller |
| 2013/0030433 A1 | 1/2013 | Heard |
| 2013/0035680 A1 | 2/2013 | Ben-Haim et al. |
| 2013/0035685 A1 | 2/2013 | Fischer et al. |
| 2013/0053840 A1 | 2/2013 | Krapohl et al. |
| 2013/0072856 A1 | 3/2013 | Frankhouser et al. |
| 2013/0072857 A1 | 3/2013 | Frankhouser et al. |
| 2013/0079762 A1 | 3/2013 | Twomey et al. |
| 2013/0085510 A1 | 4/2013 | Stefanchik et al. |
| 2013/0103023 A1 | 4/2013 | Monson et al. |
| 2013/0103024 A1 | 4/2013 | Monson et al. |
| 2013/0110145 A1 | 5/2013 | Weitzman |
| 2013/0116686 A1* | 5/2013 | Akagane .......... A61B 18/1445 606/41 |
| 2013/0123776 A1 | 5/2013 | Monson et al. |
| 2013/0123777 A1 | 5/2013 | Monson et al. |
| 2013/0123782 A1 | 5/2013 | Trees et al. |
| 2013/0123822 A1 | 5/2013 | Wellman et al. |
| 2013/0131660 A1 | 5/2013 | Monson et al. |
| 2013/0158659 A1 | 6/2013 | Bergs et al. |
| 2013/0158660 A1 | 6/2013 | Bergs et al. |
| 2013/0165929 A1 | 6/2013 | Muir et al. |
| 2013/0214025 A1 | 8/2013 | Zemlok et al. |
| 2013/0217967 A1 | 8/2013 | Mohr et al. |
| 2013/0253256 A1 | 9/2013 | Griffith et al. |
| 2013/0253480 A1 | 9/2013 | Kimball et al. |
| 2013/0253498 A1 | 9/2013 | Germain et al. |
| 2013/0274734 A1 | 10/2013 | Maass et al. |
| 2013/0277410 A1 | 10/2013 | Fernandez et al. |
| 2013/0282038 A1 | 10/2013 | Dannaher et al. |
| 2013/0296843 A1 | 11/2013 | Boudreaux et al. |
| 2013/0296908 A1 | 11/2013 | Schulte et al. |
| 2013/0334989 A1 | 12/2013 | Kataoka |
| 2013/0338661 A1 | 12/2013 | Behnke, II |
| 2013/0345689 A1 | 12/2013 | Ruddenklau et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005653 A1 | 1/2014 | Shelton, IV et al. |
| 2014/0005656 A1 | 1/2014 | Mucilli et al. |
| 2014/0005661 A1 | 1/2014 | Shelton, IV et al. |
| 2014/0005662 A1 | 1/2014 | Shelton, IV et al. |
| 2014/0005676 A1 | 1/2014 | Shelton, IV et al. |
| 2014/0005678 A1 | 1/2014 | Shelton, IV et al. |
| 2014/0005680 A1 | 1/2014 | Shelton, IV et al. |
| 2014/0005681 A1 | 1/2014 | Gee et al. |
| 2014/0005702 A1 | 1/2014 | Timm et al. |
| 2014/0005705 A1 | 1/2014 | Weir et al. |
| 2014/0005708 A1 | 1/2014 | Shelton, IV et al. |
| 2014/0005718 A1 | 1/2014 | Shelton, Iv et al. |
| 2014/0012299 A1 | 1/2014 | Stoddard et al. |
| 2014/0014544 A1 | 1/2014 | Bugnard et al. |
| 2014/0066962 A1 | 3/2014 | Robertson et al. |
| 2014/0087569 A1 | 3/2014 | Lee |
| 2014/0107538 A1 | 4/2014 | Wiener et al. |
| 2014/0114327 A1 | 4/2014 | Boudreaux et al. |
| 2014/0121569 A1 | 5/2014 | Schafer et al. |
| 2014/0135804 A1 | 5/2014 | Weisenburgh, II et al. |
| 2014/0155921 A1 | 6/2014 | Price et al. |
| 2014/0160280 A1 | 6/2014 | Sigmon, Jr. |
| 2014/0180274 A1 | 6/2014 | Kabaya et al. |
| 2014/0194868 A1 | 7/2014 | Sanai et al. |
| 2014/0194874 A1 | 7/2014 | Dietz et al. |
| 2014/0194875 A1 | 7/2014 | Reschke et al. |
| 2014/0207135 A1 | 7/2014 | Winter |
| 2014/0243864 A1 | 8/2014 | Voegele et al. |
| 2014/0246475 A1 | 9/2014 | Hall et al. |
| 2014/0263541 A1 | 9/2014 | Leimbach et al. |
| 2014/0263552 A1 | 9/2014 | Hall et al. |
| 2014/0276659 A1 | 9/2014 | Juergens et al. |
| 2014/0276754 A1 | 9/2014 | Gilbert et al. |
| 2014/0276797 A1 | 9/2014 | Batchelor et al. |
| 2014/0276806 A1 | 9/2014 | Heim |
| 2014/0276970 A1 | 9/2014 | Messerly et al. |
| 2015/0032150 A1 | 1/2015 | Ishida et al. |
| 2015/0045819 A1 | 2/2015 | Houser et al. |
| 2015/0066067 A1 | 3/2015 | Stulen |
| 2015/0073460 A1 | 3/2015 | Stulen |
| 2015/0080876 A1 | 3/2015 | Worrell et al. |
| 2015/0080887 A1 | 3/2015 | Sobajima et al. |
| 2015/0094703 A1 | 4/2015 | Zikorus et al. |
| 2015/0112335 A1 | 4/2015 | Boudreaux et al. |
| 2015/0119914 A1 | 4/2015 | Neurohr et al. |
| 2015/0119915 A1 | 4/2015 | Neurohr et al. |
| 2015/0119916 A1 | 4/2015 | Dietz et al. |
| 2015/0123348 A1 | 5/2015 | Robertson et al. |
| 2015/0157355 A1 | 6/2015 | Price et al. |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0182251 A1 | 7/2015 | Messerly et al. |
| 2015/0182276 A1 | 7/2015 | Wiener et al. |
| 2015/0182277 A1 | 7/2015 | Wiener et al. |
| 2015/0196318 A1 | 7/2015 | Messerly et al. |
| 2015/0238260 A1 | 8/2015 | Nau, Jr. |
| 2015/0250495 A1 | 9/2015 | Robertson et al. |
| 2015/0257780 A1 | 9/2015 | Houser |
| 2015/0257781 A1 | 9/2015 | Houser et al. |
| 2015/0265308 A1 | 9/2015 | Houser et al. |
| 2015/0272659 A1 | 10/2015 | Boudreaux et al. |
| 2015/0272660 A1 | 10/2015 | Boudreaux et al. |
| 2015/0282879 A1 | 10/2015 | Ruelas |
| 2015/0313667 A1 | 11/2015 | Allen, IV |
| 2015/0320481 A1 | 11/2015 | Cosman, Jr. et al. |
| 2015/0327883 A1 | 11/2015 | Messerly et al. |
| 2015/0328484 A1 | 11/2015 | Messerly et al. |
| 2015/0340586 A1 | 11/2015 | Wiener et al. |
| 2015/0351789 A1 | 12/2015 | Robertson et al. |
| 2016/0030076 A1 | 2/2016 | Faller et al. |
| 2016/0045248 A1 | 2/2016 | Unger et al. |
| 2016/0051316 A1 | 2/2016 | Boudreaux |
| 2016/0074108 A1 | 3/2016 | Woodruff et al. |
| 2016/0089209 A1 | 3/2016 | Parihar et al. |
| 2016/0089533 A1 | 3/2016 | Turner et al. |
| 2016/0095617 A1 | 4/2016 | Price et al. |
| 2016/0106509 A1 | 4/2016 | Worrell et al. |
| 2016/0120563 A1 | 5/2016 | Messerly et al. |
| 2016/0128762 A1 | 5/2016 | Harris et al. |
| 2016/0144204 A1 | 5/2016 | Akagane |
| 2016/0157927 A1 | 6/2016 | Corbett et al. |
| 2016/0175029 A1 | 6/2016 | Witt et al. |
| 2016/0192999 A1 | 7/2016 | Stulen et al. |
| 2016/0199125 A1 | 7/2016 | Jones |
| 2016/0206342 A1 | 7/2016 | Robertson et al. |
| 2016/0262786 A1 | 9/2016 | Madan et al. |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0296249 A1 | 10/2016 | Robertson |
| 2016/0296250 A1 | 10/2016 | Olson et al. |
| 2016/0296251 A1 | 10/2016 | Olson et al. |
| 2016/0296252 A1 | 10/2016 | Olson et al. |
| 2016/0296270 A1 | 10/2016 | Strobl et al. |
| 2016/0317217 A1 | 11/2016 | Batross et al. |
| 2016/0324537 A1 | 11/2016 | Green et al. |
| 2016/0346001 A1 | 12/2016 | Vakharia et al. |
| 2016/0367281 A1 | 12/2016 | Gee et al. |
| 2016/0374709 A1 | 12/2016 | Timm et al. |
| 2017/0000516 A1 | 1/2017 | Stulen et al. |
| 2017/0000541 A1 | 1/2017 | Yates et al. |
| 2017/0000542 A1 | 1/2017 | Yates et al. |
| 2017/0000552 A1 | 1/2017 | Asher et al. |
| 2017/0000553 A1 | 1/2017 | Wiener et al. |
| 2017/0000554 A1 | 1/2017 | Yates et al. |
| 2017/0056058 A1 | 3/2017 | Voegele et al. |
| 2017/0086876 A1 | 3/2017 | Wiener et al. |
| 2017/0086908 A1 | 3/2017 | Wiener et al. |

(56) References Cited

U.S. PATENT DOCUMENTS

| | | |
|---|---|---|
| 2017/0086909 A1 | 3/2017 | Yates et al. |
| 2017/0086910 A1 | 3/2017 | Wiener et al. |
| 2017/0086911 A1 | 3/2017 | Wiener et al. |
| 2017/0086912 A1 | 3/2017 | Wiener et al. |
| 2017/0086913 A1 | 3/2017 | Yates et al. |
| 2017/0086914 A1 | 3/2017 | Wiener et al. |
| 2017/0105757 A1 | 4/2017 | Weir et al. |
| 2017/0105782 A1 | 4/2017 | Scheib et al. |
| 2017/0105786 A1 | 4/2017 | Scheib et al. |
| 2017/0105791 A1 | 4/2017 | Yates et al. |
| 2017/0119426 A1 | 5/2017 | Akagane |
| 2017/0135751 A1 | 5/2017 | Rothweiler et al. |
| 2017/0143371 A1 | 5/2017 | Witt et al. |
| 2017/0143877 A1 | 5/2017 | Witt et al. |
| 2017/0164994 A1 | 6/2017 | Smith |
| 2017/0164997 A1 | 6/2017 | Johnson et al. |
| 2017/0189095 A1 | 7/2017 | Danziger et al. |
| 2017/0189096 A1 | 7/2017 | Danziger et al. |
| 2017/0196586 A1 | 7/2017 | Witt et al. |
| 2017/0196587 A1 | 7/2017 | Witt et al. |
| 2017/0202571 A1 | 7/2017 | Shelton, IV et al. |
| 2017/0202572 A1 | 7/2017 | Shelton, IV et al. |
| 2017/0202573 A1 | 7/2017 | Witt et al. |
| 2017/0202591 A1 | 7/2017 | Shelton, IV et al. |
| 2017/0202592 A1 | 7/2017 | Shelton, IV et al. |
| 2017/0202594 A1 | 7/2017 | Shelton, IV et al. |
| 2017/0202595 A1 | 7/2017 | Shelton, IV |
| 2017/0202596 A1 | 7/2017 | Shelton, IV et al. |
| 2017/0202597 A1 | 7/2017 | Shelton, IV et al. |
| 2017/0202598 A1 | 7/2017 | Shelton, IV et al. |
| 2017/0202599 A1 | 7/2017 | Shelton, IV et al. |
| 2017/0202605 A1 | 7/2017 | Shelton, IV et al. |
| 2017/0202607 A1 | 7/2017 | Shelton, IV et al. |
| 2017/0202608 A1 | 7/2017 | Shelton, IV et al. |
| 2017/0202609 A1 | 7/2017 | Shelton, IV et al. |
| 2017/0207467 A1 | 7/2017 | Shelton, IV et al. |
| 2017/0209167 A1 | 7/2017 | Nield |
| 2017/0238991 A1 | 8/2017 | Worrell et al. |
| 2017/0245875 A1 | 8/2017 | Timm et al. |
| 2017/0312014 A1 | 11/2017 | Strobl et al. |
| 2017/0312015 A1 | 11/2017 | Worrell et al. |
| 2017/0312016 A1 | 11/2017 | Strobl et al. |
| 2017/0312017 A1 | 11/2017 | Trees et al. |
| 2017/0312018 A1 | 11/2017 | Trees et al. |
| 2017/0312019 A1 | 11/2017 | Trees et al. |
| 2017/0319265 A1 | 11/2017 | Yates et al. |
| 2017/0325874 A1 | 11/2017 | Noack et al. |
| 2017/0348064 A1 | 12/2017 | Stewart et al. |
| 2018/0014872 A1 | 1/2018 | Dickerson |
| 2018/0028257 A1 | 2/2018 | Yates et al. |
| 2018/0042658 A1 | 2/2018 | Shelton, IV et al. |
| 2018/0064961 A1 | 3/2018 | Wiener et al. |
| 2018/0078277 A1 | 3/2018 | Illizaliturri-Sanchez et al. |
| 2018/0098785 A1 | 4/2018 | Price et al. |
| 2018/0098808 A1 | 4/2018 | Yates et al. |
| 2018/0146976 A1 | 5/2018 | Clauda et al. |
| 2018/0177545 A1 | 6/2018 | Boudreaux et al. |
| 2018/0235691 A1 | 8/2018 | Voegele et al. |
| 2018/0280083 A1 | 10/2018 | Parihar et al. |
| 2019/0021783 A1 | 1/2019 | Asher et al. |
| 2019/0105067 A1 | 4/2019 | Boudreaux et al. |
| 2019/0201048 A1 | 7/2019 | Stulen et al. |
| 2019/0209201 A1 | 7/2019 | Boudreaux et al. |
| 2019/0262030 A1 | 8/2019 | Faller et al. |
| 2019/0274700 A1 | 9/2019 | Robertson et al. |
| 2019/0282288 A1 | 9/2019 | Boudreaux |
| 2019/0282292 A1 | 9/2019 | Wiener et al. |
| 2020/0015883 A1 | 1/2020 | Batross et al. |
| 2020/0022724 A1 | 1/2020 | Worrell et al. |
| 2020/0030021 A1 | 1/2020 | Yates et al. |
| 2020/0054382 A1 | 2/2020 | Yates et al. |
| 2020/0078085 A1 | 3/2020 | Yates et al. |
| 2020/0078609 A1 | 3/2020 | Messerly et al. |
| 2020/0085465 A1 | 3/2020 | Timm et al. |
| 2020/0113624 A1 | 4/2020 | Worrell et al. |
| 2020/0138473 A1 | 5/2020 | Shelton, IV et al. |
| 2020/0222135 A1 | 7/2020 | Stolen et al. |
| 2020/0229833 A1 | 7/2020 | Vakharia et al. |
| 2020/0229834 A1 | 7/2020 | Olson et al. |
| 2020/0237434 A1 | 7/2020 | Scheib et al. |
| 2020/0261141 A1 | 8/2020 | Wiener et al. |
| 2020/0268433 A1 | 8/2020 | Wiener et al. |
| 2021/0052313 A1 | 2/2021 | Shelton, IV et al. |
| 2021/0100578 A1 | 4/2021 | Weir et al. |
| 2021/0100579 A1 | 4/2021 | Shelton, IV et al. |
| 2021/0177481 A1 | 6/2021 | Shelton, IV et al. |
| 2021/0177496 A1 | 6/2021 | Shelton, IV et al. |
| 2021/0186553 A1 | 6/2021 | Green et al. |
| 2021/0186554 A1 | 6/2021 | Green et al. |
| 2021/0196263 A1 | 7/2021 | Shelton, IV et al. |
| 2021/0196265 A1 | 7/2021 | Shelton, IV et al. |
| 2021/0196266 A1 | 7/2021 | Shelton, IV et al. |
| 2021/0196267 A1 | 7/2021 | Shelton, IV et al. |
| 2021/0196268 A1 | 7/2021 | Shelton, IV et al. |
| 2021/0196269 A1 | 7/2021 | Shelton, IV et al. |
| 2021/0196270 A1 | 7/2021 | Shelton, IV et al. |
| 2021/0196271 A1 | 7/2021 | Shelton, IV et al. |
| 2021/0196301 A1 | 7/2021 | Shelton, IV et al. |
| 2021/0196302 A1 | 7/2021 | Shelton, IV et al. |
| 2021/0196305 A1 | 7/2021 | Strobl |
| 2021/0196306 A1 | 7/2021 | Estera et al. |
| 2021/0196307 A1 | 7/2021 | Shelton, IV |
| 2021/0196334 A1 | 7/2021 | Sarley et al. |
| 2021/0196335 A1 | 7/2021 | Messerly et al. |
| 2021/0196336 A1 | 7/2021 | Faller et al. |
| 2021/0196343 A1 | 7/2021 | Shelton, IV et al. |
| 2021/0196344 A1 | 7/2021 | Shelton, IV et al. |
| 2021/0196345 A1 | 7/2021 | Messerly et al. |
| 2021/0196346 A1 | 7/2021 | Leuck et al. |
| 2021/0196349 A1 | 7/2021 | Fiebig et al. |
| 2021/0196350 A1 | 7/2021 | Fiebig et al. |
| 2021/0196351 A1 | 7/2021 | Sarley et al. |
| 2021/0196352 A1 | 7/2021 | Messerly et al. |
| 2021/0196353 A1 | 7/2021 | Gee et al. |
| 2021/0196354 A1 | 7/2021 | Shelton, IV et al. |
| 2021/0196355 A1 | 7/2021 | Shelton, IV et al. |
| 2021/0196356 A1 | 7/2021 | Shelton, IV et al. |
| 2021/0196357 A1 | 7/2021 | Shelton, IV et al. |
| 2021/0196358 A1 | 7/2021 | Shelton, IV et al. |
| 2021/0196359 A1 | 7/2021 | Shelton, IV et al. |
| 2021/0196360 A1 | 7/2021 | Shelton, IV et al. |
| 2021/0196361 A1 | 7/2021 | Shelton, IV et al. |
| 2021/0196362 A1 | 7/2021 | Shelton, IV et al. |
| 2021/0196363 A1 | 7/2021 | Shelton, IV et al. |
| 2021/0196364 A1 | 7/2021 | Shelton, IV et al. |
| 2021/0196365 A1 | 7/2021 | Shelton, IV et al. |
| 2021/0196366 A1 | 7/2021 | Shelton, IV et al. |
| 2021/0196367 A1 | 7/2021 | Salguero et al. |
| 2021/0212744 A1 | 7/2021 | Shelton, IV et al. |
| 2021/0220036 A1 | 7/2021 | Shelton, IV et al. |
| 2021/0236195 A1 | 8/2021 | Asher et al. |

FOREIGN PATENT DOCUMENTS

| | | |
|---|---|---|
| CN | 1233944 A | 11/1999 |
| CN | 1253485 A | 5/2000 |
| CN | 2460047 Y | 11/2001 |
| CN | 1634601 A | 7/2005 |
| CN | 1640365 A | 7/2005 |
| CN | 1694649 A | 11/2005 |
| CN | 1775323 A | 5/2006 |
| CN | 1922563 A | 2/2007 |
| CN | 2868227 Y | 2/2007 |
| CN | 1951333 A | 4/2007 |
| CN | 101035482 A | 9/2007 |
| CN | 101040799 A | 9/2007 |
| CN | 101467917 A | 1/2009 |
| CN | 101396300 A | 4/2009 |
| CN | 101474081 A | 7/2009 |
| CN | 101516285 A | 8/2009 |
| CN | 101674782 A | 3/2010 |
| CN | 101883531 A | 11/2010 |
| CN | 102100582 A | 6/2011 |
| CN | 102149312 A | 8/2011 |

(56) References Cited

FOREIGN PATENT DOCUMENTS

| | | | |
|---|---|---|---|
| CN | 202027624 U | 11/2011 |
| CN | 102792181 A | 11/2012 |
| CN | 101313865 B | 1/2013 |
| CN | 103281982 A | 9/2013 |
| CN | 103379853 A | 10/2013 |
| CN | 203468630 U | 3/2014 |
| CN | 104013444 A | 9/2014 |
| CN | 102160045 A | 8/2017 |
| DE | 3904558 A1 | 8/1990 |
| DE | 9210327 U1 | 11/1992 |
| DE | 4300307 A1 | 7/1994 |
| DE | 4323585 A1 | 1/1995 |
| DE | 19608716 C1 | 4/1997 |
| DE | 29623113 U1 | 10/1997 |
| DE | 20004812 U1 | 9/2000 |
| DE | 20021619 U1 | 3/2001 |
| DE | 10042606 A1 | 8/2001 |
| DE | 10201569 A1 | 7/2003 |
| DE | 102012109037 A1 | 4/2014 |
| EP | 0136855 B1 | 9/1984 |
| EP | 0171967 A2 | 2/1986 |
| EP | 1839599 A1 | 10/1987 |
| EP | 0336742 A2 | 4/1989 |
| EP | 0342448 A1 | 11/1989 |
| EP | 0424685 B1 | 5/1991 |
| EP | 0443256 A1 | 8/1991 |
| EP | 0456470 A1 | 11/1991 |
| EP | 0238667 B1 | 2/1993 |
| EP | 0598976 A2 | 1/1994 |
| EP | 0677275 A2 | 3/1995 |
| EP | 0482195 B1 | 1/1996 |
| EP | 0695535 A1 | 2/1996 |
| EP | 0705571 A1 | 4/1996 |
| EP | 0741996 A2 | 11/1996 |
| EP | 0612570 B1 | 6/1997 |
| EP | 1108394 A2 | 6/2001 |
| EP | 1138264 A1 | 10/2001 |
| EP | 0908148 B1 | 1/2002 |
| EP | 1229515 A2 | 8/2002 |
| EP | 1285634 A1 | 2/2003 |
| EP | 0908155 B1 | 6/2003 |
| EP | 0705570 B1 | 4/2004 |
| EP | 0765637 B1 | 7/2004 |
| EP | 0870473 B1 | 9/2005 |
| EP | 0624346 B1 | 11/2005 |
| EP | 1594209 A1 | 11/2005 |
| EP | 1199044 B1 | 12/2005 |
| EP | 1609428 A1 | 12/2005 |
| EP | 1199043 B1 | 3/2006 |
| EP | 1433425 B1 | 6/2006 |
| EP | 1256323 B1 | 9/2006 |
| EP | 1698289 A2 | 9/2006 |
| EP | 1704824 A1 | 9/2006 |
| EP | 1749479 A1 | 2/2007 |
| EP | 1815950 A1 | 8/2007 |
| EP | 1844720 A1 | 10/2007 |
| EP | 1862133 A1 | 12/2007 |
| EP | 1875875 A1 | 1/2008 |
| EP | 1199045 B1 | 6/2008 |
| EP | 1964530 A1 | 9/2008 |
| EP | 1972264 A1 | 9/2008 |
| EP | 1974771 A1 | 10/2008 |
| EP | 1435852 B1 | 12/2008 |
| EP | 1498082 B1 | 12/2008 |
| EP | 1707131 B1 | 12/2008 |
| EP | 1997438 A2 | 12/2008 |
| EP | 1477104 B1 | 1/2009 |
| EP | 2014218 A2 | 1/2009 |
| EP | 2042112 A2 | 4/2009 |
| EP | 2060238 A1 | 5/2009 |
| EP | 1832259 B1 | 6/2009 |
| EP | 2074959 A1 | 7/2009 |
| EP | 1747761 B1 | 10/2009 |
| EP | 2106758 A1 | 10/2009 |
| EP | 2111813 A1 | 10/2009 |
| EP | 2131760 A1 | 12/2009 |
| EP | 2200145 A1 | 6/2010 |
| EP | 1214913 B1 | 7/2010 |
| EP | 2238938 A1 | 10/2010 |
| EP | 2298154 A2 | 3/2011 |
| EP | 1510178 B1 | 6/2011 |
| EP | 1946708 B1 | 6/2011 |
| EP | 2305144 A1 | 6/2011 |
| EP | 2335630 A1 | 6/2011 |
| EP | 1502551 B1 | 7/2011 |
| EP | 2361562 A1 | 8/2011 |
| EP | 2365608 A2 | 9/2011 |
| EP | 2420197 A2 | 2/2012 |
| EP | 2422721 A2 | 2/2012 |
| EP | 1927321 B1 | 4/2012 |
| EP | 2510891 A1 | 10/2012 |
| EP | 1767164 B1 | 1/2013 |
| EP | 2316359 B1 | 3/2013 |
| EP | 2578172 A2 | 4/2013 |
| EP | 1586275 B1 | 5/2013 |
| EP | 1616529 B1 | 9/2013 |
| EP | 2668922 A1 | 12/2013 |
| EP | 2583633 B1 | 10/2014 |
| EP | 2076195 B1 | 12/2015 |
| EP | 2113210 81 | 3/2016 |
| EP | 2227155 B1 | 7/2016 |
| EP | 2859858 B1 | 12/2016 |
| ES | 2115068 T3 | 6/1998 |
| GB | 1482943 A | 8/1977 |
| GB | 2032221 A | 4/1980 |
| GB | 2317566 A | 4/1998 |
| GB | 2379878 B | 11/2004 |
| GB | 2447767 B | 8/2011 |
| JP | S 50-100891 A | 8/1975 |
| JP | S 59-68513 U | 5/1984 |
| JP | S 59141938 A | 8/1984 |
| JP | S 62-221343 A | 9/1987 |
| JP | S 62-227343 A | 10/1987 |
| JP | 62-292153 A | 12/1987 |
| JP | S 62-292154 A | 12/1987 |
| JP | S 63-109386 A | 5/1988 |
| JP | S 63-315049 A | 12/1988 |
| JP | H 01-151452 A | 3/1989 |
| JP | H 01-198540 A | 8/1989 |
| JP | H 02-71510 U | 5/1990 |
| JP | H 02-286149 A | 11/1990 |
| JP | H 02-292193 A | 12/1990 |
| JP | H 03-37061 A | 2/1991 |
| JP | H 04-25707 U | 2/1992 |
| JP | H 04-64351 A | 2/1992 |
| JP | H 04-30508 U | 3/1992 |
| JP | H 04-150847 A | 5/1992 |
| JP | H 04-152942 A | 5/1992 |
| JP | H 0541716 A | 2/1993 |
| JP | 05-095955 A | 4/1993 |
| JP | H 05-115490 A | 5/1993 |
| JP | H 06-70938 A | 3/1994 |
| JP | H 06-104503 A | 4/1994 |
| JP | H 06-217988 A | 8/1994 |
| JP | H 06-507081 A | 8/1994 |
| JP | H 07-500514 A | 1/1995 |
| JP | H 7-508910 A | 10/1995 |
| JP | H 07-308323 A | 11/1995 |
| JP | H 08-24266 A | 1/1996 |
| JP | H08229050 A | 9/1996 |
| JP | H 08-275951 A | 10/1996 |
| JP | H 08-299351 A | 11/1996 |
| JP | H 08-336544 A | 12/1996 |
| JP | H 08-336545 A | 12/1996 |
| JP | H 09-503146 A | 3/1997 |
| JP | H 09-135553 A | 5/1997 |
| JP | H09130655 A | 5/1997 |
| JP | H 09-140722 A | 6/1997 |
| JP | H 10-5237 A | 1/1998 |
| JP | 10127654 A | 5/1998 |
| JP | H 10-295700 A | 11/1998 |
| JP | H 11-501543 A | 2/1999 |
| JP | H 11-128238 A | 5/1999 |
| JP | H 11-192235 A | 7/1999 |

(56) References Cited

FOREIGN PATENT DOCUMENTS

| | | |
|---|---|---|
| JP | H 11-253451 A | 9/1999 |
| JP | H 11-318918 A | 11/1999 |
| JP | 2000-041991 A | 2/2000 |
| JP | 2000-070279 A | 3/2000 |
| JP | 2000-210299 A | 8/2000 |
| JP | 2000-271145 A | 10/2000 |
| JP | 2000-287987 A | 10/2000 |
| JP | 2000271142 A | 10/2000 |
| JP | 2002-542690 A | 12/2000 |
| JP | 2001-029353 A | 2/2001 |
| JP | 2001-502216 A | 2/2001 |
| JP | 2001-309925 A | 11/2001 |
| JP | 2002059380 A | 2/2002 |
| JP | 2002-177295 A | 6/2002 |
| JP | 2002-186901 A | 7/2002 |
| JP | 2002-204808 A | 7/2002 |
| JP | 2002-238919 A | 8/2002 |
| JP | 2002-263579 A | 9/2002 |
| JP | 2002-301086 A | 10/2002 |
| JP | 2002-306504 A | 10/2002 |
| JP | 2002-330977 A | 11/2002 |
| JP | 2003-000612 A | 1/2003 |
| JP | 2003-010201 | 1/2003 |
| JP | 2003-510158 A | 3/2003 |
| JP | 2003-116870 A | 4/2003 |
| JP | 2003-126104 A | 5/2003 |
| JP | 2003-126110 A | 5/2003 |
| JP | 2003-153919 A | 5/2003 |
| JP | 2003-310627 A | 5/2003 |
| JP | 2007-229454 A | 9/2003 |
| JP | 2003-530921 A | 10/2003 |
| JP | 2003-339730 A | 12/2003 |
| JP | 2004-129871 A | 4/2004 |
| JP | 2004-147701 A | 5/2004 |
| JP | 2005003496 A | 1/2005 |
| JP | 2005027026 A | 1/2005 |
| JP | 2005-040222 A | 2/2005 |
| JP | 2005-066316 A | 3/2005 |
| JP | 2005-074088 A | 3/2005 |
| JP | 2005-507679 A | 3/2005 |
| JP | 2005-534451 A | 11/2005 |
| JP | 2005337119 A | 12/2005 |
| JP | 2006-006410 A | 1/2006 |
| JP | 2006068396 A | 3/2006 |
| JP | 2006081664 A | 3/2006 |
| JP | 2006-512149 A | 4/2006 |
| JP | 2006114072 A | 4/2006 |
| JP | 2006-116194 A | 5/2006 |
| JP | 2006-158525 A | 6/2006 |
| JP | 2006-218296 A | 8/2006 |
| JP | 2006217716 A | 8/2006 |
| JP | 2006-288431 A | 10/2006 |
| JP | 2007037568 A | 2/2007 |
| JP | 2007-050181 A | 3/2007 |
| JP | 2007-524459 A | 8/2007 |
| JP | 2007-527747 A | 10/2007 |
| JP | 2007-296369 A | 11/2007 |
| JP | 200801876 A | 1/2008 |
| JP | 2008-036390 A | 2/2008 |
| JP | 200833644 A | 2/2008 |
| JP | 2008-508065 A | 3/2008 |
| JP | 2008-119250 A | 5/2008 |
| JP | 2008-515562 A | 5/2008 |
| JP | 2008-521503 A | 6/2008 |
| JP | 2008188160 A | 8/2008 |
| JP | D1339835 S | 8/2008 |
| JP | 2008-212679 A | 9/2008 |
| JP | 2008-536562 A | 9/2008 |
| JP | 2008-284374 A | 11/2008 |
| JP | 2009-511206 A | 3/2009 |
| JP | 2009-082711 A | 4/2009 |
| JP | 2009-517181 A | 4/2009 |
| JP | 4262923 B2 | 5/2009 |
| JP | 2009-523567 A | 6/2009 |
| JP | 2009-148557 A | 7/2009 |
| JP | 2009-236177 A | 10/2009 |
| JP | 2009-254819 A | 11/2009 |
| JP | 2010-000336 A | 1/2010 |
| JP | 2010-009686 A | 1/2010 |
| JP | 2010-514923 A | 5/2010 |
| JP | 2010-121865 A | 6/2010 |
| JP | 2010-534522 A | 11/2010 |
| JP | 2010-540186 A | 12/2010 |
| JP | 2011-505198 A | 2/2011 |
| JP | 2012/075899 A | 4/2012 |
| JP | 2012071186 A | 4/2012 |
| JP | 2012-235658 A | 11/2012 |
| JP | 5208761 B2 | 6/2013 |
| JP | 2015-515339 A | 5/2015 |
| JP | 5714508 B2 | 5/2015 |
| JP | 5836543 B1 | 12/2015 |
| KR | 100789356 B1 | 12/2007 |
| RU | 2154437 C1 | 8/2000 |
| RU | 22035 U1 | 3/2002 |
| RU | 2201163 C2 | 3/2003 |
| RU | 2304934 C2 | 8/2007 |
| RU | 2405603 C1 | 12/2010 |
| RU | 2013119977 A | 11/2014 |
| SU | 850068 A1 | 7/1981 |
| WO | WO-8103272 A1 | 11/1981 |
| WO | WO 92/22259 A2 | 12/1992 |
| WO | WO 93/08757 A1 | 5/1993 |
| WO | WO 93/14708 A1 | 8/1993 |
| WO | WO 93/16646 A1 | 9/1993 |
| WO | WO 93/20877 A1 | 10/1993 |
| WO | WO 9400059 A1 | 1/1994 |
| WO | WO 94/21183 A1 | 9/1994 |
| WO | WO 94/24949 A1 | 11/1994 |
| WO | WO 95/09572 A1 | 4/1995 |
| WO | WO 95/34259 A1 | 12/1995 |
| WO | WO 96/30885 A1 | 10/1996 |
| WO | WO 96/39086 A1 | 12/1996 |
| WO | WO-9800069 A1 | 1/1998 |
| WO | WO 98/16156 A1 | 4/1998 |
| WO | WO 98/26739 A1 | 6/1998 |
| WO | WO 98/35621 A1 | 8/1998 |
| WO | WO 98/37815 A1 | 9/1998 |
| WO | WO 98/47436 A1 | 10/1998 |
| WO | WO 99/20213 A1 | 4/1999 |
| WO | WO-9923960 A1 | 5/1999 |
| WO | WO 99/52489 A1 | 10/1999 |
| WO | WO-0024330 A1 | 5/2000 |
| WO | WO 00/64358 A2 | 11/2000 |
| WO | WO 00/74585 A2 | 12/2000 |
| WO | WO 01/24713 A1 | 4/2001 |
| WO | WO-0128444 A1 | 4/2001 |
| WO | WO 01/54530 A1 | 8/2001 |
| WO | WO 01/67970 A1 | 9/2001 |
| WO | WO-0172251 A1 | 10/2001 |
| WO | WO 01/95810 A2 | 12/2001 |
| WO | WO 02/24080 A2 | 3/2002 |
| WO | WO 02/38057 A1 | 5/2002 |
| WO | WO 02/062241 A1 | 8/2002 |
| WO | WO 03/082133 A1 | 10/2003 |
| WO | WO-03095028 A1 | 11/2003 |
| WO | WO 2004/012615 A1 | 2/2004 |
| WO | WO 2004/026104 A2 | 4/2004 |
| WO | WO 2004/032754 A2 | 4/2004 |
| WO | WO 2004/032762 A1 | 4/2004 |
| WO | WO 2004/032763 A2 | 4/2004 |
| WO | WO 2004/037095 A2 | 5/2004 |
| WO | WO 2004/060141 A2 | 7/2004 |
| WO | WO-2004078051 A2 | 9/2004 |
| WO | WO 2004/098426 A1 | 11/2004 |
| WO | WO 2004/112618 A2 | 12/2004 |
| WO | WO 2006/063199 A2 | 6/2005 |
| WO | WO 2005/117735 A2 | 12/2005 |
| WO | WO 2005/122917 A1 | 12/2005 |
| WO | WO 2006/012797 A1 | 2/2006 |
| WO | WO 2006/042210 A2 | 4/2006 |
| WO | WO 2006/058223 A2 | 6/2006 |
| WO | WO 2006/083988 A1 | 8/2006 |
| WO | WO 2006/101661 A2 | 9/2006 |
| WO | WO 2006/119139 A2 | 11/2006 |

(56) References Cited

FOREIGN PATENT DOCUMENTS

| WO | WO 2006/119376 A2 | 11/2006 |
|---|---|---|
| WO | WO 2006/129465 A1 | 12/2006 |
| WO | WO 2007/008703 A2 | 1/2007 |
| WO | WO 2007/008710 A2 | 1/2007 |
| WO | WO 2007/038538 A1 | 4/2007 |
| WO | WO 2007/040818 A1 | 4/2007 |
| WO | WO 2007/047380 A2 | 4/2007 |
| WO | WO 2007/047531 A2 | 4/2007 |
| WO | WO 2007/056590 A1 | 5/2007 |
| WO | WO 2007/087272 A2 | 8/2007 |
| WO | WO 2007/089724 A2 | 8/2007 |
| WO | WO 2007/143665 A2 | 12/2007 |
| WO | WO 2008/016886 A2 | 2/2008 |
| WO | WO 2008/042021 A1 | 4/2008 |
| WO | WO 2008/049084 A2 | 4/2008 |
| WO | WO 2008/051764 A2 | 5/2008 |
| WO | WO 2008/089174 A2 | 7/2008 |
| WO | WO 2008/118709 A1 | 10/2008 |
| WO | WO 2008/130793 A1 | 10/2008 |
| WO | WO 2009/010565 A1 | 1/2009 |
| WO | WO 2009/018067 A1 | 2/2009 |
| WO | WO 2009/018406 A2 | 2/2009 |
| WO | WO 2009/027065 A1 | 3/2009 |
| WO | WO 2009/046234 A2 | 4/2009 |
| WO | WO 2009/073402 A2 | 6/2009 |
| WO | WO 2009/088550 A2 | 7/2009 |
| WO | WO 2009/120992 A2 | 10/2009 |
| WO | WO 2009/141616 A1 | 11/2009 |
| WO | WO 2010/017149 A1 | 2/2010 |
| WO | WO-2010027109 A1 | 3/2010 |
| WO | WO 2010/068783 A1 | 6/2010 |
| WO | WO-2010104755 A1 | 9/2010 |
| WO | WO 2011/008672 A2 | 1/2011 |
| WO | WO 2011/044338 A2 | 4/2011 |
| WO | WO-2011044343 A2 | 4/2011 |
| WO | WO 2011/052939 A2 | 5/2011 |
| WO | WO 2011/060031 A1 | 5/2011 |
| WO | WO 2011/100321 A2 | 8/2011 |
| WO | WO 2011/144911 A1 | 11/2011 |
| WO | WO 2012/044597 A1 | 4/2012 |
| WO | WO-2012044606 A2 | 4/2012 |
| WO | WO 2012/061722 A2 | 5/2012 |
| WO | WO-2012088535 A1 | 6/2012 |
| WO | WO 2012/128362 A1 | 9/2012 |
| WO | WO 2012/135705 A1 | 10/2012 |
| WO | WO 2012/135721 A1 | 10/2012 |
| WO | WO-2012/150567 A1 | 11/2012 |
| WO | WO 2013/018934 A1 | 2/2013 |
| WO | WO 2013/062978 A2 | 5/2013 |
| WO | WO 2014/092108 A1 | 6/2014 |
| WO | WO 2016/009921 A1 | 12/2016 |

OTHER PUBLICATIONS

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
AST Products, Inc., "Principles of Video Contact Angle Analysis," 20 pages, (2006).
Lim et al., "A Review of Mechanism Used in Laparoscopic Surgical Instruments," Mechanism and Machine Theory, vol. 38, pp. 1133-1147, (2003).
Gooch et al., "Recommended Infection-Control Practices for Dentistry, 1993," Published: May 28, 1993; [retrieved on Aug. 23, 2008] Retrieved from the internet: URL: http//wonder.cdc.gov/wonder/prevguid/p0000191/p0000191.asp (15 pages).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Incropera et al., "Fundamentals of Heat and Mass Transfer", Wiley, New York (1990). (Book—not attached).
F. A. Duck, "Optical Properties of Tissue Including Ultraviolet and Infrared Radiation," pp. 43-71 in *Physical Properties of Tissue* (1990).
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Campbell et al., "Thermal Imaging in Surgery," p. 19-3, in *Medical infrared Imaging*, N. A. Diakides and J. D. Bronzino, Eds. (2008).
Sullivan, "Cost-Constrained Selection of Strand Diameter and Number in a Litz-Mire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
Graff. K.F., "Elastic Wave Propagation in a Curved Sonic Transmission Line," IEEE Transactions on Sonics and Ultrasonics, SU-17(1), 1-6 (1970).
Makarov, S. N., Ochmann, M., Desinger, K., "The longitudinal vibration response of a curved fiber used for laser ultrasound surgical therapy," Journal of the Acoustical Society of America 102, 1191-1199 (1997).
Morley, L. S. D., "Elastic Waves in a Naturally Curved Rod," Quarterly Journal of Mechanics and Applied Mathematics, 14: 155-172 (1961).
Walsh, S. J., White, R. G., "Vibrational Power Transmission in Curved Beams," Journal of Sound and Vibration, 233(3), 455-488 (2000).
http://www.apicalinstr.com/generators.htm.
http://www.dotmed.com/listing/electrosurical-unit/ethicon/ultracision-g110-/1466724.
http:/www.ethicon.com/gb-en/healthcare-professionals/produds/energy-devices/capital//ge . . . .
http://www.4-traders.com/JOHNSON-JOHNSON-4832/news/Johnson-Johnson-Ethicon-E . . . .
http://www.medicalexpo.com/medical-manufacturer/electrosurgical-generator-6951.html.
http://www.megadyne.com/es generator.php.
http://www.valleylab.com/product/es/generators/index.html.
Covidien 501 (k) Summary Sonicision, dated Feb. 24, 2011 (7 pages).
Gerhard, Glen C., "Surgical Electrotechnology: Quo Vadis?," IEEE Transactions on Biomedical Engineering, vol. BME-31, No. 12, pp. 787-792, Dec. 1984.
Fowler, K.R., "A Programmable, Arbitrary Waveform Electrosurgical Device," IEEE Engineering in Medicine and Biology Society 10th Annual International Conference, pp. 1324, 1325 (1988).
LaCourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Henriques. F.C., "Studies in thermal injury V. The predictability and the significance of thermally induced rate processes leading to irreversible epidermal injury." Archives of Pathology, 434, pp. 489-502 (1947).
Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

(56) References Cited

OTHER PUBLICATIONS

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
Wall et al., "Thermal modification of collagen," J Shoulder Elbow Surg, No. 8, pp. 339-344 (Jul./Aug. 1999).
Wells et al., "Altered Mechanical Behavior of Epicardium Under Isothermal Biaxial Loading," Transactions of the ASME, Journal of Biomechanical Engineering, vol. 126, pp. 492-497 (Aug. 2004).
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Humphrey, J.D., "Continuum Thermomechanics and the Clinical Treatment of Disease and Injury," Appl. Mech. Rev., vol. 56, No. 2 pp. 231-260 (Mar. 2003).
National Semiconductors Temperature Sensor Handbook—http://www.national.com/appinfo/tempsensors/files/temphb.pdf; accessed online: Apr. 1, 2011.
Chen et al., "Heat-induced changes in the mechanics of a collagenous tissue: pseudoelastic behavior at 37° C," Journal of Biomechanics, 31, pp. 211-216 (1998).
Kurt Gieck & Reiner Gieck, *Engineering Formulas* § Z.7 (7th ed. 1997).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Wright, et al., "Time-Temperature Equivalence of Heat-Induced Changes in Cells and Proteins," Feb. 1998. ASME Journal of Biomechanical Engineering, vol. 120, pp. 22-26.
Covidien Brochure, [Value Analysis Brief], LigaSure Advance™ Pistol Grip, dated Rev. Apr. 2010 (7 pages).
Covidien Brochure, LigaSure Impact™ Instrument LF4318, dated Feb. 2013 (3 pages).
Covidien Brochure, LigaSure Atlas™ Hand Switching Instruments, dated Dec. 2008 (2 pages).
Covidien Brochure, The LigaSure™ 5 mm Blunt Tip Sealer/Divider Family, dated Apr. 2013 (2 pages).
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Douglas, S.C. "Introduction to Adaptive Filter". Digital Signal Processing Handbook. Ed. Vijay K. Madisetti and Douglas B. Williams. Boca Raton: CRC Press LLC, 1999.
Leonard I. Malis, M.D., "The Value of Irrigation During Bipolar Coagulation," 1989.
Covidien Brochure, The LigaSure Precise™ Instrument, dated Mar. 2011 (2 pages).
Jang, J. et al. "Neuro-fuzzy and Soft Computing." Prentice Hall, 1997, pp. 13-89, 199-293, 335-393, 453-496, 535-549.
Erbe Electrosurgery VIO® 200 S, (2012), p. 7, 12 pages, accessed Mar. 31, 2014 at http://www.erbe-med.com/erbe/media/Marketingmaterialien/85140170 ERBE EN VIO 200 S D027541.
Hörmann et al., "Reversible and irreversible denaturation of collagen fibers." Biochemistry, 10, pp. 932-937 (1971).
Dean, D.A., "Electrical Impedance Spectroscopy Study of Biological Tissues," J. Electrostat, 66(3-4), Mar. 2008, pp. 165-177. Accessed Apr. 10, 2018: https://www.ncbi.nlm.nih.gov/pmc/articles/PMC2597841/.
Moraleda et al., A Temperature Sensor Based on a Polymer Optical Fiber Macro-Bend, Sensors 2013, 13, 13076-13089, doi: 10.3390/s131013076, ISSN 1424-8220.

\* cited by examiner

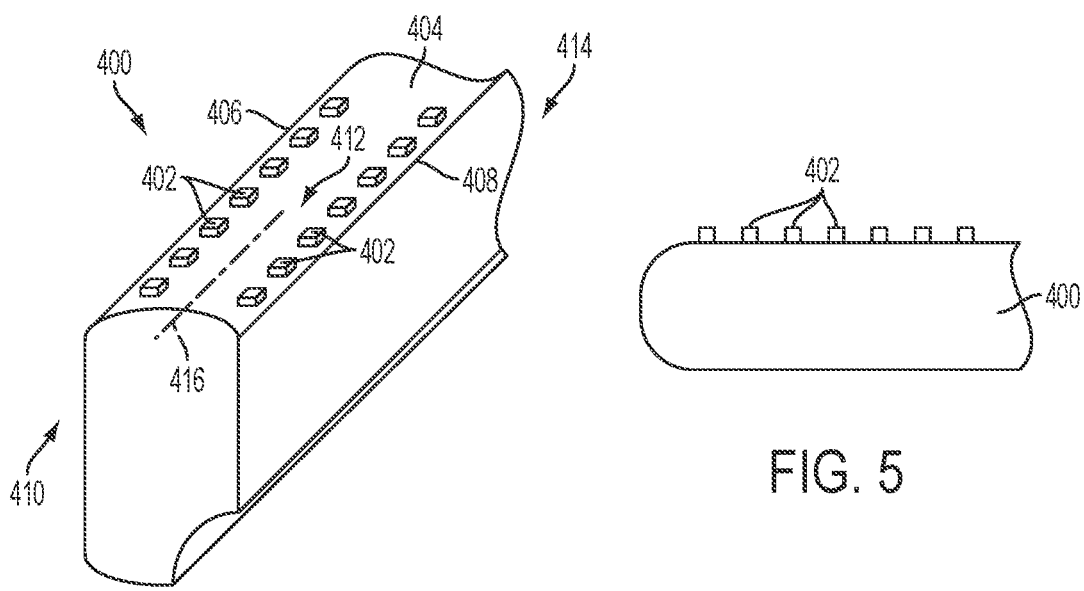
FIG. 4
FIG. 5
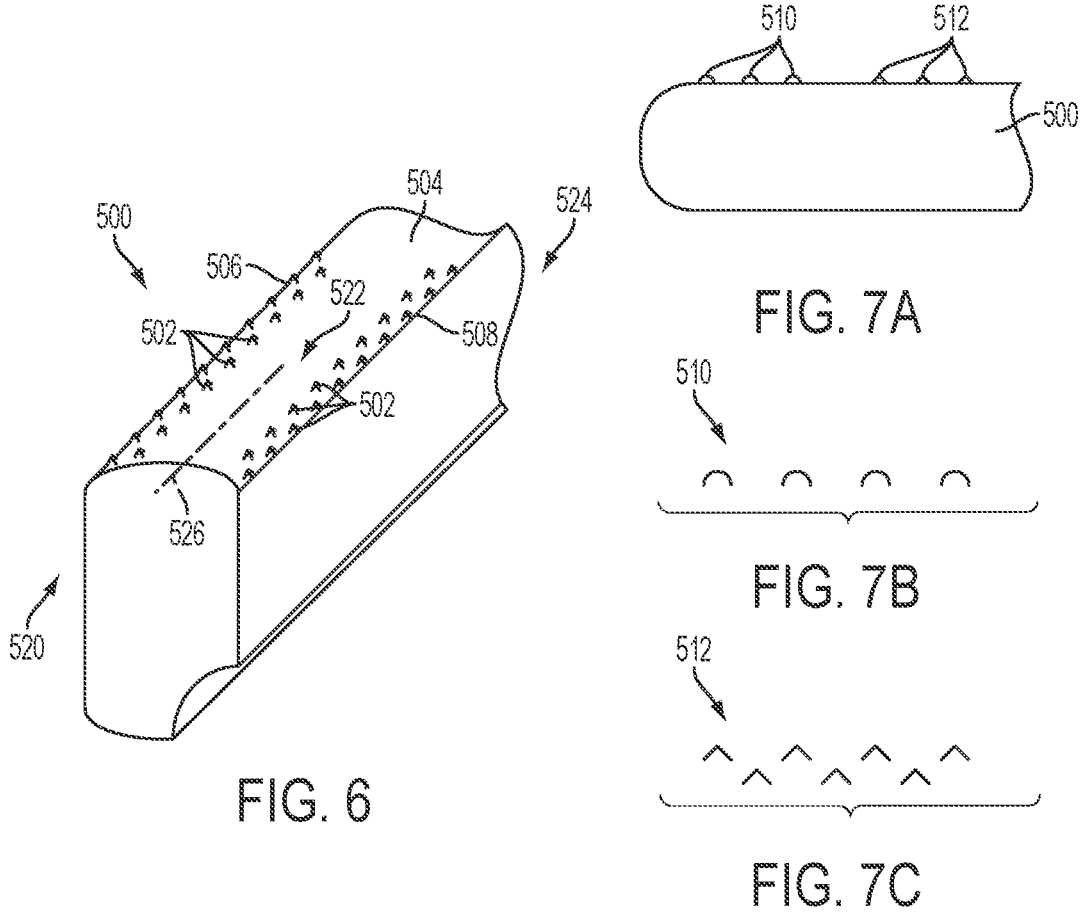
FIG. 6
FIG. 7A
FIG. 7B
FIG. 7C

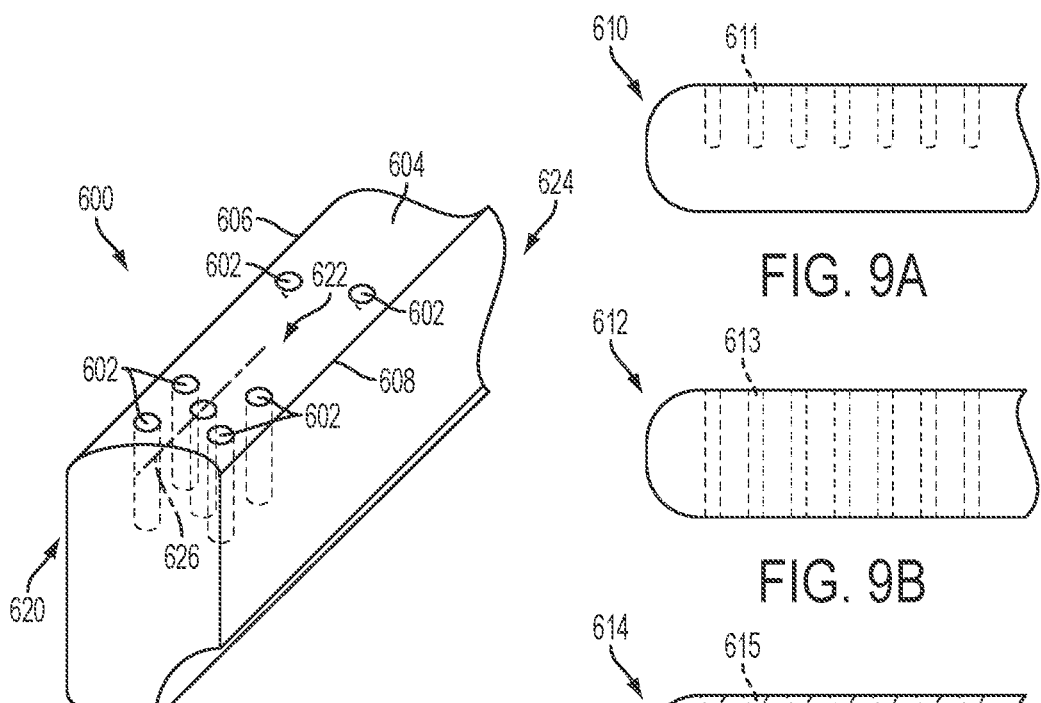
FIG. 8
FIG. 9A
FIG. 9B
FIG. 9C
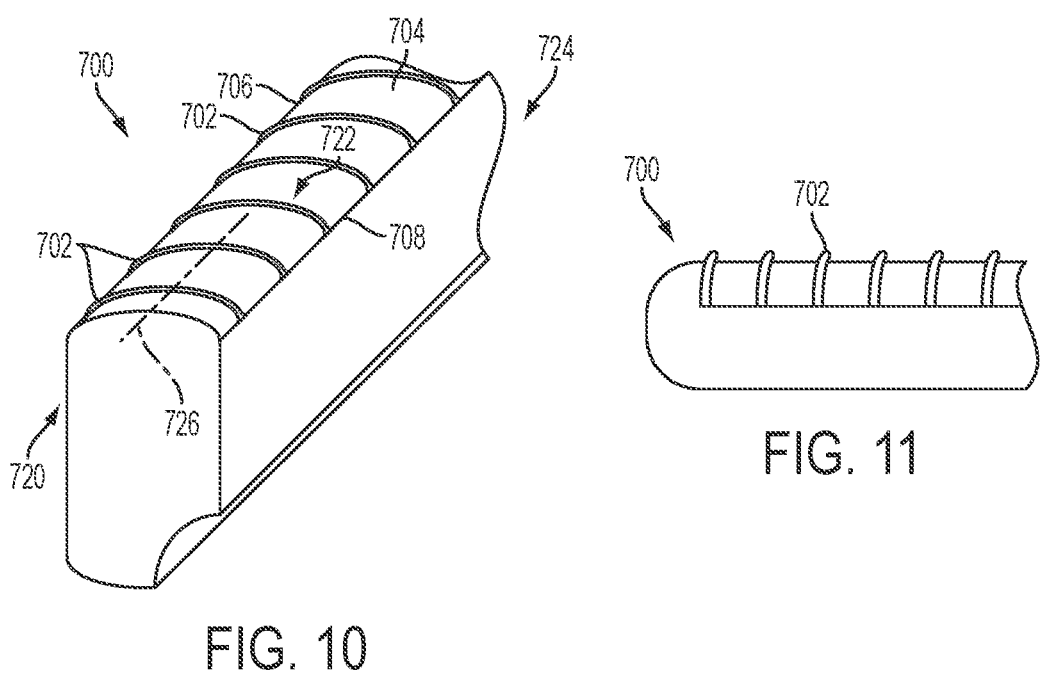
FIG. 10
FIG. 11

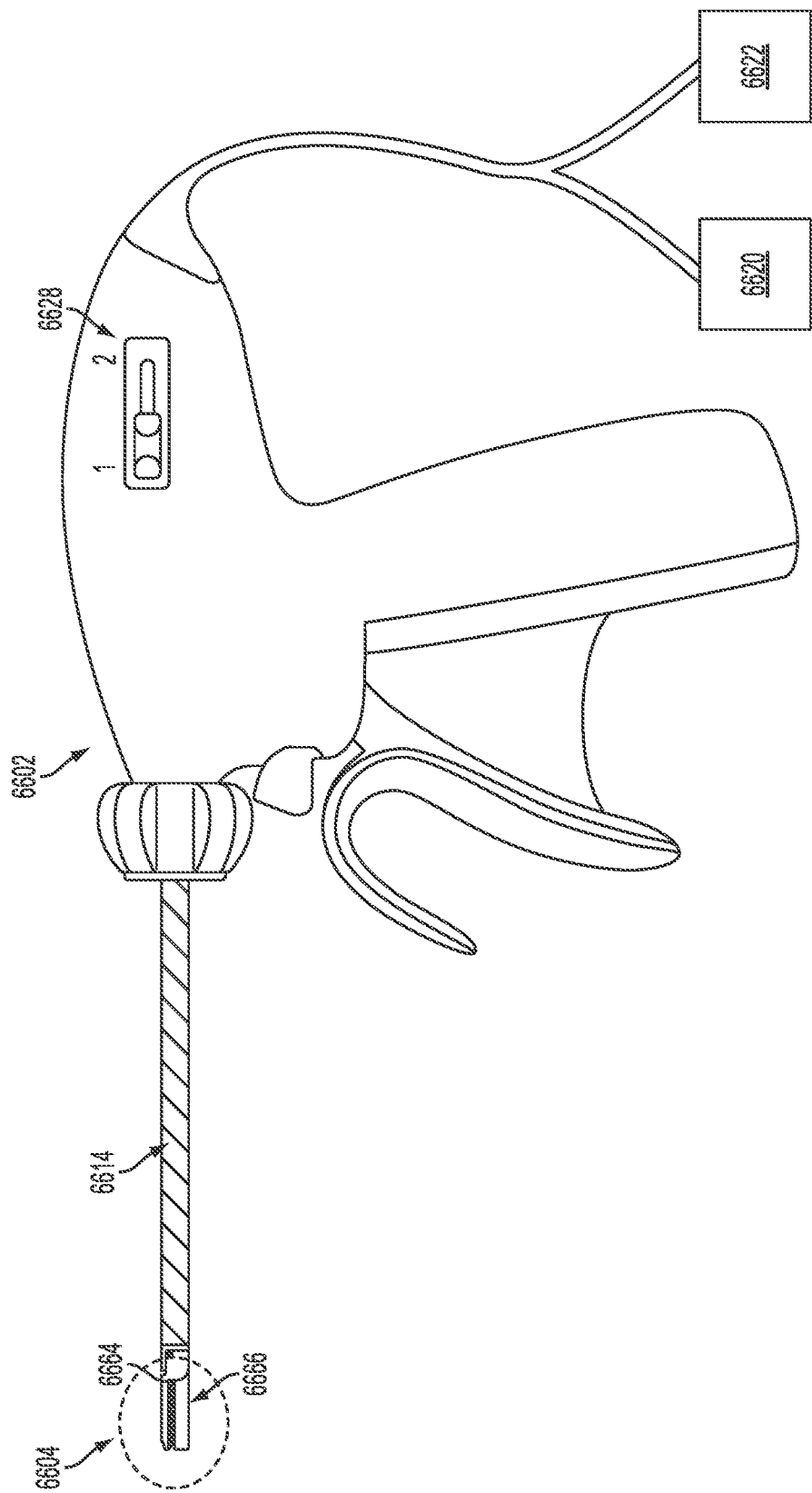

ULTRASONIC AND ELECTROSURGICAL DEVICES

CROSS-REFERENCE TO RELATED APPLICATIONS

This application is a divisional application claiming priority under 35 U.S.C. § 121 to U.S. patent application Ser. No. 13/843,295, entitled ULTRASONIC AND ELECTROSURGICAL DEVICES, filed Mar. 15, 2013, now U.S. Patent Application Publication No. US 2014/0135804, which claims the benefit of U.S. Provisional Patent Application Ser. No. 61/726,890, filed Nov. 15, 2012, entitled ULTRASONIC AND ELECTROSURGICAL DEVICES, the disclosures of which are hereby incorporated by reference in their entirety.

INTRODUCTION

The present disclosure is related generally to ultrasonic and electrical surgical devices. More particularly, the present disclosure is related to various blade features for ultrasonic blades to improve tissue grasping, various seals and fluid egress features to prevent build up and accumulation of tissue and other bodily materials encountered during surgery on the distal portion of the tube(s) and the nearby portion of the blade of ultrasonic surgical devices, clamp closure mechanisms for ultrasonic end effectors to provide uniform clamp force, rotation mechanisms for ultrasonic transducers and devices, and combined electrosurgical and ultrasonic devices to provide tissue cutting and spot coagulation.

Ultrasonic surgical devices, such as ultrasonic scalpels, are used in many applications in surgical procedures by virtue of their unique performance characteristics. Depending upon specific device configurations and operational parameters, ultrasonic surgical devices can provide substantially simultaneous transection of tissue and hemostasis by coagulation, desirably minimizing patient trauma. An ultrasonic surgical device comprises a proximally-positioned ultrasonic transducer and an instrument coupled to the ultrasonic transducer having a distally-mounted end effector comprising an ultrasonic blade to cut and seal tissue. The end effector is typically coupled either to a handle and/or a robotic surgical implement via a shaft. The blade is acoustically coupled to the transducer via a waveguide extending through the shaft. Ultrasonic surgical devices of this nature can be configured for open surgical use, laparoscopic, or endoscopic surgical procedures including robotic-assisted procedures.

Ultrasonic energy cuts and coagulates tissue using temperatures lower than those used in electrosurgical procedures. Vibrating at high frequencies (e.g., 55,500 times per second), the ultrasonic blade denatures protein in the tissue to form a sticky coagulum. Pressure exerted on tissue by the blade surface in combination with a clamping mechanism collapses blood vessels and allows the coagulum to form a hemostatic seal. A surgeon can control the cutting speed and coagulation by the force applied to the tissue by the end effector, the time over which the force is applied and the selected excursion level of the end effector.

Also used in many surgical applications are electrosurgical devices. Electrosurgical devices apply electrical energy to tissue in order to treat tissue. An electrosurgical device may comprise an instrument having a distally-mounted end effector comprising one or more electrodes. The end effector can be positioned against tissue such that electrical current is introduced into the tissue. Electrosurgical devices can be configured for bipolar or monopolar operation. During bipolar operation, current is introduced into and returned from the tissue by active and return electrodes, respectively, of the end effector. During monopolar operation, current is introduced into the tissue by an active electrode of the end effector and returned through a return electrode (e.g., a grounding pad) separately located on a patient's body. Heat generated by the current flow through the tissue may form haemostatic seals within the tissue and/or between tissues and thus may be particularly useful for sealing blood vessels, for example. The end effector of an electrosurgical device sometimes also comprises a cutting member that is movable relative to the tissue and the electrodes to transect the tissue.

Electrical energy applied by an electrosurgical device can be transmitted to the instrument by a generator. The electrical energy may be in the form of radio frequency ("RF") energy. RF energy is a form of electrical energy that may be in the frequency range of 300 kHz to 1 MHz. During its operation, an electrosurgical device can transmit low frequency RF energy through tissue, which causes ionic agitation, or friction, in effect resistive heating, thereby increasing the temperature of the tissue. Because a sharp boundary may be created between the affected tissue and the surrounding tissue, surgeons can operate with a high level of precision and control, without sacrificing adjacent tissues or critical structures. The low operating temperatures of RF energy may be useful for removing, shrinking, or sculpting soft tissue while simultaneously sealing blood vessels. RF energy may work particularly well on connective tissue, which is primarily comprised of collagen and shrinks when contacted by heat.

SUMMARY

In one embodiment, an ultrasonic surgical instrument comprises a waveguide comprising a proximal end and a distal end, wherein the proximal end is coupled to an ultrasonic transducer; an end effector coupled to the distal end of the waveguide; a tube comprising a lumen, wherein the waveguide is located within the lumen; a clamp arm pivotably connected to the tube; and a tissue accumulation impedance mechanism configured to prevent tissue from accumulating in the lumen.

In another embodiment of the ultrasonic surgical instrument, the tissue accumulation impedance mechanism comprises a boot barrier configured to create a seal between the tube and the end effector.

In another embodiment of the ultrasonic surgical instrument, the boot barrier is sealed to the tube using one or more retention features.

In another embodiment of the ultrasonic surgical instrument, the boot barrier comprises a cavity.

In another embodiment of the ultrasonic surgical instrument, the cavity is rounded to allow fluid to flow out of the cavity.

In another embodiment of the ultrasonic surgical instrument, the boot barrier comprises a plurality of contact points with the blade.

In another embodiment of the ultrasonic surgical instrument, the tissue accumulation impedance mechanism comprises one or more apertures in the tube.

In another embodiment of the ultrasonic surgical instrument, the apertures comprise one or more windows.

In another embodiment of the ultrasonic surgical instrument the apertures comprise one or more holes.

In another embodiment of the ultrasonic surgical instrument, the distal portion comprises a hemispherical cross section.

In another embodiment of the ultrasonic surgical instrument, the tube comprises one or more ribs formed on an inner side of the tube.

In another embodiment of the ultrasonic surgical instrument, the tissue accumulation impedance mechanism comprises a pump configured to provide a positive pressure flow between the blade and the tube, wherein the positive pressure flow prevents tissue ingress into the lumen.

In another embodiment of the ultrasonic surgical instrument, the pump or the outlet of the pump is located distally to a distal-most overmolded seal located within the lumen.

In another embodiment of the ultrasonic surgical instrument the tissue accumulation impedance mechanism comprises a slidable tube disposed within the lumen, the slidable tube slidable from a first position to a second position, wherein in the first position the slidable tube is disposed over the blade, and the second position the blade is exposed.

In one embodiment, an ultrasonic surgical instrument comprises a waveguide comprising a proximal end and a distal end, wherein the proximal end is coupled to an ultrasonic transducer; an end effector coupled to the distal end of the waveguide, the end effector comprising at least one tissue retention feature; a clamp arm operatively coupled to the end effector.

In another embodiment of the ultrasonic surgical instrument, the at least one tissue retention feature comprises one or more indentations/grooves/notches/texture formed in the end effector.

In another embodiment of the ultrasonic surgical instrument, the one or more indentations comprise triangular teeth.

In another embodiment of the ultrasonic surgical instrument, the one or more indentations comprise holes.

In another embodiment of the ultrasonic surgical instrument, the one or more indentations comprise horizontal trenches.

In another embodiment of the ultrasonic surgical instrument, the at least on tissue retention feature comprises one or more projections from the end effector.

In another embodiment of the ultrasonic surgical instrument, the one or more projections comprise triangular teeth.

In another embodiment of the ultrasonic surgical instrument, the one or more projections comprise blocks.

In another embodiment of the ultrasonic surgical instrument, the one or more projections comprise horizontal bumps.

In another embodiment of the ultrasonic surgical instrument, the one or more projections comprise circular bumps.

In another embodiment of the ultrasonic surgical instrument, the at least one tissue retention feature is disposed over an entire length of the blade.

In another embodiment of the ultrasonic surgical instrument, the at least one tissue retention feature is disposed over a discrete section of the blade.

In one embodiment, an ultrasonic surgical instrument comprises a waveguide comprising a proximal end and a distal end, wherein the proximal end is coupled to an ultrasonic transducer; an end effector operatively coupled to the distal end of the waveguide guide; a rotation shroud configured to rotate the waveguide; and a rotation stop mechanism coupled to the rotation shroud prevent rotation of the rotation knob beyond a predetermined rotation.

In another embodiment of the ultrasonic surgical instrument, the shroud comprises at least one channel; at least one boss, the at least one boss located within the at least one channel, wherein the at least one boss has a predetermined lateral movement limit, wherein when the at least one boss reaches the predetermined lateral movement limit, the at least one boss prevents further rotation of the rotation knob.

In another embodiment of the ultrasonic surgical instrument, the rotation stop comprises a gate comprising a first wing and a second wing, wherein the first and second wings are disposed at an angle, wherein the gate is disposed within the shroud and the gate allows a predetermined angle of rotation of the shroud.

In one embodiment, an ultrasonic surgical instrument comprises a waveguide comprising a proximal end and a distal end, wherein the proximal end is coupled to an ultrasonic transducer; an end effector coupled to the distal end of the waveguide; a clamp arm operatively coupled to the end effector; a tube disposed over the waveguide, wherein the tube comprises a counter deflection element, wherein the counter deflection element is configured to allow deflection of the blade, wherein the deflection of the blade counteracts a force placed on the blade by the clamp arm in a clamped position.

In one embodiment, a surgical instrument comprises a waveguide comprising a proximal end and a distal end, wherein the proximal end is coupled to a signal source, the signal source configured to provide an ultrasonic signal and an electrosurgical signal; an end effector coupled to the waveguide; a clamp arm operatively coupled to the end effector; and a sealing button, wherein the sealing button causes the surgical instrument to deliver the electrosurgical signal to the end effector and/or the clamp arm for a first period and the sealing button causes the surgical instrument to deliver the ultrasonic signal to the blade for a second period, wherein the second period is subsequent to the first period.

In another embodiment of the surgical instrument, the sealing button causes the surgical instrument to deliver the ultrasonic signal to the end effector prior to transmitting the electrosurgical signal to the end effector and/or clamp arm.

In another embodiment of the surgical instrument, the sealing button causes the surgical instrument to only deliver the ultrasonic signal to the end effector resulting in haemostatic transection of tissue. A separate spot coagulation button is provided on the handle. When the spot coagulation button is depressed, an electrosurgical signal is provided to either the end effector or the clamp arm or both to effect spot coagulation of tissue.

In another embodiment of the surgical instrument, wherein the electrosurgical signal is a monopolar RF signal.

In another embodiment of the surgical instrument, wherein the electrosurgical signal is a bipolar RF signal.

In one embodiment, a surgical instrument comprises a waveguide comprising a proximal end and a distal end, wherein the proximal end is coupled to an ultrasonic transducer; an end effector coupled to the distal end of the waveguide; a tube disposed over the waveguide; a cam surface formed on or in an outer surface of the tube; and a clamp arm, wherein the clamp arm is operatively coupled to the cam surface.

In another embodiment of the surgical instrument, a pivot pin is located within a hole defined by the end effector, the pivot pin operatively coupled to the clamp arm, wherein the clamp arm pivots about the pivot pin.

In another embodiment of the surgical instrument, the pivot pin is located at the distal most node of the waveguide.

In another embodiment of the surgical instrument, the tube is actuatable and the clamp arm is cammed open and closed against the end effector through relative motion between the tube and the end effector.

In one embodiment, a surgical instrument comprises a waveguide comprising a proximal end and a distal end, wherein the proximal end is coupled to an ultrasonic transducer; an end effector coupled to the distal end of the waveguide, the end effector defining a pin hole; a rigid pin disposed within the pin hole; a clamp arm operatively connected to the outer tube; and a four-bar linkage; wherein the four-bar linkage is operatively coupled to the clamp arm and the rigid pin, wherein the four-bar linkage is actuatable via end effector translation to move the clamp arm to a clamped position.

In another embodiment of the surgical instrument, an outer tube is coupled to the four-bar linkage and the outer-tube actuates the four-bar linkage from a first position to a second position.

In one embodiment, an ultrasonic surgical instrument comprises a waveguide comprising a proximal end and a distal end, wherein the proximal end is coupled to an ultrasonic transducer; an end effector coupled to the distal end of the waveguide, wherein the end effector is partially coated with thermally and electrically insulative material such that the distal end of the end effector comprises one or more exposed sections.

In another embodiment of the ultrasonic surgical instrument end effector, the one or more exposed areas are symmetrical.

In another embodiment of the ultrasonic surgical instrument end effector, the one or more exposed areas are asymmetrical.

In another embodiment of the ultrasonic surgical instrument end effector, the one or more exposed sections are separated by one or more coated sections.

In one embodiment, an ultrasonic surgical instrument comprises a waveguide comprising a proximal end and a distal end, wherein the proximal end is coupled to an ultrasonic transducer; an end effector coupled to the distal end of the waveguide, and a clamp arm is operatively connected to the end effector, wherein the clamp arm is partially coated with thermally and electrically insulative material such that the distal end of the clamp arm comprises one or more exposed sections.

In another embodiment of the ultrasonic surgical instrument clamp arm, the one or more exposed areas are symmetrical.

In another embodiment of the ultrasonic surgical instrument clamp arm, the one or more exposed areas are asymmetrical.

In another embodiment of the ultrasonic surgical instrument clamp arm, the one or more exposed sections are separated by one or more coated sections.

In one embodiment, an ultrasonic surgical instrument comprises a waveguide comprising a proximal end and a distal end, wherein the proximal end is coupled to an ultrasonic transducer; an end effector coupled to the distal end of the waveguide, and a clamp arm is operatively connected to the end effector, wherein the end effector and the clamp arm are partially coated with thermally and electrically insulative material such that the distal end of the end effector and clamp arm comprise one or more exposed sections.

In another embodiment of the ultrasonic surgical instrument, the one or more exposed areas are symmetrical.

In another embodiment of the ultrasonic surgical instrument, the one or more exposed areas are asymmetrical.

In another embodiment of the ultrasonic surgical instrument, the one or more exposed sections are separated by one or more coated sections.

The foregoing is a summary and thus may contain simplifications, generalizations, inclusions, and/or omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

The foregoing summary is illustrative only and is not intended to be in any way limiting. In addition to the illustrative aspects, embodiments, and features described above, further aspects, embodiments, and features will become apparent by reference to the drawings and the following detailed description.

FIGURES

The novel features of the embodiments described herein are set forth with particularity in the appended claims. The embodiments, however, both as to organization and methods of operation may be better understood by reference to the following description, taken in conjunction with the accompanying drawings as follows.

FIG. 4 illustrates one embodiment of an ultrasonic blade with protruding block-like grasping features formed on a grasping portion of the blade.

FIG. 5 is a side view of the ultrasonic blade shown in FIG. 4, according to one embodiment.

FIG. 6 illustrates one embodiment of an ultrasonic blade with protruding bump-like or spike-like grasping features formed on a grasping portion of the blade.

FIG. 7A is a side view of the ultrasonic blade shown in FIG. 6, according to one embodiment.

FIG. 7B shows bump-like protrusions, according to one embodiment.

FIG. 7C shows spike-like protrusions, according to one embodiment.

FIG. 8 illustrates one embodiment of an ultrasonic blade with cavity-like grasping features formed on a grasping portion of the blade.

FIG. 9A is a side view of the ultrasonic blade shown in FIG. 8 having cylindrical cavity-like grasping features partially formed into the grasping portion of the blade, according to one embodiment.

FIG. 9B is a side view of the ultrasonic blade shown in FIG. 8 having cylindrical cavity-like grasping features formed through the grasping portion of the blade, according to one embodiment.

FIG. 9C is a side view of the ultrasonic blade shown in FIG. 8 having conical cavity-like grasping features partially formed into the grasping portion of the blade, according to one embodiment.

FIG. 10 illustrates one embodiment of an ultrasonic blade with transverse bump-like grasping features formed on a grasping portion of the blade.

FIG. 11 is a side view of the ultrasonic blade shown in FIG. 10, according to one embodiment.

FIG. 74A illustrates the gate in a left-biased position such that the rotation knob can be rotated approximately 690 degrees clockwise until a contoured extrusion element on the rotation knob makes contact with the right wing of the gate so that the left wing of the gate prevents motion by reacting statically against the shroud, according to one embodiment.

FIG. 74B illustrates the rotation knob rotated back 360° until it knocks the right wing of the gate into a right-biased position, according to one embodiment.

FIG. 74C illustrates the rotation knob after it knocks the right wing of the gate into a right-biased position, according to one embodiment.

FIG. 76A illustrates the gate in a left-biased position such that the rotation knob comprising a tactile feedback element can be rotated approximately 690 degrees clockwise until a contoured extrusion element on the rotation knob makes contact with the right wing of the gate so that the left wing of the gate prevents motion by reacting statically against the shroud, according to one embodiment.

FIG. 76B illustrates the rotation knob comprising a tactile feedback element rotated back 360° until it knocks the right wing of the gate into a right-biased position, according to one embodiment.

FIG. 76C illustrates the rotation knob comprising a tactile feedback element after it knocks the right wing of the gate into a right-biased position, according to one embodiment.

FIGS. 84-93 illustrate various embodiments of ultrasonic blades partially coated with an electrically insulative material to provide thermal insulation at the tissue contact area to minimize adhesion of tissue to the blade, where the lighter shade regions of the blade represent the coated portions and the darker shaded regions of the blade represent exposed surfaces that enable RF current to flow from the exposed region of the blade, through the tissue, and the movable jaw member. It is conceivable that this feature may be employed on the blade, the clamp arm, or both.

Figure 94:
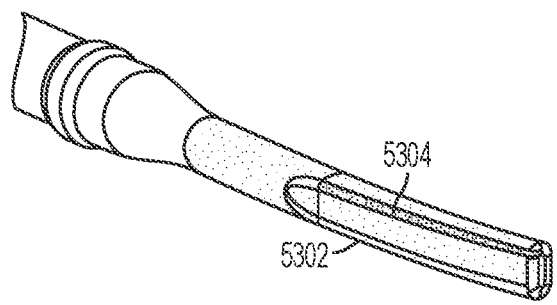
Figure 95:
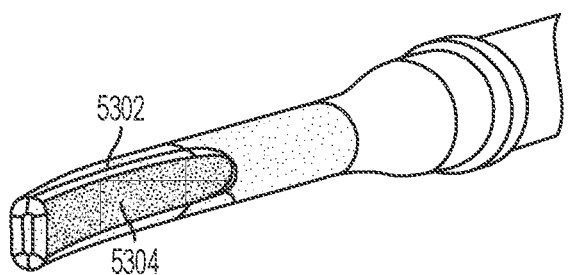

FIGS. 94-95 illustrate embodiments of two ultrasonic blades with non-symmetrical exposed surface, where the blades are coated with an electrically insulative material to provide thermal insulation at the tissue contact area to minimize adhesion of tissue to the blade, where the lighter shade regions of the blade represent the coated portions and the darker shaded regions of the blade represent exposed surfaces that enable RF current to flow from the exposed region of the blade, through the tissue, and the movable jaw member. It is conceivable that this feature may be employed on the blade, the clamp arm, or both.

Figure 96:
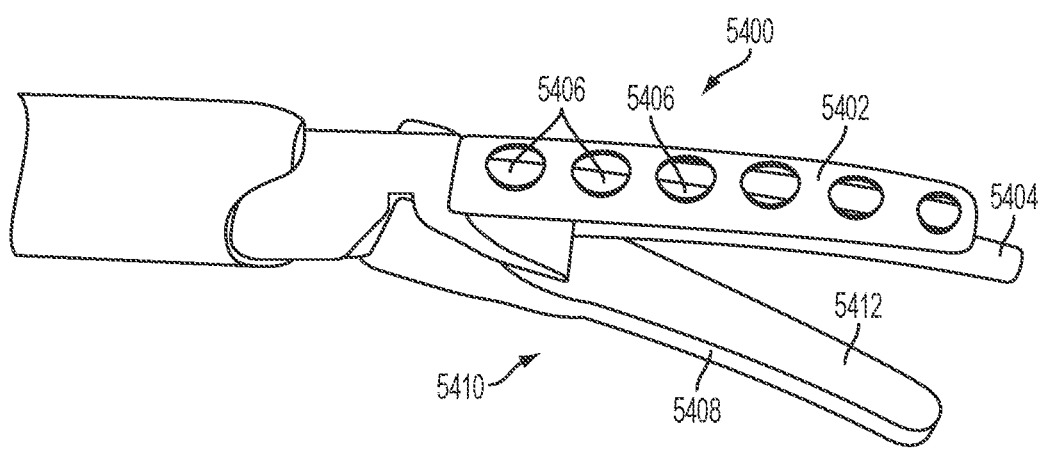

FIG. 96 is a perspective view of one embodiment of an ultrasonic end effector comprising a metal heat shield.

Figure 97:
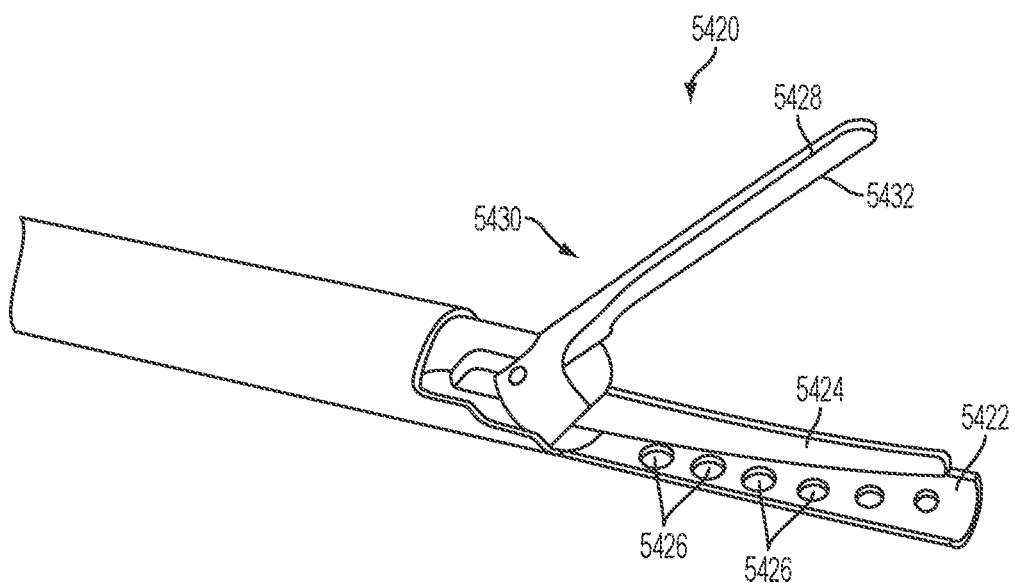

FIG. 97 is a perspective view of another embodiment of an ultrasonic end effector comprising a retractable metal heat shield.

Figure 98:
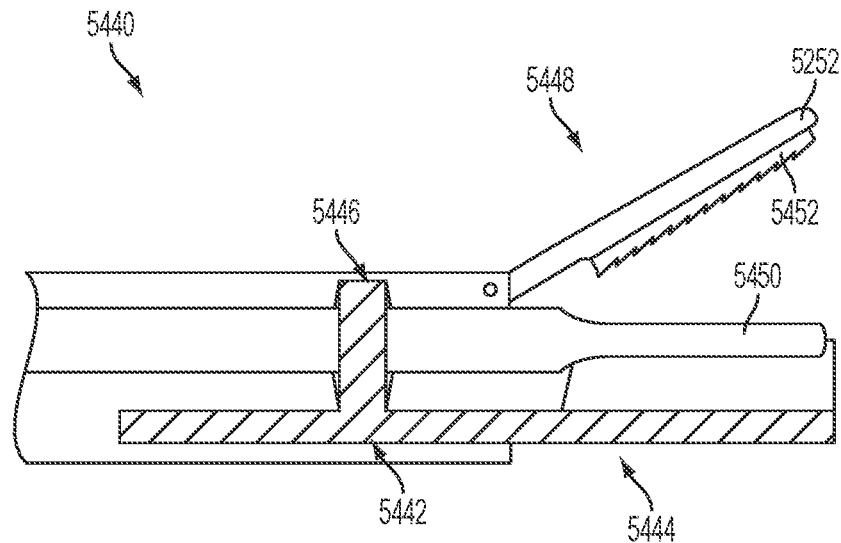

FIG. 98 is a side view of another embodiment of an ultrasonic end effector comprising a heat shield shown in cross-section.

Figure 99:
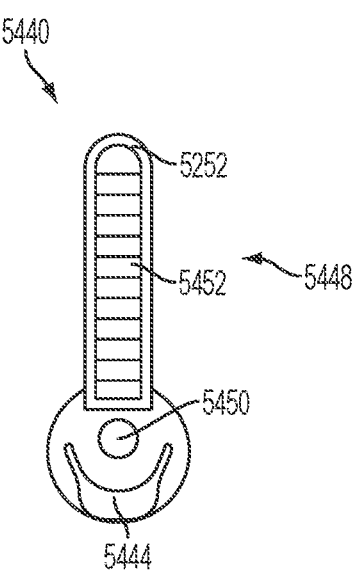

FIG. 99 is a front view of the ultrasonic end effector shown in FIG. 98, according to one embodiment.

Figure 100:
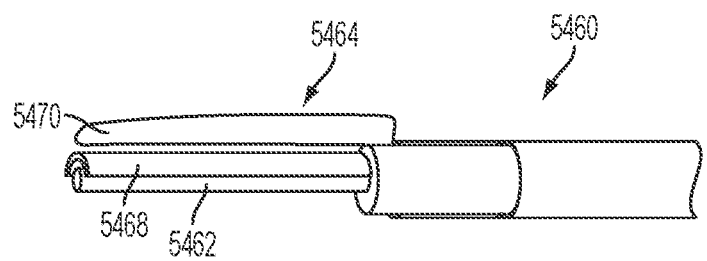

FIG. 100 illustrates one embodiment of a clamp arm comprising a movable jaw member shown in a closed position and a dual purpose rotatable heat shield located below the ultrasonic blade.

Figure 101:
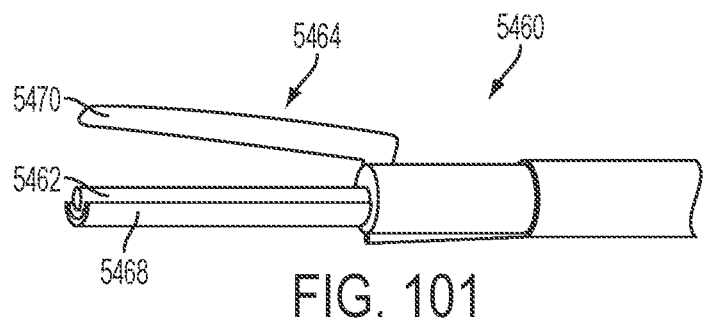

FIG. 101 illustrates one embodiment of a movable jaw member shown in an open position and a dual purpose rotatable heat shield rotated such that it is interposed between the movable jaw member and the blade.

Figure 102:
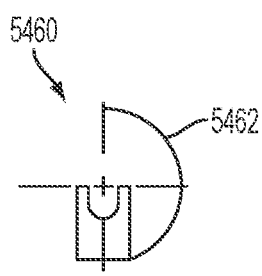

FIG. 102 illustrates an end view of one embodiment of a dual purpose rotatable heat shield rotated in a first position.

Figure 103:
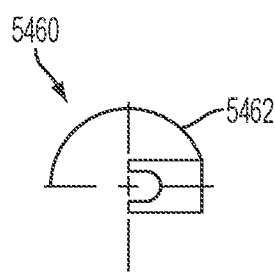

FIG. 103 illustrates an end view of one embodiment of the dual purpose rotatable heat shield rotated in a second position.

Figure 104:
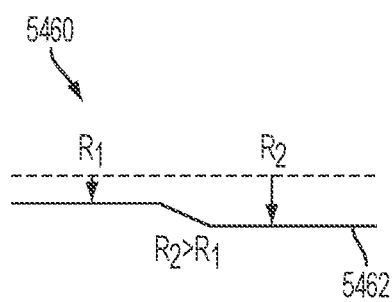

FIG. 104 is a top profile view of one embodiment of a heat shield showing a tapered portion of the shield.

Figure 105:
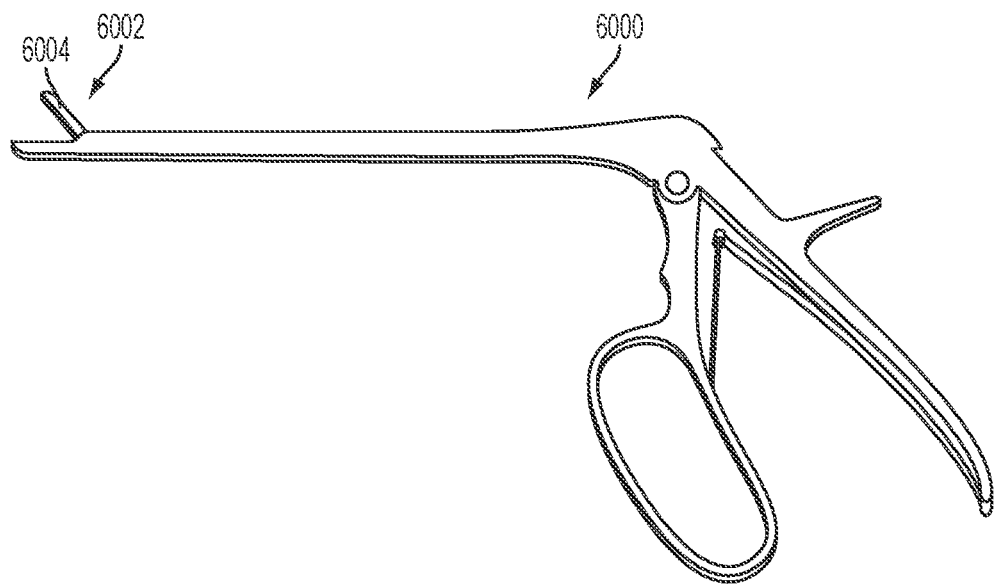

FIG. 105 illustrates a conventional rongeur surgical instrument.

Figure 106:
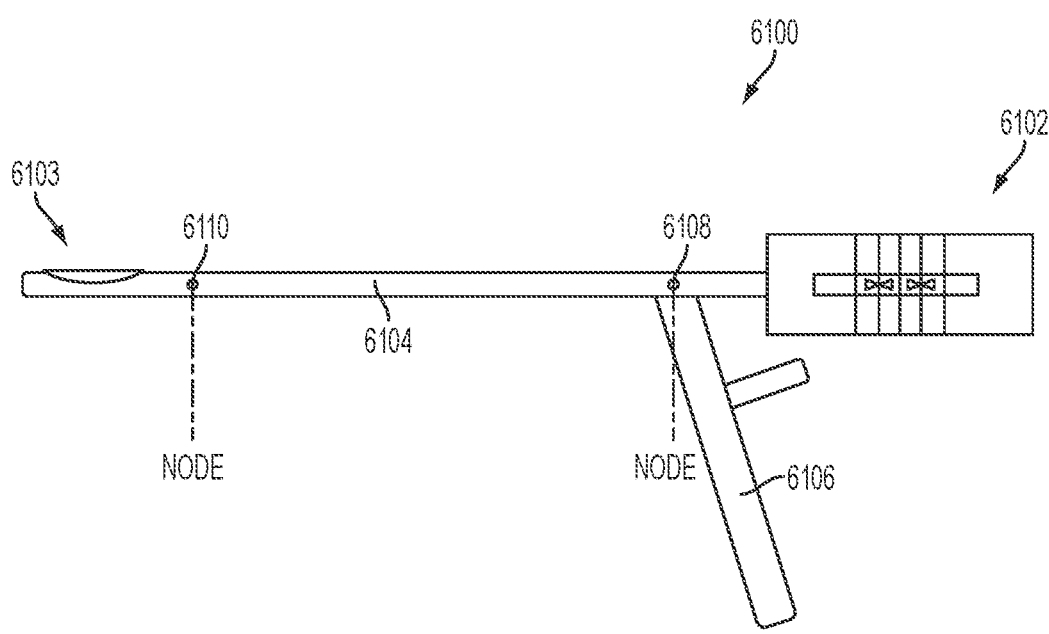

FIG. 106 illustrates one embodiment of an ultrasonic energy driven rongeur device.

Figure 107:
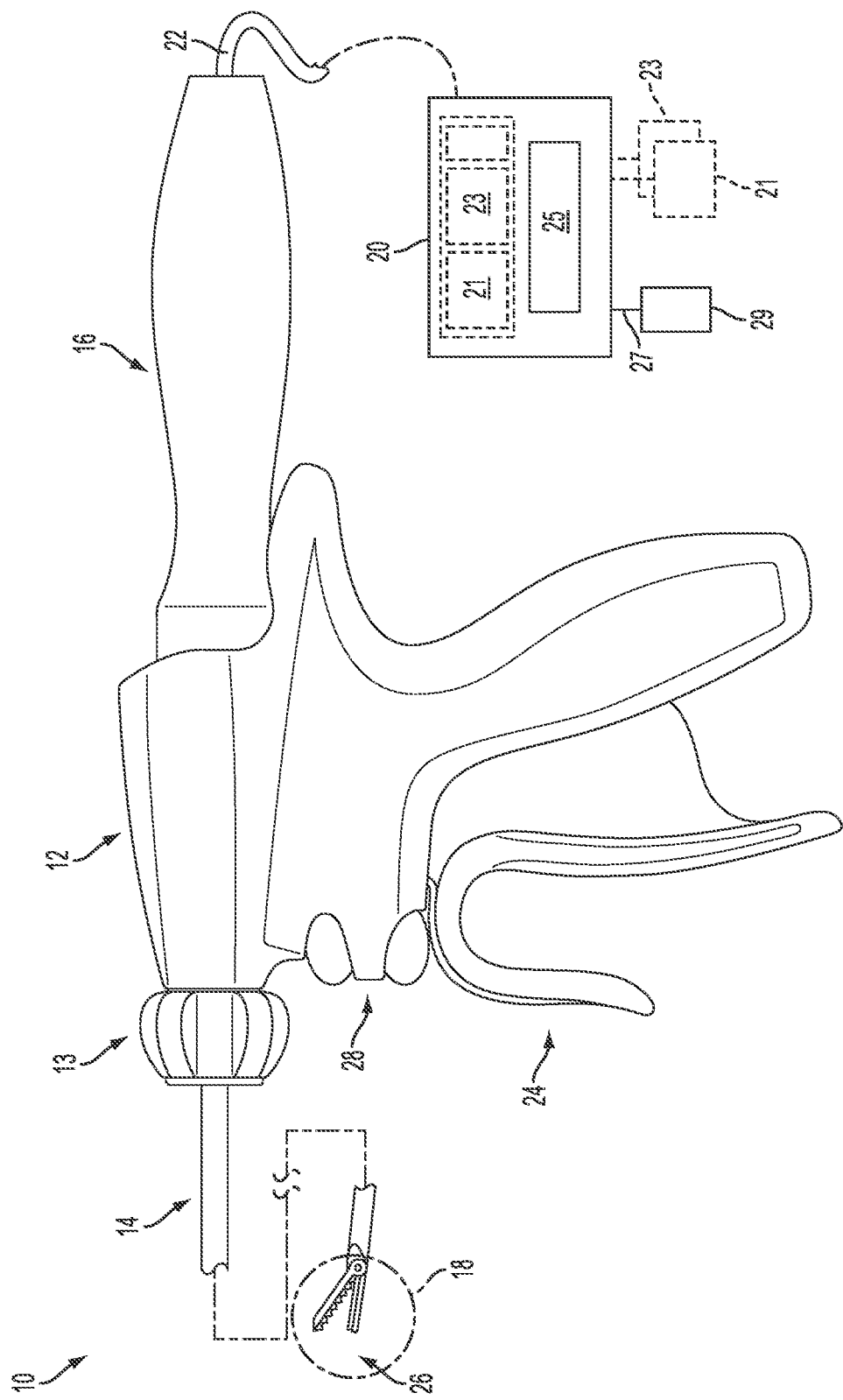

FIG. 107 illustrates one embodiment of a surgical system including a surgical instrument and an ultrasonic generator.

Figure 108:
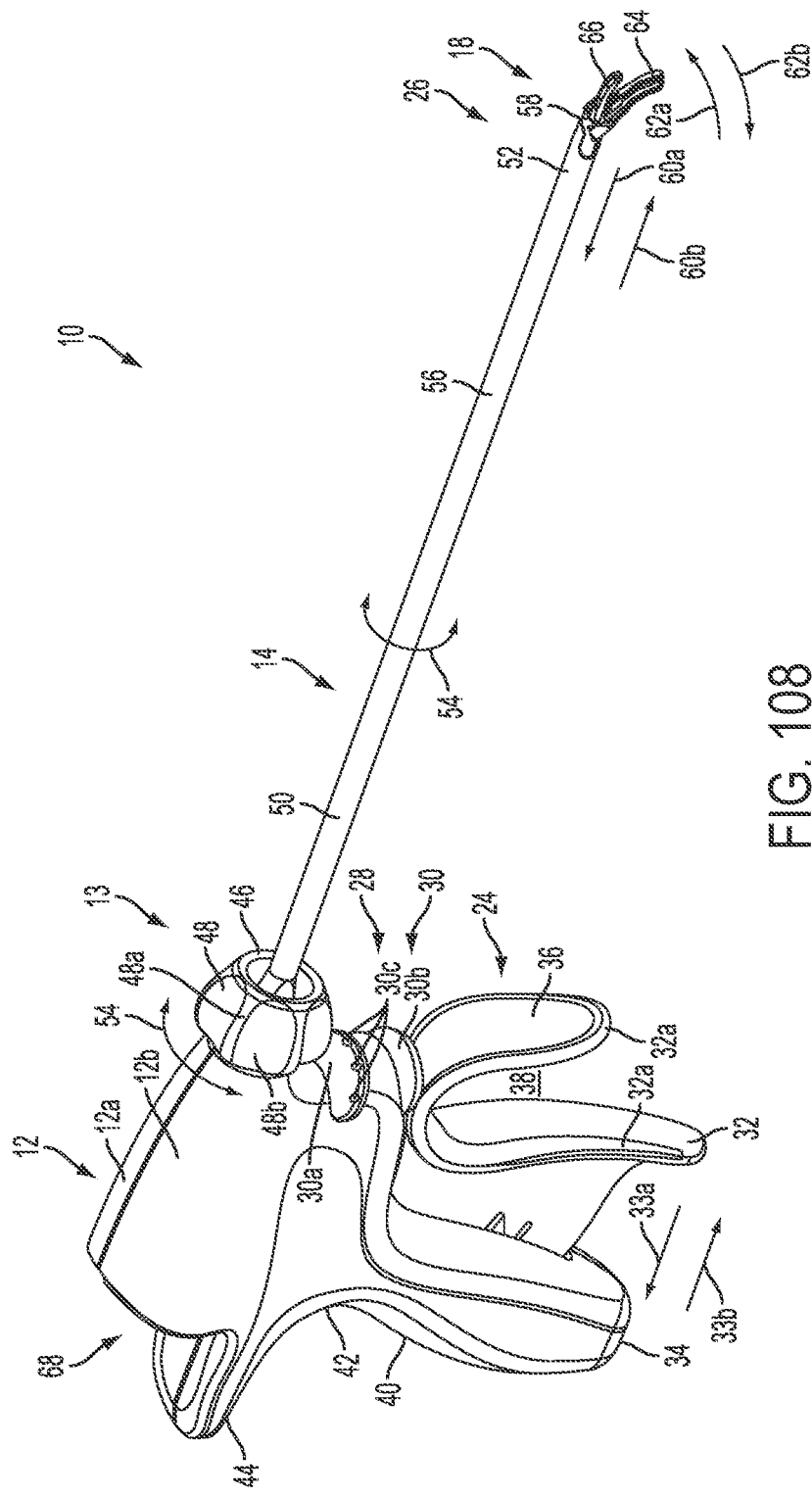

FIG. 108 illustrates one embodiment of the surgical instrument shown in FIG. 107.

Figure 109:
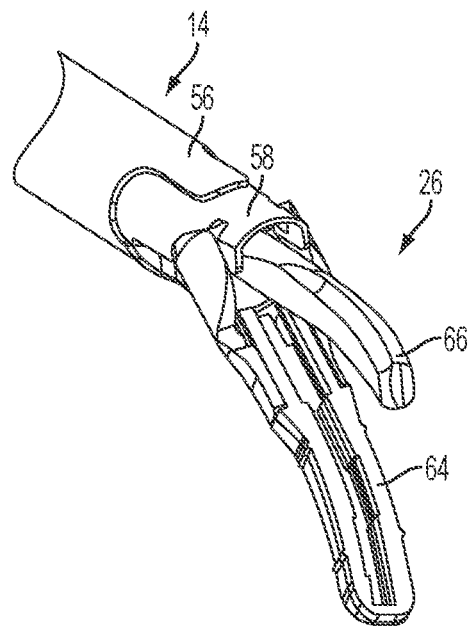

FIG. 109 illustrates one embodiment of an ultrasonic end effector.

Figure 110:
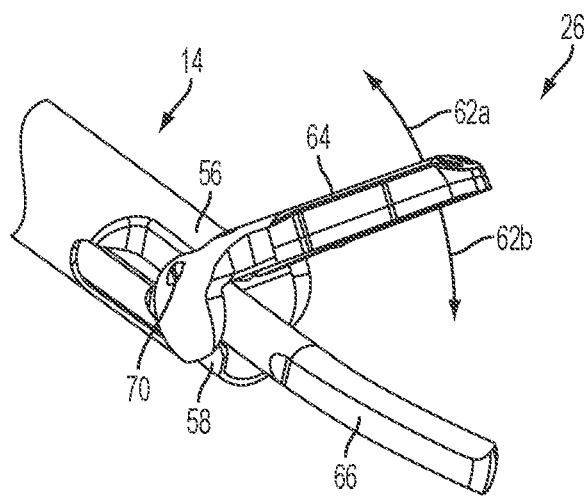

FIG. 110 illustrates another embodiment of an ultrasonic end effector.

Figure 111:
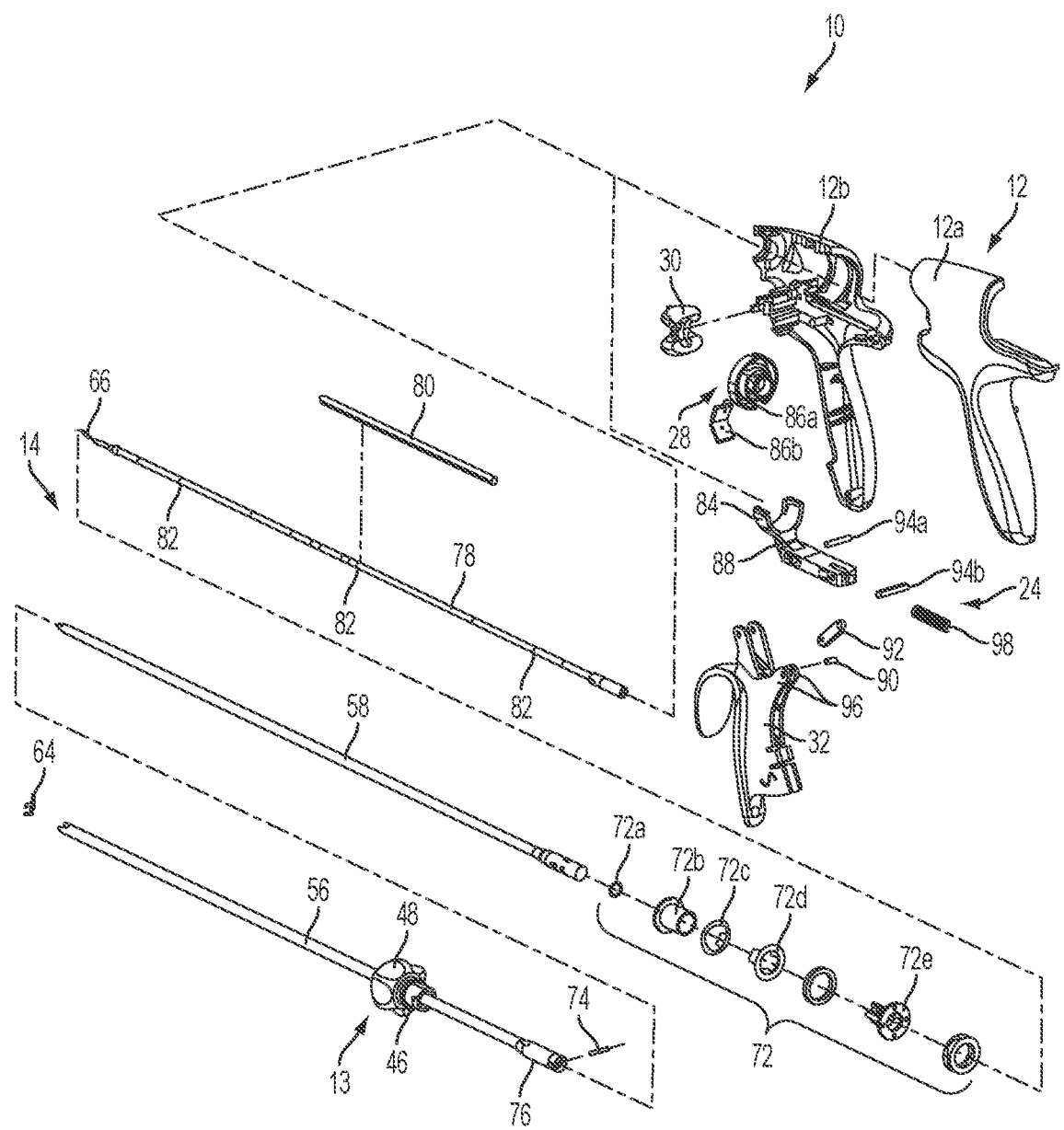

FIG. 111 illustrates an exploded view of one embodiment of the surgical instrument shown in FIG. 107.

Figure 112A:
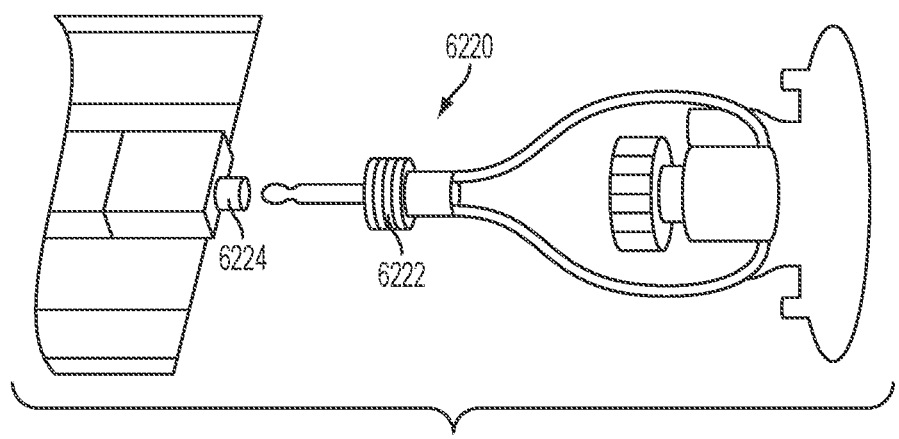
Figure 112B:
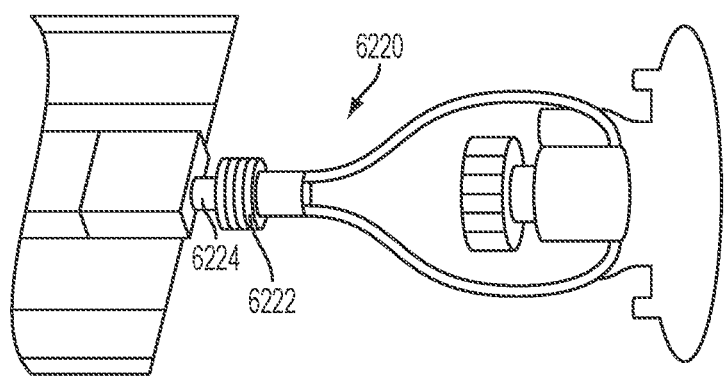
Figure 113A:
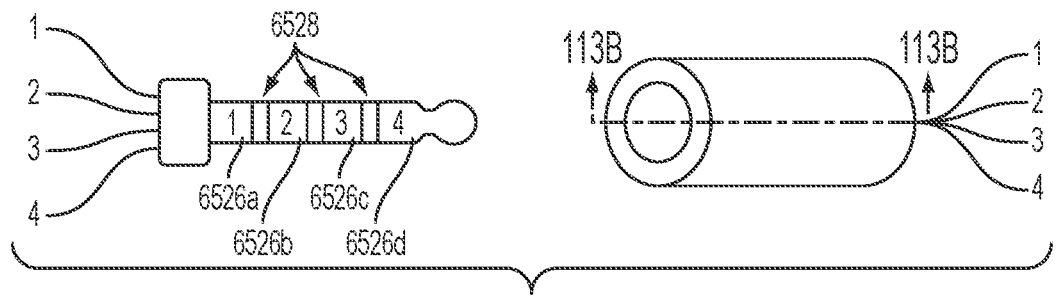
Figure 113B:
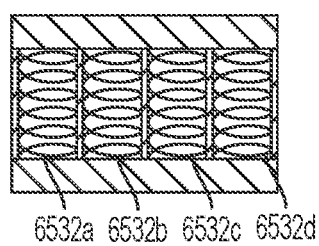
Figure 113C:
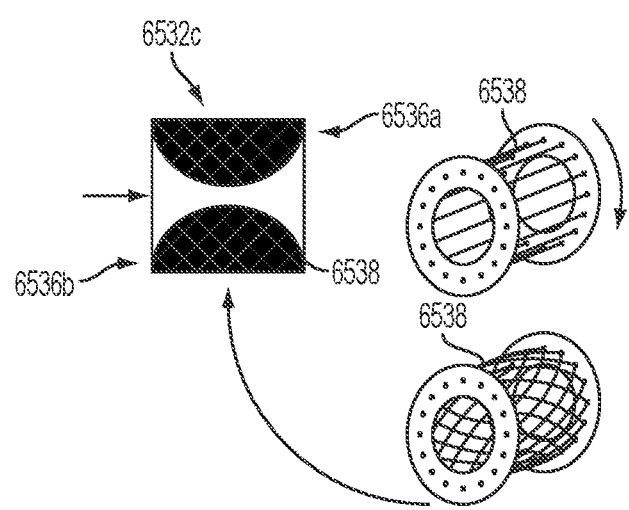

FIGS. 112A and 112B illustrate one embodiment of an unlimited rotation connection for an integrated transducer FIGS. 113A-113C illustrate one embodiment of an unlimited rotation connection for an integrated transducer.

Figure 114A:
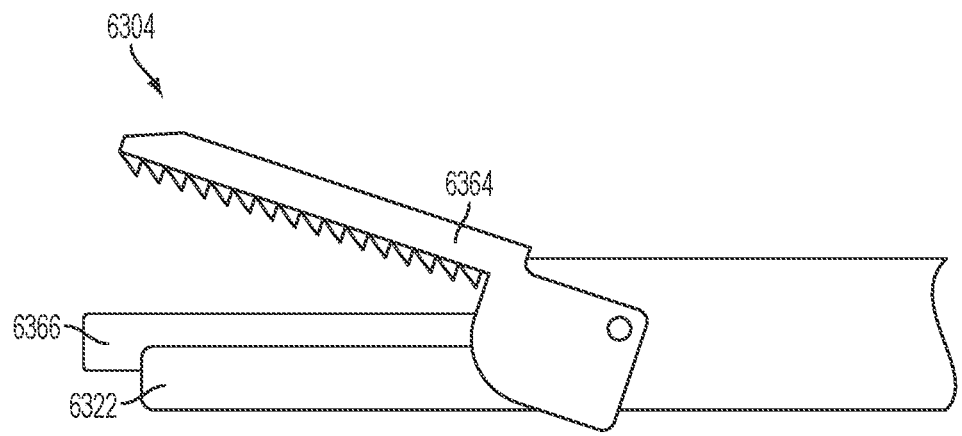
Figure 114B:
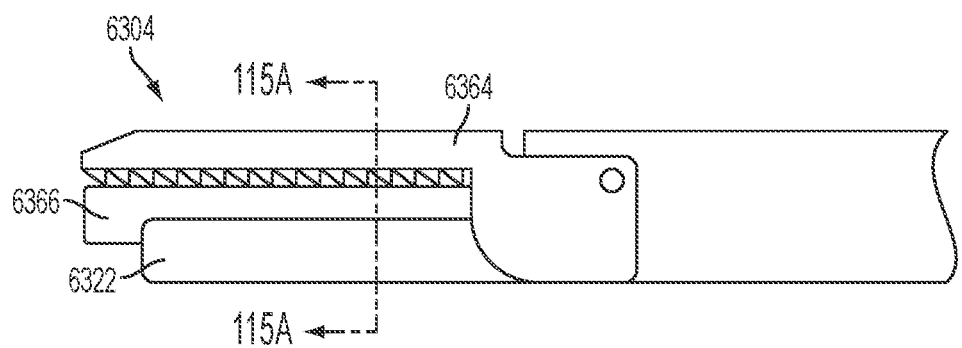

FIGS. 114A and 114B illustrate one embodiment of an integrated RF/ultrasonic surgical end effector.

FIGS. 115A-115I illustrate various electrode arrangements for the integrated RF/ultrasonic surgical end effector of FIGS. 114A and 114B.

Figure 116A:
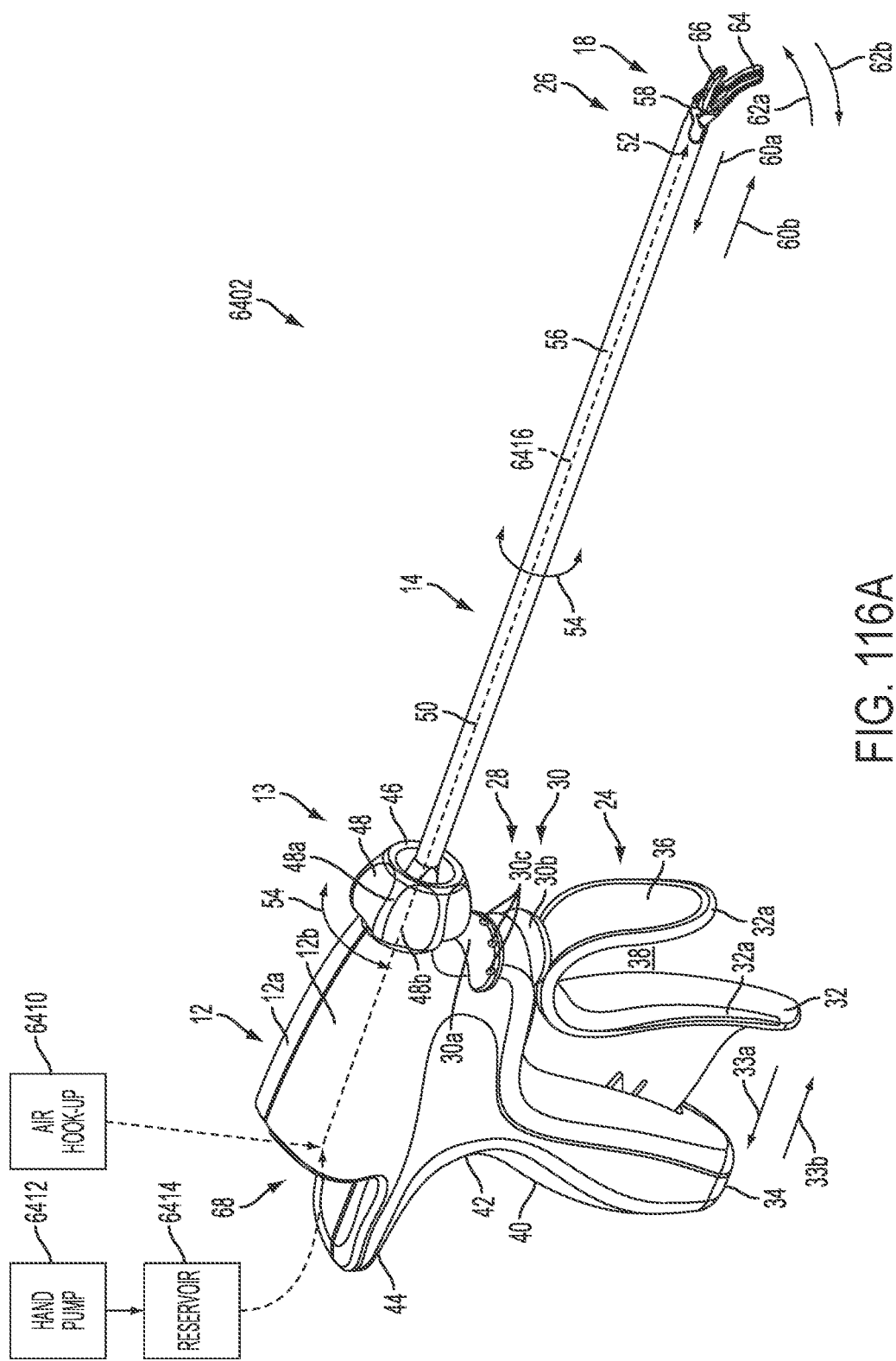

FIG. 116A illustrates one embodiment of an air cooled surgical instrument.

Figure 116B:
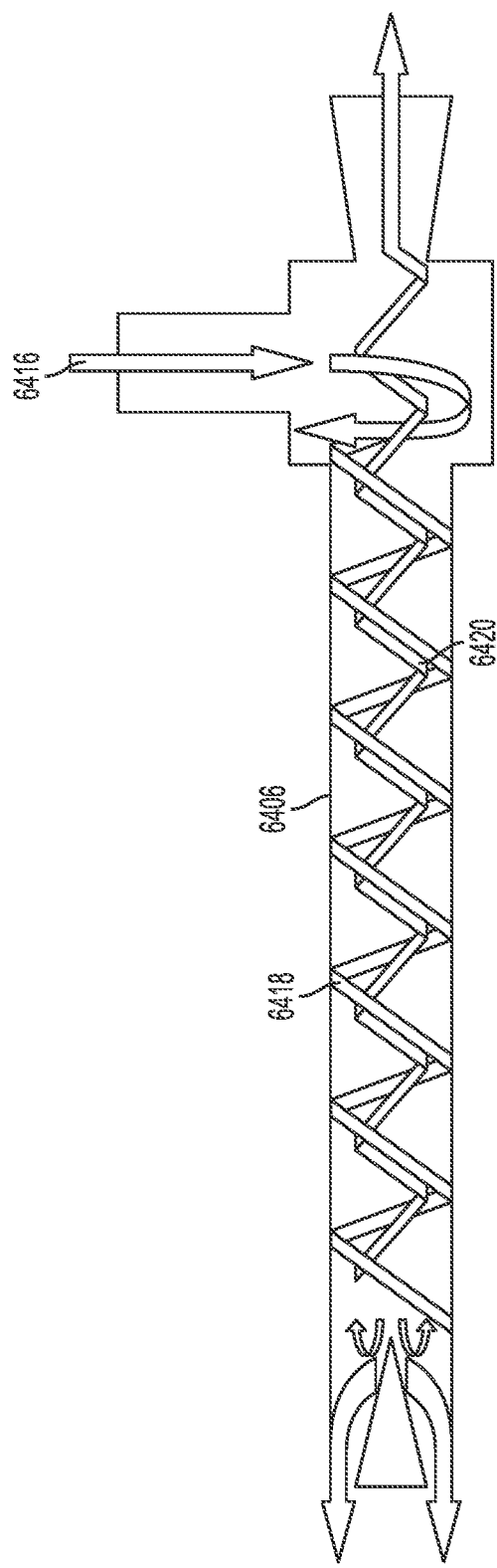

FIG. 116B illustrates one embodiment of a vortex tube.

FIG. 117 illustrates one embodiment of an integrated RF/ultrasonic surgical instrument comprising a double pole double throw switch.

Figure 118:
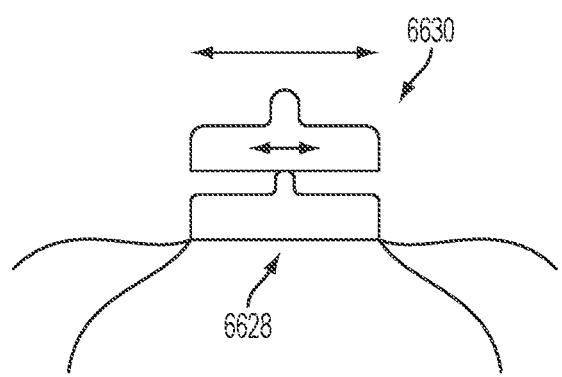
Figure 119A:
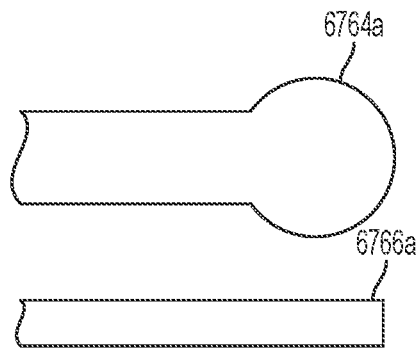
Figure 119B:
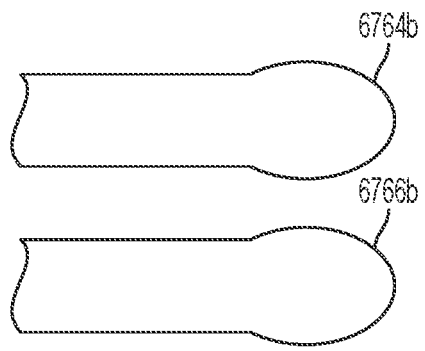
Figure 119C:
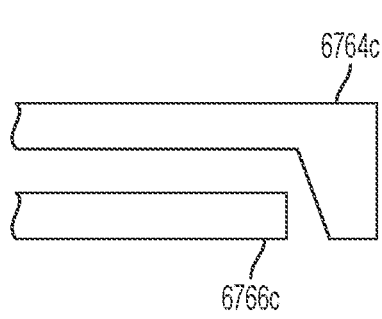
Figure 119D:
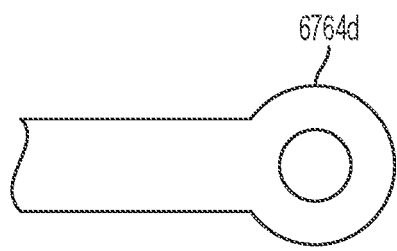
Figure 119E:
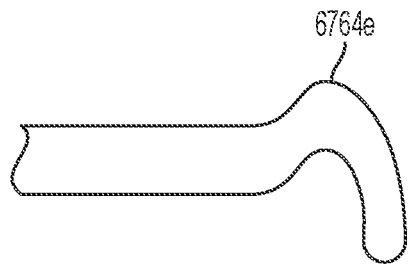

FIG. 118 illustrates one embodiment of a double pole double throw switch.

FIGS. 119A-119E illustrate various embodiments of combination RF/ultrasonic end effectors.

Figure 120A:
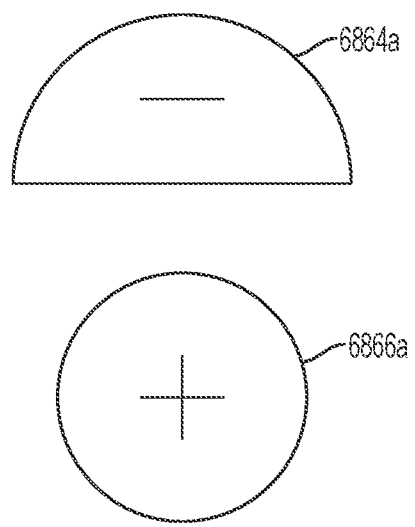
Figure 120B:
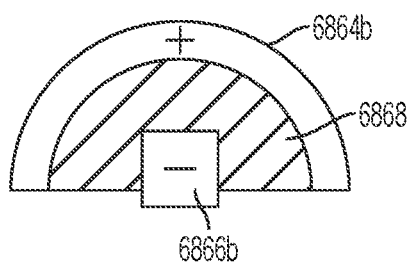
Figure 120C:
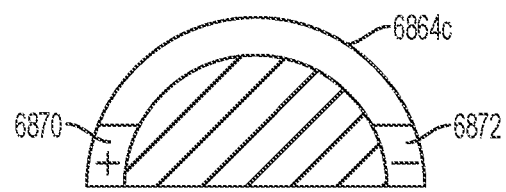

FIGS. 120A-120C illustrate various embodiments of bipolar combination RF/ultrasonic end effectors.

Figure 121A:
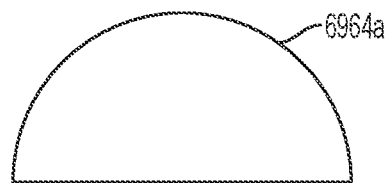
Figure 121B:
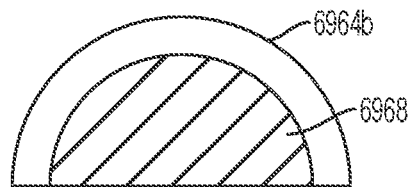
Figure 121C:
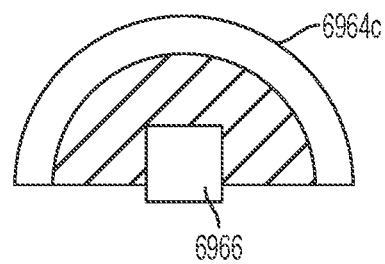

FIGS. 121A-121C illustrate various embodiments of monopolar combination RF/ultrasonic end effectors.

DESCRIPTION

Before explaining the various embodiments of the ultrasonic and electrical surgical devices in detail, it should be noted that the various embodiments disclosed herein are not limited in their application or use to the details of construction and arrangement of parts illustrated in the accompanying drawings and description. Rather, the disclosed embodiments are may be positioned or incorporated in other embodiments, variations and modifications thereof, and may be practiced or carried out in various ways. Accordingly, embodiments of the ultrasonic and electrical surgical devices disclosed herein are illustrative in nature and are not meant to limit the scope or application thereof. Furthermore, unless otherwise indicated, the terms and expressions employed herein have been chosen for the purpose of describing the embodiments for the convenience of the reader and are not to limit the scope thereof. In addition, it should be understood that any one or more of the disclosed embodiments, expressions of embodiments, and/or examples thereof, can be combined with any one or more of the other disclosed embodiments, expressions of embodiments, and/or examples thereof, without limitation.

In the following description, like reference characters designate like or corresponding parts throughout the several views. Also, in the following description, it is to be understood that terms such as front, back, inside, outside, top, bottom and the like are words of convenience and are not to be construed as limiting terms. Terminology used herein is not meant to be limiting insofar as devices described herein, or portions thereof, may be attached or utilized in other orientations. The various embodiments will be described in more detail with reference to the drawings.

In various embodiments, the present disclosure is related to various embodiments of ultrasonic blades comprising various grasping features. Conventional ultrasonic blades lack grasping features. Such grasping features may be desirable on a gripping surface of an ultrasonic blade to provide additional gripping and to prevent tissue milking during grasping and treatment, which in some cases may improve hemostasis. Tissue milking occurs when a tissue section slides, or milks, out of the jaws of a surgical device during treatment. The present disclosure provides various blade modification features to prevent tissue milking, as well as provide better grasping forces.

In various embodiments, the present disclosure is related to various embodiments of devices configured to prevent ingress of surgical matter, e.g., fluid and tissue, in the space between an ultrasonic blade and an inner or outer tube distal of the distal seal. Two main categories of embodiments are described. First, a pressure or energy source attached to the blade-tube subassembly prevents fluid or tissue ingress into the space between the blade and the inner tube. Second, a flexible membrane(s) attached to either the blade or the inner tube prevents fluid or tissue ingress.

In various embodiments, the present disclosure also is related to various embodiments of alternate closure mechanisms for ultrasonic devices. Present ultrasonic devices utilize a tube-in-tube (TnT) closure mechanism to enable closure of the clamp arm, referred to herein as a movable jaw member, against an active length of the ultrasonic blade. The present embodiments of alternate closure mechanisms for ultrasonic devices may yield several advantages. For example, there may be differences among the drag force of actuating the inner tube against the outer tube resulting in variation in device clamp force. Additionally, the pivot location of the clamp arm on the outer tube causes a sharp angular closure, and results in a non-uniform closure profile. Furthermore, present device mechanism may be sensitive to variation in components, as the stackup links the inner and outer tube at the location of the insulated pin, which currently resides near the proximal end of the tube assembly.

In various embodiments, the present disclosure also is related to various embodiments of shaft assembly/transducer rotation limiters to limit the rotation of the shaft and ultrasonic transducer.

In various embodiments, the present disclosure also is related to various embodiments of shaft/ultrasonic transducer rotation systems to provide unlimited continuous rotation of an ultrasonic device. In various embodiments, tactile feedback may be provided to the user before a hard stop is hit.

In various embodiments, the present disclosure also is related to various embodiments of an integrated RF/ultrasonic instrument electrically connected to provide RF spot coagulation energy for pre- or post-ultrasonic treatment of tissues with an ultrasonic/RF generator. The integrated ultrasonic instrument enables the touch up of diffuse bleeding (capillary bleeding, cut site oozing) or pre-treatment of tissue without the need for coupling pressure and improves the coupling pressure needed for ultrasonic instruments to couple the blade to tissue such that friction-based tissue effect is effective. The integrated ultrasonic instrument reduces (1) difficulty in applying enough pressure to generate haemostatic effect in loosely supported (i.e., un-clamped) tissue or (2) coupling pressure that generates too much tissue disruption that, in many cases, makes the diffuse bleeding worse. In one embodiment, a four-lead jack connector is mated with a slidable female mating plug to electrically isolate a secondary RF generator from the ultrasonic transducer when switching between RF energy and ultrasonic energy.

In various embodiments, the present disclosure is also directed to ultrasonic blades comprising heat shields. The heat shields may be fixed, translatable or rotatable. The heat shield also may be used to conduct RF energy to target tissue.

In various embodiments, the present disclosure also is related to coated ultrasonic/RF blades. Ultrasonic blades are coated with an electrically insulative material to provide thermal insulation at the tissue contact area to minimize adhesion of tissue to the blade. Conventional ultrasonic devices utilize one mode of treatment, which limits versatility. For example, conventional ultrasonic devices may be used for blood vessel sealing and transecting tissue. Bipolar or monopolar RF may offer added benefits such as a method for spot coagulation and pretreatment of tissue. Incorporating ultrasonic and RF may provide versatility and increase effectiveness. However, conventional ultrasonic devices utilize coatings to provide reduced friction and thermal insulation at the distal end of the blade. These coatings are electrically insulative, and therefore limit current flow thus decreasing RF effectiveness. Additionally, current density may influence effectiveness. In order to incorporate both modes into one device, a masking or selective coating removal process may be required. Creating an exposed area on the surface of the blade may provide a suitable path for current flow. It is conceivable that the same principles may be applied to the clamping member as well.

General Surgical Instrument Overview

Before launching into a description of various embodiments, the present disclosures turns to the description of FIGS. 107-111, which describes various embodiments of a surgical system in which various embodiments of the ultrasonic and electrical surgical devices described in connection with FIGS. 1-106 may be practiced. Accordingly, FIG. 107 is a right side view of one embodiment of an ultrasonic surgical instrument 10. In the illustrated embodiment, the ultrasonic surgical instrument 10 may be employed in various surgical procedures including laparoscopic, endoscopic or traditional open surgical procedures. In one example embodiment, the ultrasonic surgical instrument 10 comprises a handle assembly 12, an elongated shaft assembly 14, and an ultrasonic transducer 16. The handle assembly 12 comprises a trigger assembly 24, a distal rotation assembly 13, and an activation switch assembly 28. The elongated shaft assembly 14 comprises an end effector assembly 26, which comprises elements to dissect tissue or mutually grasp, cut, and coagulate vessels and/or tissue, and actuating elements to actuate the end effector assembly 26. The handle assembly 12 is adapted to receive the ultrasonic transducer 16 at the proximal end. The ultrasonic transducer 16 is mechanically engaged to the elongated shaft assembly 14 and portions of the end effector assembly 26. The ultrasonic transducer 16 is electrically coupled to a generator 20 via a cable 22. Although the majority of the drawings depict a multiple end effector assembly 26 for use in connection with laparoscopic surgical procedures, the ultrasonic surgical instrument 10 may be employed in more traditional open surgical procedures and in other embodiments, may be configured for use in laparoscopic or endoscopic procedures. For the purposes herein, the ultrasonic surgical instrument 10 is described in terms of an laparoscopic instrument; however, it is contemplated that an open and/or endoscopic version of the ultrasonic surgical instrument 10 also may include the same or similar operating components and features as described herein.

In various embodiments, the generator 20 comprises several functional elements, such as modules and/or blocks. Different functional elements or modules may be configured for driving different kinds of surgical devices. For example, an ultrasonic generator module 21 may drive an ultrasonic device, such as the ultrasonic surgical instrument 10. In some example embodiments, the generator 20 also comprises an electrosurgery/RF generator module 23 for driving an electrosurgical device (or an electrosurgical embodiment of the ultrasonic surgical instrument 10). In various embodiments, the generator 20 may be formed integrally within the handle assembly 12. In such implementations, a battery would be co-located within the handle assembly 12 to act as the energy source.

In some embodiments, the electrosurgery/RF generator module 23 may be configured to generate a therapeutic and/or a sub-therapeutic energy level. In the example embodiment illustrated in FIG. 107, the generator 20 includes a control system 25 integral with the generator 20, and a foot switch 29 connected to the generator via a cable 27. The generator 20 may also comprise a triggering mechanism for activating a surgical instrument, such as the instrument 10. The triggering mechanism may include a power switch (not shown) as well as a foot switch 29. When activated by the foot switch 29, the generator 20 may provide energy to drive the acoustic assembly of the surgical instrument 10 and to drive the end effector 18 at a predetermined excursion level or provide the therapeutic/sub-therapeutic electromagnetic/RF energy. The generator 20 drives or excites the acoustic assembly at any suitable resonant frequency of the acoustic assembly and/or drives the therapeutic/sub-therapeutic electromagnetic/RF energy.

In one embodiment, the electrosurgical/RF generator module 23 may be implemented as an electrosurgery unit (ESU) capable of supplying power sufficient to perform bipolar electrosurgery using RF energy. In one embodiment, the ESU can be a bipolar ERBE ICC 350 sold by ERBE USA, Inc. of Marietta, Ga. In bipolar electrosurgery applications, as previously discussed, a surgical instrument having an active electrode and a return electrode can be utilized, wherein the active electrode and the return electrode can be positioned against, or adjacent to, the tissue to be treated such that current can flow from the active electrode to the return electrode through the tissue. Accordingly, the electrosurgical/RF module 23 generator may be configured for therapeutic purposes by applying electrical energy to the tissue T sufficient for treating the tissue (e.g., cauterization).

In one embodiment, the electrosurgical/RF generator module 23 may be configured to deliver a sub-therapeutic RF signal to implement a tissue impedance measurement module. In one embodiment, the electrosurgical/RF generator module 23 comprises a bipolar RF generator as described in more detail below. In one embodiment, the electrosurgical/RF generator module 12 may be configured to monitor electrical impedance Z, of tissue T and to control the characteristics of time and power level based on the tissue T by way of a return electrode on provided on a clamp member of the end effector assembly 26. Accordingly, the electrosurgical/RF generator module 23 may be configured for sub-therapeutic purposes for measuring the impedance or other electrical characteristics of the tissue T. Techniques and circuit configurations for measuring the impedance or other electrical characteristics of tissue T are discussed in more detail in commonly assigned U.S. Patent Publication No. 2011/0015631, titled "Electrosurgical Generator for Ultrasonic Surgical Instruments," the disclosure of which is herein incorporated by reference in its entirety.

A suitable ultrasonic generator module 21 may be configured to functionally operate in a manner similar to the GEN300 sold by Ethicon Endo-Surgery, Inc. of Cincinnati, Ohio as is disclosed in one or more of the following U.S. patents, all of which are incorporated by reference herein: U.S. Pat. No. 6,480,796 (Method for Improving the Start Up of an Ultrasonic System Under Zero Load Conditions); U.S. Pat. No. 6,537,291 (Method for Detecting Blade Breakage Using Rate and/or Impedance Information); U.S. Pat. No. 6,662,127 (Method for Detecting Presence of a Blade in an Ultrasonic System); U.S. Pat. No. 6,678,899 (Method for Detecting Transverse Vibrations in an Ultrasonic Surgical System); U.S. Pat. No. 6,977,495 (Detection Circuitry for Surgical Handpiece System); U.S. Pat. No. 7,077,853 (Method for Calculating Transducer Capacitance to Determine Transducer Temperature); U.S. Pat. No. 7,179,271 (Method for Driving an Ultrasonic System to Improve Acquisition of Blade Resonance Frequency at Startup); and U.S. Pat. No. 7,273,483 (Apparatus and Method for Alerting Generator Function in an Ultrasonic Surgical System).

It will be appreciated that in various embodiments, the generator 20 may be configured to operate in several modes. In one mode, the generator 20 may be configured such that the ultrasonic generator module 21 and the electrosurgical/RF generator module 23 may be operated independently. Alternatively, the ultrasonic generator module 21 may be configured to selectively apply either ultrasonic energy or either therapeutic sub-therapeutic RF energy to the end effector.

For example, the ultrasonic generator module 21 may be activated to apply ultrasonic energy to the end effector assembly 26 and subsequently, either therapeutic sub-therapeutic RF energy may be applied to the end effector assembly 26 by the electrosurgical/RF generator module 23. As previously discussed, the subtherapeutic electrosurgical/RF energy may be applied to tissue clamped between clamp elements of the end effector assembly 26 to measure tissue impedance to control the activation, or modify the activation, of the ultrasonic generator module 21. Tissue impedance feedback from the application of the subtherapeutic energy also may be employed to activate a therapeutic level of the electrosurgical/RF generator module 23 to seal the tissue (e.g., vessel) clamped between claim elements of the end effector assembly 26.

In another embodiment, the ultrasonic generator module 21 and the electrosurgical/RF generator module 23 may be activated simultaneously. In one example, the ultrasonic generator module 21 is simultaneously activated with a sub-therapeutic RF energy level to measure tissue impedance simultaneously while the ultrasonic blade of the end effector assembly 26 cuts and coagulates the tissue (or vessel) clamped between the clamp elements of the end effector assembly 26. Such feedback may be employed, for example, to modify the drive output of the ultrasonic generator module 21. In another example, the ultrasonic generator module 21 may be driven simultaneously with electrosurgical/RF generator module 23 such that the ultrasonic blade portion of the end effector assembly 26 is employed for cutting the damaged tissue while the electrosurgical/RF energy is applied to electrode portions of the end effector clamp assembly 26 for sealing the tissue (or vessel). Alternatively, the ultrasonic and the electrosurgical/RF energy can be employed sequentially with a single activation to achieve a desired tissue effect.

When the generator 20 is activated via the triggering mechanism, in one embodiment electrical energy is continuously applied by the generator 20 to a transducer stack or assembly of the acoustic assembly. In another embodiment, electrical energy is intermittently applied (e.g., pulsed) by the generator 20. A phase-locked loop in the control system of the generator 20 may monitor feedback from the acoustic assembly. The phase lock loop adjusts the frequency of the electrical energy sent by the generator 20 to match the resonant frequency of the selected longitudinal mode of vibration of the acoustic assembly. In addition, a second feedback loop in the control system 25 maintains the electrical current supplied to the acoustic assembly at a preselected constant level in order to achieve substantially constant excursion at the end effector 18 of the acoustic assembly. In yet another embodiment, a third feedback loop in the control system 25 monitors impedance between electrodes located in the end effector assembly 26. Although FIGS. 107-111 show a manually operated ultrasonic surgical instrument, it will be appreciated that ultrasonic surgical instruments may also be used in robotic applications, for example, as described herein, as well as combinations of manual and robotic applications.

In ultrasonic operation mode, the electrical signal supplied to the acoustic assembly may cause the distal end of the end effector 18 to vibrate longitudinally in the range of, for example, approximately 20 kHz to 250 kHz. According to various embodiments, the blade 22 may vibrate in the range of about 40 kHz to 56 kHz, for example, at about 50.0 kHz. In other embodiments, the blade 22 may vibrate at other frequencies including, for example, about 31 kHz or about 80 kHz. The excursion of the vibrations at the blade can be controlled by, for example, controlling the amplitude of the electrical signal applied to the transducer assembly of the acoustic assembly by the generator 20. As noted above, the triggering mechanism of the generator 20 allows a user to activate the generator 20 so that electrical energy may be continuously or intermittently supplied to the acoustic assembly. The generator 20 also has a power line for insertion in an electro-surgical unit or conventional electrical outlet. It is contemplated that the generator 20 can also be powered by a direct current (DC) source, such as a battery. The generator 20 can comprise any suitable generator, such as Model No. GEN04, and/or Model No. GEN11 available from Ethicon Endo-Surgery, Inc.

FIG. 108 is a left perspective view of one example embodiment of the ultrasonic surgical instrument 10 showing the handle assembly 12, the distal rotation assembly 13, the elongated shaft assembly 14, and the end effector assembly 26. In the illustrated embodiment the elongated shaft assembly 14 comprises a distal end 52 dimensioned to mechanically engage the end effector assembly 26 and a proximal end 50 that mechanically engages the handle assembly 12 and the distal rotation assembly 13. The proximal end 50 of the elongated shaft assembly 14 is received within the handle assembly 12 and the distal rotation assembly 13. More details relating to the connections between the elongated shaft assembly 14, the handle assembly 12, and the distal rotation assembly 13 are provided in the description of FIG. 98.

In the illustrated embodiment, the trigger assembly 24 comprises a trigger 32 that operates in conjunction with a fixed handle 34. The fixed handle 34 and the trigger 32 are ergonomically formed and adapted to interface comfortably with the user. The fixed handle 34 is integrally associated with the handle assembly 12. The trigger 32 is pivotally movable relative to the fixed handle 34 as explained in more detail below with respect to the operation of the ultrasonic surgical instrument 10. The trigger 32 is pivotally movable in direction 33A toward the fixed handle 34 when the user applies a squeezing force against the trigger 32. A spring element 98 (FIG. 111) causes the trigger 32 to pivotally move in direction 33B when the user releases the squeezing force against the trigger 32.

In one example embodiment, the trigger 32 comprises an elongated trigger hook 36, which defines an aperture 38 between the elongated trigger hook 36 and the trigger 32. The aperture 38 is suitably sized to receive one or multiple fingers of the user therethrough. The trigger 32 also may comprise a resilient portion 32a molded over the trigger 32 substrate. The overmolded resilient portion 32a is formed to provide a more comfortable contact surface for control of the trigger 32 in outward direction 33B. In one example embodiment, the overmolded resilient portion 32a may be provided over a portion of the elongated trigger hook 36. The proximal surface of the elongated trigger hook 32 remains uncoated or coated with a non-resilient substrate to enable the user to easily slide their fingers in and out of the aperture 38. In another embodiment, the geometry of the trigger forms a fully closed loop which defines an aperture suitably sized to receive one or multiple fingers of the user therethrough. The fully closed loop trigger also may comprise a resilient portion molded over the trigger substrate.

In one example embodiment, the fixed handle 34 comprises a proximal contact surface 40 and a grip anchor or saddle surface 42. The saddle surface 42 rests on the web where the thumb and the index finger are joined on the hand. The proximal contact surface 40 has a pistol grip contour that receives the palm of the hand in a normal pistol grip with no rings or apertures. The profile curve of the proximal contact surface 40 may be contoured to accommodate or receive the palm of the hand. A stabilization tail 44 is located towards a more proximal portion of the handle assembly 12. The stabilization tail 44 may be in contact with the uppermost web portion of the hand located between the thumb and the index finger to stabilize the handle assembly 12 and make the handle assembly 12 more controllable.

In one example embodiment, the switch assembly 28 may comprise a toggle switch 30. The toggle switch 30 may be implemented as a single component with a central pivot 304 located within inside the handle assembly 12 to eliminate the possibility of simultaneous activation. In one example embodiment, the toggle switch 30 comprises a first projecting knob 30a and a second projecting knob 30b to set the power setting of the ultrasonic transducer 16 between a minimum power level (e.g., MIN) and a maximum power level (e.g., MAX). In another embodiment, the rocker switch may pivot between a standard setting and a special setting. The special setting provides one or more special programs to be implemented by the device. The toggle switch 30 rotates about the central pivot as the first projecting knob 30a and the second projecting knob 30b are actuated. The one or more projecting knobs 30a, 30b are coupled to one or more arms that move through a small arc and cause electrical contacts to close or open an electric circuit to electrically energize or de-energize the ultrasonic transducer 16 in accordance with the activation of the first or second projecting knobs 30a, 30b. The toggle switch 30 is coupled to the generator 20 to control the activation of the ultrasonic transducer 16. The toggle switch 30 comprises one or more electrical power setting switches to activate the ultrasonic transducer 16 to set one or more power settings for the ultrasonic transducer 16. The forces required to activate the toggle switch 30 are directed substantially toward the saddle point 42, thus avoiding any tendency of the instrument to rotate in the hand when the toggle switch 30 is activated.

In one example embodiment, the first and second projecting knobs 30a, 30b are located on the distal end of the handle assembly 12 such that they can be easily accessible by the user to activate the power with minimal, or substantially no, repositioning of the hand grip, making it suitable to maintain control and keep attention focused on the surgical site (e.g., a monitor in a laparoscopic procedure) while activating the toggle switch 30. The projecting knobs 30a, 30b may be configured to wrap around the side of the handle assembly 12 to some extent to be more easily accessible by variable finger lengths and to allow greater freedom of access to activation in awkward positions or for shorter fingers.

In the illustrated embodiment, the first projecting knob 30a comprises a plurality of tactile elements 30c, e.g., textured projections or "bumps" in the illustrated embodiment, to allow the user to differentiate the first projecting knob 30a from the second projecting knob 30b. It will be appreciated by those skilled in the art that several ergonomic features may be incorporated into the handle assembly 12. Such ergonomic features are described in U.S. Pat. No. 8,623,027, entitled "Ergonomic Surgical Instruments" which is incorporated by reference herein in its entirety.

In one example embodiment, the toggle switch 30 may be operated by the hand of the user. The user may easily access the first and second projecting knobs 30a, 30b at any point while also avoiding inadvertent or unintentional activation at any time. The toggle switch 30 may readily operated with a finger to control the power to the ultrasonic assembly 16 and/or to the ultrasonic assembly 16. For example, the index finger may be employed to activate the first contact portion 30a to turn on the ultrasonic assembly 16 to a maximum (MAX) power level. The index finger may be employed to activate the second contact portion 30b to turn on the ultrasonic assembly 16 to a minimum (MIN) power level. In another embodiment, the rocker switch may pivot the instrument 10 between a standard setting and a special setting. The special setting provides one or more special programs to be implemented by the instrument 10. The toggle switch 30 may be operated without the user having to look at the first or second projecting knob 30a, 30b. For example, the first projecting knob 30a or the second projecting knob 30b may comprise a texture or projections to tactilely differentiate between the first and second projecting knobs 30a, 30b without looking.

In other embodiments, the trigger 32 and/or the toggle switch 30 may be employed to actuate the electrosurgical/RF generator module 23 individually or in combination with activation of the ultrasonic generator module 21.

In one example embodiment, the distal rotation assembly 13 is rotatable without limitation in either direction about a longitudinal axis "T." The distal rotation assembly 13 is mechanically engaged to the elongated shaft assembly 14. The distal rotation assembly 13 is located on a distal end of the handle assembly 12. The distal rotation assembly 13 comprises a cylindrical hub 46 and a rotation knob 48 formed over the hub 46. The hub 46 mechanically engages the elongated shaft assembly 14. The rotation knob 48 may comprise fluted polymeric features and may be engaged by a finger (e.g., an index finger) to rotate the elongated shaft assembly 14. The hub 46 may comprise a material molded over the primary structure to form the rotation knob 48. The rotation knob 48 may be overmolded over the hub 46. The hub 46 comprises an end cap portion 46a that is exposed at the distal end. The end cap portion 46a of the hub 46 may contact the surface of a trocar during laparoscopic procedures. The hub 46 may be formed of a hard durable plastic such as polycarbonate to alleviate any friction that may occur between the end cap portion 46a and the trocar. The rotation knob 48 may comprise "scallops" or flutes formed of raised ribs 48a and concave portions 48b located between the ribs 48a to provide a more precise rotational grip. In one example embodiment, the rotation knob 48 may comprise a plurality of flutes (e.g., three or more flutes). In other embodiments, any suitable number of flutes may be employed. The rotation knob 48 may be formed of a softer polymeric material overmolded onto the hard plastic material. For example, the rotation knob 48 may be formed of pliable, resilient, flexible polymeric materials including Versaflex® TPE alloys made by GLS Corporation, for example. This softer overmolded material may provide a greater grip and more precise control of the movement of the rotation knob 48. It will be appreciated that any materials that provide adequate resistance to sterilization, are biocompatible, and provide adequate frictional resistance to surgical gloves may be employed to form the rotation knob 48.

In one example embodiment, the handle assembly 12 is formed from two (2) housing portions or shrouds comprising a first portion 12a and a second portion 12b. From the perspective of a user viewing the handle assembly 12 from the distal end towards the proximal end, the first portion 12a is considered the right portion and the second portion 12b is considered the left portion. Each of the first and second portions 12a, 12b includes a plurality of interfaces 69 (FIG. 111) dimensioned to mechanically align and engage each another to form the handle assembly 12 and enclosing the internal working components thereof. The fixed handle 34, which is integrally associated with the handle assembly 12, takes shape upon the assembly of the first and second portions 12a and 12b of the handle assembly 12. A plurality of additional interfaces (not shown) may be disposed at various points around the periphery of the first and second portions 12a and 12b of the handle assembly 12 for ultrasonic welding purposes, e.g., energy direction/deflection points. The first and second portions 12a and 12b (as well as the other components described below) may be assembled together in any fashion known in the art. For example, alignment pins, snap-like interfaces, tongue and groove interfaces, locking tabs, adhesive ports, may all be utilized either alone or in combination for assembly purposes.

In one example embodiment, the elongated shaft assembly 14 comprises a proximal end 50 adapted to mechanically engage the handle assembly 12 and the distal rotation assembly 13; and a distal end 52 adapted to mechanically engage the end effector assembly 26. The elongated shaft assembly 14 comprises an outer tubular sheath 56 and a reciprocating tubular actuating member 58 located within the outer tubular sheath 56. The proximal end of the tubular reciprocating tubular actuating member 58 is mechanically engaged to the trigger 32 of the handle assembly 12 to move in either direction 60A or 60B in response to the actuation and/or release of the trigger 32. The pivotably moveable trigger 32 may generate reciprocating motion along the longitudinal axis "T." Such motion may be used, for example, to actuate the jaws or clamping mechanism of the end effector assembly 26. A series of linkages translate the pivotal rotation of the trigger 32 to axial movement of a yoke coupled to an actuation mechanism, which controls the opening and closing of the jaws of the clamping mechanism of the end effector assembly 26. The distal end of the tubular reciprocating tubular actuating member 58 is mechanically engaged to the end effector assembly 26. In the illustrated embodiment, the distal end of the tubular reciprocating tubular actuating member 58 is mechanically engaged to a clamp arm assembly 64, which is pivotable about a pivot point 70, to open and close the clamp arm assembly 64 in response to the actuation and/or release of the trigger 32. For example, in the illustrated embodiment, the clamp arm assembly 64 is movable in direction 62A from an open position to a closed position about a pivot point 70 when the trigger 32 is squeezed in direction 33A. The clamp arm assembly 64 is movable in direction 62B from a closed position to an open position about the pivot point 70 when the trigger 32 is released or outwardly contacted in direction 33B.

In one example embodiment, the end effector assembly 26 is attached at the distal end 52 of the elongated shaft assembly 14 and includes a clamp arm assembly 64 and a blade 66. The jaws of the clamping mechanism of the end effector assembly 26 are formed by clamp arm assembly 64 and the blade 66. The blade 66 is ultrasonically actuatable and is acoustically coupled to the ultrasonic transducer 16. The trigger 32 on the handle assembly 12 is ultimately connected to a drive assembly, which together, mechanically cooperate to effect movement of the clamp arm assembly 64. Squeezing the trigger 32 in direction 33A moves the clamp arm assembly 64 in direction 62A from an open position, wherein the clamp arm assembly 64 and the blade 66 are disposed in a spaced relation relative to one another, to a clamped or closed position, wherein the clamp arm assembly 64 and the blade 66 cooperate to grasp tissue therebetween. The clamp arm assembly 64 may comprise a clamp pad 69 to engage tissue between the blade 66 and the clamp arm 64. Releasing the trigger 32 in direction 33B moves the clamp arm assembly 64 in direction 62B from a closed relationship, to an open position, wherein the clamp arm assembly 64 and the blade 66 are disposed in a spaced relation relative to one another.

The proximal portion of the handle assembly 12 comprises a proximal opening 68 to receive the distal end of the ultrasonic assembly 16. The ultrasonic assembly 16 is inserted in the proximal opening 68 and is mechanically engaged to the elongated shaft assembly 14.

In one example embodiment, the elongated trigger hook 36 portion of the trigger 32 provides a longer trigger lever with a shorter span and rotation travel. The longer lever of the elongated trigger hook 36 allows the user to employ multiple fingers within the aperture 38 to operate the elongated trigger hook 36 and cause the trigger 32 to pivot in direction 33B to open the jaws of the end effector assembly 26. For example, the user may insert three fingers (e.g., the middle, ring, and little fingers) in the aperture 38. Multiple fingers allows the surgeon to exert higher input forces on the trigger 32 and the elongated trigger hook 36 to activate the end effector assembly 26. The shorter span and rotation travel creates a more comfortable grip when closing or squeezing the trigger 32 in direction 33A or when opening the trigger 32 in the outward opening motion in direction 33B lessening the need to extend the fingers further outward. This substantially lessens hand fatigue and strain associated with the outward opening motion of the trigger 32 in direction 33B. The outward opening motion of the trigger may be spring-assisted by spring element 98 (FIG. 111) to help alleviate fatigue. The opening spring force is sufficient to assist the ease of opening, but not strong enough to adversely impact the tactile feedback of tissue tension during spreading dissection.

For example, during a surgical procedure either the index finger may be used to control the rotation of the elongated shaft assembly 14 to locate the jaws of the end effector assembly 26 in a suitable orientation. The middle and/or the other lower fingers may be used to squeeze the trigger 32 and grasp tissue within the jaws. Once the jaws are located in the desired position and the jaws are clamped against the tissue, the index finger can be used to activate the toggle switch 30 to adjust the power level of the ultrasonic transducer 16 to treat the tissue. Once the tissue has been treated, the user the may release the trigger 32 by pushing outwardly in the distal direction against the elongated trigger hook 36 with the middle and/or lower fingers to open the jaws of the end effector assembly 26. This basic procedure may be performed without the user having to adjust their grip of the handle assembly 12.

FIGS. 109-110 illustrate the connection of the elongated shaft assembly 14 relative to the end effector assembly 26. As previously described, in the illustrated embodiment, the end effector assembly 26 comprises a clamp arm assembly 64 and a blade 66 to form the jaws of the clamping mechanism. The blade 66 may be an ultrasonically actuatable blade acoustically coupled to the ultrasonic transducer 16. The trigger 32 is mechanically connected to a drive assembly. Together, the trigger 32 and the drive assembly mechanically cooperate to move the clamp arm assembly 64 to an open position in direction 62A wherein the clamp arm assembly 64 and the blade 66 are disposed in spaced relation relative to one another, to a clamped or closed position in direction 62B wherein the clamp arm assembly 64 and the blade 66 cooperate to grasp tissue therebetween. The clamp arm assembly 64 may comprise a clamp pad 69 to engage tissue between the blade 66 and the clamp arm 64. The distal end of the tubular reciprocating tubular actuating member 58 is mechanically engaged to the end effector assembly 26. In the illustrated embodiment, the distal end of the tubular reciprocating tubular actuating member 58 is mechanically engaged to the clamp arm assembly 64, which is pivotable about the pivot point 70, to open and close the clamp arm assembly 64 in response to the actuation and/or release of the trigger 32. For example, in the illustrated embodiment, the clamp arm assembly 64 is movable from an open position to a closed position in direction 62B about a pivot point 70 when the trigger 32 is squeezed in direction 33A. The clamp arm assembly 64 is movable from a closed position to an open position in direction 62A about the pivot point 70 when the trigger 32 is released or outwardly contacted in direction 33B.

As previously discussed, the clamp arm assembly 64 may comprise electrodes electrically coupled to the electrosurgical/RF generator module 23 to receive therapeutic and/or sub-therapeutic energy, where the electrosurgical/RF energy may be applied to the electrodes either simultaneously or non-simultaneously with the ultrasonic energy being applied to the blade 66. Such energy activations may be applied in any suitable combinations to achieve a desired tissue effect in cooperation with an algorithm or other control logic.

FIG. 111 is an exploded view of the ultrasonic surgical instrument 10 shown in FIG. 108. In the illustrated embodiment, the exploded view shows the internal elements of the handle assembly 12, the handle assembly 12, the distal rotation assembly 13, the switch assembly 28, and the elongated shaft assembly 14. In the illustrated embodiment, the first and second portions 12a, 12b mate to form the handle assembly 12. The first and second portions 12a, 12b each comprises a plurality of interfaces 69 dimensioned to mechanically align and engage one another to form the handle assembly 12 and enclose the internal working components of the ultrasonic surgical instrument 10. The rotation knob 48 is mechanically engaged to the outer tubular sheath 56 so that it may be rotated in circular direction 54 up to 360°. The outer tubular sheath 56 is located over the reciprocating tubular actuating member 58, which is mechanically engaged to and retained within the handle assembly 12 via a plurality of coupling elements 72. The coupling elements 72 may comprise an O-ring 72a, a tube collar cap 72b, a distal washer 72c, a proximal washer 72d, and a thread tube collar 72e. The reciprocating tubular actuating member 58 is located within a reciprocating yoke 84, which is retained between the first and second portions 12a, 12b of the handle assembly 12. The yoke 84 is part of a reciprocating yoke assembly 88. A series of linkages translate the pivotal rotation of the elongated trigger hook 32 to the axial movement of the reciprocating yoke 84, which controls the opening and closing of the jaws of the clamping mechanism of the end effector assembly 26 at the distal end of the ultrasonic surgical instrument 10. In one example embodiment, a four-link design provides mechanical advantage in a relatively short rotation span, for example.

In one example embodiment, an ultrasonic transmission waveguide 78 is disposed inside the reciprocating tubular actuating member 58. The distal end 52 of the ultrasonic transmission waveguide 78 is acoustically coupled (e.g., directly or indirectly mechanically coupled) to the blade 66 and the proximal end 50 of the ultrasonic transmission waveguide 78 is received within the handle assembly 12. The proximal end 50 of the ultrasonic transmission waveguide 78 is adapted to acoustically couple to the distal end of the ultrasonic transducer 16 as discussed in more detail below. The ultrasonic transmission waveguide 78 is isolated from the other elements of the elongated shaft assembly 14 by a protective sheath 80 and a plurality of isolation elements 82, such as silicone rings. The outer tubular sheath 56, the reciprocating tubular actuating member 58, and the ultrasonic transmission waveguide 78 are mechanically engaged by a pin 74. The switch assembly 28 comprises the toggle switch 30 and electrical elements 86a, 86b to electrically energize the ultrasonic transducer 16 in accordance with the activation of the first or second projecting knobs 30a, 30b.

In one example embodiment, the outer tubular sheath 56 isolates the user or the patient from the ultrasonic vibrations of the ultrasonic transmission waveguide 78. The outer tubular sheath 56 generally includes a hub 76. The outer tubular sheath 56 is threaded onto the distal end of the handle assembly 12. The ultrasonic transmission waveguide 78 extends through the opening of the outer tubular sheath 56 and the isolation elements 82 isolate the ultrasonic transmission waveguide 24 from the outer tubular sheath 56. The outer tubular sheath 56 may be attached to the waveguide 78 with the pin 74. The hole to receive the pin 74 in the waveguide 78 may occur nominally at a displacement node. The waveguide 78 may screw or snap into the hand piece handle assembly 12 by a stud. Flat portions on the hub 76 enable the assembly to be torqued to a required level. In one example embodiment, the hub 76 portion of the outer tubular sheath 56 is preferably constructed from plastic and the tubular elongated portion of the outer tubular sheath 56 is fabricated from stainless steel. Alternatively, the ultrasonic transmission waveguide 78 may comprise polymeric material surrounding it to isolate it from outside contact.

In one example embodiment, the distal end of the ultrasonic transmission waveguide 78 may be coupled to the proximal end of the blade 66 by an internal threaded connection, preferably at or near an antinode. It is contemplated that the blade 66 may be attached to the ultrasonic transmission waveguide 78 by any suitable means, such as a welded joint or the like. Although the blade 66 may be detachable from the ultrasonic transmission waveguide 78, it is also contemplated that the single element end effector (e.g., the blade 66) and the ultrasonic transmission waveguide 78 may be formed as a single unitary piece.

In one example embodiment, the trigger 32 is coupled to a linkage mechanism to translate the rotational motion of the trigger 32 in directions 33A and 33B to the linear motion of the reciprocating tubular actuating member 58 in corresponding directions 60A and 60B. The trigger 32 comprises a first set of flanges 98 with openings formed therein to receive a first yoke pin 92a. The first yoke pin 92a is also located through a set of openings formed at the distal end of the yoke 84. The trigger 32 also comprises a second set of flanges 96 to receive a first end 92a of a link 92. A trigger pin 90 is received in openings formed in the link 92 and the second set of flanges 96. The trigger pin 90 is received in the openings formed in the link 92 and the second set of flanges 96 and is adapted to couple to the first and second portions 12a, 12b of the handle assembly 12 to form a trigger pivot point for the trigger 32. A second end 92b of the link 92 is received in a slot 384 formed in a proximal end of the yoke 84 and is retained therein by a second yoke pin 94b. As the trigger 32 is pivotally rotated about the pivot point 190 formed by the trigger pin 90, the yoke translates horizontally along longitudinal axis "T" in a direction indicated by arrows 60A, 60B.

Ultrasonic Blades with Various Grasping Features

FIGS. 1-11 illustrates various embodiments of ultrasonic blades comprising grasping features. Such grasping features may be included on a gripping surface of an ultrasonic blade to provide additional gripping and prevent tissue milking during grasping and treatment, which in some cases may improve hemostasis. Tissue milking occurs when a tissue section slides, or milks, out of the jaws of a surgical device during treatment. Blade modification features discussed below can prevent tissue milking, as well as provide better grasping forces.

A minimum grasping force for an ultrasonic clamp arm in a medical forceps having a movable jaw member is about 2.25 lb-f when clamped on a dry chamois while the device is inactive. During activation, however, the tissue may milk out of the jaws either proximally or distally. The blade 100 comprising the tooth-like grasping features 102 for an ultrasonic shears device can help prevent tissue milking as well as provide better grasping forces.

Grasping features may take the form of several shapes as described in connection with FIGS. 1-11, for example. The grasping features could be located only on a portion of the blade, such as, for example, the distal tip, the center of the blade, the proximal section, or any portion of the blade. In another embodiment, the grasping features may be located along the entire length or a portion of the blade. In some embodiments, the features illustrated and described with respect to FIGS. 1-11 could be located longitudinally on a portion of the blade, such as, for example, configured along a center line of the blade, the left side of the blade, the right side of the blade, or both the right and left side of the blade. In another embodiment, the grasping features may be configured along the entire width of the blade. Grasping features may include, for example, teeth machined into the blade, teeth protruding from the surface of the blade, protruding blocks, protruding bumps or spikes, holes formed in the blade, or protruding elongated bumps. These and other blade grasping features are described hereinbelow in connection with FIGS. 1-11.

Figure 1:
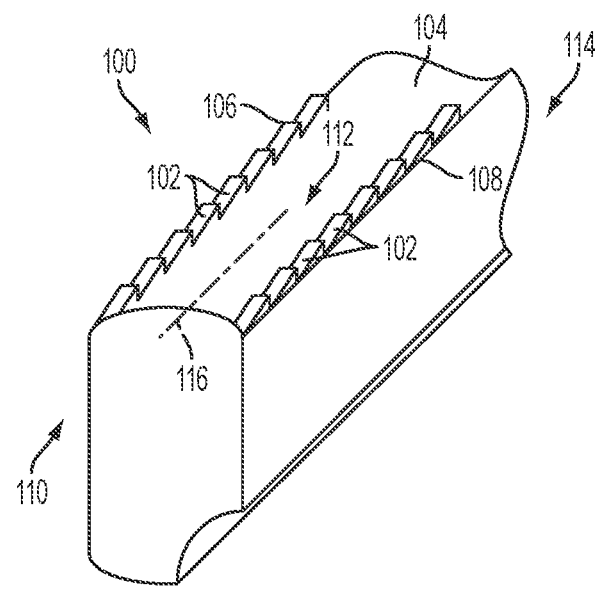
FIG. 1 illustrates one embodiment of an ultrasonic blade with tooth-like grasping features formed on a grasping surface of the blade.

FIG. 1 illustrates one embodiment of an ultrasonic blade 100 with tooth-like grasping features 102 formed on a grasping surface 104 of the blade 100. In the embodiment illustrated in FIG. 1 the tooth-like grasping features 102 are formed along lateral portions 106, 108 of the grasping surface 104 of the blade 100, e.g., the left side of the blade 100 and the right side of the blade 100. In one embodiment, the tooth-like grasping features 102 may be formed along the entire active length or a portion of the blade 100. Elements of the tooth-like grasping features 102 may be uniformly or variable spaced. In other embodiments, the tooth-like grasping features 102 could be located only on a portion of the blade 100, such as, for example, the distal tip 110, the center 112 of the blade 100, the proximal section 114, or any portion of the blade 100. In another embodiment, the tooth-like grasping features 102 may be located along the entire length or a portion of the blade 100. In some embodiments, the tooth-like grasping features 102 could be located longitudinally on a portion of the blade 100, such as, for example, configured along a center line 116 of the blade 100, the left side 108 of the blade 100, the right side 106 of the blade 100, or both the right and left side of the blade 100. In another embodiment, the tooth-like grasping features 102 may be configured along the entire width of the blade 100. The tooth-like grasping features 102 may be configured to trap tissue and prevent disengagement during activation to prevent tissue milking, as well as provide better grasping forces. Accordingly, the tooth-like grasping features 102 formed on the blade 100 improve tissue grasping. The embodiments, however, are not limited in this context.

Figure 2:
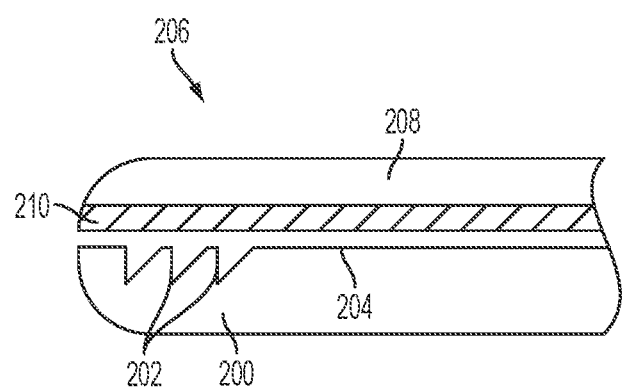
FIG. 2 illustrates one embodiment of the ultrasonic blade with tooth-like grasping features formed on a grasping portion of the blade, where the teeth are machined into the grasping portion of the blade.

FIG. 2 illustrates one embodiment of an ultrasonic blade 200 with tooth-like grasping features 202 formed on a grasping portion 204 of the blade 200 where the teeth are machined into the grasping portion 204 of the blade 200. In the embodiment illustrated in FIG. 2, the blade 200 is part of a medical forceps 206 having a movable jaw member 208, which is commonly referred to as a clamp arm. The movable jaw member 208 comprises a clamp pad 210 to engage tissue between the blade 200 and the movable jaw member 208, e.g., clamp arm. In one embodiment, the tooth-like grasping features 202 may be formed along the entire active length or a portion of the blade 200. Elements of the tooth-like grasping features 202 may be uniformly or variable spaced. Although not shown, the tooth-like grasping features 202 may be formed across the grasping surface 204 of the blade 200, may be formed as multiple rows along the lateral portions of the blade 200 as shown in FIG. 1, or may be formed as a single row along the longitudinal portion of the grasping surface 204 of the blade 200. The tooth-like grasping features 202 may be configured to trap tissue and prevent disengagement during activation to prevent tissue milking, as well as provide better grasping forces. Accordingly, the tooth-like grasping features 202 formed on the blade 200 improve tissue grasping. The embodiments, however, are not limited in this context.

Figure 3:
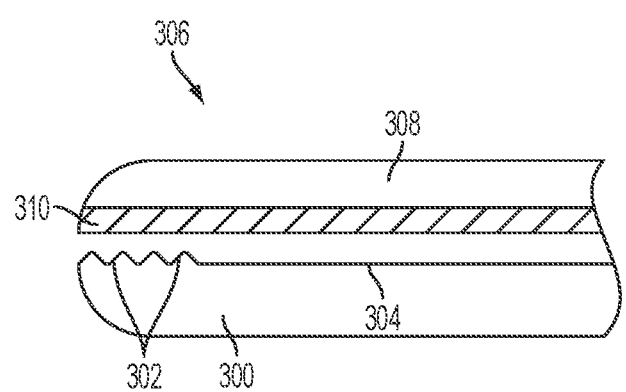
FIG. 3 illustrates one embodiment of the ultrasonic blade with tooth-like grasping features formed on a grasping portion of the blade, where the teeth protrude from the grasping portion of the blade.

FIG. 3 illustrates one embodiment of an ultrasonic blade 300 with tooth-like grasping features 302 formed on a grasping portion 304 of the blade 300, where the teeth 302 protrude from the grasping portion 304 of the blade 300. In the embodiment illustrated in FIG. 3, the blade 300 is part of a medical forceps 306 having a movable jaw member 308, which is commonly referred to as a clamp arm. The movable jaw member 308 comprises a clamp pad 310 to engage tissue between the blade 300 and the movable jaw member 308, e.g., clamp arm. In one embodiment, the tooth-like grasping features 302 may be formed along the entire active length or a portion of the blade 300. Elements of the tooth-like grasping features 302 may be uniformly or variable spaced. Although not shown, the tooth-like grasping features 302 may be formed across the grasping surface 304 of the blade 300, may be formed as multiple rows along the lateral portions of the blade 300 as shown in FIG. 1, or may be formed as a single row along the longitudinal portion of the grasping surface 304 of the blade 300. The tooth-like grasping features 302 may be configured to trap tissue and prevent disengagement during activation to prevent tissue milking, as well as provide better grasping forces. Accordingly, the tooth-like grasping features 302 formed on the blade 300 improve tissue grasping. The embodiments, however, are not limited in this context.

FIG. 4 illustrates one embodiment of an ultrasonic blade 400 with protruding block-like grasping features 402 formed on a grasping 404 portion of the blade 400. FIG. 5 is a side view of the ultrasonic blade shown in FIG. 4. In the embodiment illustrated in FIGS. 4 and 5 the block-like grasping features 402 are formed along lateral portions 406, 408 of the grasping surface 404 of the blade 400. In one embodiment, the block-like grasping features 402 may be formed along the entire active length or a portion of the blade 400. Elements of the block-like grasping features 402 may be uniformly or variable spaced. In other embodiments, the block-like grasping features 402 could be located only on a portion of the blade 400, such as, for example, the distal tip 410, the center 412 of the blade 400, the proximal section 414, or any portion of the blade 400. In another embodiment, the block-like grasping features 402 may be located along the entire length or a portion of the blade 400. In some embodiments, the block-like grasping features 402 could be located longitudinally on a portion of the blade 400, such as, for example, configured along a center line 416 of the blade 400, the left side 408 of the blade 400, the right side 406 of the blade 400, or both the right and left side of the blade 400. In another embodiment, the block-like grasping features 402 may be configured along the entire width of the blade 400. The block-like grasping features 402 may be configured to trap tissue and prevent disengagement during activation to prevent tissue milking, as well as provide better grasping forces. Accordingly, the block-like grasping features 402 formed on the blade 400 improve tissue grasping. The embodiments, however, are not limited in this context.

FIG. 6 illustrates one embodiment of an ultrasonic blade 500 with protruding grasping features 502 formed on a grasping portion 504 of the blade 500. FIG. 7A is a side view of the ultrasonic blade 500 shown in FIG. 6 and FIG. 7B shows the protruding grasping features 502 in the form of bump-like protrusions 510 whereas FIG. 7C shows the protruding grasping features 502 in the form of spike-like protrusions 512. In the embodiment illustrated in FIGS. 6 and 7A the protruding grasping features 502 are formed along lateral portions 506, 508 of the grasping surface 504 of the blade 500. In one embodiment, the grasping features 502 may be formed along the entire active length or a portion of the blade 500. Elements of the grasping features 502 may be uniformly or variable spaced. In other embodiments, the grasping features 502 could be located only on a portion of the blade 500, such as, for example, the distal tip 520, the center 522 of the blade 500, the proximal section 524, or any portion of the blade 500. In another embodiment, the grasping features 502 may be located along the entire length or a portion of the blade 500. In some embodiments, the grasping features 502 could be located longitudinally on a portion of the blade 500, such as, for example, configured along a center line 526 of the blade 500, the left side 508 of the blade 500, the right side 506 of the blade 500, or both the right and left side of the blade 500. In another embodiment, the grasping features 502 may be configured along the entire width of the blade 500. The grasping features 502 may be configured to trap tissue and prevent disengagement during activation to prevent tissue milking, as well as provide better grasping forces. Accordingly, the grasping features 502 formed on the blade 500 improve tissue grasping. The embodiments, however, are not limited in this context.

FIG. 8 illustrates one embodiment of an ultrasonic blade 600 with cavity-like grasping features 602 formed on a grasping portion 604 of the blade 600. FIG. 9A is a side view of an ultrasonic blade 600 having cylindrical cavity-like grasping features 611 partially formed into the grasping portion of the blade 610. FIG. 9B is a side view of an ultrasonic blade 600 having cylindrical cavity-like grasping features 613 formed through a grasping portion of the blade 612. FIG. 9C is a side view of an ultrasonic blade 600 having conical cavity-like grasping features 615 partially formed into the grasping portion of the blade 614. In the embodiment illustrated in FIGS. 8 and 9A-C, the cavity-like grasping features 602 are distributed along portions of the grasping surface 604 of the blade 600. In one embodiment, the grasping features 602 may be formed along the entire active length or a portion of the blade 600. Elements of the grasping features 602 may be uniformly or variable spaced. In other embodiments, the grasping features 602 could be located only on a portion of the blade 600, such as, for example, the distal tip 620, the center 622 of the blade 600, the proximal section 624, or any portion of the blade 600. In another embodiment, the grasping features 602 may be located along the entire length or a portion of the blade 600. In some embodiments, the grasping features 602 could be located longitudinally on a portion of the blade 600, such as, for example, configured along a center line 626 of the blade 600, the left side 608 of the blade 600, the right side 606 of the blade 600, or both the right and left side of the blade 600. In another embodiment, the grasping features 602 may be configured along the entire width of the blade 600. The grasping features 602 may be configured to trap tissue and prevent disengagement during activation to prevent tissue milking, as well as provide better grasping forces. Accordingly, the grasping features 602 formed on the blade 600 improve tissue grasping. The embodiments, however, are not limited in this context.

FIG. 10 illustrates one embodiment of an ultrasonic blade 700 with transverse bump-like grasping features 702 formed on a grasping portion 704 of the blade 700. FIG. 11 is a side view of the ultrasonic blade 700 shown in FIG. 10. In the embodiment illustrated in FIGS. 10 and 11, the transverse bump-like grasping features 702 are distributed transversally along across of the grasping surface 704 of the blade 700. In one embodiment, the transverse bump-like grasping features 702 may be formed along the entire active length or a portion of the blade 700. Elements of the transverse bump-like grasping features 702 may be uniformly or variable spaced. In other embodiments, the transverse bump-like grasping features 702 could be located only on a portion of the blade 700, such as, for example, the distal tip 720, the center 722 of the blade 700, the proximal section 724, or any portion of the blade 700. In another embodiment, the transverse bump-like grasping features 702 may be located along the entire length or a portion of the blade 700. In some embodiments, the transverse bump-like grasping features 702 could be located longitudinally on a portion of the blade 700, such as, for example, configured along a center line 726 of the blade 700, the left side 708 of the blade 700, the right side 706 of the blade 700, or both the right and left side of the blade 700. In another embodiment, the transverse bump-like grasping features 702 may be configured along the entire width of the blade 700. The transverse bump-like grasping features 702 may be configured to trap tissue and prevent disengagement during activation to prevent tissue milking, as well as provide better grasping forces. Accordingly, the transverse bump-like grasping features 702 formed on the blade 700 improve tissue grasping. The embodiments, however, are not limited in this context.

Figure 12:
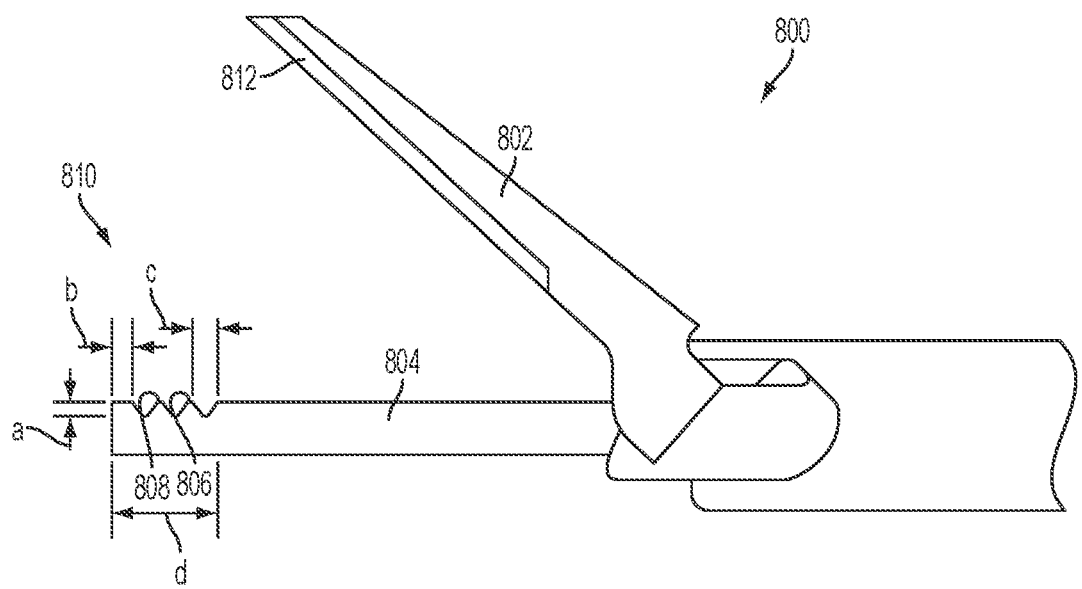
FIG. 12 is a side view of one embodiment of an end effector assembly comprising medical forceps having a movable jaw member and an ultrasonic blade having protrusions in the form of tooth-like grasping features formed on a grasping surface of the blade.
Figure 13:
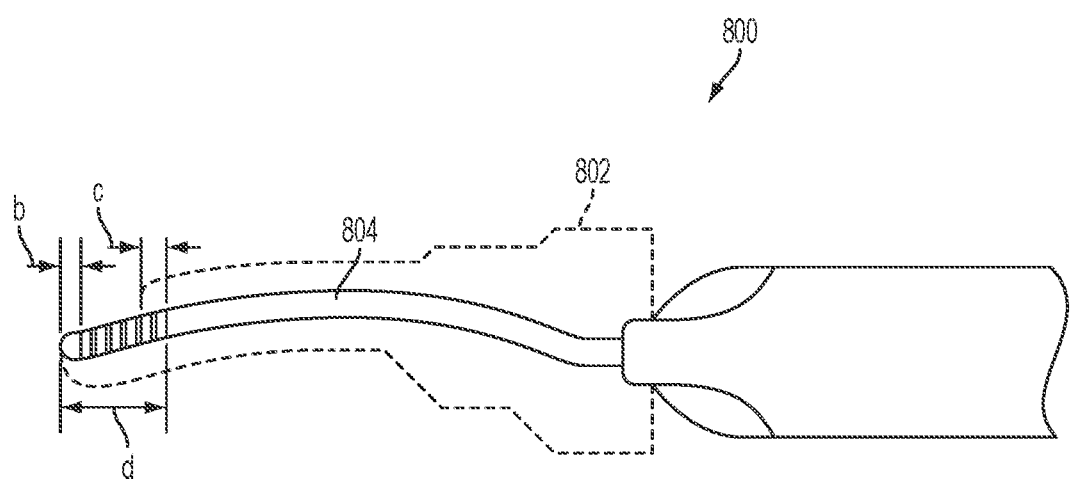
FIG. 13 is a top view of one embodiment of the medical forceps shown in FIG. 12 with the movable jaw member drawn in phantom line to show the ultrasonic blade positioned below the movable jaw member.

FIG. 12 is a side view of one embodiment of an end effector assembly comprising medical forceps 800 having a movable jaw member 802 and an ultrasonic blade 804 having protrusions 806 in the form of tooth-like grasping features formed in the grasping surface 808 of the blade 804. FIG. 13 is a top view of one embodiment of the medical forceps 800 shown in FIG. 12 with the movable jaw member 802 drawn in phantom line to show the ultrasonic blade 804 positioned below the movable jaw member 802.

In one embodiment, the protrusions 806 (e.g., teeth) may be defined by several dimensions. A first dimension "a" represents the height of a protrusion 806 (e.g., tooth). In one embodiment, the dimension "a" may be about 0.12 mm to 0.18 mm. A second dimension "b" represents the width of a protrusion 806 (e.g., tooth). In one embodiment, the dimension "b" may be about 0.2 mm. A third dimension "c" represents the spacing between each protrusion 806. In one embodiment, the dimension "c" is about 0.5 mm. The protrusions 806 may cover, in one embodiment, a distance represented by dimension "d" which can be as little as 2 mm of the blade 804 to provide additional grasping strength. The 2 mm of protrusions 806 may comprise any percentage of the blade 804, such as, for example, 13% of a 15 mm blade. In one embodiment, the height of the protrusion 806 near the distal end 810 of the blade 804 may be approximately 2.3 mm. In one embodiment, the protrusions 806 may comprise about 5% of the total height of the blade 804. In various embodiments, the protrusions 806 may include a pitch of 0.3 mm-1.0 mm, a depth of approximately 0.08 mm-0.8 mm, and an angle of approximately 5-90 degrees. In various embodiments, the protrusions 806 may be in the form of blocks, bumps, spikes, or speed bumps, as previously described. These alternate embodiments of the protrusions 806 would be formed having similar dimensions as the protrusions 806 described in connection with FIGS. 12 and 13 to have a similar affect on tissue, e.g., statistically better tissue grasping forces and preventing tissue milking.

In one embodiment, the protrusions 806 may mate with alternating features formed on the clamp arm 802 or tissue pad 812 portion of the medical forceps 800. In another embodiment, this mating is neither necessary nor required. In one non-mating embodiment, grasping efficiency may be increased by 64% using three features in the form of teeth. The presence of the features does not affect the tissue transection ability of the blade 804. In one embodiment, the blade 804 may comprise protrusions 806 along the entire active length of the blade 804. The protrusions 806 may be configured to trap tissue and prevent disengagement during activation. Various embodiments of protrusions 806 may include blade teeth, horizontal trenches, or cavities, as previously described.

FIGS. 14-18 illustrate various embodiments of ultrasonic blades comprising blade features is to address tissue milking. As previously discussed, tissue milking is defined as the event in which tissue begins to slip out of the jaws of an ultrasonic medical forceps having a movable jaw member and an ultrasonic blade upon device activation. This event increases the difficulty of manipulating tissue in low accessibility conditions. To address this and other issues, the present disclosure provides three embodiments to improve the grasping ability during ultrasonic activation. At least one embodiment of each of the disclosed ultrasonic blades employs repeated features across the active length of the blade. These features are designed to trap tissue and prevent disengagement during activation. Based on the testing, the following embodiments have shown between a 30% and 40% improvement in grasping force during activation over conventional ultrasonic blades. The three embodiments provide ultrasonic blade teeth geometries in the form of blade teeth, horizontal trenches, and holes (e.g., cavities) as described hereinbelow in connection with FIGS. 14-18 to prevent disengagement of tissue from the blade and clamp arm upon ultrasonic activation of the device and to improve tissue grasping ability prior to and during ultrasonic activation. In various embodiments, the ultrasonic blades comprise tissue trapping features to improve grasping ability and prevent tissue disengagement during ultrasonic activation of the blade.

Figure 14:
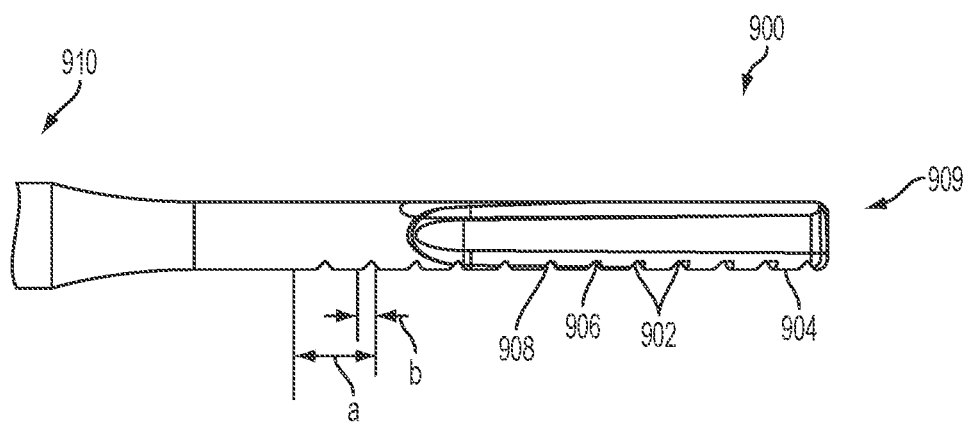
FIG. 14 is a side view illustrating one embodiment of an ultrasonic blade comprising tooth-like grasping features having triangular grooves formed on a grasping surface of the blade.
Figure 15:
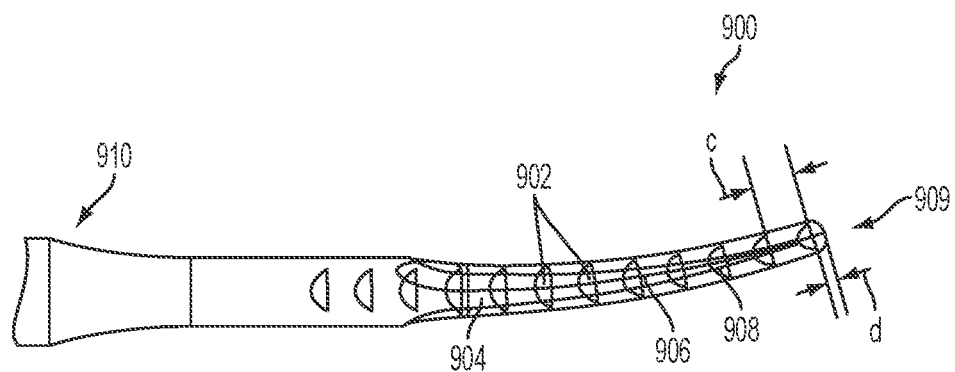
FIG. 15 is a top view of the ultrasonic blade shown in FIG. 14, according to one embodiment.

FIG. 14 is a side view illustrating one embodiment of an ultrasonic blade 900 comprising tooth-like grasping features 902 having triangular grooves formed on a grasping surface 904 of the blade 900. FIG. 15 is a top view of the ultrasonic blade 900 shown in FIG. 14. The blade 900 comprises a proximal end 910 and a distal end 909. The blade 900 comprises tissue trapping features 902 in the form of triangular grooves repeated along a portion of or the entire longitudinal length of the blade 900. A distal side 906 toward the distal end 909 of the blade 900 of each feature 902 may be a surface perpendicular to the longitudinal axis of the blade 900 followed by an angled surface 908 that tapers off in a proximal direction 910. In one embodiment, the features 902 may be characterized by dimensions a, b, c, and d. In one embodiment, dimension "a" represents the heights of the feature 902, which may be approximately 0.010", "b" represents the width of the feature 902, which may be approximately 0.020", "c" represents the distance between the features 902, which may be approximately 0.055", and "d" represents the distance from the most distal feature 902 to the distal 909 tip of the blade 900, which may be approximately 0.015". In one embodiment, the features 902 may be evenly spaced along the longitudinal length of the blade 900. In another embodiment, the triangular grooves grasping features 902 may be unevenly spaced along the longitudinal length of the blade 900. In the illustrated embodiment, the blade 900 comprises 12 evenly spaced triangular grooves grasping features 902 along the longitudinal length of the blade 900.

Figure 16:
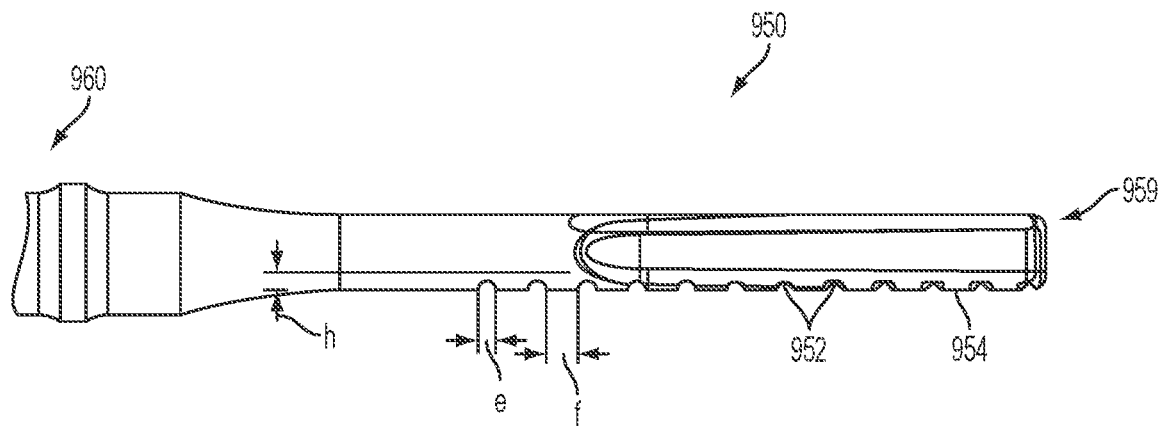
FIG. 16 is a side view illustrating one embodiment of an ultrasonic blade comprising tooth-like grasping features including horizontal trenches having repeated semicircular grooves formed on a grasping surface of the blade.
Figure 17:
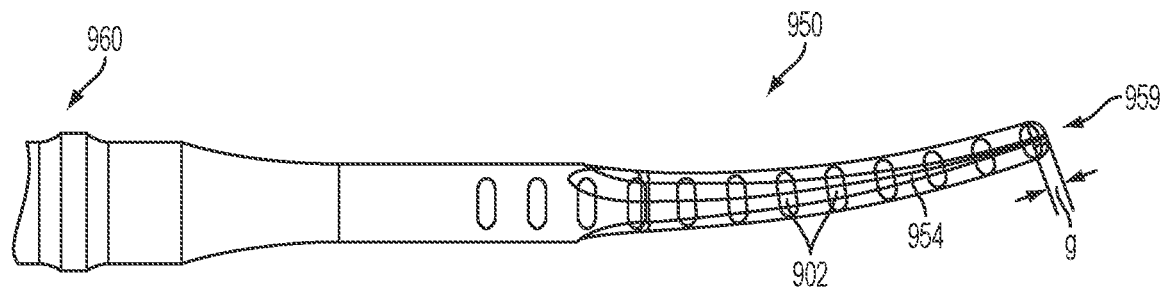
FIG. 17 is a top view of the ultrasonic blade shown in FIG. 16, according to one embodiment.

FIG. 16 is a side view illustrating one embodiment of an ultrasonic blade 950 with tooth-like grasping features 952 including horizontal trenches having repeated semicircular grooves formed on a grasping surface 954 of the blade 950. FIG. 17 is a top view of the ultrasonic blade 950 shown in FIG. 16. The blade 950 comprises a proximal end 960 and a distal end 959. The blade 950 comprises tissue trapping features 952 in the form of horizontal trenches having semicircular grooves repeated along the longitudinal length of the blade 950. In one embodiment, the features 952 may be characterized by dimensions e, f, g, and h. In one embodiment, dimension "e" represents the diameter of the grooves, which may be approximately 0.020", "f" represents the distance between each of the features 952, which may be approximately 0.057", "g" represents the distance from the most distal feature 952 to the distal 909 tip of the blade 950, which may be approximately 0.015", and "h" represents the depth of the grooves which may be approximately 0.005". In one embodiment, the features 952 may be evenly spaced along the longitudinal length of the blade 950. In another embodiment, the semicircular groove grasping features 952 may be unevenly spaced along the longitudinal length of the blade 950. In the illustrated embodiment, the blade 950 comprises 12 evenly spaced semicircular groove grasping features 952 along the longitudinal length of the blade 950.

Figure 18:
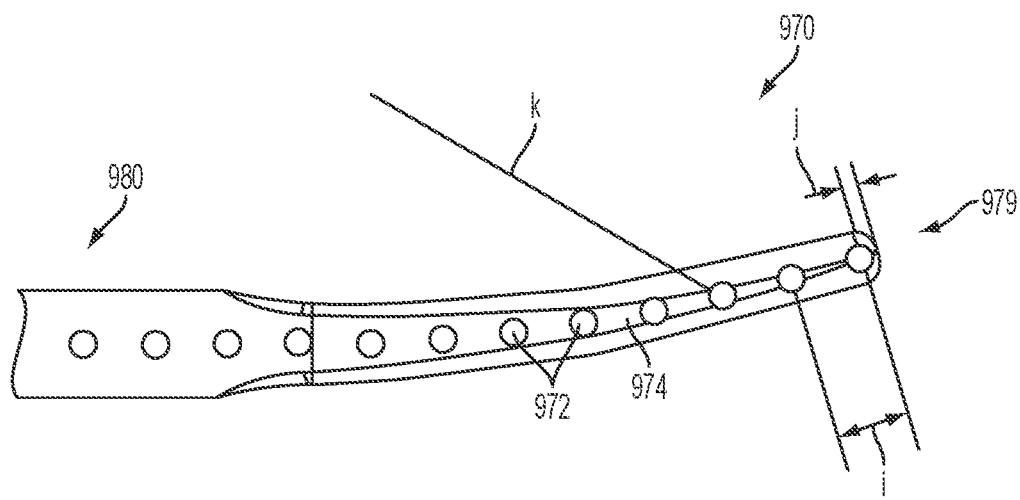
FIG. 18 is a top view illustrating one embodiment of an ultrasonic blade comprising grasping features including cavities formed on a grasping surface of the blade.

FIG. 18 is a top view illustrating one embodiment of an ultrasonic blade 970 comprising grasping features 972 including cavities or holes formed on a grasping surface 974 of the blade 970. The blade 970 comprises a proximal end 980 and a distal end 979. The blade 970 comprises tissue trapping features 972 in the form of circular elements repeated along the longitudinal length of the blade 970. In one embodiment, the features 972 may be characterized by dimensions i, j, and k. In one embodiment, dimension "k" represents the diameter of a circular element, which may be approximately 0.020", "i" represents the distance between each of the circular features 972, which may be approximately 0.057", and "j" represents the distance from the most distal feature 972' to the distal 979 tip of the blade 970, which may be approximately 0.015". In one embodiment, the circular features 972 may be evenly spaced along the longitudinal length of the blade 970. In another embodiment, the circular features 972 may be unevenly spaced along the longitudinal length of the blade 970. In the illustrated embodiment, the blade 970 comprises 12 evenly spaced circular grasping features 972 along the longitudinal length of the blade 970.

Ingress Prevention

The present disclosure describes various embodiments of devices to prevent surgical matter, such as fluid or tissue, for example, from entering the space between an ultrasonic blade and an inner tube distal of the blade's distal seal. Two main categories of embodiments are described. First, a pressure or energy source attached to the blade-tube subassembly prevents fluid or tissue ingress into the space between the blade and the inner tube. Second, a flexible membrane(s) attached to either the blade or the inner tube prevents fluid or tissue ingress.

Figure 32:
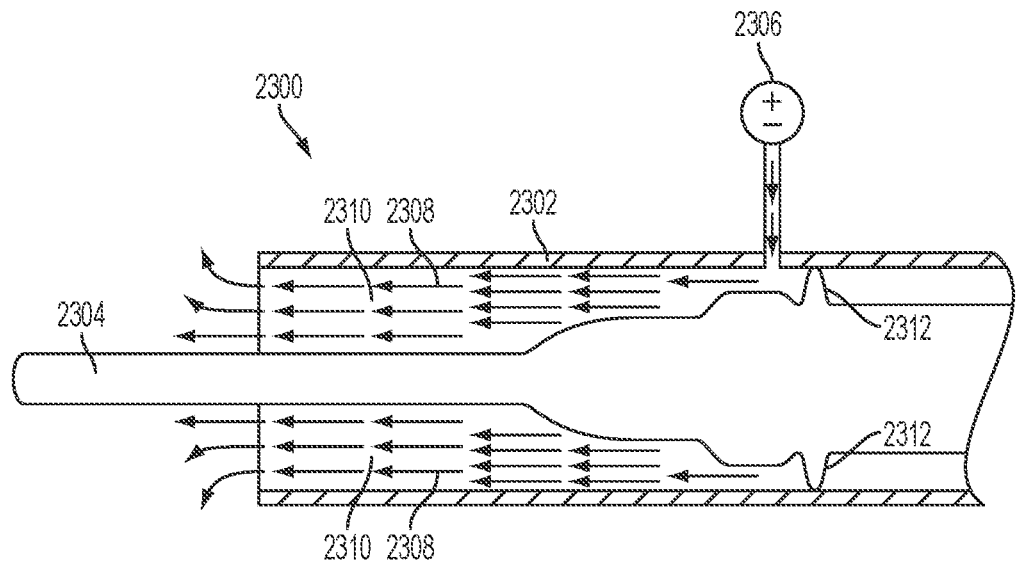
FIG. 32 illustrates one embodiment of a positive pressure fluid flow system to apply a positive pressure fluid flow between an outer tube and an ultrasonic blade at distal end thereof employing a pump or pump outlet located distal of a distal node.

In one embodiment, surgical matter in the form of fluid or tissue, for example, could be prevented from entering the distal inner tube area by the application of a constant pressure of a fluid medium (e.g., air, $CO_2$ or saline solution) in the distal direction. FIG. 32 illustrates one embodiment of a positive pressure fluid flow system 2300 comprising a pump and/or pump outlet 2306 located distal of the distal seal. In the illustrated embodiment, the external pump and/or pump outlet 2306 is fluidically coupled to the device distal of the distal node of an ultrasonic blade 2304. Air or other fluid medium 2308 is pumped into the space 2310 between the blade 2304 and the inner tube 2302, forcing particulates and/or bodily fluids out of that space 2310. As illustrated in FIG. 32, the pump and/or pump outlet 2306 is fluidically coupled to the space 2310 between the tube 2302 and the blade 2304 at a point distal from a distal blade seal 2312, e.g., an O-ring or overmolded seal. Thus, the positive pressure fluid flow 2308 is directed to the distal end of the device to prevent accumulation of surgical matter in the space 2310.

Figure 49:
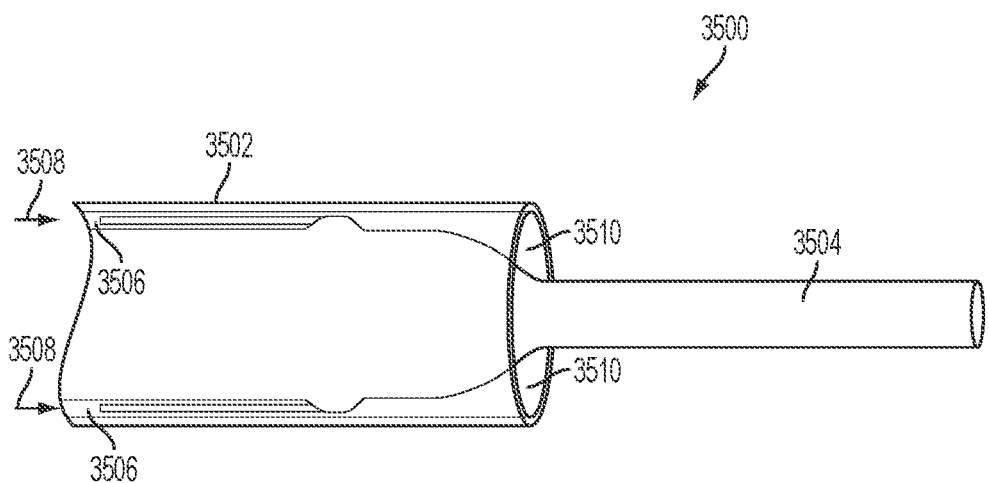
FIG. 49 illustrates one embodiment of a positive fluid pressure system in which air is pumped down the length of the inner tube.

FIG. 49 illustrates one embodiment of a positive fluid pressure system 3500 in which air 3508 is pumped down the length of the inner tube 3502 through space 3506. The air 3508 prevents surgical matter from entering the space 3510 between the ultrasonic blade 3504 and the inner tube 3502. FIG. 49 shows a similar concept to that shown in FIG. 32, but the distal node does not have a seal to the inner tube

3502. Rather, air 3508 is pumped down the full length of the inner tube 3502 to prevent fluid and/or tissue ingress.

Figure 26:
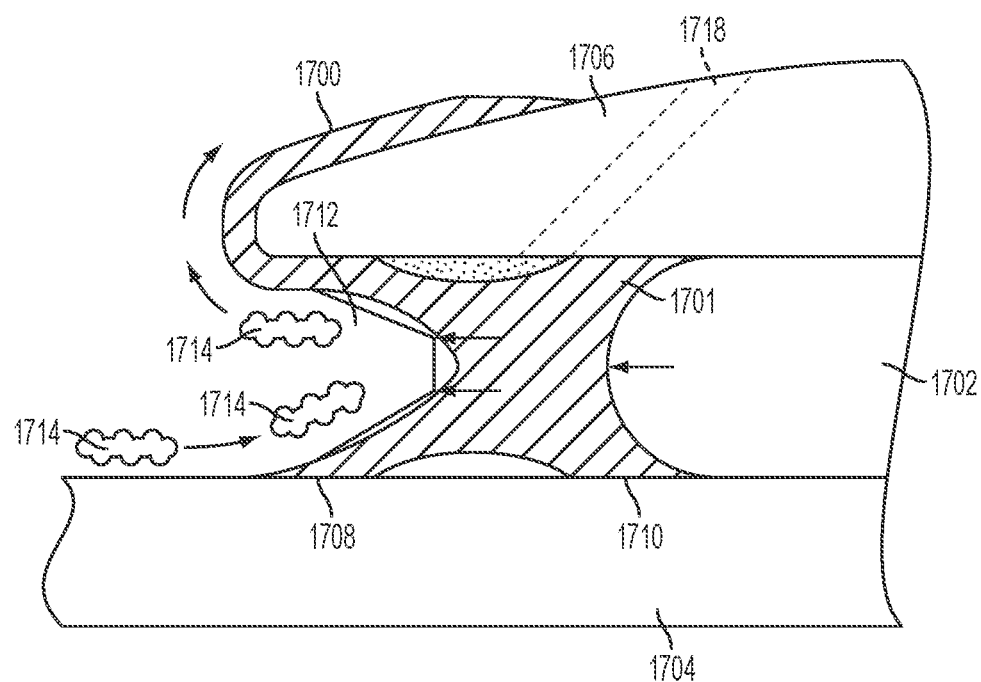
FIG. 26 illustrates one embodiment of a hybrid system comprising a contoured seal comprising a flexible membrane that acts as a pump to force surgical matter out of a distal inner tube area.

FIG. 26 illustrates one embodiment of a hybrid system comprising a contoured seal 1700 comprising a flexible membrane 1701 that acts as a pump to force surgical matter 1714 out of a distal tube 1706 area. The pressurized flexible membrane 1701 blocks tissue ingress by contact. The flexible membrane 1701 is attached to the inner tube 1706 and sealed to the ultrasonic blade 1704. Thus, the relative movement between the blade 1704 and the distal tube 1706 causes the flexible membrane 1701 to act in a pump-like manner to force fluids, tissue, or other surgical matter to flow along the contour of the flexible membrane 1701 and out of the inner tube 1706 area. The contoured seal 1700 seals a space 1702 between a portion of an ultrasonic blade 1704 and a tube 1706. The contoured seal 1700 has two points of contact 1708, 1710 with the ultrasonic blade 1704 to minimize friction and interference and to provide a double seal. A cavity 1712 is defined by the contoured seal 1700 for collecting surgical matter 1714. In an alternative embodiment, a separate duct 1718 may be provided to apply a positive pressure to the flexible membrane of the contoured seal 1700 to expel the surgical matter 1714 from the cavity 1712.

In various other embodiments, a boot barrier (or seal, for example) may be added to an end effector portion of an ultrasonic instrument to prevent the buildup of surgical matter on the end effector. The boot barrier seals the ultrasonic blade to the distal ends of one or more tube(s) near to the proximal end of the tissue effecting portion of the ultrasonic blade. The boot barrier may be made from any suitable materials including compliant, thermally robust material that has a relatively low coefficient of friction in order to minimize the seal load on the blade. Materials suitable for the boot barrier may include, for example, silicone rubber, parylene coated silicon rubber, Tetrafluoroethylene-hexafluoropropylene (FEP), which has similar properties to those of Polytetrafluoroethylene (PTFE) otherwise known in the trade as Teflon, shrink tubing, or any similar material. In another embodiment, the blade may be coated to reduce power draw of the instrument due to inclusion of the boot barrier.

The boot barrier seals to the blade and may provide slight interference to the blade. Where the boot barrier seals to the blade, the boot barrier does not provide vertical reaction for clamping/bending of the blade in order to keep the load on the blade (from the boot) minimized. The boot barrier may seal to the outer diameter of the tube(s), the inner diameter of the tube(s) or both. One or more retention features may be provided on the blade and/or the tube(s) for retaining the boot to the blade and/or the tube(s). In one embodiment, the retention features may also be located on the boot barrier itself.

Generally, the boot barrier prevents build up and accumulation of surgical matter such as, for example, tissue, blood, melted fat, and other related materials encountered during surgery, between the distal portion of the tube(s) and the nearby portion of the blade of the ultrasonic surgery device. This build up and accumulation may result in large and inconsistent mechanical loads on the system resulting in procedure interruptions due to high impedance either causing resonance issues or causing the system to bog down and potentially stop during activation. The tube(s) are needed to protect tissue and users from the ultrasonically active blade and, in the case of shears-type device, to support and/or drive a clamp arm. Ideally, the ultrasonic blade is as active (ultrasonically) as possible in the proximal portion of its tissue effecting length. Solutions that maximize this ultrasonic activity also elongate the portion of the blade between its most distal node and the proximal end its tissue effecting length. The result is a relatively large annular volume that accumulates tissue, blood, fat, etc. with the aforementioned issues.

Figure 19:
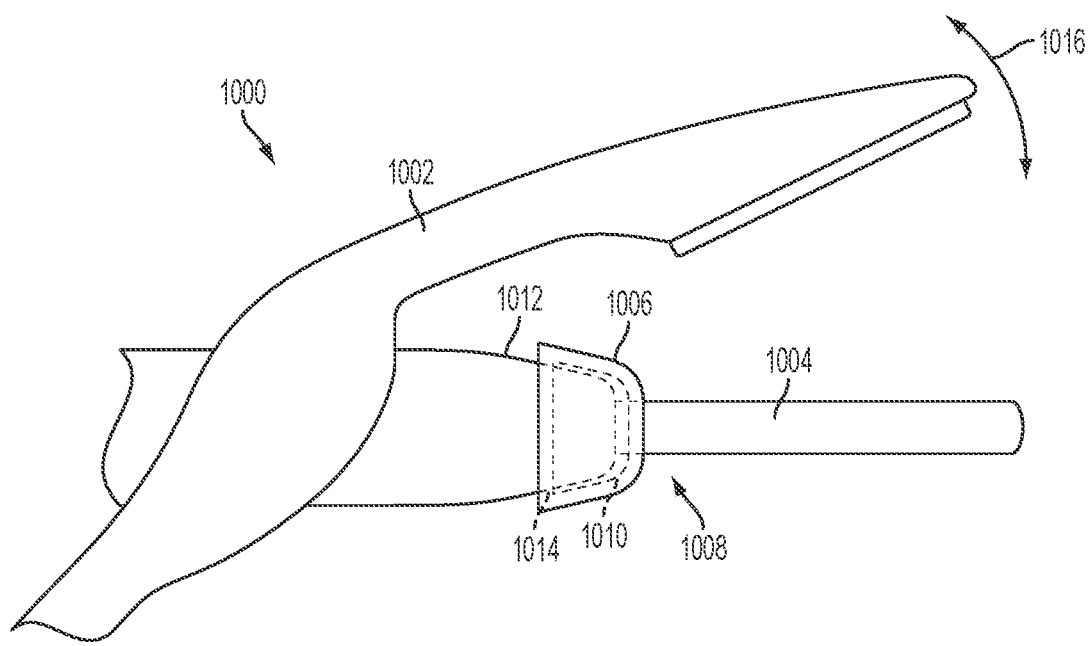
FIG. 19 illustrates one embodiment of an end effector assembly comprising a medical forceps having a movable jaw member and an ultrasonic blade with a flexible seal positioned over a proximal portion of the blade and a distal portion of a tube to seal the blade to an outer diameter of the tube.

FIG. 19 illustrates one embodiment of an end effector assembly 1000 comprising a medical forceps having a movable jaw member 1002 and an ultrasonic blade 1004. The jaw member 1002 is movable in direction 1016. A flexible boot barrier 1006 is positioned over a proximal portion 1008 of the blade 1004 and a distal portion of a tube 1010 to seal the blade 1004 to an outer diameter 1012 of the tube 1010. A retention feature 1014 may be provided on the outer diameter 1012 of the tube 1010 to keep the boot barrier 1006 in place. As previously discussed, the boot barrier 1006 may be made from silicone rubber or other similar materials. In one embodiment, the boot barrier 1006 may be coated with a lubricious material such as parylene, for example, to reduce friction. In an alternative embodiment, the blade 1104 may be coated with similar lubricious materials to reduce friction. Reducing friction between the blade 1004 and the boot barrier 1006 reduces power draw due to the inclusion of the boot barrier 1006.

Figure 20:
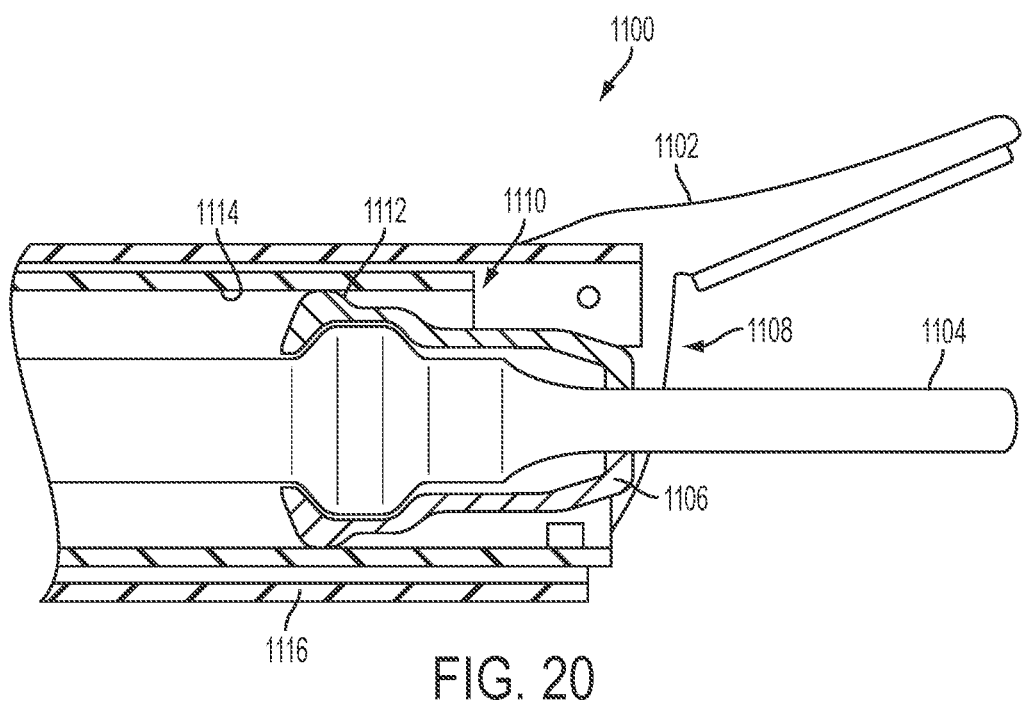
FIG. 20 illustrates one embodiment of an end effector assembly comprising a medical forceps having a movable jaw member and an ultrasonic blade with a flexible seal positioned over a proximal portion of the blade and within a distal portion of a tube to seal the blade to an inner diameter of the tube.

FIG. 20 illustrates one embodiment of an end effector assembly 1100 comprising a medical forceps having a movable jaw member 1102 and an ultrasonic blade 1104. A flexible seal 1106 positioned over a proximal portion 1108 of the blade 1104 and within a distal portion 1110 of an inner tube 1112 to seal the blade 1104 to an inner diameter 1114 of the inner tube 1112. The inner tube 1112 is slidably movable within an outer tube 1116.

Figure 21:
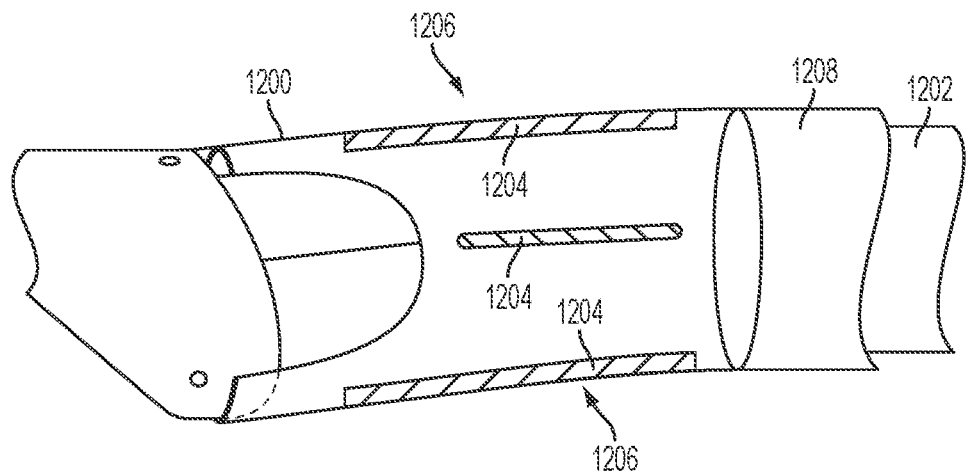
FIG. 21 illustrates one embodiment of a slotted inner tube to conceal a lengthwise portion of an ultrasonic blade where the slots provide fluid egress to discharge surgical matter that may accumulate in a space between the blade and the inner tube.
Figure 22:
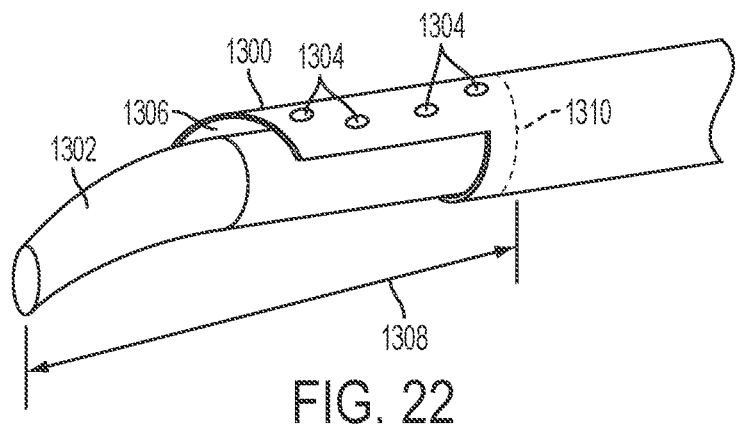
FIG. 22 illustrates one embodiment of a perforated mutilated inner tube to conceal a lengthwise portion of an ultrasonic blade where the perforations provide fluid egress to discharge surgical matter that may accumulate in a space between the blade and the inner tube.

FIG. 21 illustrates one embodiment of a slotted inner tube 1200 to conceal a lengthwise portion of an ultrasonic blade 1202. Slots 1204 provide fluid/tissue egress to discharge surgical matter that may accumulate in a space 1206 between the blade 1202 and the inner tube 1200. Fluid/tissue egress through the slots 1204 at the distal end of an ultrasonic device prevents the accumulation of surgical matter. In ultrasonic laparoscopic shears, for example, an overmolded silicone distal seal 1208 is provided on or near the distal node of the blade 1202. A boot barrier may be overmolded, positioned just distal to the clamp arm edge, which could prevent tissue pinching, and anchored to the inner tube 1200, or positioned within the inner tube 1200 and non-visible to the user as shown in FIG. 22, for example. In these devices, there is approximately 13 mm length of the blade 1202 that is concealed by the outer tube (not shown) and the inner tube 1200 before the distal seal 1208 is present. Surgical matter, such as fluid, blood, fat, or other tissue, can become lodged in that space between the outer diameter of the blade 1202 and the inner diameter of the inner tube 1200. In other instruments comprising similar shears, the length of exposed blade may increase thus increasing the chance of tissue lodging therein. This could result in increased transection times as the fluid/tissue becomes a heat sink or in relaxed pressure on the blade if the fluid/tissue hardens from applied blade heat. Additionally, if an RF modality is to be added to ultrasonic lap shears technology, tissue and fluid could cause a short circuit if the RF energy is allowed to flow from the blade through tissue that is inside the inner tube, rather than the desired energy path along the active (exposed) length of the blade. Thus a boot or distal tissue ingress prevention method or mechanism is provided as described herein below in connection with FIGS. 21-23 where surgical matter such as fluid or tissue is expelled from between the inner tube 1200 and the blade 1202 by slots 1204, windows, apertures, or perforations formed in the inner tube 1200.

FIG. 22 illustrates one embodiment of a perforated inner tube 1300 to conceal a lengthwise portion of an ultrasonic blade 1302. The inner tube 1300 is perforated with holes 1304 to allow surgical matter such as fluids/tissue to escape. The perforations 1304 provide fluid/tissue egress to discharge surgical matter that may accumulate in a space 1306 between the blade 1302 and the inner tube 1300. In the illustrated embodiment, the inner tube 1300 comprises a 180° half circle and is perforated with holes 1304 to allow fluids/tissue to escape. The tube 1300 is located between the active blade 1302 and the distal most overmold 1310 portion, which is located a distance 1308 from the distal tip of the blade 1302.

Figure 23:
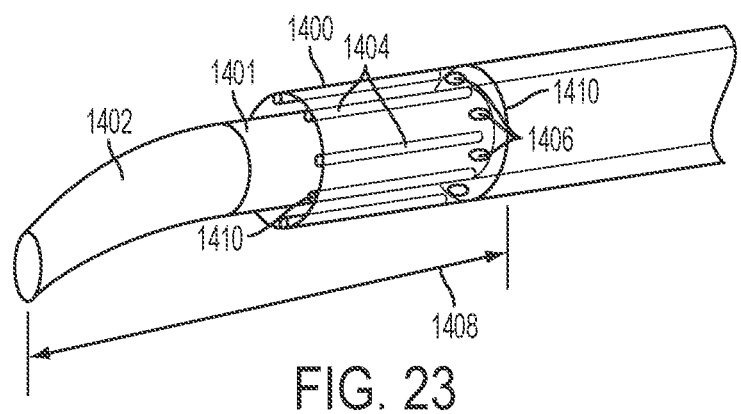
FIG. 23 illustrates one embodiment of a fluid-directing ribbed and perforated inner tube to conceal a lengthwise portion of an ultrasonic blade where the fluid-directing ribs and perforations provide fluid egress to discharge surgical matter that may accumulate in a space between the blade and the inner tube.

FIG. 23 illustrates one embodiment of a fluid-directing ribbed and perforated inner tube 1400 to conceal a lengthwise portion 1401 of an ultrasonic blade 1402. Fluid-directing ribs 1404 perforations 1406 provide fluid egress to discharge surgical matter that may accumulate in a space 1410 between the blade 1402 and the inner tube 1400. The distal most overmold is located at a distance 1408 from the distal tip of the blade 1402. In the illustrated embodiment, the ribs 1404 radiate inward and comprise holes 1406 located between each rib. The ribs 1404 have a clearance with respect to the blade 1402. The spacing of the ribs 1404 is such that only fluids can pass, not solids of appreciable size. The channeling configuration raises fluid velocity and raises likelihood of clearing out of holes 1406.

Figure 24:
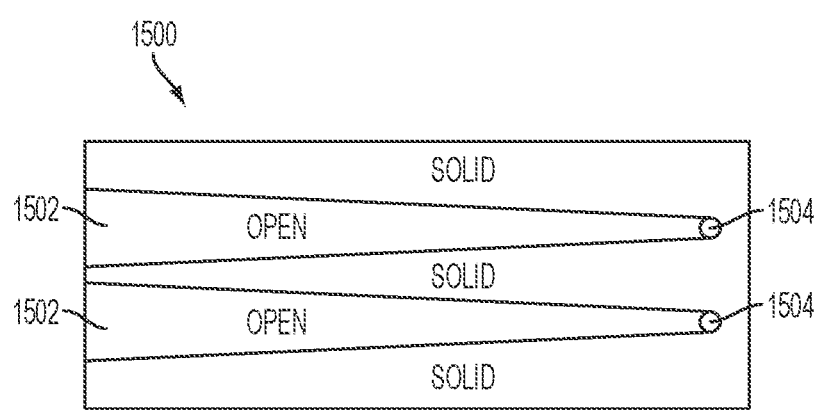
FIG. 24 is one embodiment of a fluid-directing ribbed and perforated inner tube comprising converging ducts

FIG. 24 is one embodiment of a fluid-directing ribbed and perforated inner tube 1500 comprising converging ducts 1502. In one embodiment, the converging ducts 1502 are fluidically coupled to apertures 1504 to provide fluid egress to discharge surgical matter.

Figure 25:
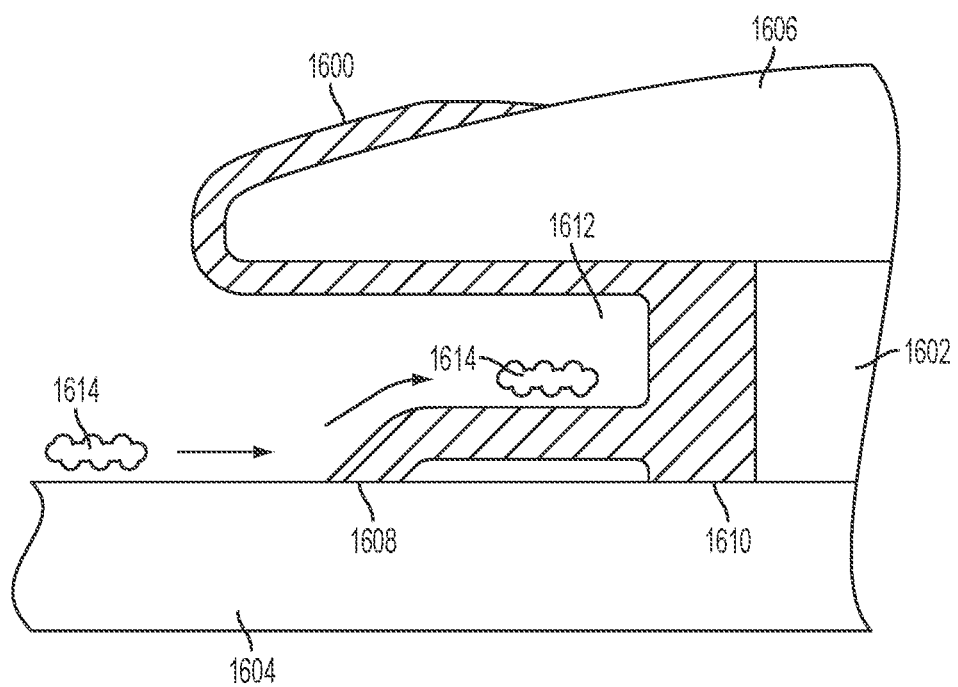
FIG. 25 illustrates one embodiment of a contoured seal to seal a space between a portion of an ultrasonic blade and an outer tube, where the flexible seal having two points of contact and defining a cavity for collecting surgical matter.

FIG. 25 illustrates one embodiment of a contoured seal 1600 to seal a space 1602 between a portion of an ultrasonic blade 1604 distal to the distal seal and a tube 1606. The contoured flexible seal 1600 has two points of contact 1608, 1610 with the ultrasonic blade 1604 to minimize friction and interference and to provide a double seal. A cavity 1612 is defined by the contoured flexible seal 1600 for collecting surgical matter 1614.

Figure 27:
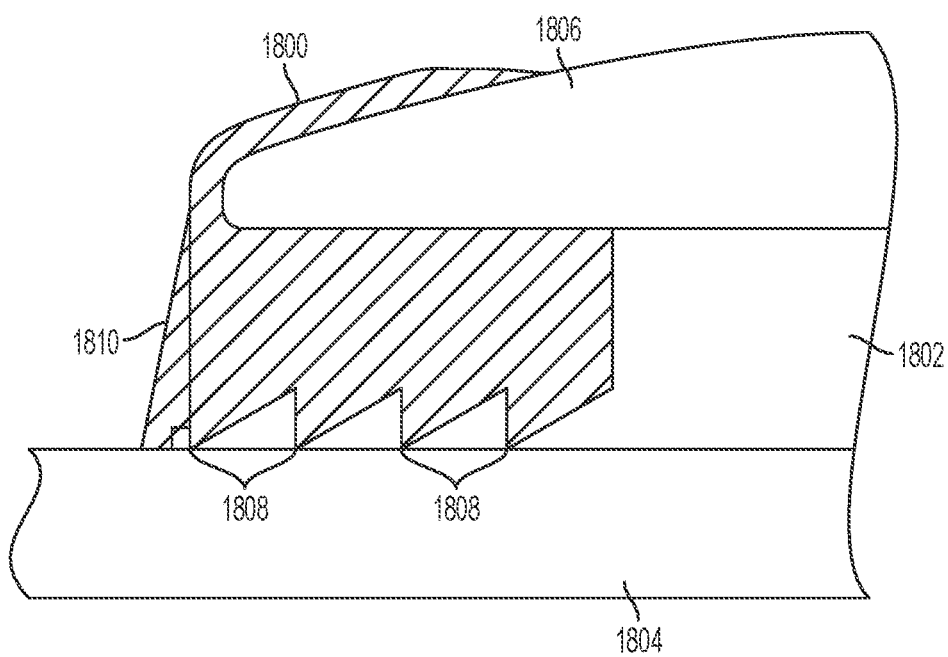
FIG. 27 illustrates one embodiment of a seal to seal a space between a portion of an ultrasonic blade and the tube, the flexible seal multiple points of contact and a low interference point of contact.

FIG. 27 illustrates one embodiment of a seal 1800 to seal a space 1802 between a portion of an ultrasonic blade 1804 distal to the distal seal and a tube 1806. The flexible seal 1800 has multiple points of contact 1808 to provide low interference point of contact between the seal 1800 and the blade 1804. The multiple points of contact 1808 reduce fluid wicking up the shaft of the blade 1804. A nose portion 1810 of the seal 1800 and the multiple points of contact 1808 block surgical matter from entering into the space 1802 between the blade 1804 and the tube 1806.

Figure 28:
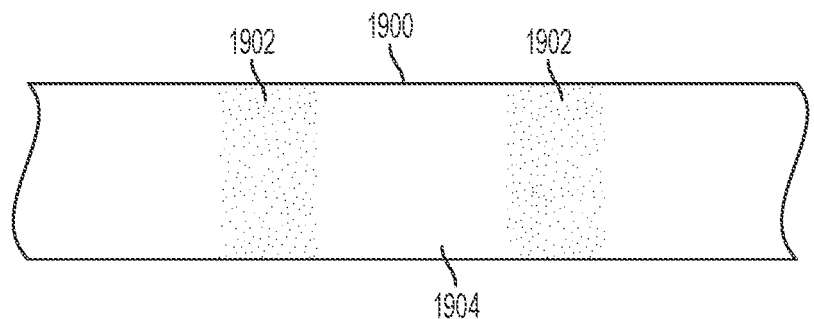
FIG. 28 illustrates etched areas formed on an outer surface of an ultrasonic blade to prevent tissue ingress, according to one embodiment.

FIG. 28 illustrates etched areas 1902 formed on an outer surface 1904 of an ultrasonic blade 1900 to prevent fluid/tissue ingress along the blade due to blade vibration.

Figure 29:
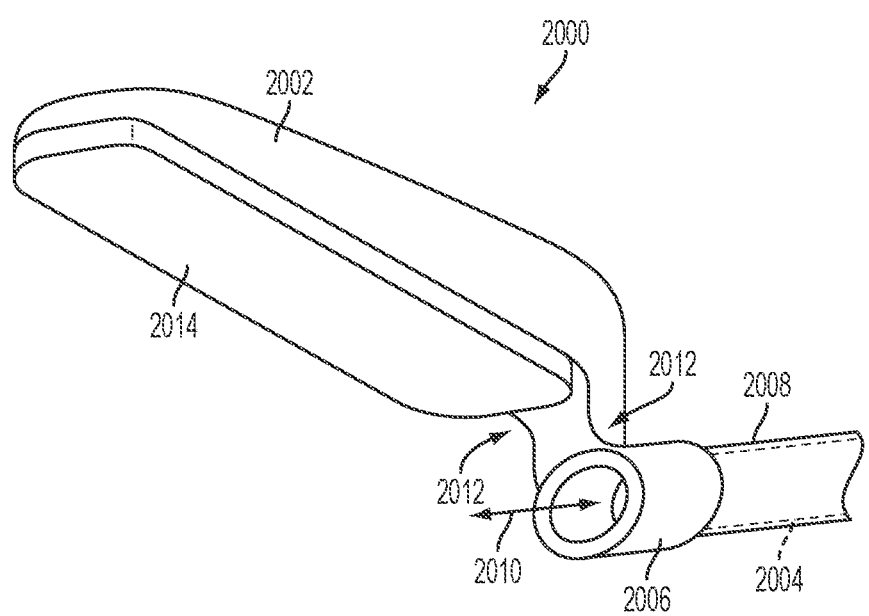
FIG. 29 illustrates one embodiment of an end effector assembly comprising a medical forceps having a movable jaw member and a slidable ultrasonic blade partially retracted within a tube.

FIG. 29 illustrates one embodiment of an end effector assembly 2000 comprising a medical forceps having a movable jaw 2002 member and a slidable ultrasonic blade 2004 partially retracted within a seal 2006. The movable jaw member 2002 comprises a clamp pad 2014 having a living hinge formed by necked down regions 2012 at the interface of the clamp pad 2014 and the seal 2006. The blade 2004 is slidable in direction 2010 and is received within the seal 2006. The seal 2006 is coupled to an inner tube 2008 to seal the blade 2004 to the tube 2008 and prevent fluid/tissue migration proximally.

Figure 30:
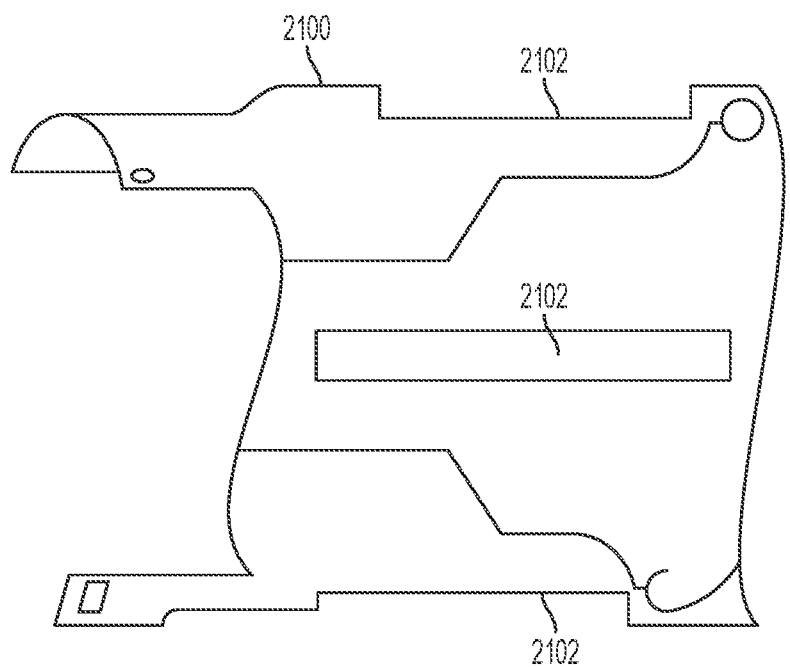
FIG. 30 illustrates one embodiment of an inner tube having machined windows formed therein to allow drainage between the inner and outer tubes.

FIG. 30 illustrates one embodiment of an inner tube 2100 having machined windows 2102 formed therein. The windows 2102 allow drainage between the inner 2100 and an outer tube. This embodiment may be an alternative to the embodiment show in FIG. 21, for example.

Figure 31:
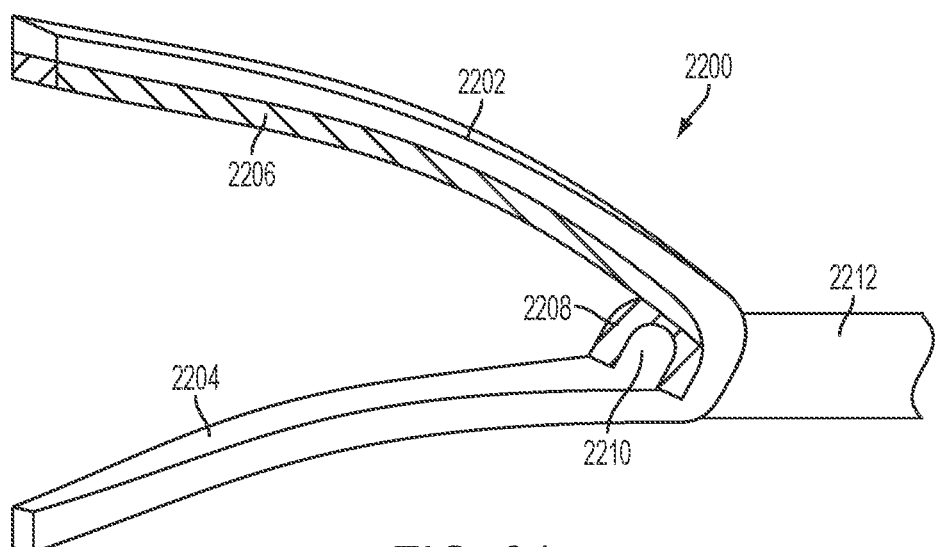
FIG. 31 illustrates one embodiment of an end effector assembly comprising a medical forceps having a movable jaw member and an ultrasonic blade where the movable jaw member includes a pad with a tissue stop to deflect surgical matter where the tissue stop portion is contoured to the movable jaw member to cover an opening of the inner tube.

FIG. 31 illustrates one embodiment of an end effector assembly 2200 comprising a medical forceps having a movable jaw member 2202 and an ultrasonic blade 2204. The movable jaw member 2202 comprises an extended clamp arm pad 2206 that follows the contour of the movable jaw member 2202 (e.g., clamp arm) into the space around the blade 2204 to cover the opening of the inner tube with a tissue stop element 2208. The tissue stop element 2208 deflects surgical matter and prevents it from entering the space between the blade 2204 and the inner tube 2212. The tissue stop element 2208 is contoured to the movable jaw member 2202 to cover an opening 2210 of the inner tube 2212. In one embodiment, the clamp arm pad 2206 is machined with the tissue stop 2208 element to provide minimal interference between the blade 2204 and the tube 2212. The pad 2206 and/or the tissue stop element 2208 may be made of a lubricious material such as Teflon to minimize the load on the blade 2204.

Figure 38:
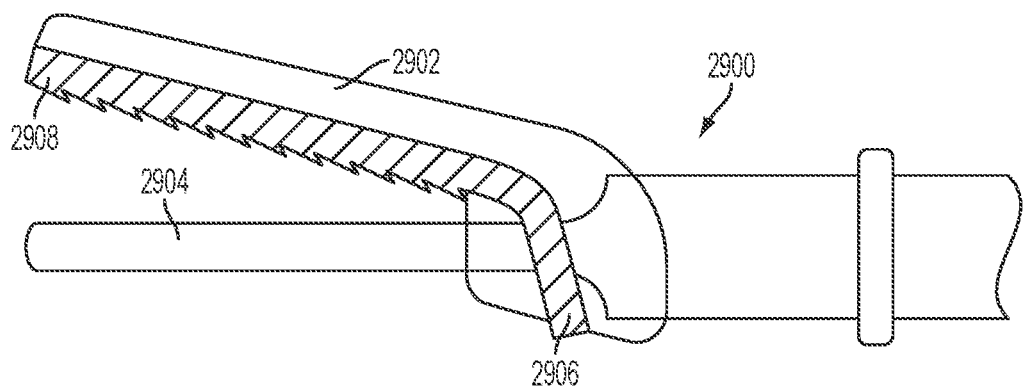
FIG. 38 illustrates one embodiment of an end effector assembly comprising a medical forceps having a movable jaw member and an ultrasonic blade where the movable jaw member comprises a deflector pad to deflect surgical matter.

FIG. 38 illustrates one embodiment of an end effector assembly 2900 comprising a medical forceps having a movable jaw member 2902 and an ultrasonic blade 2904. The movable jaw member 2902 comprises a clamp arm pad 2908 having a deflector pad 2906 to deflect surgical matter.

Figure 39:
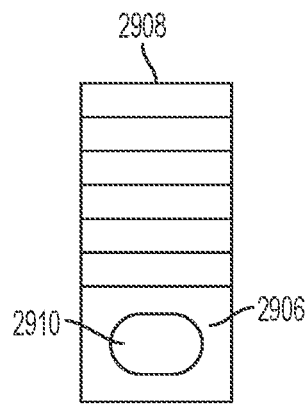
FIG. 39 is a front view of the deflector pad shown in FIG. 38, according to one embodiment.

FIG. 39 is a front view of the clamp arm pad 2908 and deflector pad 2906 shown in FIG. 38. An aperture 2910 is provided in the deflector pad 2906 to receive the ultrasonic blade 2904 therethrough.

Figure 33:
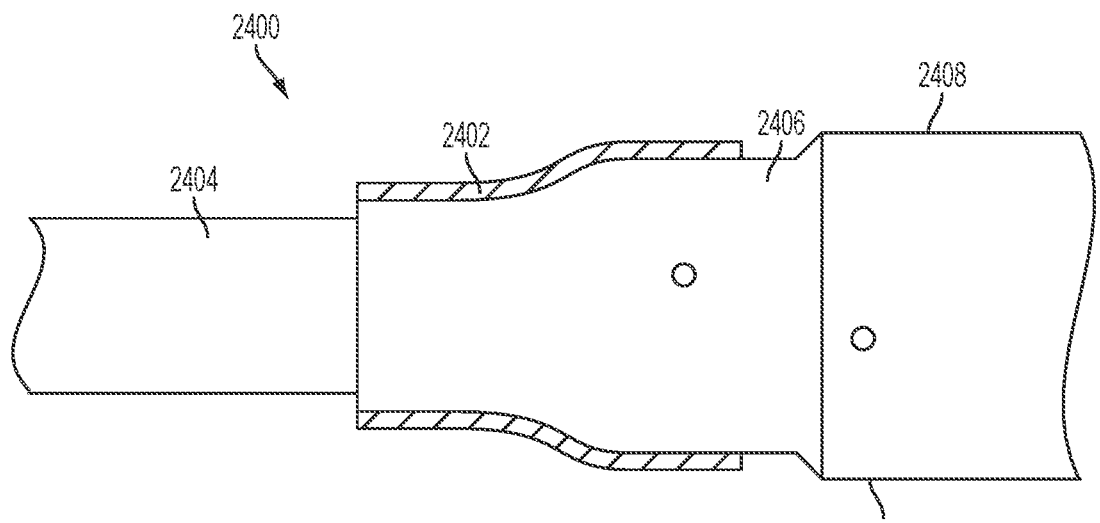
FIG. 33 illustrates a portion of an end effector assembly comprising an ultrasonic blade including one embodiment of a flexible seal to seal the ultrasonic blade to a tube at a distal node, according to one embodiment.

FIG. 33 illustrates a portion of an end effector assembly 2400 comprising an ultrasonic blade 2404 including one embodiment of a boot barrier 2402 to seal the ultrasonic blade 2404 to a tube 2406 distal to the distal node 2410 of the blade. In one embodiment, the boot barrier 2402 seals the blade 2404 to an inner tube 2406 which is disposed within an outer tube 2408. In the embodiment illustrate din FIG. 33, the boot barrier 2402 may be formed of FEP to cover high stress regions of the blade 2404. In the illustrated embodiment, the outer tube 2408 ends at a blade distal node 2410.

Figure 34:
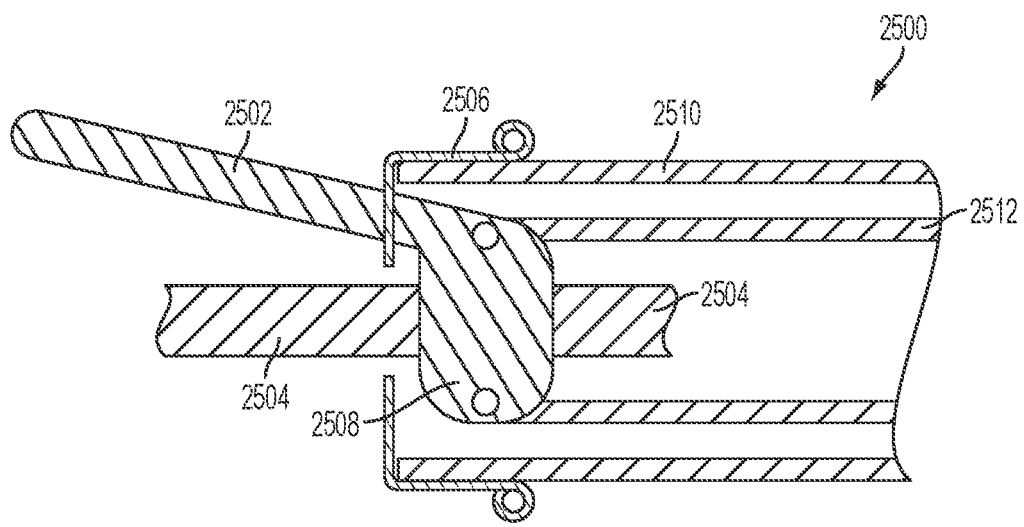
FIG. 34 illustrates one embodiment of an end effector assembly comprising a medical forceps having a movable jaw member and an ultrasonic blade including a flexible seal positioned distal to an edge of the movable jaw member and anchored to a tube to prevent tissue pinching.

FIG. 34 illustrates one embodiment of an end effector assembly 2500 comprising a medical forceps having a movable jaw member 2502 and an ultrasonic blade 2504 including a flexible seal 2506 positioned distal to an edge 2508 of the movable jaw member 2502 and anchored to an outer tube 2510 to prevent tissue pinching. An inner tube 2512 is positioned within the outer tube 2510. The blade 2504 is positioned within the inner tube 2512.

Figure 35:
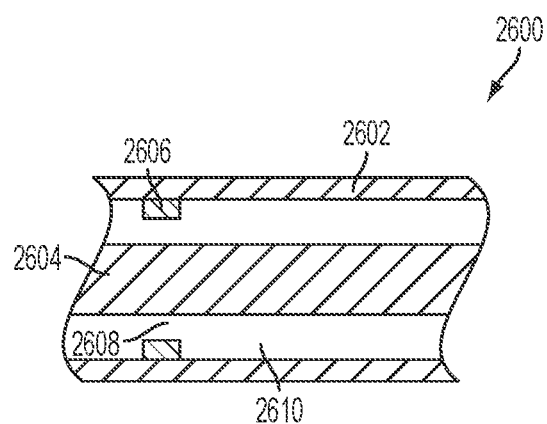
FIG. 35 illustrates one embodiment of a seal positioned within an inner tube and an ultrasonic blade positioned within the inner tube.

FIG. 35 illustrates one embodiment of an end effector assembly 2600 comprising a seal 2606 positioned within an inner tube 2602 and an ultrasonic blade 2604 positioned within the inner tube 2602 such that it is non-visible to the user. The seal 2602 may either be a low friction material to minimize load on the blade 2604 or a small clearance 2608 may be provided between the seal 2606 and the blade 2604 to prevent contact with the blade. The seal 2606 seals the space 2610 defined between the blade 2604 distal to the distal seal and an inner diameter of the inner tube 2602 to prevent the accumulation of surgical matter therein.

Figure 36:
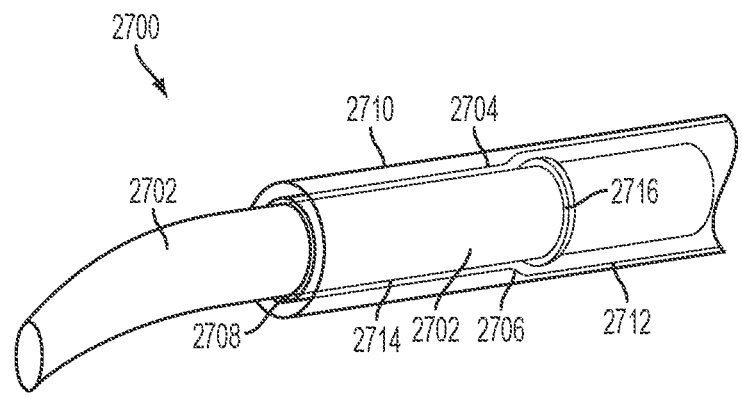
FIG. 36 illustrates one embodiment of a seal mechanism for an ultrasonic blade having a tapered inner tube portion distal to the last seal where the inner tube necks down to a smaller diameter at a distal end defining a reduce entry space for surgical matter.

FIG. 36 illustrates one embodiment of a seal mechanism 2700 for an ultrasonic blade 2702 having a tapered inner tube 2704 portion distal to the blade distal seal 2716 where the inner tube 2704 necks down 2706 to a smaller diameter at a distal end defining a reduced entry space 2708 for surgical matter. A conventional outer tube 2710 is provided over the tapered inner tube 2704. The diameter of the inner tube portion 2712 proximal to the necked down region 2706 is greater than the diameter of the inner tube portion 2714 distal to the necked down region 2706. In one embodiment, the necked down region 2706 coincides with the location just distal to the distal-most overmold 2716. In one embodiment, the inner tube 2704 may be necked down for a portion distal to the distal-most seal, to provide less open space for fluids and solids to enter.

Figure 37:
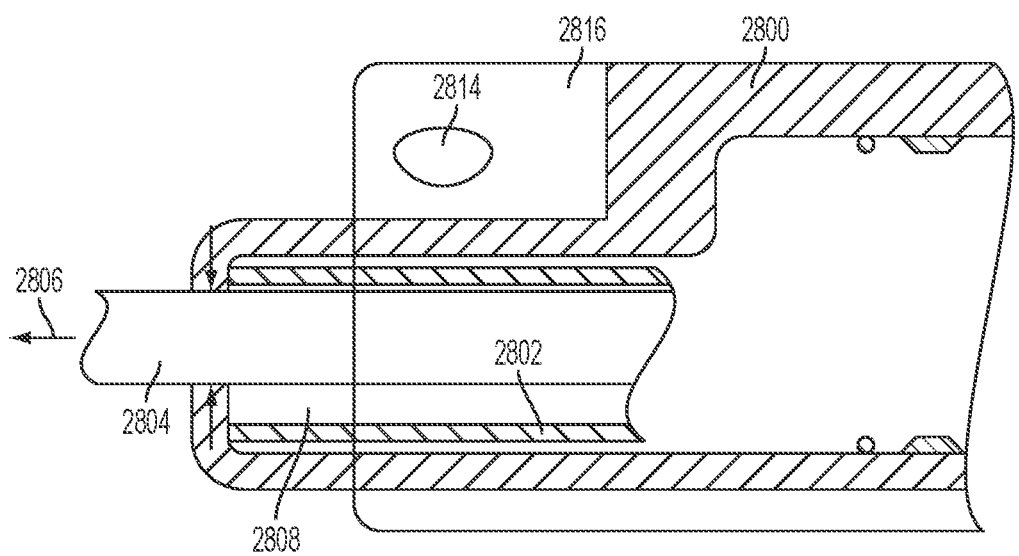
FIG. 37 illustrates one embodiment of an overmolded flexible seal located over an inner tube that an ultrasonic blade punctures through during assembly.

FIG. 37 illustrates one embodiment of an overmolded flexible seal 2800 located over an inner tube 2802 that an ultrasonic blade 2804 punctures through during assembly. As shown, as the blade 2804 is moved distally in direction 2806 during device assembly, the blade 2804 breaks through the overmolded flexible seal 2800 to seal the space 2808 between the blade 2804 and the inner tube 2802. A clamp arm pivot hole 2814 in the outer tube distal clevis 2816 enables a movable jaw member to open and close. An outer tube distal clevis 2816 is located on a distal end of an outer tube. In one embodiment, the clevis 2816 can be welded on the distal end of the outer tube.

Figure 40:
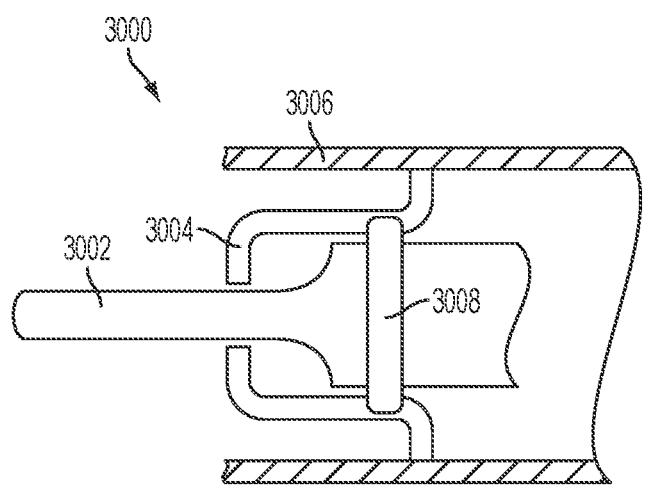
FIG. 40 illustrates one embodiment of a seal system for an ultrasonic blade.

FIG. 40 illustrates one embodiment of a seal system 3000 for an ultrasonic blade 3002. A flexible seal 3004 seals the ultrasonic blade 3002 distal to a distal seal portion 3008. In one embodiment, the flexible seal 3004 seals the blade 3002 to the inner diameter of the inner tube 3006.

Figure 41:
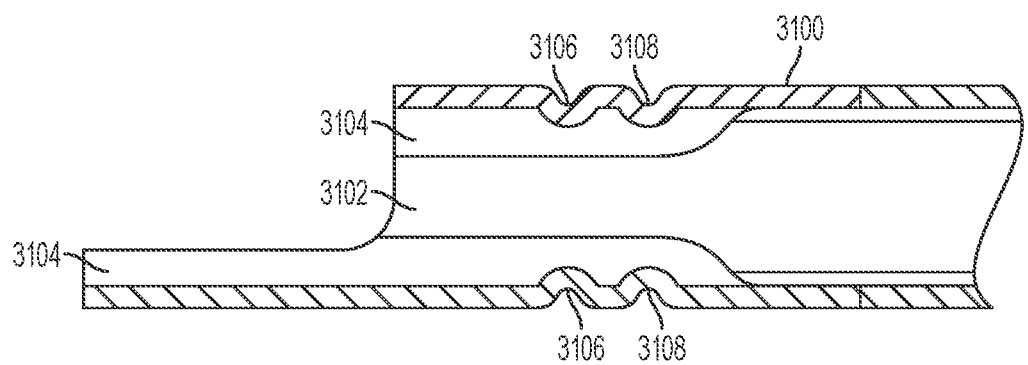
FIG. 41 illustrates one embodiment of a contoured inner tube or component that attaches to an inner tube to provide a circuitous path for fluid.

FIG. 41 illustrates one embodiment of a contoured inner tube 3102 or component that attaches to an inner tube 3100 to provide a circuitous path 3104 for fluid. An area of the inner tube 3100 comprises a locally swaged pair of grooves 3106, 3108 that may be employed to locate an O-ring that would touch the blade or provide a circuitous path to prevent ingress of fluids during use.

Figure 42:
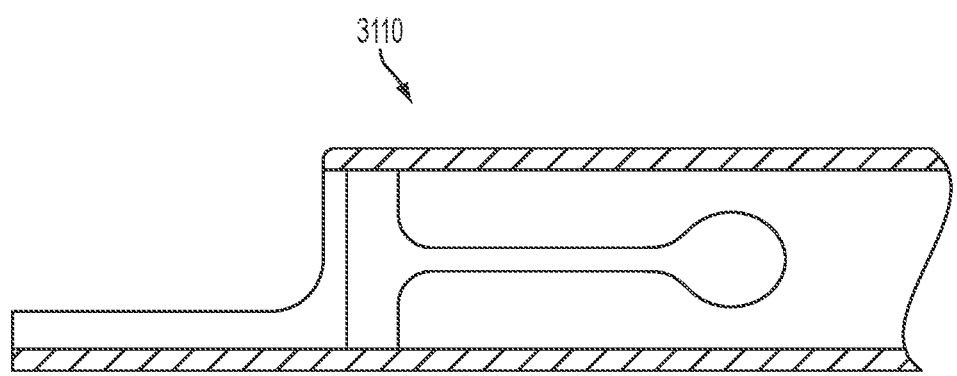
FIG. 42 illustrates one embodiment of a molded component with compliant arms that serve to block the distal opening of a tube assembly and is attached via the arms going around a pin in the blade at a node location.

FIG. 42 illustrates one embodiment of a molded component 3110 with compliant arms that serves to block the distal opening of a tube assembly and is attached via arms going around a pin in the blade at a node location.

Figure 43:
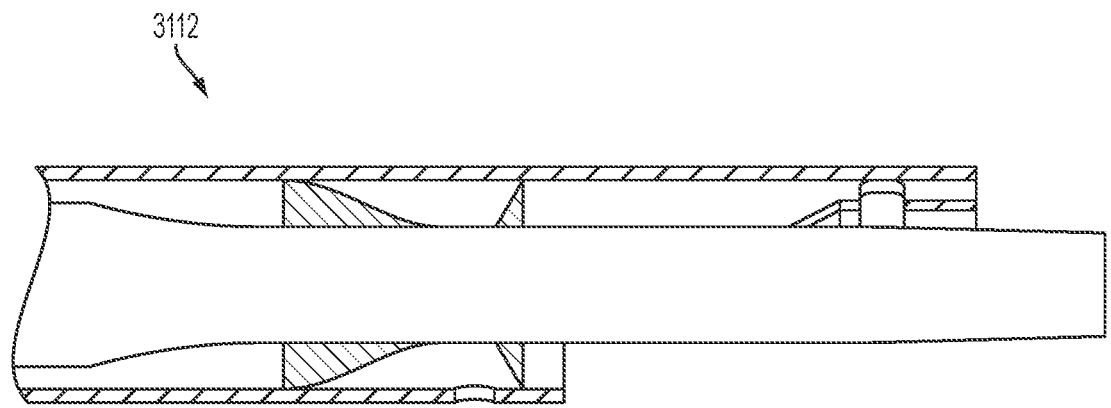
FIG. 43 illustrates one embodiment of an overmolded silicone bumper that adheres to the inside of an inner tube.
Figure 44:
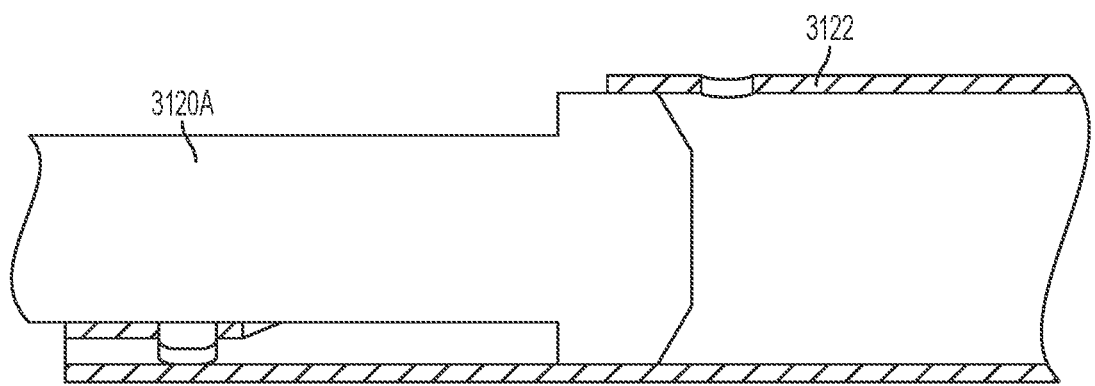
FIGS. 44-47 illustrate one embodiment of how a pair of mandrels can be inserted into an inner tube from both ends to form the overmolded bumper in FIG. 43.
Figure 45:
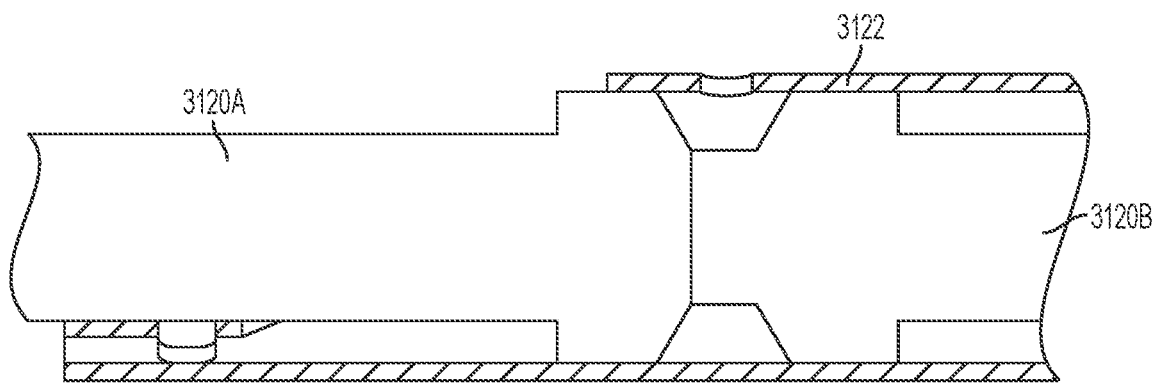
Figure 46:
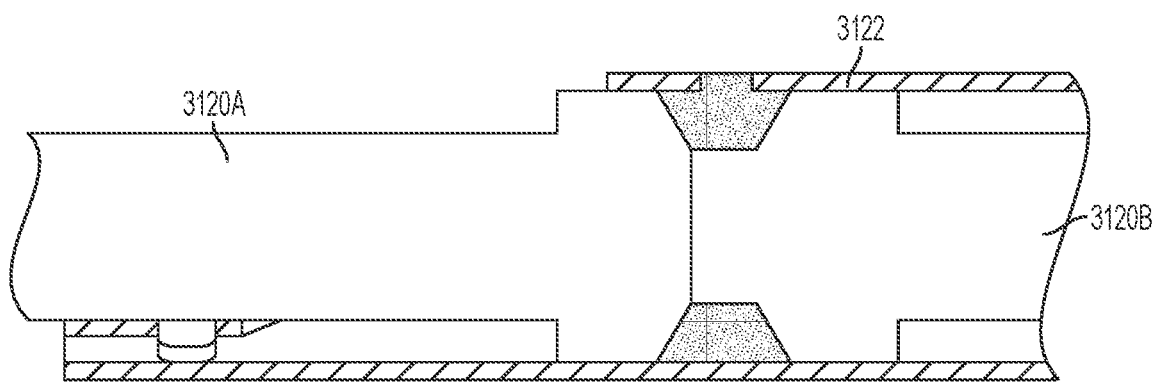
Figure 47:
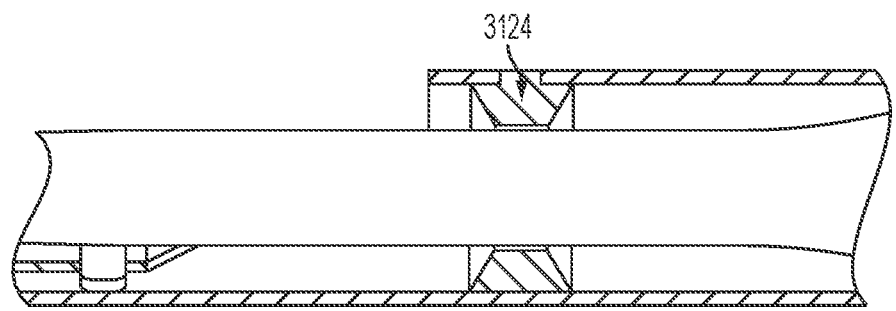

FIG. 43 illustrates one embodiment of an overmolded silicone bumper 3112 that adheres to the inside of an inner tube. The bumper 3112 prevents fluid ingress and does not nominally touch the blade so there is no increase in blade loading during use.

FIGS. 44-47 illustrate one embodiment of how a pair of mandrels 3120A, 3120B can be inserted into an inner 3122 tube from both ends. The mandrels 3120A, 3120B combine to form an overmold channel into which the silicone (or equivalent) bumper 3124 material would be injected. The mandrels would then be removed leaving just the bumper 3124.

Figure 48:
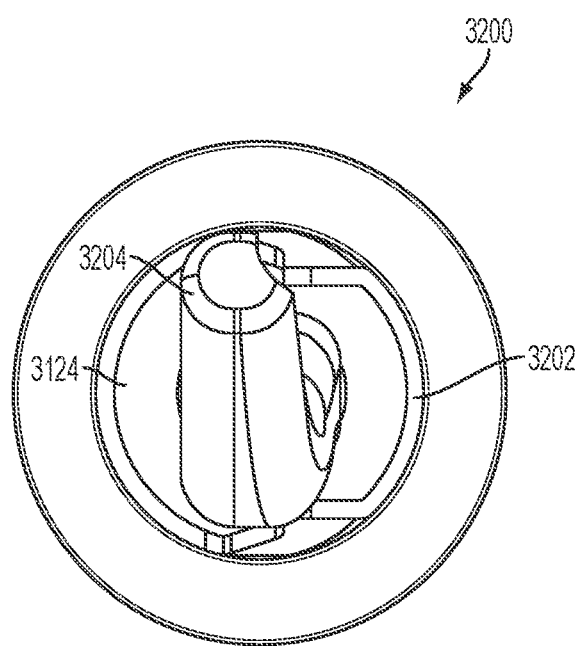
FIG. 48 illustrates one embodiment of an overmolded material affixed to an inner tube that does not seal to the ultrasonic blade.

FIG. 48 illustrates an end view of a seal system 3200 comprising an overmolded bumper 3124 affixed to an inner tube 3202 that does not seal to an ultrasonic blade 3204. In the illustrated embodiment, the seal system 3200 is an end view of the tube assembly shown in FIG. 47 with the molded bumper 3124 in place.

Figure 50:
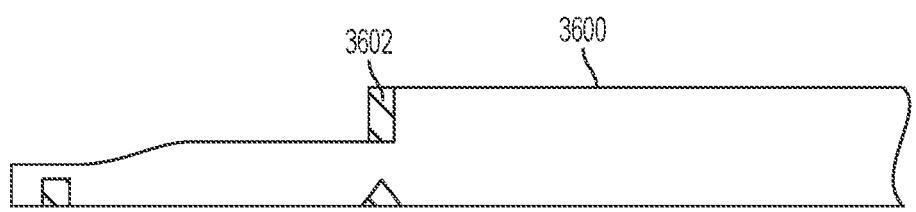
FIG. 50 illustrates one embodiment of an inner tube having a silicone seal attached thereto at minimal interference with ultrasonic blade.

FIG. 50 illustrates one embodiment of an inner tube 3600 comprising having a silicone seal 3602 attached thereto at minimal interference with an ultrasonic blade.

Figure 51:
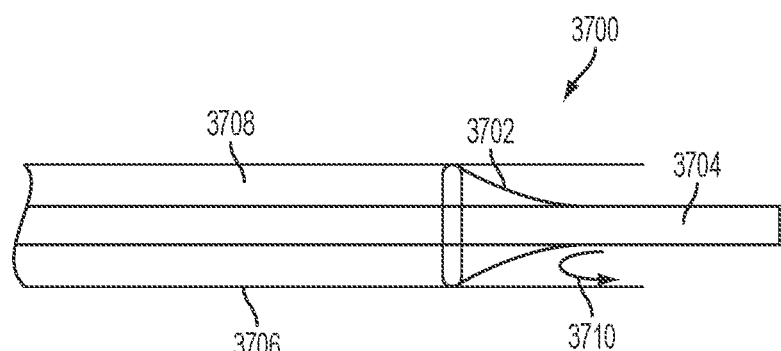
FIG. 51 illustrates one embodiment of seal system for sealing an ultrasonic blade to a tube.

FIG. 51 illustrates one embodiment of seal system 3700 for sealing an ultrasonic blade 3704 to a tube 3706. In the illustrated embodiment, the sealing system 3700 comprises a funnel 3702 to prevent ingress of surgical matter in the space 3708 between the blade 3704 distal to the distal node and the inner tube 3706. The funnel 3702 deflects surgical matter distally 3710.

Figure 52:
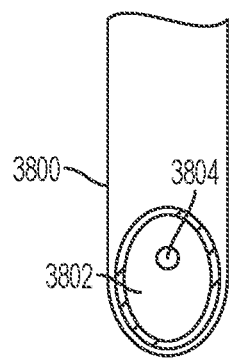
FIG. 52 illustrates one embodiment of a flexible seal located over an inner tube that an ultrasonic blade punctures through during assembly.

FIG. 52 illustrates one embodiment of a flexible seal 3802 located over an inner tube 3800 that an ultrasonic blade punctures through and dilates at location 3804 during assembly.

Figure 53:
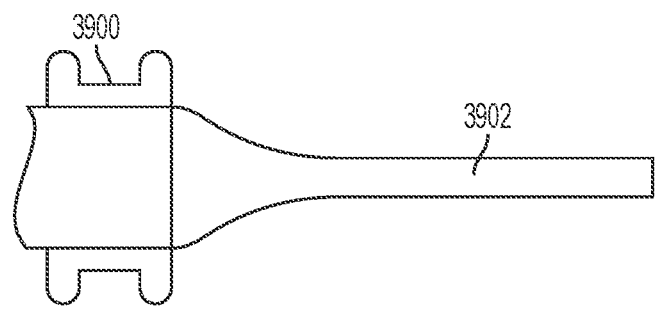
FIG. 53 illustrates one embodiment of an overmolded flexible seal attached to an ultrasonic blade distal of a distal seal.

FIG. 53 illustrates one embodiment of an overmolded flexible seal 3900 attached to an ultrasonic blade 3902 distal of the distal node.

Figure 54:
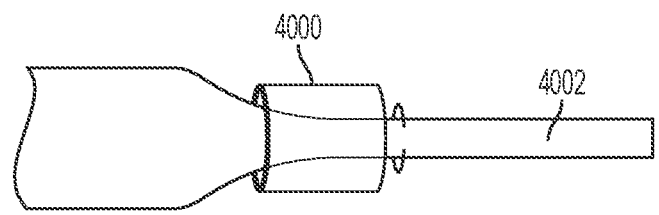
FIG. 54 illustrates one embodiment of an overmolded flexible seal attached to an ultrasonic blade distal of a distal seal.

FIG. 54 illustrates one embodiment of an overmolded flexible seal 4000 attached to an ultrasonic blade 4002 distal of the distal node. In one embodiment, the overmolded flexible seal 4000 is made from an FEP material.

Figure 55:
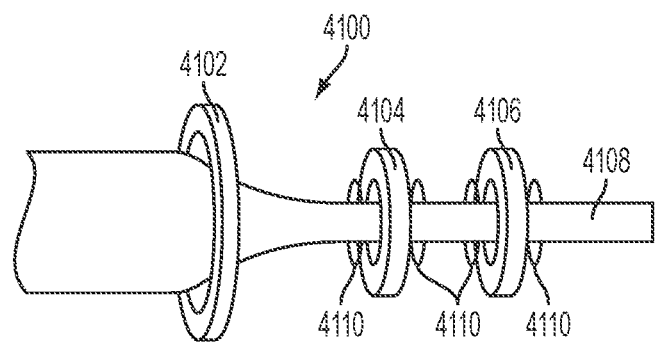
FIG. 55 illustrates one embodiment of a sealing system comprising multiple toroidal seals to seal an ultrasonic blade distal of a distal seal.

FIG. 55 illustrates one embodiment of a sealing system 4100 comprising multiple toroidal seals 4102, 4104, 4106 to seal an ultrasonic blade 4108 distal of the distal node. The toroidal seals 4102, 4104, 4106 are suspended by small overmolded features 4110 that do not interfere with the blade 4108.

Figure 56:
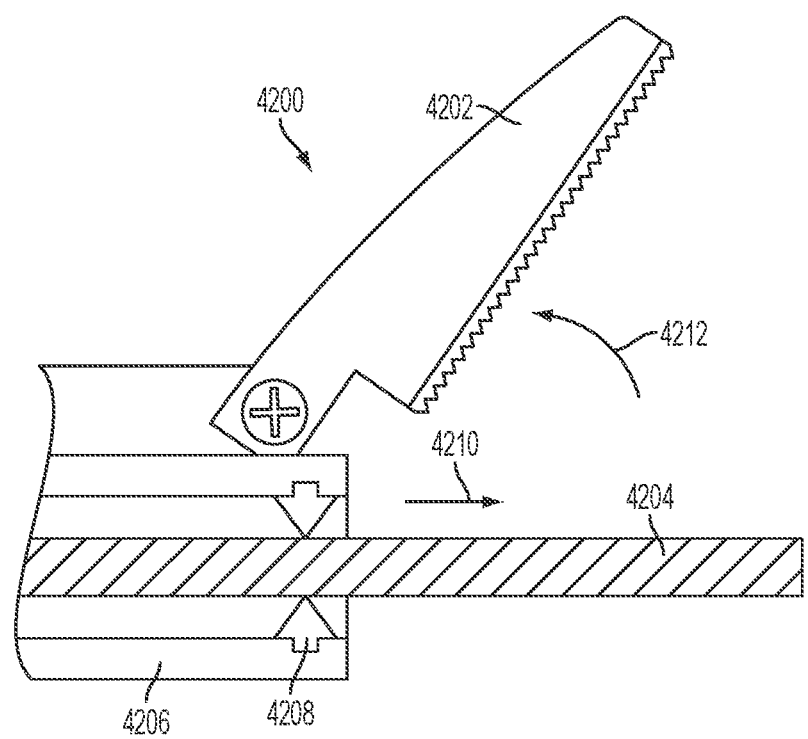
FIG. 56 illustrates one embodiment of an end effector assembly comprising a medical forceps having a movable jaw member in an open position, an ultrasonic blade, and a slidably movable inner tube including a wiping seal.

FIG. 56 illustrates one embodiment of an end effector assembly 4200 comprising a medical forceps having a movable jaw member 4202 in an open position, an ultrasonic blade 4204, and a slidably movable inner tube 4206 including a wiping seal 4208. As illustrated in FIG. 56, the slidably movable inner tube 4206 moves distally in direction 4210 as the jaw member 4212 opens in direction 4212. The wiping seal 4208 surrounds the blade 4204. As the jaw member 4202 opens in direction 4212 the wiping seal 4208 moves distally in direction 4210 along with the inner tube 4206 to wipe surgical matter off the blade 4204.

Figure 57:
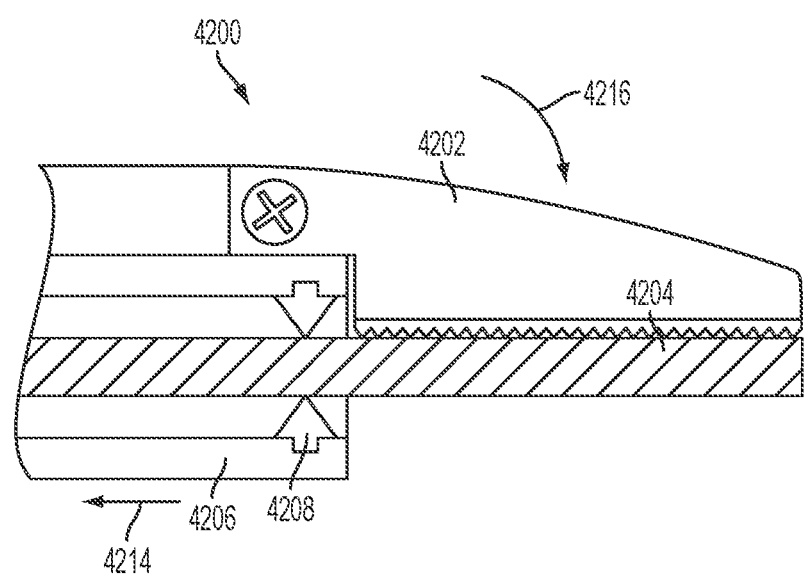
FIG. 57 illustrates one embodiment of the end effector assembly shown in FIG. 56 comprising a medical forceps having a movable jaw member in a closed position.

FIG. 57 illustrates one embodiment of the end effector assembly 4200 shown in FIG. 56 comprising a medical forceps having a movable jaw member 4202 in a closed position. As shown in FIG. 57, as the jaw member 4202 closes in direction 4216, the inner tube 4206 moves proximally in direction 4214 to retract the wiping seal 4208. To wipe the blade 4204 with the wiping seal 4208, the jaw member 4202 is opened as described in connection with FIG. 56.

Figure 58:
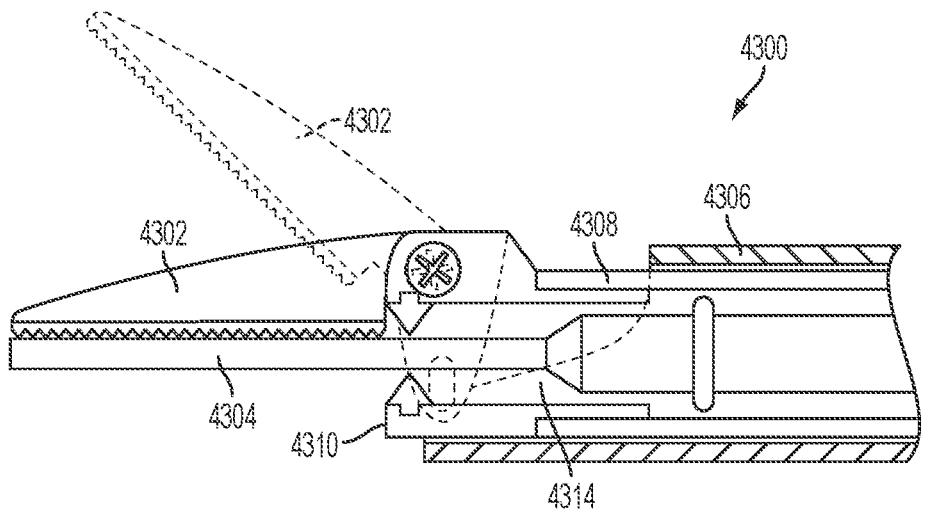
FIG. 58 illustrates one embodiment of an end effector assembly comprising a medical forceps having a movable jaw member in an open position shown in phantom line and a closed position shown in solid line, an ultrasonic blade, a slidably movable outer tube, and a fixed inner tube with a flexible seal located over the blade.

FIG. 58 illustrates one embodiment of an end effector assembly 4300 comprising a medical forceps having a movable jaw member 4302 in a closed position shown in solid line and in an open position shown in phantom line, an ultrasonic blade 4304, a slidably movable outer tube 4306, and a fixed inner tube 4308 with an overmolded flexible seal 4310 located on the inner tube 4308 over the blade 4304.

Figure 59:
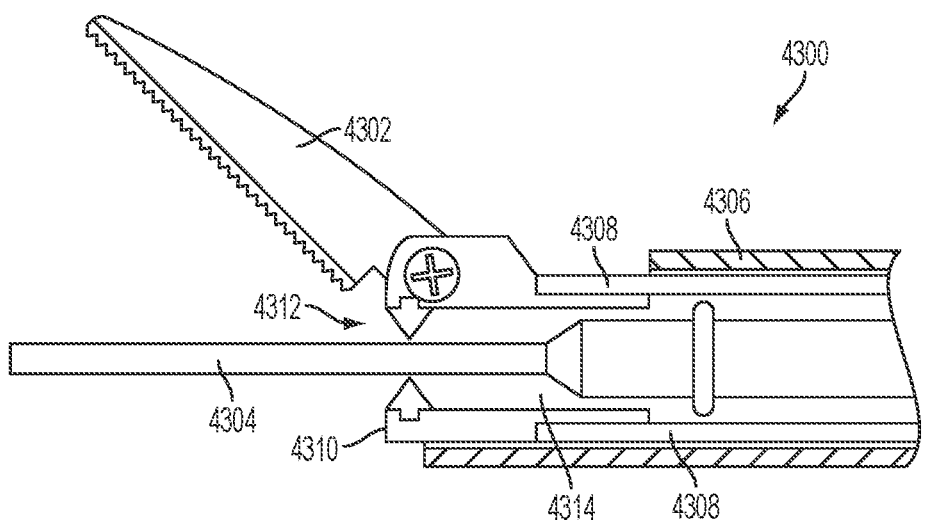
FIG. 59 illustrates one embodiment of an end effector assembly comprising a medical forceps having a movable jaw member in an open position, an ultrasonic blade, a slidably movable outer tube, and a fixed inner tube with a flexible seal overmolded on the inner tube.

FIG. 59 illustrates one embodiment of the end effector assembly 4300 comprising the movable jaw member 4302 in an open position. As shown in FIG. 59, as the jaw member 4202 is opened the overmolded flexible seal 4310 seals the throat 4312 of the device to prevent surgical matter from entering the space 4314 between the blade 4304 and the inner tube 4308.

Alternate Closure Mechanisms for Ultrasonic Devices

Present ultrasonic devices utilize a tube-in-tube (TnT) closure mechanism to enable closure of the clamp arm, referred to herein as a movable jaw member, against an active length of the ultrasonic blade. The following embodiments of alternate closure mechanisms for ultrasonic devices may yield several advantages. For example, there may be differences among the drag force of actuating the inner tube against the outer tube results in variation in device clamp force. Additionally, the pivot location of the clamp arm on the outer tube causes a sharp angular closure, and magnifies the impact to a non-uniform closure profile. Furthermore, the predicate device mechanism may be sensitive to variation in components, as the stackup links the inner and outer tube at the location of the insulated pin, which currently sits near the proximal end of the tube assembly.

One embodiment of an ultrasonic device comprising an alternate closure mechanism is described hereinbelow in connection with FIGS. 60-62. In one embodiment, the ultrasonic device comprises a vibrating blade with a through hole at distal node, an actuator mechanism, an outer tube with cam surfaces at a distal end, and a clamp arm. In another embodiment, the clamp arm is rotatedly fixed to the vibrating blade. In another embodiment, the clamp arm is cammed open and closed (against vibrating blade) through relative motion between the outer tube and vibrating blade. In yet another embodiment, one or more pivots of the clamp arm are positioned at a distal node of the vibrating blade. An illustrative example is discussed hereinbelow.

Figure 60:
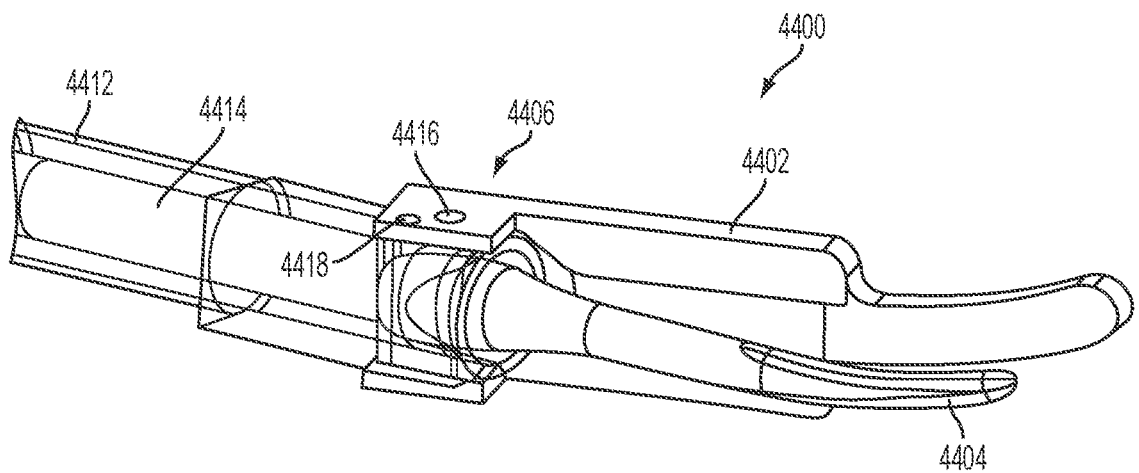
FIG. 60 is a perspective view of one embodiment of an end effector assembly comprising a medical forceps having a movable jaw member and an ultrasonic blade where the movable jaw member is rotatably attached to a distal node.

FIG. 60 is a perspective view of one embodiment of an end effector assembly 4400 comprising a medical forceps having a movable jaw member 4402 and an ultrasonic blade 4404 where the movable jaw member is rotatably attached to a distal node 4406. The outer tube 4412 is shown transparent to show the ultrasonic waveguide 4414 located therein. FIG. 61 is a side view of the end effector assembly 4400 shown in FIG. 60 with the movable jaw member 4402 in an open position and shown transparent to show outer tube cam slots 4408, 4410 to rotate the movable jaw member 4402 upon relative motion between the blade 4404 and the outer tube 4412. FIG. 62 illustrates one embodiment of the end effector assembly 4400 showing the movable jaw member 4402 pivot 4416.

Figure 61:
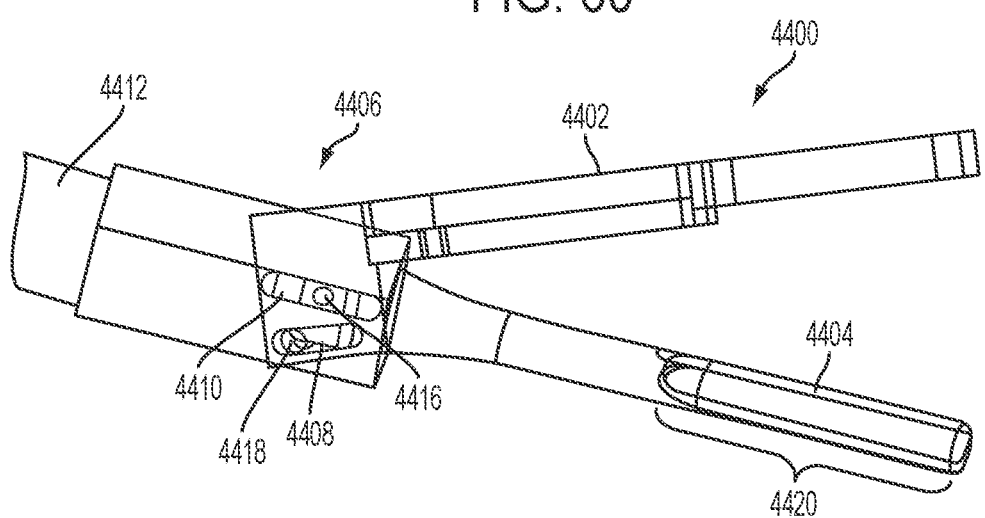
FIG. 61 is a side view of one embodiment of the end effector assembly shown in FIG. 60 with the movable jaw member in an open position and shown transparent to show outer tube cam slots to rotate the movable jaw member upon relative motion between the blade and the outer tube.
Figure 62:
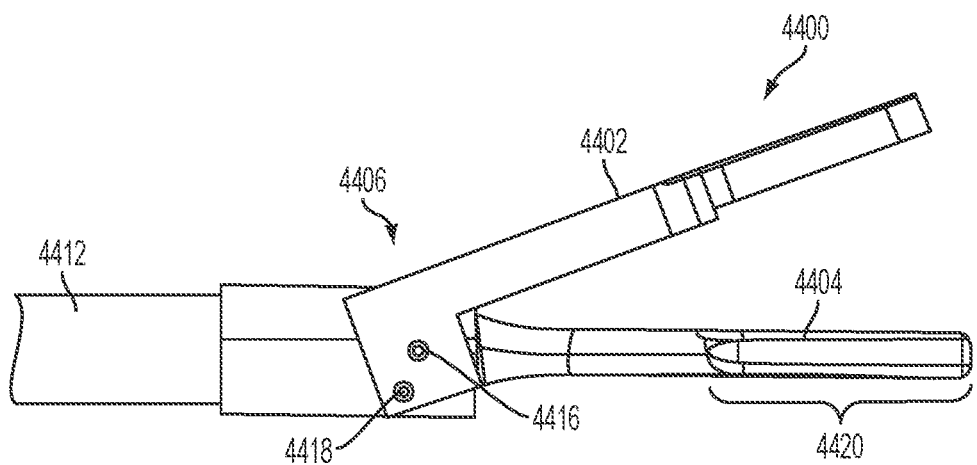
FIG. 62 illustrates one embodiment of the end effector assembly shown in FIG. 60 showing the movable jaw member pivot.

With reference now to FIGS. 60-62, in one embodiment, the movable jaw member 4402 (e.g., clamp arm) is rotatably anchored directly to the blade 4404. The anchoring is accomplished through eliminating the inner tube and attaching the movable jaw member 4402 at the most distal node 4406 of the blade 4404 so as not to interfere with the acoustical train of the device. The attachment may be made through the use of a through hole and insulated pin 4416 attached to the movable jaw member 4402, although other attachment means may be used and are contemplated, such as, for example, pins, screws, snap fits, overmolds or the like. Additionally, the outer tube 4412 contains a cam surface, which locates a second pin 4418 attached to the movable jaw member 4402 such that the movable jaw member 4402 rotates about the pivot at pin 4416 in the blade 4404 when there is relative motion between the blade 4404 and the outer tube 4412. Furthermore, additional geometries for the cam surface are contemplated, such as splines, curves, and the like. As shown in the embodiment of FIG. 62, the pivot location at pin 4416 is positioned in a more proximal location than current devices. The benefits of anchoring the movable jaw member 4402 to the blade 4404 at the distal node 4406 allows for a more parallel closure along the active portion 4420 of the blade 4404, ultimately creating a more uniform pressure profile. In one embodiment, the configuration described in connection with FIGS. 60-62 operates at lower temperatures and can eliminate the need for a polyimide clamp arm pad within the movable jaw member 4402. Although not shown in the embodiment of FIG. 62, the outer tube 4412 may extend longitudinally along the axis of the blade, to prevent tissue from contacting the non-active blade 4404 surface Another embodiment of an ultrasonic device comprising an alternate closure mechanism is described in connection with FIGS. 63-67 hereinbelow. The current closure mechanism experiences frictional losses caused by the relative motion of the inner tube against the outer tube and the inner tube against the blade overmolds. These frictional losses can be attributed to decreased tissue feedback experienced by users. In addition, the clamp force and pressure profile associated with tube-in-tube closure may be sensitive to component variation. More consistent sealing and transection ability can be achieved either by tighter tolerances or decreasing the number of components involved in closure. To address these and other issues, in one embodiment the ultrasonic device comprises a vibrating blade with a hole through the distal node, an outer tube, a clamp arm, and a rigid link. In another embodiment, the clamp arm is coupled to the vibrating blade with a rigid link and system of revolute joints. An illustrative example is discussed hereinbelow.

Figure 63:
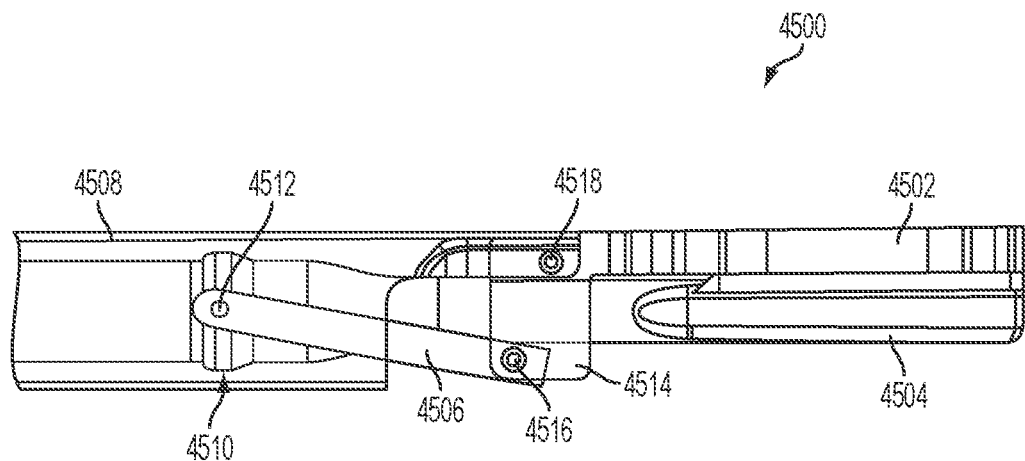
FIG. 63 is a side view of one embodiment of an end effector assembly comprising a medical forceps having a movable jaw member in a closed position and an ultrasonic blade, the end effector assembly comprising a linkage to open and close the movable jaw member by employing relative motion between the outer tube and the blade.
Figure 64:
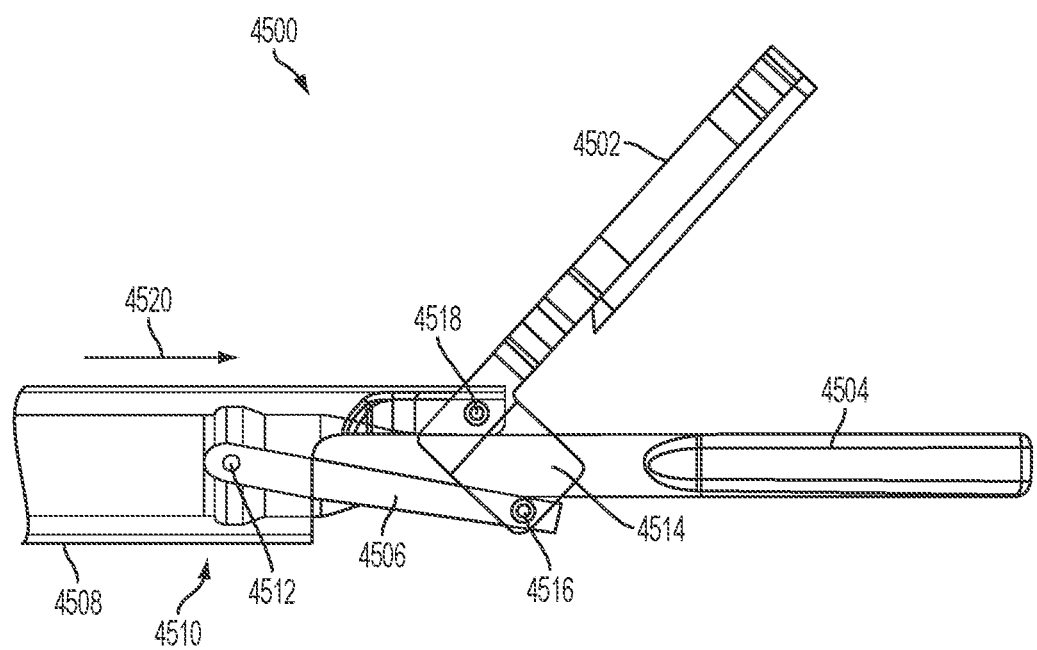
FIG. 64 is a side view of the end effector assembly shown in FIG. 63 with the movable jaw member in an open position, according to one embodiment.
Figure 65:
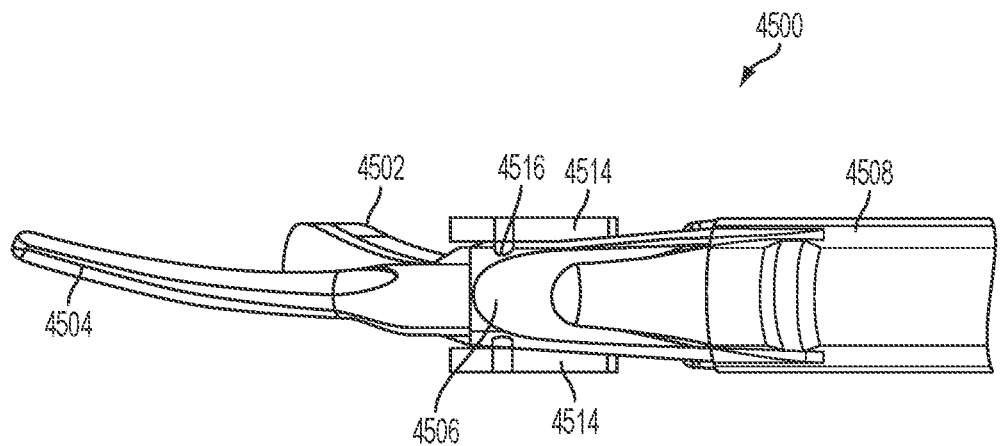
FIG. 65 is a bottom view of the end effector assembly shown in FIG. 63 with the movable jaw member in an open position, according to one embodiment.
Figure 66:
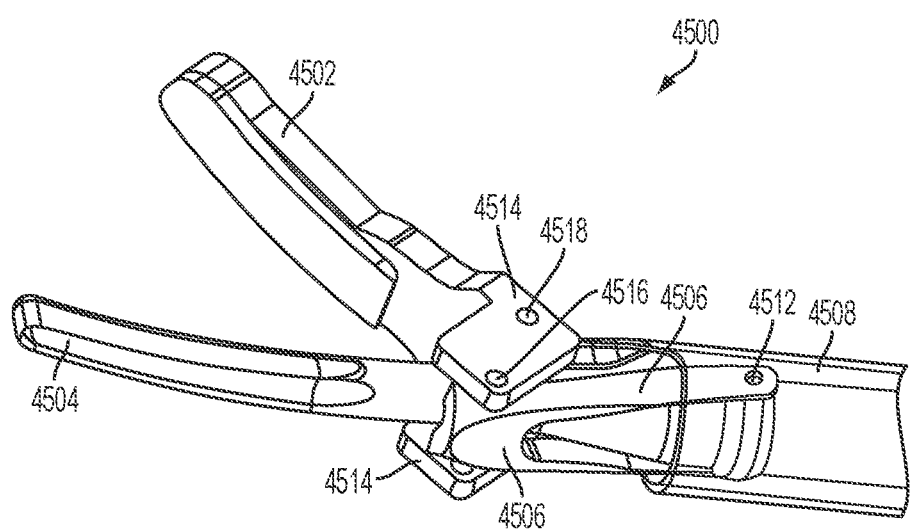
FIG. 66 is a perspective view of the end effector assembly shown in FIG. 63 with the movable jaw member in an open position, according to one embodiment.
Figure 67:
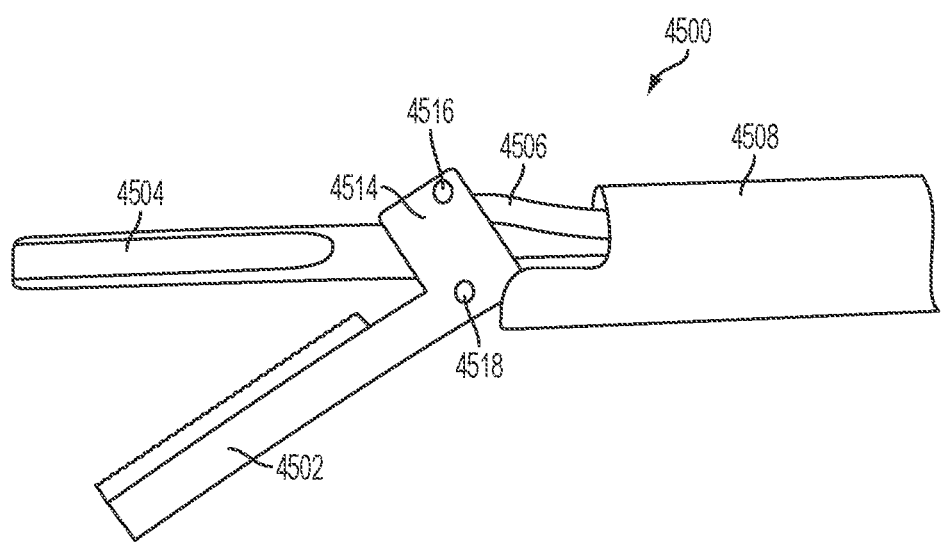
FIG. 67 is a perspective view of the end effector assembly shown in FIG. 63 with the movable jaw member in an open position, according to one embodiment.

FIG. 63 is a side view of one embodiment of an end effector assembly 4500 comprising a medical forceps having a movable jaw member 4502 in a closed position and an ultrasonic blade 4504. The end effector assembly 4500 comprises a linkage 4506 to open and close the movable jaw member 4502 by employing relative motion between the outer tube 4508 and the blade 4504. FIG. 64 is a side view of the end effector assembly 4500 shown in FIG. 63 with the movable jaw member 4502 in an open position. FIG. 65 is a bottom view of the end effector assembly 4500 shown in FIG. 63 with the movable jaw member 4502 in an open position. FIG. 66 is a perspective view of the end effector assembly 4500 shown in FIG. 63 with the movable jaw member 4502 in an open position. FIG. 67 is a perspective view of the end effector assembly 4500 shown in FIG. 63 with the movable jaw member 4502 in an open position.

With reference now to FIGS. 63-67, in one embodiment, the linkage 4506 may be a four bar linkage configured to actuate the movable jaw member 4502 (e.g., clamp arm) by utilizing relative motion between the outer tube 4508 and the blade 4504. The inner tube may be replaced with the rigid link 4506. The link 4506 may be pinned to the blade 4504 through the distal node 4510, although other fastening means are contemplated such as pins, screws, snap fits, and the like. Locating a pin 4512 at the distal node 4510 minimizes interference to the acoustic train of the ultrasonic device. The link 4506 is subsequently pinned to a bottom portion 4514 of the movable jaw member 4502 via pin 4516 and a second pivot of the movable jaw member 4502 is pinned to an end of the outer tube 4508 via pin 4518. Clamping may be achieved by displacing the outer tube 4508 forward relative to the blade 4504 in direction 4520. The link 4506 component ensures that the distance between the distal node 4510 and the lower pivot of the clamp arm remains constant. The presence of the link 4506 forces the movable jaw member 4502 to rotate as the outer tube 4508 is displaced in direction 4520. In one embodiment, the rigid link 4506 may comprise a small stainless steel component formed from progressive stamping, although other materials and manufacturing processes are contemplated, such as metal injection molding (MIM), polymers formed from plastic injection molding, and the like. The use of a rigid link 4506 also allows simplification of a trigger assembly. For example, a trigger assembly for actuating the inner tube may be removed. The use of a four bar linkage 4506 also reduces frictional losses in the tube assembly and results in a decrease in accumulated pressure profile variations.

Yet another embodiment of an ultrasonic device comprising an alternate closure mechanism is described in connection with FIGS. 68-70 hereinbelow. The embodiment illustrated in FIGS. 68-70 addresses issues such as tolerance accumulation between the blade, movable jaw member, inner tube, insulated pin, and rotation knob of existing ultrasonic devices.

Figure 68:
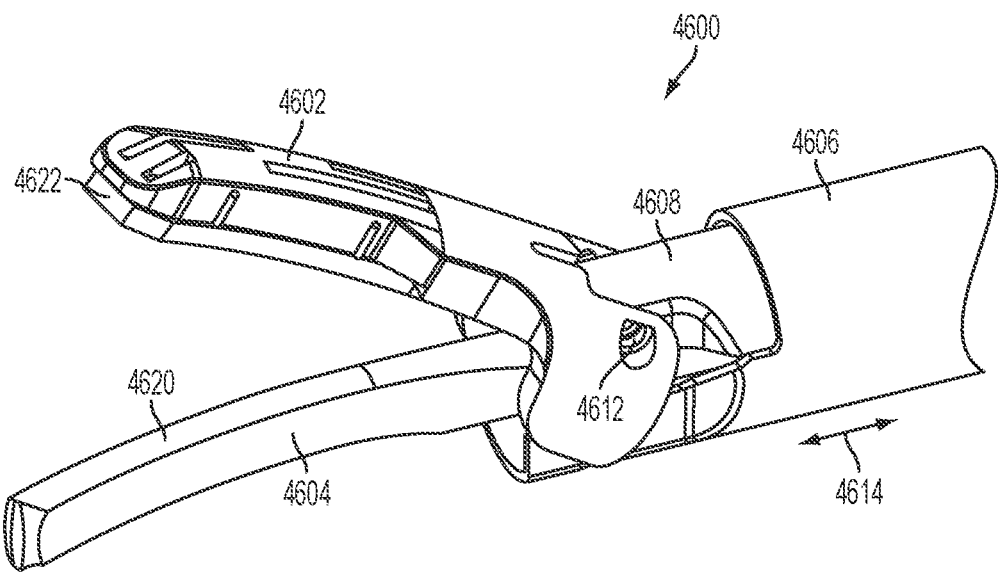
FIG. 68 is a perspective view of one embodiment of an end effector assembly comprising a medical forceps having a movable jaw member and an ultrasonic blade with the movable jaw member shown in an open position, where an outer tube is translated with respect to the blade to open and close the movable jaw member.

FIG. 68 is a perspective view of one embodiment of an end effector assembly 4600 comprising a medical forceps having a movable jaw member 4602 and an ultrasonic blade 4604 with the movable jaw member 4602 shown in an open position. An inner tube 4608 is translated with respect to the blade 4604 to open and close the movable jaw member 4602. FIG. 69 is a perspective view of the inner tube 4608 with the outer tube 4606 removed. The inner tube 4608 is operatively coupled to the end effector assembly 4600 shown in FIG. 68. FIG. 70 is a perspective view of a notch portion 4610 of the inner tube 4608 shown in FIG. 69.

Figure 69:
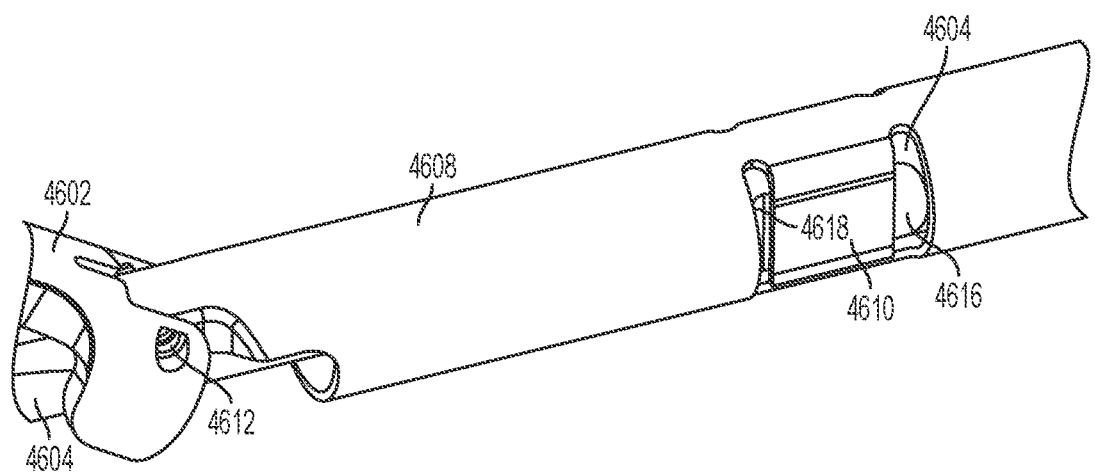
FIG. 69 is a perspective view of the inner tube with the outer tube removed, where the inner tube is operatively coupled to the end effector assembly shown in FIG. 68, according to one embodiment.
Figure 70:
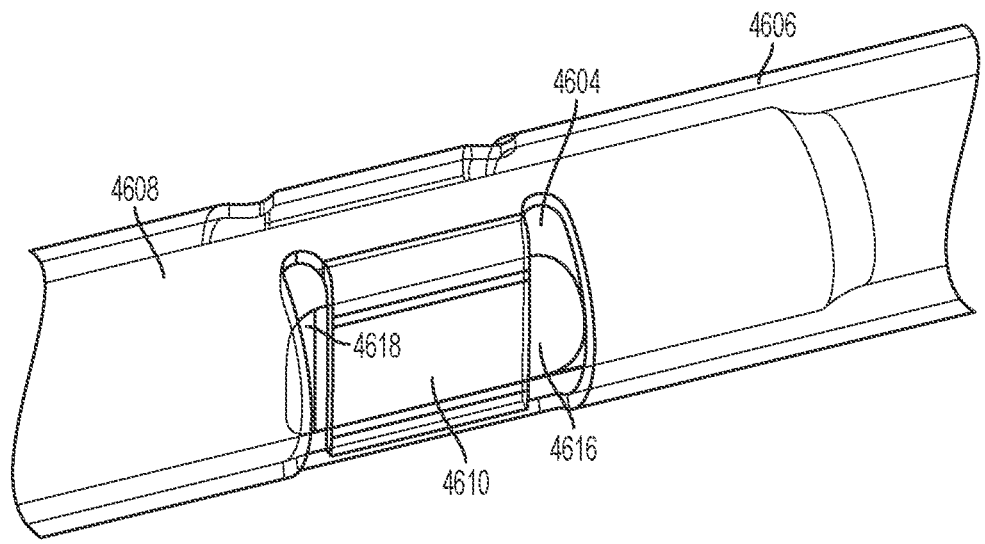
FIG. 70 is a perspective view of a notch portion of the inner tube shown in FIG. 69, according to one embodiment.

With reference now to FIGS. 68-70, in one embodiment, the inner tube 4608 is configured to translate with respect to the blade 4604 to move the movable jaw member 4602 (e.g., clamp arm) and to generate clamp pressure against the blade 4604. In the embodiment illustrated in FIGS. 68-70, the movable jaw member 4602 is attached and pivots at pivot 4612 on the inner tube 4608. The outer tube 4606 translates in direction 4614 to pivot the movable jaw member 4602. The inner tube 4608 has a notched region 4610 as shown in FIGS. 69 and 70, that is squeezed inwardly into notches 4616, 4618 formed in the blade 4604 that would be located at the node location of the blade 4604. In one embodiment, the blade 4604 portion in the notched region 4610 location may be coated with a thin layer of silicone overmold to provide tight relationship between the inner tube 4608 and the blade 4604. such tight relationship provides good movable jaw member 4602 clocking with respect to the blade 4604 cutting surface 4620 (FIG. 68). As shown in FIG. 68, in one embodiment, a clamp arm pad 4622 also may be provided on the inside portion of the movable jaw member 4602.

Figure 71:
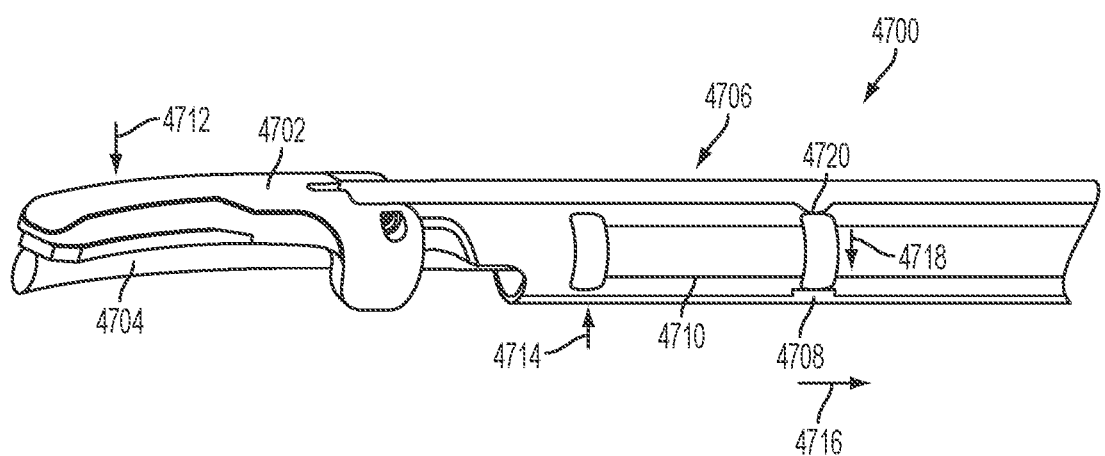
FIG. 71 illustrates one embodiment of an end effector assembly comprising a medical forceps having a movable jaw member in a closed position, an ultrasonic blade, and a shaft assembly configured to counteract deflection of the blade.

FIG. 71 illustrates one embodiment of an end effector assembly 4700 comprising a medical forceps having an end effector with a movable jaw member 4702 in a closed position, an ultrasonic blade 4704, and a shaft assembly 4706 configured to counteract deflection of the blade 4704. A counter deflection element 4720 is provided on an inner tube 4710 at one of the blade nodes 4718 proximal to the distal node 4714 to counteract deflection of the blade 4704 by the movable jaw member 4702. In one embodiment, a downward 4712 deflection of the blade 4704 by the movable jaw member 4702 is counteracted by the downward reaction force of counter deflection element 4720 at the node 4718 proximal to the distal node 4714. In one embodiment, the counter deflection element 4720 may comprise a bulge into the inner lumen to provide downward counter force to the clamping force. In another embodiment, a window 4708 may be cut into the inner tube 4710 to allow a downward force to deflect the blade 4704 without making contact with the opposing wall of the inner tube 4710.

Any of the inner tubes and/or outer tubes disclosed herein may be coated with a polymer used as moisture and dielectric barriers. Among them, parylene C may be selected due to its combination of barrier properties, cost, and other processing advantages. Parylene is the trade name for a variety of chemical vapor deposited poly(p-xylylene), for example. The polymer coating is used to prevent shorting in the shaft from the blade to adjacent metal parts. In one embodiment, the just the inner tube (e.g., actuator) may be coated to prevent it from shorting to the blade which is one "pole" in the combined ultrasonic and bipolar (RF) device, where the other "pole" is the outer tube and the clamp arm. The inner tube insulation provides a more robust and space efficient electrical insulating barrier than an intervening plastic tube, which may be considered an alternative embodiment.

Transducer Support and Limited Rotation with Single Component

In one embodiment, a shaft rotation limiter comprises a single piece which interfaces with a transducer flange by a threaded connection. The rotation limiter provides radial support through a component fixed in the shroud channels. The amount of rotation is limited by the allowed lateral motion of the component in the shroud channels as it is threaded along the transducer. One example of a shaft rotation limiter is described in connection with FIG. 72 hereinbelow.

Figure 72:
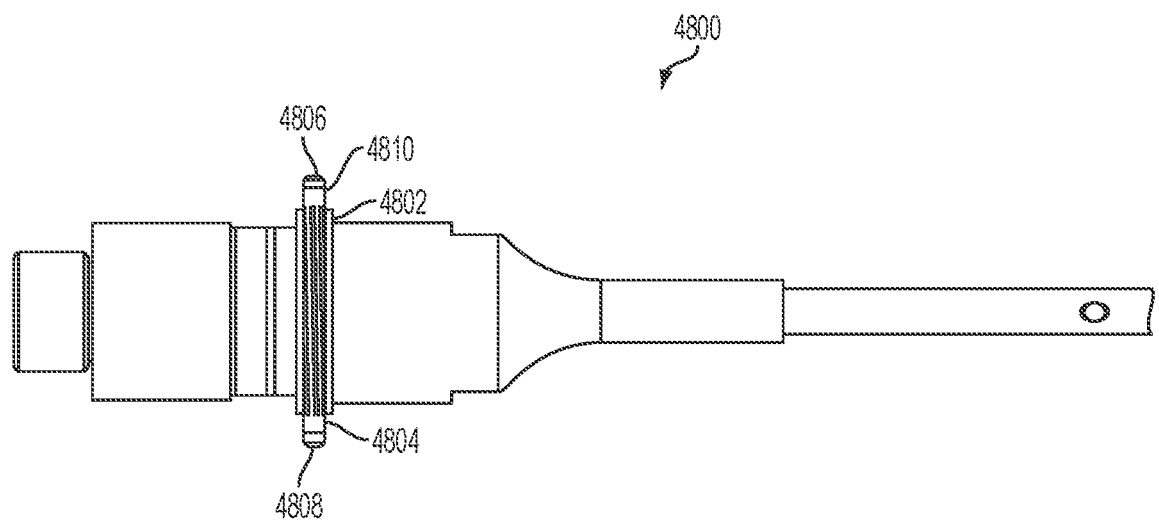
FIG. 72 illustrates one embodiment of an ultrasonic transducer having a modified flange incorporating external threads to allow transducer rotation.

FIG. 72 illustrates one embodiment of an ultrasonic transducer 4800 having a modified flange 4802 incorporating external threads 4804 to allow transducer rotation. In the illustrated embodiment, the transducer flange 4802 is modified to incorporate external threads 4804. The external threads 4804 may mate with a component 4810 having internal threads and at least two protruding bosses 4806, 4808. The protruding bosses 4806, 4808 engage into channels in the device shroud and limit transducer rotation. The shroud illustrated in FIG. 72 is described in further detail in relation to embodiments listed below. The component 4810 with the threaded inner diameter interfaces with the transducer 4800 by threaded connection. Since the component 4810 is limited in transverse travel by the shroud channels, it provides radial support. The component 4810 with the threaded inner diameter translates rotational movement of the transducer 4800 to a lateral motion of the component 4810. Rotation of the blade or transducer 4800 can be provided by a fixed rotation knob. Rotating the knob may cause the internally threaded component 4810 to translate laterally and rotation would be limited when the component 4810 can no longer translate. The lateral movement may be defined by the length of the channel in the shroud or the length of the threaded flange 4802 on the transducer. The shroud allows rotations in excess of 360°. The amount of rotation of the transducer 4800 is limited by the allowed lateral motion of the component 4810 in the shroud channels (not shown).

Limited Rotation of Ultrasonic Device with Rotation>360°

Figure 73:
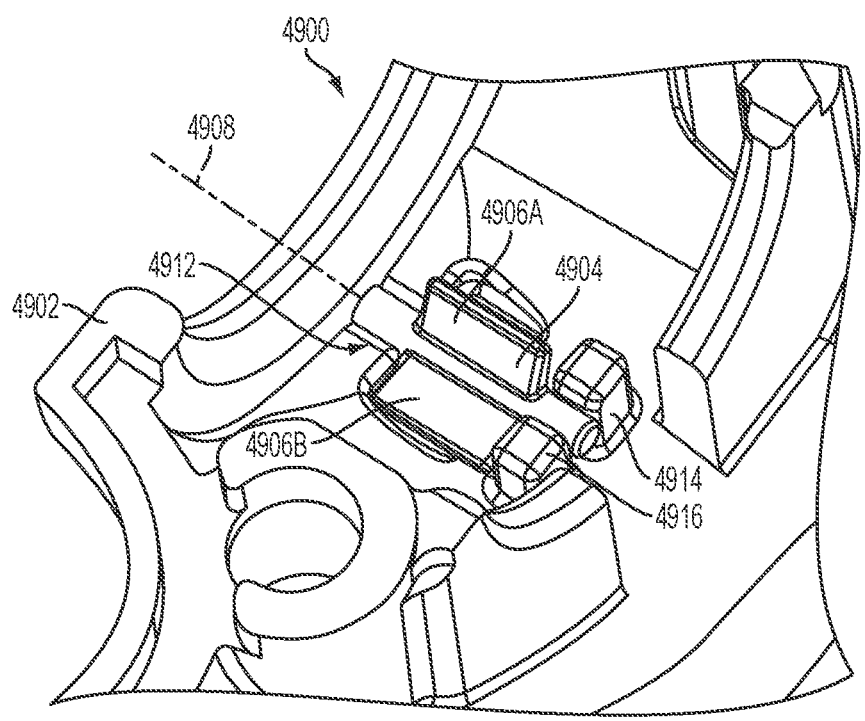
FIG. 73 is a sectional view of one embodiment of an ultrasonic transducer rotation system comprising a shroud and a gate fitted into one-half of the shroud.

FIG. 73 is a sectional view of an ultrasonic transducer rotation system 4900 comprising a shroud 4902 and a gate 4904 fitted into one-half of the shroud 4902. In the illustrated embodiment, the gate 4904 is L-shaped and has two wings 4906A, 4906B (right and left wings, respectively) extending at a fixed angle from a central axis 4908 positioned within a portion of the shroud 4902. One additional component, as well as modifications of a rotation knob and the right-hand or left-hand shroud 4902, allow for approximately 690° of rotation—almost two full rotations. The rotation knob is used by the operator to rotate the shaft and ultrasonic transducer of the device. The additional component is referred to herein as the gate 4904. The gate 4904 is rotationally moveable about axis 4908 within the shroud 4902 to two positions. The rotation knob will have an additional contoured extrusion element that extends to make contact with the gate 4904. Where the gate 4904 is inserted into the shroud 4902 there will be a minimum amount of frictional contact between the shroud 4902 and the gate 4904 to keep the gate 4904 in place while it is not in contact with the rotation knob. The gate 4904 in the shroud 4902 is constrained by a cylindrical hole 4912 and two bosses 4914, 4916 with a slight undercut. The axis 4908 of the gate 4904 that sits in the cylindrical hole 4912 would be constrained in part by features on the rotation knob. The gate 4904 can be made of a rigid metal or a single stamped metal part or injection molded from plastic. The gate 4904 can either snap into place in the shroud 4902 or be ultrasonically welded or heat staked to the shroud 4902 in such a fashion to allow free rotation of the gate 4904 about axis 4908.

Figure 74A:
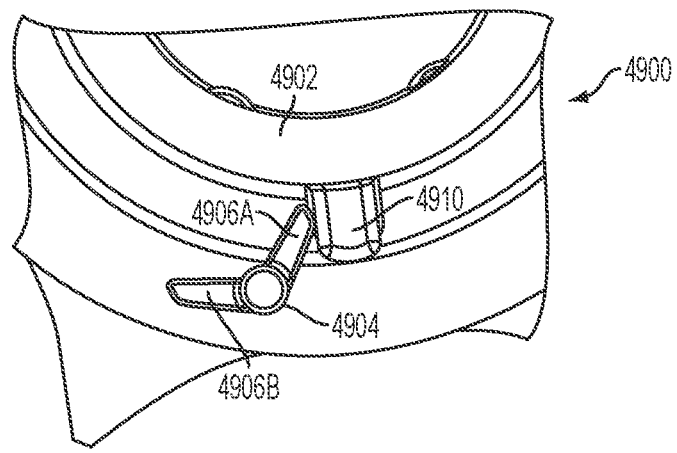
FIGS. 74A-74C illustrate the dynamics of the gate interaction with a rotation knob, according to one embodiment.
Figure 74B:
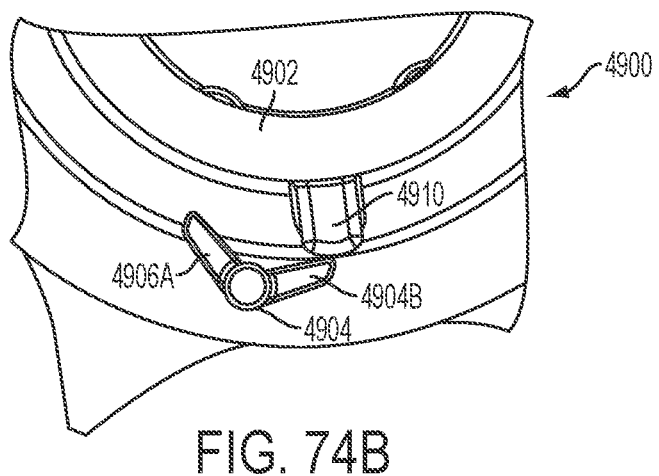
Figure 74C:
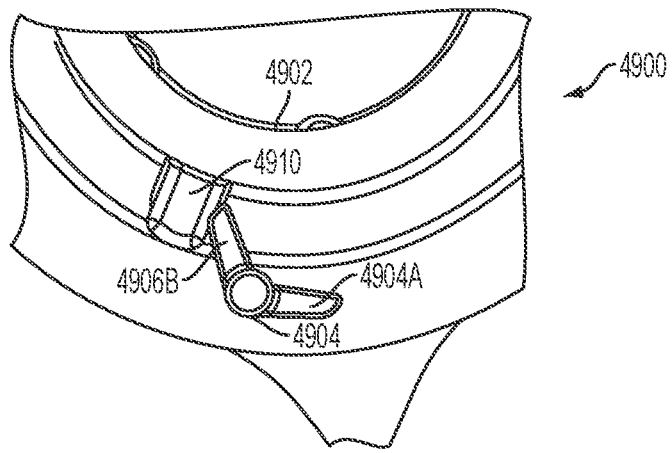

FIGS. 74A-74C illustrate the dynamics of the gate/rotation knob interaction. FIG. 74A illustrates the gate 4904 in a left-biased position such that the rotation knob can be rotated 690° clockwise until a contoured extrusion element 4910 on the rotation knob makes contact with the right wing 4906A of the gate 4904 so that the left wing 4906B of the gate 4904 prevents motion by reacting statically against the shroud 4902. Thus, at the starting point, the rotation knob contoured extrusion element 4910 is contacting the outside of the right wing 4906A of the gate 4904 and is constrained to only move in a counter-clockwise direction.

FIG. 74B illustrates the rotation knob rotated back 360 degrees until it rotates the right wing 4906A of the gate 4904 into a right-biased position. Upon full 360° rotation the rotation knob extrusion 4910 contacts the inside of the right wing 4906A of the gate 4904, rotating the gate 4904 to the right as the knob rotates around.

FIG. 74C illustrates the rotation knob after it rotates the right wing 4906A of the gate 4904 into a right-biased position. Subsequently, the rotation knob can be rotated an additional 330° until the contoured extrusion element 4910 of the rotation knob contacts the left wing 4906B of the gate 4904 and the right wing 4906A of the gate 4904 prevents motion by reacting statically against the shroud 4902. After 690° of rotation the rotation knob contacts the outside of the left wing 4906B of the gate 4904. The right wing 4906A of the gate 4904 is contacting the shroud 4902 and is therefore stopping further rotation of the rotation knob in the counterclockwise direction. This process can be reversed to spin the rotation knob clockwise back to its starting position.

Figure 75:
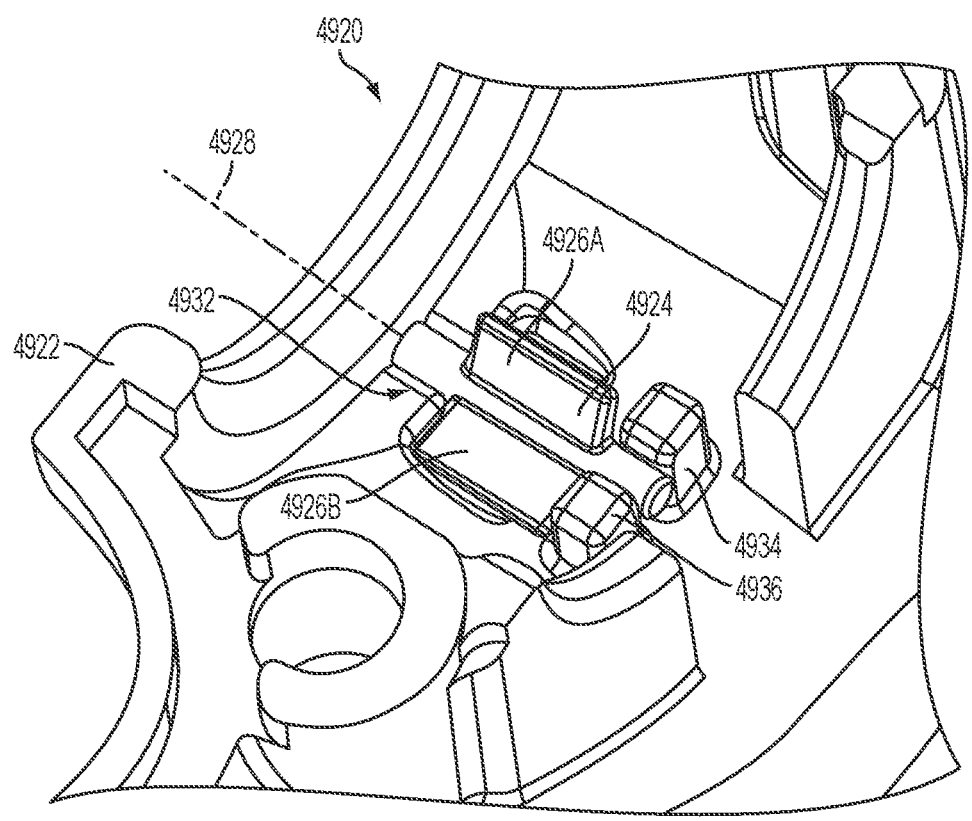
FIG. 75 is a sectional view of one embodiment of an ultrasonic transducer rotation system comprising a shroud and a gate fitted into one-half of the shroud, where the rotation system comprises a tactile feedback element.

FIG. 75 is a sectional view of an ultrasonic transducer rotation system 4920 comprising a shroud 4922 and a gate 4924 fitted into one-half of the shroud 4922, where the rotation system includes a semi-compliant element. In the illustrated embodiment, the gate 4924 is L-shaped and has two wings 4926A, 4926B (right and left wings, respectively) extending at a fixed angle from a central axis 4928 positioned within a portion of the shroud 4922. One additional component, as well as modifications of a rotation knob and the right-hand or left-hand shroud 4922, allow for approximately 690° of rotation—almost two full rotations. The rotation knob is used by the operator to rotate the device shaft and ultrasonic transducer. The additional component is referred to herein as the gate 4924. The gate 4924 is rotationally moveable about axis 4928 within the shroud 4922 to two positions. The rotation knob will have an additional contoured extrusion element that extends to make contact with the gate 4924. Where the gate 4924 is inserted into the shroud 4922 there will be a minimum amount of frictional contact between the shroud 4922 and the gate 4924 to keep the gate 4924 in place while it is not in contact with the rotation knob. The gate 4924 in the shroud 4922 is constrained by a cylindrical hole 4932 and two bosses 4934, 4936 with a slight undercut. The axis 4928 of the gate 4924 that sits in the cylindrical hole 4932 would be constrained in part by features on the rotation knob. The gate 4924 can be made of a rigid metal or injection molded from plastic. The gate 4924 can either snap into place in the shroud 4922 or be ultrasonically welded or heat staked to the shroud 4922 in such a fashion to allow free rotation of gate 4924 about axis 4928.

Unlimited (continuous) rotation of an ultrasonic shear device with an integrated transducer requires the use of additional components that may not be cost-effective. One cost-effective solution is to limit rotation of the shaft of the device, thus allowing for a direct-wired connection between the transducer and the hand activation circuit. A tactile benefit is added to the mechanism that would limit rotation but provide tactile feedback before a hard stop is hit. This tactile feedback element may enable the user to change the way they use the device, either through rotating their wrist to get additional rotation or to choose to rotate the device back to a neutral position to ensure they have enough rotation to accomplish the task they need to perform.

FIGS. 112A and 112B illustrate one embodiment of an unlimited rotation connection for an integrated transducer 6216. An unlimited rotation connection may be provided by the ultrasonic transducer rotation system 6220. The ultrasonic transducer rotation system 6220 may comprise, for example, a male plug 6222 and a female receptacle 6224. The male plug 6222 may be configured to freely rotate within the female receptacle 6224 while maintaining an electrical connection between the ultrasonic transducer 6216 and, for example, power system 6248. For example, in one embodiment, the male plug 6222 and the female receptacle 6224 may comprise a stereo plug and jack. FIG. 112A illustrates the male plug 6222 and the female receptacle 6224 in an uncoupled, or unmated, position. FIG. 112B illustrates the male plug 6222 and the female receptacle 6224 in a coupled, or mated, position. In the mated position, the male plug 6222 is able to freely rotate within the female receptacle while maintaining an electrical connection between the male plug 6222 and the female receptacle 6224.

FIGS. 113A-113C illustrate one embodiment of an unlimited rotation connection 6520. The unlimited rotation connection 6520 comprises a male plug 6522 and a female receptacle 6524. The male plug 6522 may comprise a plurality of electrodes 6526a-d coupled to an insulating tube 6528. The male plug 6522 may be coupled to a shaft/transducer assembly and may rotate in unison with the shaft/transducer assembly. In some embodiments, the first and second electrodes 6526a-6526b may be coupled to the transducer. In some embodiments, the third and fourth electrodes 6526c-6526d may be coupled to bipolar electrodes located at an end effector. In some embodiments, such as a monopolar electrode arrangement, the fourth electrode 6526d may be omitted. The plurality of electrodes 6526 may each be coupled to a wire 6530a-6530d. The female receptacle 6524 may comprise a plurality of helical contacts 6532a-6532d. The plurality of helical contacts 6532a-6532d may be positioned such that each of the helical contacts 6532a-6532d is electrically coupled to a corresponding electrode 6526a-6526d on the male plug 6522 when the male plug 6522 is inserted into the female receptacle 6524. FIG. 113B illustrates a cross-sectional view of the female receptacle 6524 take along line B-B. The female receptacle 6524 comprises a individual helical contacts 6532a-6532d separated by insulators 6534a-6534c. FIG. 113C illustrates the individual helical contact profile of a helical contact 6532a. The helical contact 6532a may comprise a first metal plate 6536a and a second metal plate 6536b. A plurality of twisted wires 6538 may be spirally twisted to assure contact between the male plug 6522 and the metal plates 6536a, 6536b. In some embodiments, the direction of the spiral may be alternated to provide increased connectivity in all directions of rotation. The twisted wires 6538 may comprise a hyperbolic shape.

The tactile feedback element is added to the limited rotation mechanism shown in FIGS. 73-74C, which includes on the rotation knob an additional contoured extrusion element 4930 that extends to make contact with the gate 4924 (the mechanism that limits rotation). In the embodiment illustrated in FIGS. 75-76C, a contoured extrusion element 4930 (FIGS. 76A-76C) located on the rotation knob can be made of a semi-compliant material. Alternatively, portions of contoured extrusion element 4930 indicated by elements 4938, may be comprised of a semi-compliant material. The semi-compliant material could be made of rubber, medium to high density rubber, silicone, thermoplastic elastomers, springy piece of stainless steel, spring steel, copper, shape memory metals, and the like. Any of these materials can be insert molded or mechanically connected to the rotation knob.

The purpose of the contoured extrusion element 4930 (FIGS. 76A-76C) on the rotation knob is to contact the gate 4924 to provide the motion needed for the gate 4924 to function. Adding compliance to the contoured extrusion element 4930 rotation knob feature enables the user to feel that they are approaching the hard stop a few degrees of rotation before the hard stop is contacted. This feedback may enable the user to change the way they use the device, either through rotating their wrist to get additional rotation or to choose to rotate the device back to a neutral position to ensure they have enough rotation to accomplish the task they need to perform.

Figure 76A:
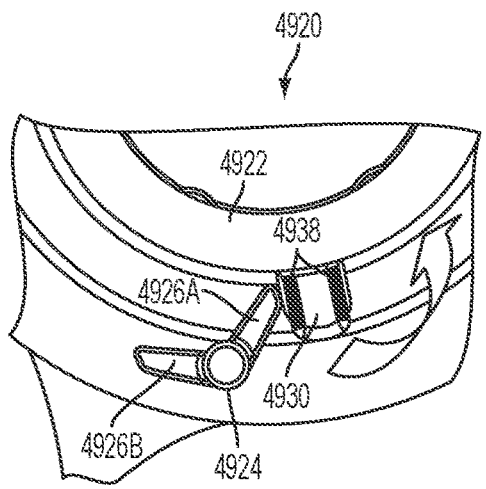
FIGS. 76A-76C illustrate the dynamics of the gate interaction with a rotation knob, where the rotation knob comprises a tactile feedback element, according to one embodiment.
Figure 76B:
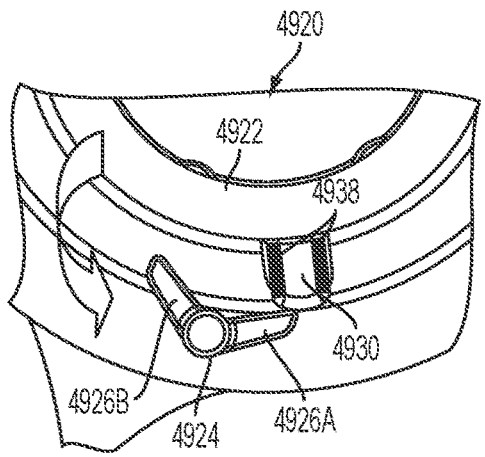
Figure 76C:
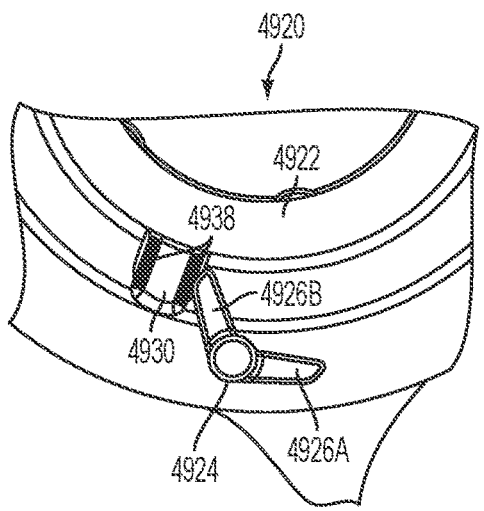

FIGS. 76A-76C illustrate the dynamics of the gate interaction with a rotation knob, where the rotation knob comprises a tactile feedback element. FIG. 76A illustrates the gate 4924 in a left-biased position such that the rotation knob can be rotated 690° clockwise until a contoured extrusion element 4930 on the rotation knob makes contact with the right wing 4906A of the gate 4924 so that the left wing 4926B of the gate 4924 prevents motion by reacting statically against the shroud 4922. Thus, at the starting point, the rotation knob contoured extrusion element 4930 is contacting the outside of the right wing 4926A of the gate 4924 and is constrained to only move in a counter-clockwise direction. A layer of (insert-molded) semi-compliant material 4938 may be located on either side or both sides of the contoured extrusion element 4930. The semi-compliant material 4938 could be made of rubber, medium to high density rubber, silicone, thermoplastic elastomers, springy piece of stainless steel, spring steel, copper, shape memory metals, and the like. Any of these semi-compliant materials 4938 can be insert molded or mechanically connected to the rotation knob.

FIG. 76B illustrates the rotation knob rotated back 360 degrees until it knocks the right wing 4926A of the gate 4924 into a right-biased position. Upon full 360° rotation the contoured extrusion element 4930 of the rotation knob contacts the inside of the right wing 4926A of the gate 4924, rotating the gate 4924 to the right as the knob rotates around. The semi-compliant material 4938 provides tactile feedback to the user.

FIG. 76C illustrates the rotation knob after it rotates the right wing 4926A of the gate 4924 into a right-biased position. Subsequently, the rotation knob can be rotated an additional 330° until the contoured extrusion element 4930 of the rotation knob contacts the left wing 4926B of the gate 4924 and the right wing 4926A of the gate 4924 prevents motion by reacting statically against the shroud 4922. After 690° of rotation the rotation knob contacts the outside of the left wing 4926B of the gate 4924. The right wing 4926A of the gate 4924 is contacting the shroud 4922 and is therefore stopping further rotation of the rotation knob in the counterclockwise direction. This process can be reversed to spin the rotation knob clockwise back to its starting position. The semi-compliant material 4938 provides tactile feedback to the user. The semi-compliant material 4938 tactile feedback element mat enable the user to change the way they use the device, either through rotating their wrist to get additional rotation or to choose to rotate the device back to a neutral position to ensure they have enough rotation to accomplish the task they need to perform.

RF Spot Coagulation with Integrated Ultrasonic/RF Generator

Figure 77:
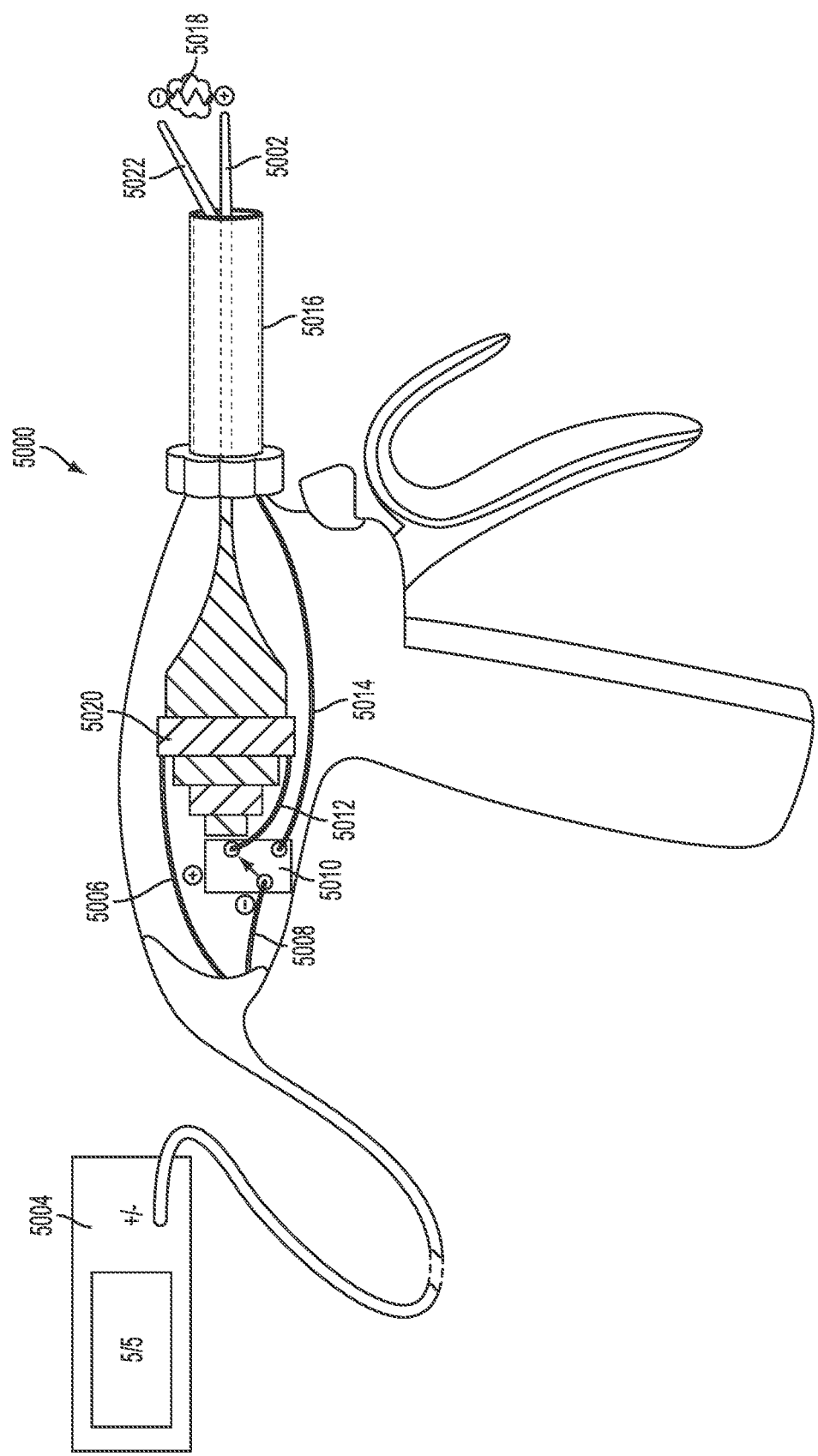
FIG. 77 illustrates one embodiment of an integrated RF/ultrasonic instrument electrically connected such that the ultrasonic blade/horn is electrically connected to a positive lead of an ultrasonic generator coupled to the instrument to provide RF spot coagulation. The clamp arm and tube are connected to the return path.

FIG. 77 illustrates an integrated RF/ultrasonic instrument 5000 electrically connected such that an ultrasonic blade/horn 5002 is electrically connected to a positive lead 5006 of an ultrasonic generator 5004 and is also coupled to an RF generator to provide spot coagulation by applying RF energy to tissue 5018. The integrated RF/ultrasonic instrument 5000 enables the touch up of diffuse bleeding (capillary bleeding, cut site oozing) without the need for ultrasonic coupling pressure. Further, the coupling pressure needed for ultrasonic instruments, to couple the blade to tissue such that friction-based tissue effect is effective, is relatively high which results in (1) difficulty in applying enough pressure to generate hemostatic effect in loosely supported (i.e., unclamped) tissue or (2) coupling pressure that generates too much tissue disruption that, in many cases, makes the diffuse bleeding worse.

In one embodiment, the integrated RF/ultrasonic instrument 5000 is wired such that the horn/blade 5002 is directly connected to the positive lead 5006 of the generator 5004. Conventional ultrasonic devices are wired such that the negative/return lead 5012 is connected to the horn/blade. A switch 5010 is provided to enable two device functionalities (1) ultrasonic and (2) bipolar (RF) to be performed. The first state of the switch 5010 connects the negative/return lead 5008 to the piezoelectric transducer (PZT) stack 5020 such that the generator 5004 drives the PZT stack 5020. The second state of the switch 5010 isolates the PZT stack 5020 and connects the negative/return 5008 to the device tube 5016 and a movable jaw member 5022 (e.g., clamp arm) through an electrical conductor 5014 and allows the generator 5004 signal to be driven through tissue 5018 located between the blade 5002 and the clamp arm 5022. The resistance in the tissue 5018 seals the vessels. Feedback signals also may be provided back to the generator 5004 to adjust signal parameters (e.g., amplitude, frequency, pulsing, modulation, etc.)

In one embodiment, the integrated RF/ultrasonic instrument 5000 may comprise a sealing button, wherein, when pressed, the generator 5004 may produce bipolar RF energy through the handpiece and into the ultrasonic blade 5002 and return through the clamp arm 5022. In one embodiment, the electrical RF current may travel around the outside of the blade 5002 and create a robust bi-polar seal. The duration of the bipolar RF energy may be about one second, after which an algorithm may cause the generator 5004 to switch to the ultrasonic power curve, wherein the blade 5002 would be activated and the cut completed in the middle of two RF seals.

Ultrasonic cutting also may provide some sealing. The application of RF energy provides added confidence that there is an RF seal in place on each side of the blade 5002.

In one embodiment, the RF/ultrasonic device comprises a blade or clamp arm or both with the distal end coated with thermally and electrically insulative material, wherein a distal end of the blade or clamp arm or both may have varying degrees of exposed (uncoated) areas that will be application dependent. In another embodiment, the exposed area on the blade or clamp arm or both may vary depending on application and may be either symmetrical or asymmetrical. In another embodiment, the exposed area on the blade may comprise at least one exposed area/segment separated by at least one coated segment. In one embodiment, a process of masking the blade or clamp arm or both to generate exposed area is provided. Alternatively, coating may be selectively removed to produce the same desired effect. Specific embodiments of such coated blades are described hereinbelow in connection with FIGS. 80-95.

Figure 78:
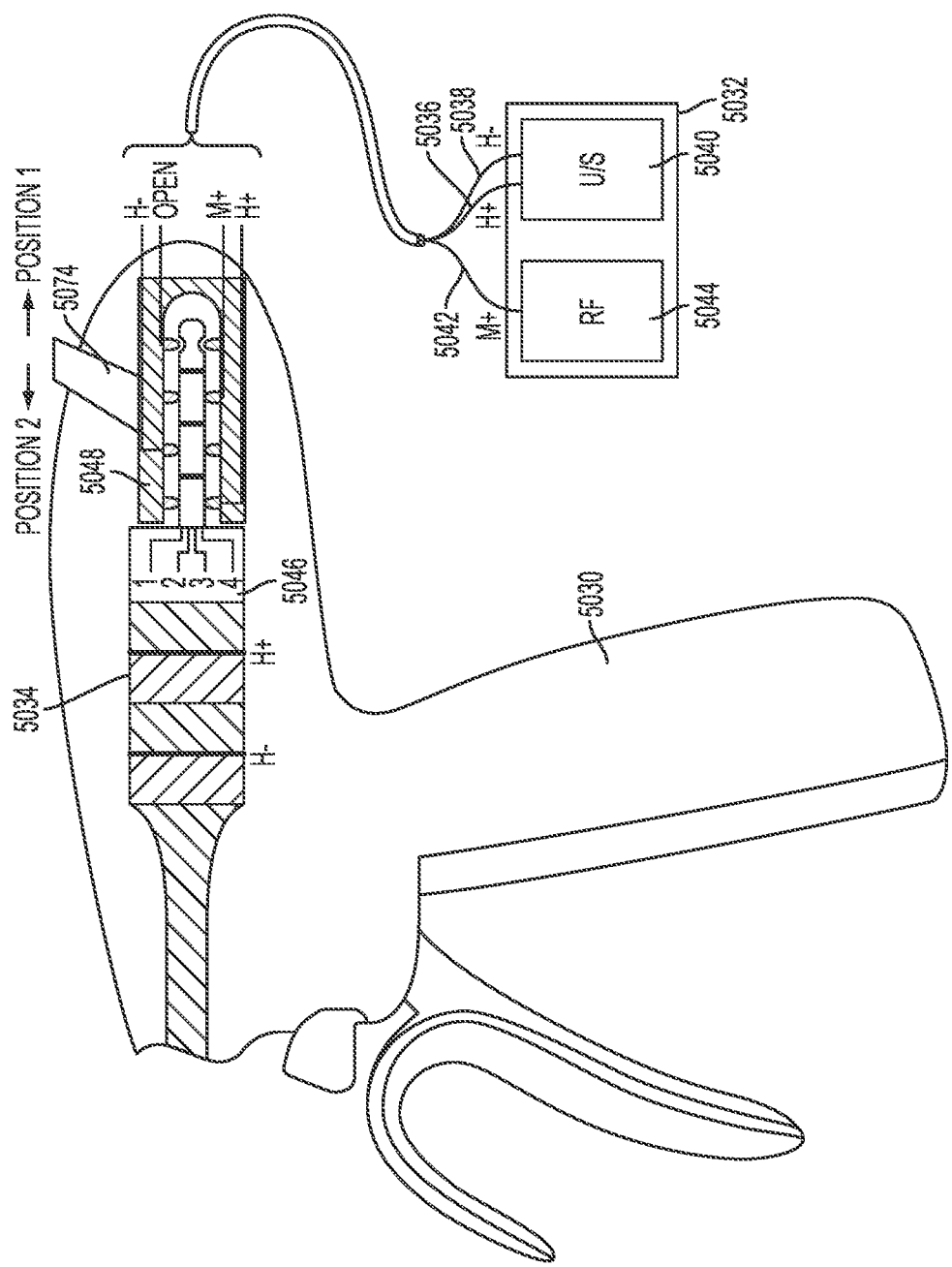
FIG. 78 illustrates one embodiment of an integrated RF/ultrasonic instrument comprising four-lead jack connector mated with a slidable female mating plug electrically connected to a generator.
Figure 79:
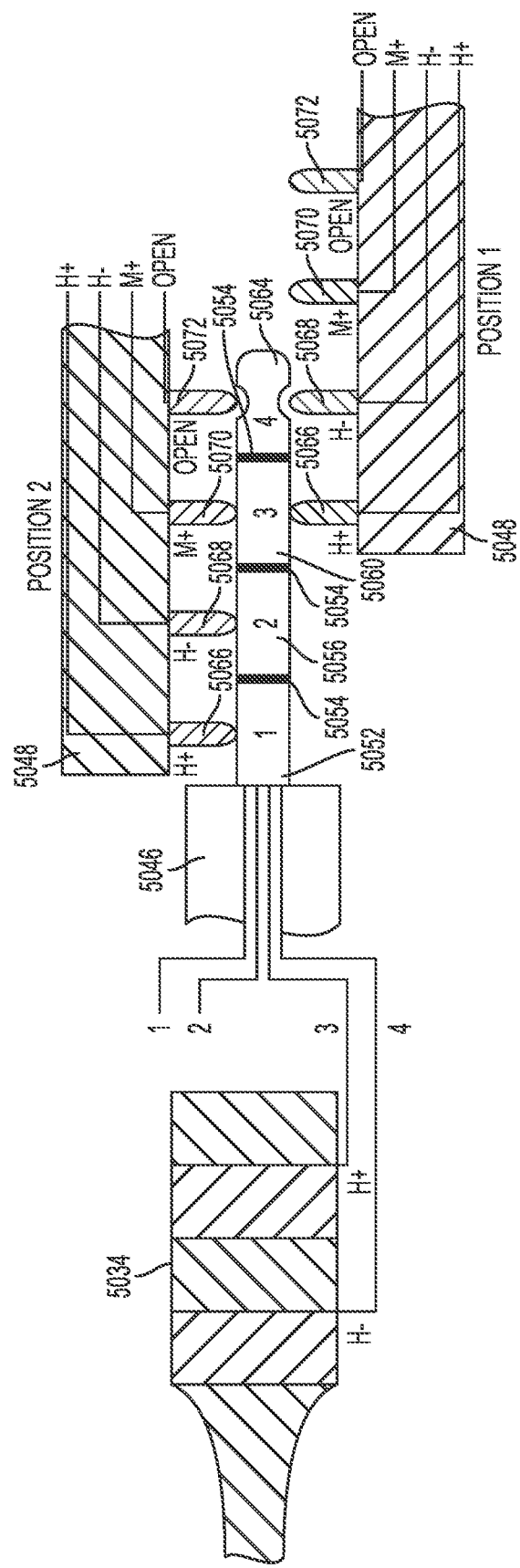
FIG. 79 is a detail view of one embodiment of a four-lead jack connector mated with a slidable female mating plug coupled to an ultrasonic transducer where position 1 provides an ultrasonic signal to the transducer, and where position 2 provides an electrosurgical signal to the device.
Figure 80:
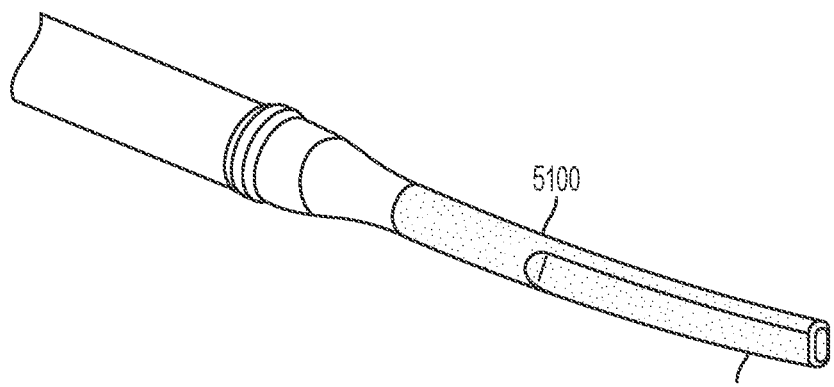
FIGS. 80-83 illustrate various embodiments of ultrasonic blades coated with an electrically insulative material to provide thermal insulation at the tissue contact area to minimize adhesion of tissue to the blade.
Figure 81:
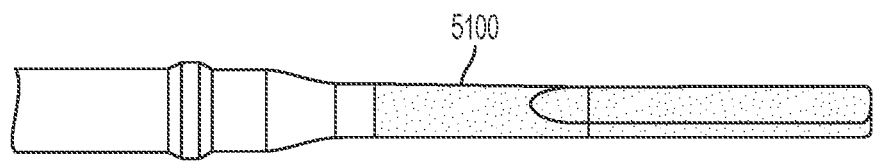
Figure 82:
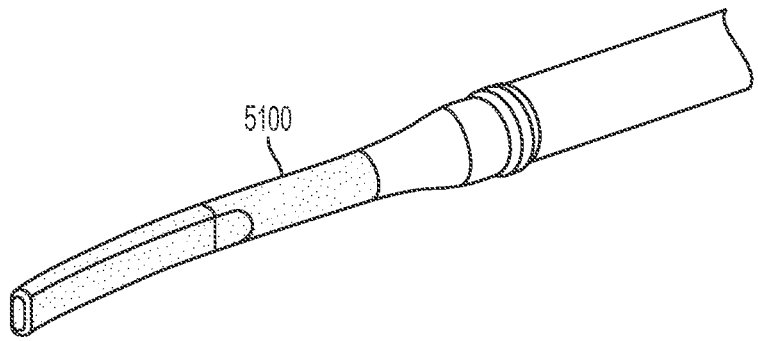
Figure 83:
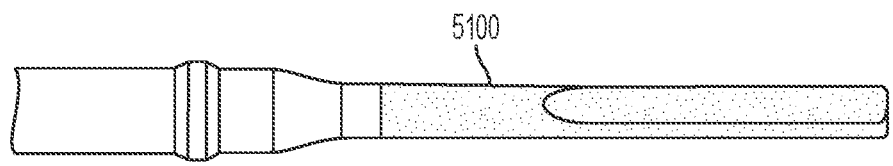
Figure 84:
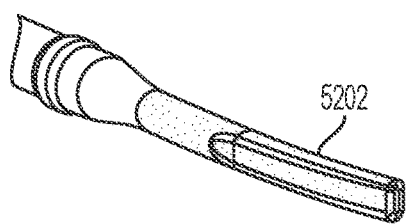
Figure 89:
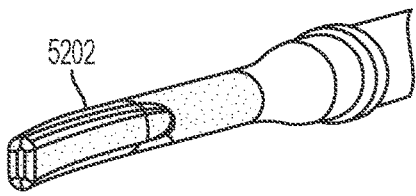
Figure 85:
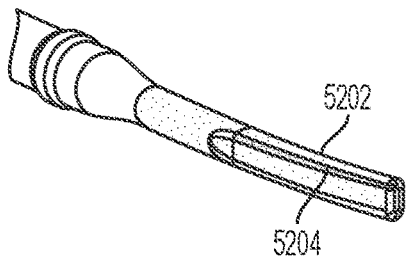
Figure 90:
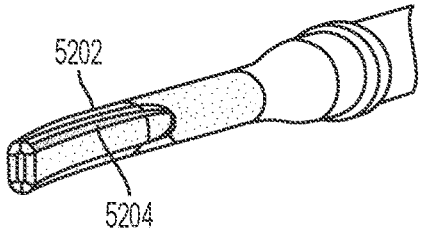
Figure 86:
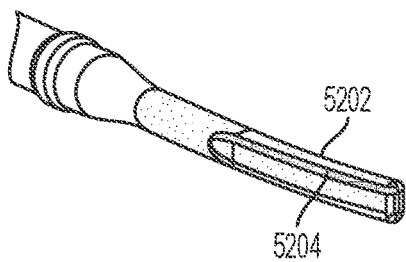
Figure 91:
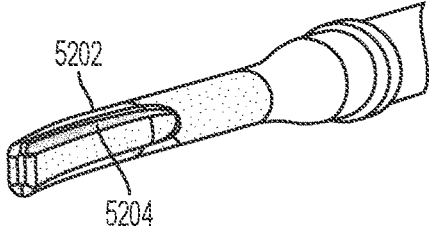
Figure 87:
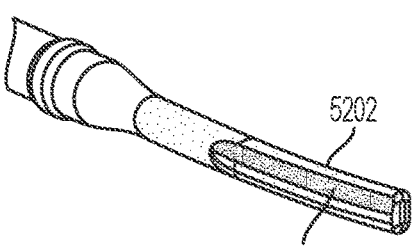
Figure 92:
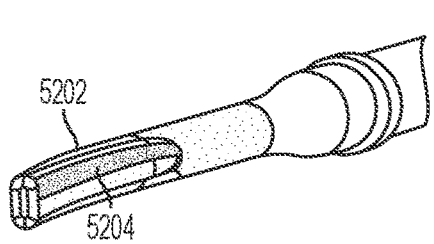
Figure 88:
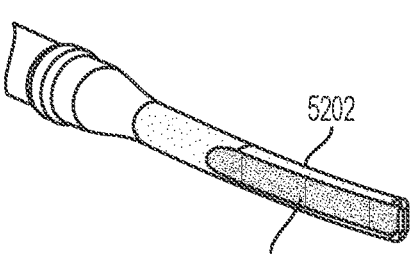
Figure 93:
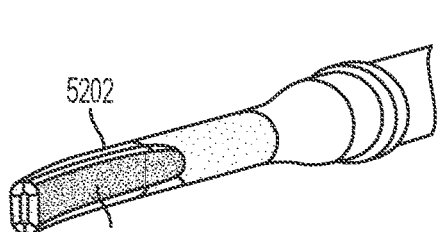

FIG. 78 illustrates one embodiment of an integrated RF/ultrasonic instrument 5030 electrically connected to an energy source such as a generator 5032 comprising four-lead jack connector 5046 is mated with a slidable female mating plug 5048. FIG. 79 is a detail view of the four-lead jack connector 5046 mated with a slidable female mating plug 5048 coupled to an ultrasonic transducer 5034. With reference to FIGS. 78-79, in one embodiment, the generator 5032 may comprise a first ultrasonic energy source such as ultrasonic generator 5040 and a second RF energy source such as an RF generator 5044 either individually or integrated into the same housing. An ultrasonic transducer 5034 is electrically connected to positive and negative leads 5036 (H+), 5038 (H−) of the ultrasonic generator 5040. A monopolar positive lead 5042 (M+) is coupled to the RF generator 5044. A four-lead jack connector 5046 is mated with a slidable female mating plug 5048 to electrically engage either 1) connection of the ultrasonic generator 5040 leads 5036, 5038 to the ultrasonic transducer 5034 or 2) connection of the monopolar RF generator 5044 lead 5042 to the transducer 5034 to prevent connecting both the ultrasonic generator 5040 and the monopolar RF generator 5044 to the transducer 5034 at the same time. In one embodiment, the female connector may be integrated in the device and the four lead jack may be mated to a generator.

A slidable switch 5074 comprises a slidable female connector 5048 configured to receive a rotatable jack connector 5046. The rotatable jack connector 5046 is used for mating with the slidable female connector 5048 for providing an electrical connection between two electrical devices, such as the transducer 5034 and the generator 5032. Referring particularly to FIG. 79, the rotatable jack connector 5046 comprises a tip terminal portion 5064 at a front end thereof, a ground terminal portion 5052 at a rear end thereof and two intermediate terminal portions 5056, 5060 to the tip and ground terminal portions 5064, 5052. The terminal portions 5052, 5056, 5060, 5064 are electrically separated from each other by dielectric insulators 5054. The ground terminal portion 5052 connects with a connecting portion of 5046. Since the structure of the rotatable mating plug 5046 is well known by those skilled in the art, detailed description thereof is omitted here. Conductive terminal portions 1, 2, 3, 4 are electrically connected to terminal portions 5052, 5056, 5060, 5064. Conductive terminal portions 1 and 2 connected to terminal portions 5052, 5056 and are isolated and are not coupled to the transducer 5034. Conductive terminal portions 3 and 4 are electrically connected to terminal portions 5060, 5064 and are electrically connected to the transducer 5034.

In one embodiment, the slidable female connector 5048 is slidable between Position 1 and Position 2. Position 1 may be configured to correspond with ultrasonic mode of operation and Position 2 may be configured to correspond with monopolar mode of operation. In Position 1, the monopolar RF lead 5042 (M+) from the monopolar RF generator 5044 is disconnected physically from the transducer 5034. The slidable female connector 5048 comprises contact portions 5066, 5068, 5070, 5072 configured to electrically engage terminal portions 5052, 5056, 5060, 5064. The slidable female connector 5048 includes an actuator portion 5074 that enables the user to slide the slidable female connector 5048 between multiple positions. As shown in particular in FIG. 79, the slidable female connector 5048 is slidably movable between Position 1 and Position 2, ultrasonic and monopolar RF modes.

Moving the slidable female connector 5048 into Position 1 places the integrated RF/ultrasonic instrument 5030 in ultrasonic mode. In this position, the contact portions 5066, 5068 are electrically engaged with terminal portions 5060, 5064 thereby electrically coupling positive and negative leads 5036 (H+), 5038 (H−) of the ultrasonic generator 5040 to the transducer 5034 through conductive terminal portions 3 and 4. In position 1, the monopolar positive lead 5042 (M+) coupled to the RF generator 5044 is physically disconnected from the transducer 5034.

Moving the slidable female connector 5048 into Position 2 places the integrated RF/ultrasonic instrument 5030 in monopolar RF mode. In this position, the contact portions 5066, 5068 are electrically engaged with terminal portions 5052, 5056 thereby electrically coupling positive and negative leads 5036 (H+), 5038 (H−) of the ultrasonic generator 5040 to isolated conductive terminal portions 1 and 2, effectively disconnecting the ultrasonic generator 5040 from the transducer 5034. In position 2, contact portion 5070 electrically engages terminal portion 5060 thereby electrically coupling the monopolar positive lead 5042 (M+) of the RF generator 5044 to the transducer 5034 through conductive terminal portion 3. Contact portion 5072 electrically engages terminal tip portion 5064, which is electrically isolated, or open.

FIGS. 114A and 114B illustrate one embodiment of an integrated RF/ultrasonic surgical instrument, for example, the integrated RF/ultrasonic surgical instrument 5030, comprising an integrated RF/ultrasonic end effector 6304. The integrated RF/ultrasonic end effector 6304 may be configured to deliver RF energy and/or ultrasonic energy to a tissue section. FIG. 114A illustrates a clamping arm 6364 in an open position. An ultrasonic blade 6366 is positioned such that the clamping arm 6364 and the ultrasonic blade 6366 may clamp tissue therebetween. The ultrasonic blade 6366 is positioned within a heat shield 6322. FIG. 114B illustrates the integrated RF/ultrasonic end effector 6304 in a clamped position.

Figure 115A:
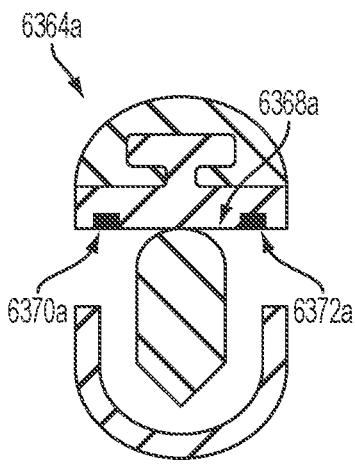
Figure 115B:
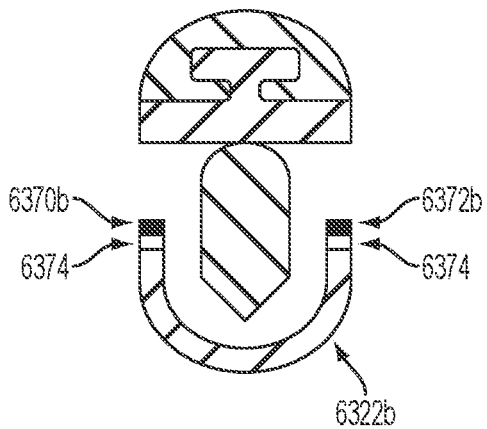
Figure 115C:
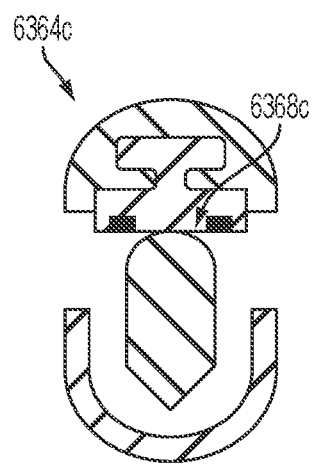
Figure 115D:
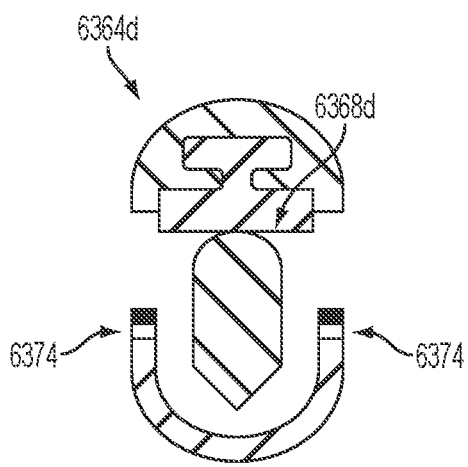
Figure 115E:
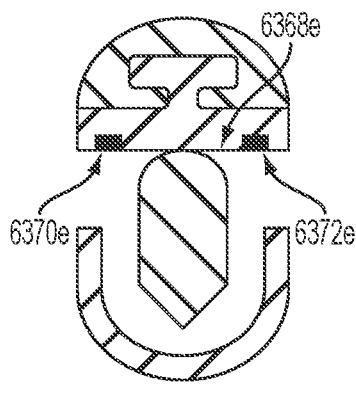
Figure 115F:
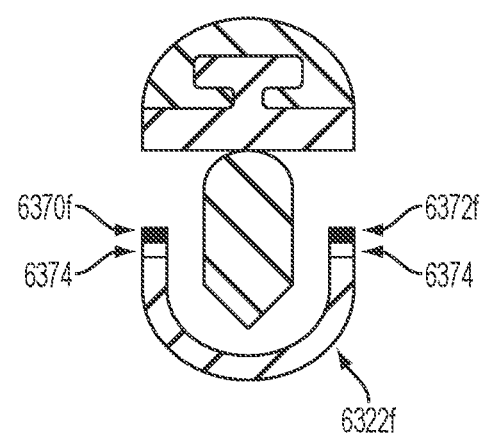

FIGS. 115A-115I illustrate various embodiments of a cross-section of the integrated RF/ultrasonic end effector 6304 taken along line A-A. As can be seen in FIGS. 115A-115I, RF electrodes 6370, 6372 may be located on and/or comprise any suitable portion of the integrated RF/ultrasonic end effector 6304. FIGS. 115A-115F illustrates various embodiments of the integrated RF/ultrasonic end effector 6304 comprising a bipolar electrode arrangement. For example, FIG. 115A illustrates one embodiment of the integrated RF/ultrasonic end effector 6304a. Positive electrodes 6370a, 6372a may be located on the tissue-facing portion of the clamp pad 6368a. The clamp arm 6364a may comprise a return, or negative, electrode. FIG. 115B illustrates one embodiment of the integrated RF/ultrasonic end effector 6304b. The positive electrodes 6370b, 6372b are located on the heat shield 6322b. An insulator 6374 may be located between the positive electrodes 6370a, 6370b and the heat shield 6322b to insulate heat shield 6322b. The clamp arm 6364b may function as the return electrode. FIG. 115C is similar to FIG. 115A, with the exception that the clamp arm 6364c extends laterally beyond the insulting clamp pad 6368c. FIG. 115D is similar to FIG. 115B, with the exception that the clamp arm 6364d extends laterally beyond the insulating clamp pad 6368d. In FIG. 115E, the clamp pad 6368e comprises a positive electrode 6370e and a negative electrode 6372e. In FIG. 115F, the heat shield 6322f comprises the positive electrode 6370f and the negative electrode 6372f

Figure 115G:
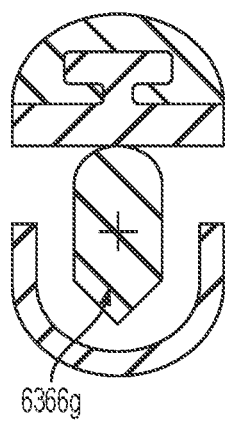
Figure 115H:
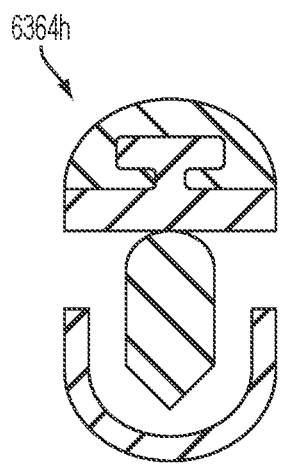
Figure 115I:
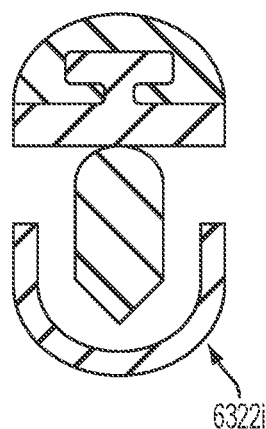

FIGS. 115G-115I illustrate various embodiments of the integrated RF/ultrasonic end effector 6304 comprising a monopolar electrode. In FIG. 115G, the ultrasonic blade 6366g comprises a monopolar electrode for delivering RF energy to a tissue section. In FIG. 115H, the clamp arm 6364h comprises the monopolar electrode. In FIG. 115I, the heat shield 6322i comprises the monopolar electrode.

FIGS. 117-118 illustrate one embodiment of an integrated RF/ultrasonic surgical instrument 6602. The integrated RF/ultrasonic instrument 6602 may comprise an insulated shaft 6614. The shaft 6614 and end effector 6604, including the jaw 6664 and ultrasonic blade 6666, may be energized with monopolar RF energy. The monopolar RF energy may be controlled by a double pole double throw (DPDT) selector switch 6628 located, for example, on the handle 6612 of the integrated RF/ultrasonic instrument 6602. The DPDT selector switch 6628 may switch the integrated RF/ultrasonic instrument 6602 from an ultrasonic generator 6620 to a monopolar RF generator 6622. FIG. 118 illustrates one embodiment of a DPDT selector switch 6628 which may be configured to switch between the ultrasonic generator 6620 and the monopolar RF generator 6622. The DPDT selector switch 6628 may comprise a user toggle 6630.

Coated Ultrasonic/RF Blades

FIGS. 80-83 illustrate various views of an ultrasonic blade 5100 coated with an electrically insulative material 5102 to provide thermal insulation at the tissue contact area to minimize adhesion of tissue to the blade 5100. Conventional ultrasonic devices utilize one mode of treatment, which limits versatility. For example, conventional ultrasonic devices may be used for blood vessel sealing and transecting tissue. Bipolar RF may offer added benefits such as a method for spot coagulation and pretreatment of tissue. Incorporating ultrasonic and RF may provide versatility and increase effectiveness. However, conventional ultrasonic devices utilize coatings to provide insulation at the distal end of the blade. These coatings are electrically insulative, and therefore limit current flow thus decreasing RF effectiveness. Additionally, current density may influence effectiveness. It may be contemplated that the entire waveguide of the blade may be coated with such coating to prevent shorting of the blade to the tube assembly return path. It is also contemplated that a similar coating and masking procedure may be employed in the clamp arm in order to provide a suitable path for current flow. In order to incorporate both energy modes into one device, a masking process for blade tip coating or coating removal process may be required. Creating an exposed area on the surface of the blade may provide a suitable path for current flow.

Accordingly, in one embodiment, an ultrasonic blade 5100 comprises a lubricious coating 5102 having properties similar to Teflon on the distal end of the blade 5100 as shown in FIGS. 80-83. The use of RF as a mode of treatment requires current to flow from the blade 5100, through tissue, and to a movable jaw member generally referred to as a clamp arm. The coating 5102 is used to provide thermal insulation at the contact area and minimize adhesion of tissue to blade 5100. However, the coating 5102 also is electrically insulative, which limits the amount of current flow. A method of masking the blade 5100 or removing coating selectively may be used to create exposed surfaces. In other embodiments, the lubricious coating 5102 provided on the blade 5100 may extend proximally so as to could coat the whole blade 5100, for example. In one embodiment, the blade 5100 may be coated back to the distal node.

FIGS. 84-93 illustrate various ultrasonic blades partially coated with an electrically insulative material to provide thermal and electrical insulation at the tissue contact area to minimize adhesion of tissue to the blade, where the lighter shade regions 5202 of the blade represent the coated portions and the darker shaded regions 5204 of the blade represent exposed surfaces that enable RF current to flow from the exposed region of the blade, through the tissue, and the movable jaw member. The exposed surface is symmetrical. The area on the blade that requires and exposed surface may be application dependent. Therefore, a different percentage of coating/exposed area has been illustrated is FIGS. 84-93. However, the embodiments are not limited to only the illustrated coverage. Although the embodiments shown in connection with FIGS. 84-93 show height-wise variation in electrically insulative blade coating, the lighter shaded regions 5202, it is contemplated within the scope of the present disclosure lengthwise variation in electrically insulative blade coating, the lighter shaded regions 5202, such that a portion of the distal tip of the blade exposed. In one example, the distal ⅓ of the sides of the blade would be exposed.

FIGS. 94-95 illustrate two ultrasonic blades with non-symmetrical exposed surfaces, where the blades are coated with an electrically insulative material to provide thermal insulation at the tissue contact area to minimize adhesion of tissue to the blade, where the lighter shade regions 5302 of the blade represent the coated portions and the darker shaded regions 5304 of the blade represent exposed surfaces that enable RF current to flow from the exposed region of the blade, through the tissue, and the movable jaw member. Current density may impact functionality and may be controlled by providing different surface areas. The surface areas do not have to be symmetrical on each side of the blade tip and may differ depending on performance. In addition, the exposed area may consist of two or more segments that are separated by at least one coated segment (not illustrated). Other coated/exposed geometries are possible as well, such as varying the depth or width of the exposed area along the axis of the blade.

In another embodiment, the blade and/or the tube assembly may be electrically charged to repel surgical matter.

FIGS. 119A-119E illustrate various embodiments of integrated RF/ultrasonic surgical end effectors. The clamp arm may comprise, for example, a circular clamp arm 6764a, 6764b, a hook clamp arm 6764c, a circular clamp arm comprising a cavity 6764d, or a curved hook clamp arm 6764e. The ultrasonic blade may comprise, for example, a rectangular ultrasonic blade 6766a, 6766c and/or an elliptical ultrasonic blade 6766b. FIGS. 120A-120C illustrate various embodiments of bipolar integrated RF/ultrasonic end effectors. In one embodiment, the clamp arm 6864a may comprise first electrode and the ultrasonic blade 6866a may comprise a second electrode. The clamp arm 6864a or the ultrasonic blade 6866a may comprise a return electrode. In some embodiments, the clamp arm 6864b may comprise an insulating pad 6868 to separate the clamp arm 6864b from the ultrasonic blade 6866b. In some embodiments, the clamp arm 6864c may comprise both a first electrode 6870 and a second electrode 6872. The first and second electrodes 6870, 6872 may be separated by an insulating portion of the clamp arm 6864c.

FIGS. 121A-121C comprise various embodiment of monopolar integrated RF/ultrasonic end effectors. In some embodiments, the entire clamp arm 6964a may comprise a monopolar electrode. In some embodiments, the clamp arm 6964*b* may comprise an insulating pad 6968. A portion of the clamp arm 6964*b* may comprise a monopolar electrode. In some embodiments, the clamp arm 6964*c* and an ultrasonic blade 6966 may comprise a single monopolar electrode.

Heat Shielded Ultrasonic Blades

FIG. 96 is a perspective view of one embodiment of an ultrasonic end effector 5400 comprising a metal heat shield 5402. The ultrasonic end effector 5400 comprises a clamp arm 5410. The clamp arm 5410 comprises a movable jaw member 5408 (clamp arm), a tissue pad 5412, an ultrasonic blade 5404, and a heat shield 5402 provided at a distance from the ultrasonic blade 5404. The heat shield 5402 is metal and contains apertures 5406 for air flow which provides cooling to the heat shield 5402 and the ultrasonic blade 5404. The heat shield 5402 is disposed opposite of the movable jaw member 5408.

FIG. 97 is a perspective view of another embodiment of an ultrasonic end effector 5420 comprising a retractable metal heat shield 5422. The ultrasonic end effector 5420 comprises a clamp arm 5430. The clamp arm 5430 comprises a movable jaw member 5428, a tissue pad 5432, an ultrasonic blade 5424, and a heat shield 5422 provided at a distance from the ultrasonic blade 5424. In another embodiment, the metal heat shield 5422 is attachable to the ultrasonic blade 5424 at the distal most node location. The attachment means also acts as a heat sink 5422 to remove heat from the blade 5424. The heat shield 5422 is metal and contains apertures 5426 for air flow which provides cooling to the heat shield 5422 and the ultrasonic blade 5424. The heat shield 5422 is disposed opposite of the movable jaw member 5428.

FIG. 98 is a side view of another embodiment of an ultrasonic end effector 5440 comprising a heat shield 5444 shown in cross-section. The ultrasonic end effector 5440 comprises a clamp arm 5448. The clamp arm 5448 comprises a movable jaw member 5252, an ultrasonic blade 5450, and a heat shield 5444 that also acts as a heat sink 5442. A pad 5452 may be provided on the blade 5450 side of the movable jaw member 5252 to grasp tissue between the pad 5452 and the blade 5450. The attachment of the heat shield 5444/heat sink 5442 is at a node location 5446. FIG. 99 is a front view of the ultrasonic end effector 5440 shown in FIG. 98, according to one embodiment.

FIGS. 100-104 illustrate various views of one embodiment of an ultrasonic end effector 5460 comprising a dual purpose rotatable heat shield 5462. FIG. 100 illustrates one embodiment of a clamp arm 5464 comprising a movable jaw member 5464 shown in a closed position and a dual purpose rotatable heat shield 5462 located below an ultrasonic blade 5468. The ultrasonic end effector 5460 comprises a clamp arm 5464 having a movable jaw member 5470, an ultrasonic blade 5468, and the dual purpose rotatable heat shield 5462. In one embodiment, the clamp arm 5464 comprises a movable jaw member 5470, which is shown in FIG. 100 in a closed position, and the rotatable heat shield 5462 is located below the ultrasonic blade 5468. In this embodiment, the heat shield 5462 is dual purposed and is rotatable about the blade 5468. The blade 5468 in this example is a straight/non-curved configuration. While the heat shield 5468 is disposed opposite of the movable jaw member 5470 (shears type end-effector), it acts as a heat shield 5462. After rotation about the blade 5468, the heat shield 5462 now is disposed between the blade 5468 and the movable jaw member 5470 providing a tissue clamping surface, backed by the blade 5468 providing strength/support for the heat shield 5468. Also, the heat shield 5468 may be configured to provide energy opposite of the energy that may be provided on the movable jaw member 5470 creating a bi-polar energy that may effect tissue.

FIG. 101 illustrates one embodiment of a movable jaw member 5470 shown in an open position and a dual purpose rotatable heat shield 5462 rotated such that it is interposed between the movable jaw member 5470 and the blade 5468.

FIG. 102 illustrates an end view of one embodiment of a dual purpose rotatable heat shield 5462 rotated in a first position. FIG. 103 illustrates an end view of one embodiment of the dual purpose rotatable heat shield 5462 rotated in a second position. With reference now to FIGS. 102-103, the rotatable heat shield 5462 has purposeful alignment that enables a tapered portion of the shield 5642 to come in between the top of the blade 5468 surface and the movable jaw member 5470. This rotation enables "back cutting" if necessary while still allowing normal activation shielding. Additionally an inner contour of the shield 5462 may be configured for contact to "clean" the tip upon rotation if necessary. Further if the shield 5462 is insulated, rotation of the shield 5462 from the stage 1 position into the stage 2 position enables RF energy to be applied for sealing only. Bottom surface of shield could have grip to assist in grasping as well when rotated to position 2.

FIG. 104 is a top profile view of one embodiment of a heat shield 5462 showing a tapered portion of the shield 5462. As shown, in one embodiment the heat shield 5462 includes a tapered portion defined by radius R1 relative to radius R2, where R2>R1.

FIGS. 116A-116B illustrates one embodiment of a cooling system for an ultrasonic surgical instrument. Air 6416 may be forced down an inner tube 6406 of the ultrasonic surgical instrument 6302 and over an ultrasonic end effector 6404. The air movement over the ultrasonic end effector 6304 may cool the ultrasonic end effector 6404. In one embodiment, cold air may be used to increase the cooling of the end effector 6404. Air 6416 may be moved in the direction of shown to cool the ultrasonic end effector 6404 through convection heat transfer from the ultrasonic end effector 6404 to the air. In some embodiments, a hospital air-line 6410 may be coupled to the ultrasonic instrument 6302 to provide compressed air flow through the inner tube 6406. In some embodiments, a hand pump 6412 and a reservoir 6414 may be located in the proximal end of the surgical instrument 6402, such as, for example, in the handle. A clinician may operate the hand pump 6412 to generate air pressure within the reservoir 6414. The hand pump 6412 may comprise, for example, a squeeze bulb. The reservoir 6414 and/or the hospital air-line 6410 may be force air over the ultrasonic end effector 6404 with each opening and/or closing of the jaws. In some embodiments, the reservoir 6414 and/or the hospital air-line 6410 may provide a continuous flow of air over the ultrasonic end effector. In some embodiments, the inner tube 6406 may comprise a vortex tub, illustrated in FIG. 116B. The vortex tube may facilitate movement of air 6416 within the inner tube 6406 to travel distally 6418 through the inner tube 6406, over the ultrasonic end effector 6404, and return 6420 to the proximal end of the inner tube 6406 which may be open to release the air. The distal end of the vortex tube may comprise a splitter to split the stream of air 6418 to cool the distal end of the ultrasonic end effector 6404.

Ultrasonic 4-Bar Closure with Application to an Ultrasonic Rongeur

FIG. 105 illustrates a conventional rongeur surgical instrument 6000. Certain orthopedic procedures such as spinal fusion are used to treat degenerative spinal disk disease. One of the most commonly used instruments is the rongeur 6000 as shown in FIG. 105 for the removal of the spinal disk, which is made up of a nucleus and a tough annulus. The rongeur 6000 uses a 4-bar linkage in combination with a clamp arm 6002 comprising a movable jaw member 6004 to take bites of the spinal disk material. Generally speaking, a number of bites (10 to 20) may be taken for complete removal of the spinal disk. The multiple use of the rongeur 6000 can be fatiguing.

Accordingly, FIG. 106 illustrates one embodiment of an ultrasonic energy driven rongeur device 6100. The ultrasonic energy driven rongeur device 6100 comprises an ultrasonic transducer 6102 is added to one member of a 4-bar mechanism. The rongeur device 6100 also comprises two elongate horizontal members. As shown in FIG. 106, only the lower horizontal member 6104 coupled to a handle 6106 is shown. The two elongate horizontal members of the ultrasonic rongeur device 6100 are each attached to one handle 6106 of the ultrasonic rongeur device 6100. The horizontal members are connected with a small link at a distal end 6103, and the forward handle 6106 is the second link. These four members approach parallel-rules. As can be seen in FIG. 106, the bottom horizontal member 6104 is basically a straight rod which does not move. In accordance with one embodiment of the present disclosure, by placing pivots 6108, 6110 of the lower horizontal member 6104 at Nodes, the lower horizontal member 6104 may be considered an ultrasonic waveguide. Accordingly, the rest of the rongeur device 6100 is attached to the lower horizontal arm 6104 at nodes. The proximal end of the lower horizontal member 6104 can be attached to an ultrasonic transducer 6102 to produce ultrasonic displacement at the distal end 6103. The amplitude of the ultrasonic displacement will aid in cutting the tissue and therefore reduce the force required by the surgeon. Not shown here is the need to insert some damping material between the two horizontal members and a sheath on the lower horizontal member 6104 to avoid contact with intervening tissue. Advantages of the ultrasonic driven rongeur device 6100 include, without limitation, a novel closure mechanism for ultrasonic instruments based on a 4-bar linkage, lower force required to take a bite of spinal disk material, reduce surgeon fatigue, and novel instrument architecture for additional applications.

While various details have been set forth in the foregoing description, it will be appreciated that the various aspects of the ultrasonic and electrosurgical devices may be practiced without these specific details. For example, for conciseness and clarity selected aspects have been shown in block diagram form rather than in detail. Some portions of the detailed descriptions provided herein may be presented in terms of instructions that operate on data that is stored in a computer memory. Such descriptions and representations are used by those skilled in the art to describe and convey the substance of their work to others skilled in the art. In general, an algorithm refers to a self-consistent sequence of steps leading to a desired result, where a "step" refers to a manipulation of physical quantities which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities.

Unless specifically stated otherwise as apparent from the foregoing discussion, it is appreciated that, throughout the foregoing description, discussions using terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

It is worthy to note that any reference to "one aspect," "an aspect," "one embodiment," or "an embodiment" means that a particular feature, structure, or characteristic described in connection with the aspect is included in at least one aspect. Thus, appearances of the phrases "in one aspect," "in an aspect," "in one embodiment," or "in an embodiment" in various places throughout the specification are not necessarily all referring to the same aspect. Furthermore, the particular features, structures or characteristics may be combined in any suitable manner in one or more aspects.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

Some or all of the embodiments described herein may generally comprise technologies for ultrasonic and RF treatment of tissue, or otherwise according to technologies described herein. In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

All of the above-mentioned U.S. patents, U.S. patent application publications, U.S. patent applications, foreign patents, foreign patent applications, non-patent publications referred to in this specification and/or listed in any Application Data Sheet, or any other disclosure material are incorporated herein by reference, to the extent not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

Although various embodiments have been described herein, many modifications, variations, substitutions, changes, and equivalents to those embodiments may be implemented and will occur to those skilled in the art. Also, where materials are disclosed for certain components, other materials may be used. It is therefore to be understood that the foregoing description and the appended claims are intended to cover all such modifications and variations as falling within the scope of the disclosed embodiments. The following claims are intended to cover all such modification and variations.

In summary, numerous benefits have been described which result from employing the concepts described herein. The foregoing description of the one or more embodiments has been presented for purposes of illustration and description. It is not intended to be exhaustive or limiting to the precise form disclosed. Modifications or variations are possible in light of the above teachings. The one or more embodiments were chosen and described in order to illustrate principles and practical application to thereby enable one of ordinary skill in the art to utilize the various embodiments and with various modifications as are suited to the particular use contemplated. It is intended that the claims submitted herewith define the overall scope.

Various aspects of the subject matter described herein are set out in the following numbered clauses:

1. An ultrasonic surgical instrument, comprising: a waveguide comprising a proximal end and a distal end, wherein the proximal end is coupled to an ultrasonic transducer; a tube defining a lumen, wherein the waveguide is located within the lumen; an end effector coupled to the distal end of the waveguide, the end effector comprising an ultrasonic blade and a clamp arm operatively coupled to the end effector; and a tissue accumulation impedance mechanism coupled to the end effector, wherein the tissue accumulation impedance mechanism is configured to prevent tissue from accumulating within the lumen.

2. The surgical instrument of clause 1, wherein the tissue accumulation impedance mechanism comprises a boot barrier configured to create a seal between the tube and the end effector.

3. The surgical instrument of clause 2, wherein the boot barrier is sealed to the tube 4. The surgical instrument of clause 2, wherein the boot is retained by the tube or end effector using one or more retention features.

5. The surgical instrument of clause 2, wherein the boot barrier is sealed to the ultrasonic blade by way of an interference fit between the boot barrier and the ultrasonic blade.

6. The surgical instrument of clause 2, wherein the boot barrier comprises a cavity.

7. The surgical instrument of clause 6, wherein the cavity is rounded to allow fluid to flow out of the cavity.

8. The surgical instrument of clause 2, wherein the boot barrier comprises a plurality of contact points with the blade.

9. The surgical instrument of claim 1, wherein the tissue accumulation impedance mechanism comprises one or more apertures in the tube.

10. The surgical instrument of claim 9, wherein the apertures comprise one or more windows.

11. The surgical instrument of claim 9, wherein the apertures comprises one or more holes.

12. The surgical instrument of claim 1, wherein the tube comprises a distal portion, wherein the distal portion comprises a half-circle cross section.

13. The surgical instrument of claim 1, wherein the tube comprises one or more ribs formed on an inner side of the tube.

14. The surgical instrument of claim 1, wherein the tissue accumulation impedance mechanism comprises a pump configured to provide a positive pressure flow between the blade and the tube, wherein the positive pressure flow prevents tissue ingress into the lumen.

15. The surgical instrument of claim 1, wherein the pump is located distally to a distal-most overmolded seal located within the lumen.

16. The surgical instrument of claim 1, wherein the tissue accumulation impedance mechanism comprises a slidable tube disposed within the lumen, the slidable tube slidable from a first position to a second position, wherein in the first position the slidable tube is disposed over the blade, and wherein in the second position the blade is exposed.

17. An ultrasonic surgical instrument comprising: z waveguide comprising a proximal end and a distal end, wherein the proximal end is coupled to a transducer; an end effector coupled to the distal end of the waveguide, the end effector comprising at least one tissue retention feature; a clamp arm operatively coupled to the end effector.

18. The surgical instrument of claim 17, wherein the at least one tissue retention feature comprises one or more indentations/grooves/notches formed in the end effector.

19. The surgical instrument of claim 18, wherein the one or more indentations comprise triangular teeth.

20. The surgical instrument of claim 18, wherein the one or more indentations comprise holes.

21. The surgical instrument of claim 18, wherein the one or more indentations comprise horizontal trenches.

22. The surgical instrument of claim 17, wherein the at least one tissue retention feature is offset from the tissue dividing crown of the end effector.

23. The surgical instrument of claim 17, wherein the at least on tissue retention feature comprises one or more projections from the end effector.

24. The surgical instrument of claim 23, wherein the one or more projections comprise triangular teeth.

25. The surgical instrument of claim 23, wherein the one or more projections comprise blocks.

26. The surgical instrument of claim 23, wherein the one or more projections comprise horizontal bumps.

27. The surgical instrument of claim 23, wherein the one or more projections comprise circular bumps.

28. The surgical instrument of claim 17, wherein the at least one tissue retention feature is disposed over an entire length of the blade.

29. The surgical instrument of claim 17, wherein the at least one tissue retention feature is disposed over a discrete section of the blade.

30. An ultrasonic surgical instrument, comprising: a waveguide comprising a proximal end and a distal end, wherein the proximal end is coupled to a transducer; an end effector operatively coupled to the distal end of the waveguide guide; a rotation shroud configured to rotate the waveguide; and a rotation stop mechanism coupled to the rotation shroud prevent rotation of the rotation knob beyond a predetermined rotation.

31. The surgical instrument of claim 30, wherein the shroud comprises: at least one channel; and at least one boss, the at least one boss located within the at least one channel, wherein the at least one boss has a predetermined lateral movement limit, wherein when the at least one boss reaches the predetermined lateral movement limit, the at least one boss prevents further rotation of the rotation knob.

32. The surgical instrument of claim 30, wherein the rotation stop comprises: a gate comprising a first wing and a second wing, wherein the first and second wings are disposed at an angle, wherein the gate is disposed within the shroud, and wherein the gate allows a predetermined angle of rotation of the shroud.

33. The surgical instrument of claim 30, wherein the rotation stop comprises a contoured extrusion element.

34. The surgical instrument of claim 33, wherein the contoured extrusion element comprises a tactile feedback element.

35. The surgical instrument of claim 34, wherein the tactile feedback element comprises a semi-compliant material selected from the group consisting of rubber, medium to high density rubber, silicone, thermoplastic elastomer, springy piece of stainless steel, spring steel, copper, shape memory metal, and combinations of any thereof.

36. An ultrasonic surgical instrument, comprising: a waveguide comprising a proximal end and a distal end, wherein the proximal end is coupled to a transducer; an end effector coupled to the distal end of the waveguide; a clamp arm operatively coupled to the end effector; and a tube disposed over the waveguide, wherein the tube comprises a counter deflection element, wherein the counter deflection element is configured to allow deflection of the blade, wherein the deflection of the blade counteracts a force placed on the blade by the clamp arm when in a clamped position.

37. A surgical instrument comprising: a waveguide comprising a proximal end and a distal end, wherein the proximal end is coupled to a signal source, the signal source configured to provide an ultrasonic signal and an electrosurgical signal; an end effector coupled to the waveguide; a clamp arm operatively coupled to the end effector; and a sealing button, wherein the sealing button causes the surgical instrument to deliver the electrosurgical signal to the end effector and the clamp arm for a first period, and wherein the sealing button causes the surgical instrument to deliver the ultrasonic signal to the blade for a second period, wherein the second period is subsequent to the first period.

38. A surgical instrument, comprising: a waveguide comprising a proximal end and a distal end, wherein the proximal end is coupled to a transducer; an end effector coupled to the distal end of the waveguide; a tube disposed over the waveguide; a cam surface formed on an outer surface of the tube; and a clamp arm operatively coupled to the cam surface.

39. The surgical instrument of claim 38, comprising: a pivot pin located within a hole defined by the end effector, the pivot pin operatively coupled to the clamp arm, wherein the clamp arm pivots about the pivot pin.

40. The surgical instrument of claim 39, wherein the pivot pin is located at the distal most node of the waveguide.

41. The surgical instrument of claim 38, wherein the tube is actuatable, and wherein the clamp arm is cammed open and closed against the end effector through relative motion between the tube and the end effector.

42. A surgical instrument, comprising: a waveguide comprising a proximal end and a distal end, wherein the proximal end is coupled to a transducer; an end effector coupled to the distal end of the waveguide, the end effector defining a pin hole; a rigid pin disposed within the pin hole; a clamp arm; and a four-bar linkage; wherein the four-bar linkage is operatively coupled to the clamp arm and the rigid pin, wherein the four-bar linkage is actuatable to move the clamp arm to a clamped position.

43. The surgical instrument of claim 40, comprising: an outer tube, wherein the outer tube is coupled to the four-bar linkage, and wherein the outer-tube actuates the four-bar linkage from a first position to a second position.

44. An ultrasonic surgical instrument, comprising: a waveguide comprising a proximal end and a distal end, wherein the proximal end is coupled to a transducer; and an end effector coupled to the distal end of the waveguide, wherein the end effector is partially coated with thermally and electrically insulative material such that the distal end of the end effector comprises one or more exposed sections.

45. The ultrasonic surgical instrument of claim 44, wherein the one or more exposed areas are symmetrical.

46. The ultrasonic surgical instrument of claim 44, wherein the one or more exposed areas are asymmetrical.

47. The ultrasonic surgical instrument of claim 44, wherein the one or more exposed sections are separated by one or more coated sections.

48. The ultrasonic surgical instrument of claim 44, wherein the waveguide is fully coated with thermally and electrically insulative material.

49. The ultrasonic surgical instrument of claim 44, wherein the waveguide is partially coated with thermally and electrically insulative material.

50. An ultrasonic surgical instrument, comprising: a waveguide comprising a proximal end and a distal end, wherein the proximal end is coupled to a transducer; and an end effector coupled to the distal end of the waveguide, a clamp arm operatively connected to the end effector wherein the clamp arm is partially coated with thermally and electrically insulative material such that the distal end of the clamp arm comprises one or more exposed sections.

51. The ultrasonic surgical instrument of claim 50, wherein the one or more exposed areas are symmetrical.

52. The ultrasonic surgical instrument of claim 50, wherein the one or more exposed areas are asymmetrical.

53. The ultrasonic surgical instrument of claim 50, wherein the one or more exposed sections are separated by one or more coated sections.

54. The ultrasonic surgical instrument of claim 50, wherein the waveguide is fully coated with thermally and electrically insulative material.

55. The ultrasonic surgical instrument of claim 50, wherein the waveguide is fully coated with thermally and electrically insulative material.

56. An ultrasonic surgical instrument, comprising: a waveguide comprising a proximal end and a distal end, wherein the proximal end is coupled to a transducer; and an end effector coupled to the distal end of the waveguide, a clamp arm operatively connected to the end effector wherein the clamp arm and the end effector are partially coated with thermally and electrically insulative material such that the distal end of the end effector and clamp arm comprise one or more exposed sections.

57. The ultrasonic surgical instrument of claim 56, wherein the one or more exposed areas are symmetrical.

58. The ultrasonic surgical instrument of claim 56, wherein the one or more exposed areas are asymmetrical.

59. The ultrasonic surgical instrument of claim 56, wherein the one or more exposed sections are separated by one or more coated sections.

60. The ultrasonic surgical instrument of claim 56, wherein the waveguide is fully coated with thermally and electrically insulative material.

61. The ultrasonic surgical instrument of claim 56, wherein the waveguide is fully coated with thermally and electrically insulative material.

62. An ultrasonic surgical instrument, comprising: ultrasonic end effector comprising an ultrasonic surgical blade and a clamp arm; and a heat shield provided at a predetermined distance from the ultrasonic blade.

63. The ultrasonic instrument of claim 62, wherein the heat shield is rotatable about the ultrasonic blade.

64. The ultrasonic instrument of 62, comprising a heat sink.

65. The ultrasonic instrument of 62, wherein the heat shield comprises a plurality of apertures.

66. The ultrasonic instrument of 62, wherein the heat shield comprises a tapered portion.

67. An integrated radio frequency (RF)/ultrasonic surgical instrument, comprising: an ultrasonic transducer; a jack connector electrically coupled to the ultrasonic transducer; and a slidable female mating plug matable with the jack connector; wherein the slidable female mating plug is slidable in multiple positions to electrically couple the ultrasonic transducer to either an ultrasonic energy source or an RF energy source.

68. The integrated radio frequency (RF)/ultrasonic surgical instrument of claim 67, wherein the jack connector is rotatable with the ultrasonic transducer.

69. The integrated radio frequency (RF)/ultrasonic surgical instrument of claim 67, wherein the jack connector is a four-lead jack connector.

70. The integrated radio frequency (RF)/ultrasonic surgical instrument of claim 67, wherein the slidable female mating plug in slidable between a first position and a second position; wherein in the first position the ultrasonic transducer is electrically coupled to the ultrasonic energy source and is electrically isolated from the RF energy source; and wherein in the second position the ultrasonic transducer is electrically coupled to the RF energy source and is electrically isolated from the ultrasonic energy source.

71. An ultrasonic energy driven rongeur device, comprising: at least one elongate member; a linkage connected to a distal end of the at least one elongate member; an ultrasonic transducer coupled to the at least one elongate member; and a pivot located at an ultrasonic node of the at least one elongate member.

72. The ultrasonic energy driven rongeur device of claim 71, comprising: a second linkage connected to a proximal end of the at least one elongate member; and a second pivot located at a second ultrasonic of the at least one elongate member.

73. The ultrasonic energy driven rongeur device of claim 71, comprising: a second elongate member above the at least one elongate member; and a damping material disposed between the least one elongate member and the second elongate member.

The invention claimed is:
1. A surgical instrument, comprising:
a waveguide comprising a proximal end and a distal end, the proximal end configured to couple to an ultrasonic transducer and one output of a radio frequency (RF) generator;
an end effector configured to cut and seal tissue, the end effector comprising an ultrasonic blade and a clamp arm, wherein the ultrasonic blade is mechanically coupled to the distal end of the waveguide and electrically coupled to the waveguide, and wherein the clamp arm comprises a movable jaw member electrically coupled to another output of the RF generator such that an electrical current can pass through the movable jaw member and the ultrasonic blade through tissue located between the movable jaw member and the ultrasonic blade; and a single electrical switch configured to electrically couple to the RF generator and the movable jaw member, wherein the single electrical switch is operable in at least two independent states, wherein in a first state the single electrical switch is configured to electrically couple an ultrasonic generator to the ultrasonic transducer to cause the ultrasonic blade to activate ultrasonically to delivery ultrasonic energy only and wherein in a second state the single electrical switch is configured to electrically isolate the ultrasonic transducer from the ultrasonic generator and to electrically couple the RF generator to the movable jaw member through an electrical conductor to cause RF electrical current only to flow through the tissue located between the ultrasonic blade and the movable jaw member, wherein the single electrical switch is operable to cause the surgical instrument to deliver electrical current only from the RF generator to the movable jaw member for a first period, and to cause the surgical instrument to deliver ultrasonic energy only to the ultrasonic blade for a second period without input from a clinician, and wherein the surgical instrument is configured such that the second period occurs after the first period in order to seal tissue before cutting tissue.

2. The surgical instrument of claim 1, wherein the ultrasonic blade and the waveguide are configured to electrically couple to a positive output of the RF generator and the movable jaw member is configured to electrically couple to a negative output of the RF generator.

3. The surgical instrument of claim 1, wherein the duration of the first and second periods is controlled by an algorithm.

4. The surgical instrument of claim 3, wherein the algorithm controls the operation of the single electrical switch to deactivate the RF generator after the first period and activate the ultrasonic generator for the second period such that the ultrasonic blade completes a cut of the tissue between two RF seals.

5. The surgical instrument of claim 4, wherein cutting the tissue with the ultrasonic blade also provides partial sealing of the tissue.

6. The surgical instrument of claim 1, wherein the ultrasonic blade comprises a coated portion and an uncoated portion, wherein the coated portion of the ultrasonic blade comprises a thermally and electrically insulative material.

7. The surgical instrument of claim 6, wherein the coated and uncoated portions of the ultrasonic blade are symmetrical.

8. The surgical instrument of claim 6, wherein the coated and uncoated portions of the ultrasonic blade are asymmetrical.

9. The surgical instrument of claim 1, wherein the movable jaw member comprises a coated portion and an uncoated portion, wherein the coated portion of the movable jaw member comprises a thermally and electrically insulative material.

10. The surgical instrument of claim 9, wherein the coated and uncoated portions of the movable jaw member are symmetrical.

11. The surgical instrument of claim 9, wherein the coated and uncoated portions of the movable jaw member are asymmetrical.

12. A surgical instrument, comprising:
an ultrasonic generator;
a radio frequency (RF) generator;
an ultrasonic transducer;
a waveguide comprising a proximal end and a distal end, the proximal end coupled to the ultrasonic transducer and one output of the RF generator;
an end effector configured to cut and seal tissue, the end effector comprising an ultrasonic blade and a clamp arm, wherein the ultrasonic blade is mechanically coupled to the distal end of the waveguide and electrically coupled to the waveguide, the clamp arm comprising a movable jaw member electrically coupled to another output of the RF generator such that an electrical current can pass through the movable jaw member and the ultrasonic blade through tissue located between the movable jaw member and the ultrasonic blade; and
a single electrical switch electrically coupled to the RF generator and the movable jaw member, wherein the single electrical switch is operable in at least two independent states, wherein in a first state the single electrical switch is configured to electrically couple the ultrasonic generator to the ultrasonic transducer to cause the ultrasonic blade to activate ultrasonically to deliver ultrasonic energy only and wherein in a second state the single electrical switch is configured to electrically isolate the ultrasonic transducer from the ultrasonic generator and to electrically couple the RF generator to the movable jaw member through an electrical conductor to cause RF electrical current only to flow through the tissue located between the ultrasonic blade and the movable jaw member, wherein the single electrical switch is operable to cause the surgical instrument to deliver electrical current only from the RF generator to the movable jaw member for a first period, and to cause the surgical instrument to deliver ultrasonic energy only to the ultrasonic blade for a second period without input from a clinician, and wherein the surgical instrument is configured such that the second period occurs after the first period in order to seal tissue before cutting tissue.

13. The surgical instrument of claim 12, wherein the ultrasonic blade and the waveguide are electrically coupled to a positive output of the RF generator and the movable jaw member is electrically coupled to a negative output of the RF generator.

14. The surgical instrument of claim 12, wherein the clamp arm comprises any one of a circular shape, a hook shape, a circular shape with a cavity, or a curved hook shape movable jaw member.

15. The surgical instrument of claim 12, wherein the ultrasonic blade comprises any one of a rectangular and elliptical shaped body.

16. The surgical instrument of claim 12, wherein the movable jaw member of the clamp arm comprises a return electrode.

17. The surgical instrument of claim 12, wherein the movable jaw member of the clamp arm comprises an insulating pad to electrically isolate the movable jaw member from the ultrasonic blade.

18. The surgical instrument of claim 12, wherein the movable jaw member of the clamp arm comprises a first and a second electrode.

19. The surgical instrument of claim 18, wherein the first and second electrodes are separated by an electrically insulating element.

20. The surgical instrument of claim 12, wherein the movable jaw member of the clamp arm comprises a first electrode and the ultrasonic blade comprises a second electrode.

* * * * *